US012503706B2

(12) United States Patent
Hansen et al.

(10) Patent No.: US 12,503,706 B2
(45) Date of Patent: Dec. 23, 2025

(54) MICROBIAL CELL WITH IMPROVED IN VIVO CONVERSION OF THEBAINE/ORIPAVINE

(71) Applicant: RIVER STONE BIOTECH LLC, Cambridge, MA (US)

(72) Inventors: Esben Halkjaer Hansen, Copenhagen (DK); Swee Chuang Lim Hallwyl, Copenhagen (DK); Hussam Hassan Nour-Eldin, Copenhagen (DK); Zeinu Mussa Belew, Copenhagen (DK)

(73) Assignee: RIVER STONE BIOTECH LLC, Cambridge, MA (US)

( * ) Notice: Subject to any disclaimer, the term of this patent is extended or adjusted under 35 U.S.C. 154(b) by 992 days.

(21) Appl. No.: 17/285,948

(22) PCT Filed: Oct. 10, 2019

(86) PCT No.: PCT/EP2019/077548
§ 371 (c)(1),
(2) Date: Apr. 16, 2021

(87) PCT Pub. No.: WO2020/078837
PCT Pub. Date: Apr. 23, 2020

(65) Prior Publication Data

US 2021/0380995 A1 Dec. 9, 2021

(30) Foreign Application Priority Data

Oct. 17, 2018 (EP) .................................... 18200911
Sep. 16, 2019 (EP) .................................... 19197480

(51) Int. Cl.
*C12N 15/81* (2006.01)
*C12N 9/02* (2006.01)
(Continued)

(52) U.S. Cl.
CPC .......... *C12N 15/81* (2013.01); *C12N 9/0071* (2013.01); *C12P 17/18* (2013.01); *C12R 2001/66* (2021.05);
(Continued)

(58) Field of Classification Search
CPC .... C12N 9/0071; C12N 15/81; C12Y 114/00; C12Y 114/13; C12Y 114/11032;
(Continued)

(56) References Cited

U.S. PATENT DOCUMENTS 9,441,233 B2 * 9/2016 Apuya .............. C12N 15/8242
11,142,780 B2 10/2021 Facchini et al.
(Continued)

FOREIGN PATENT DOCUMENTS

WO WO 2014/143744 9/2014
WO WO 2018/075670 4/2018

OTHER PUBLICATIONS

Galaine et al. Complete biosynthesis of opioids in yeast. Science (2015), 349(6252), 1095-1100 and with appended supplementary materials. (Year: 2015).*
(Continued)

*Primary Examiner* — Sean C. Barron
(74) *Attorney, Agent, or Firm* — McDonnell Boehnen Hulbert & Berghoff LLP

(57) ABSTRACT

A recombinant microbial host cell having improved in vivo conversion of reticuline and derivatives thereof (such as thebaine and/or oripavine) to relevant downstream opioids (such as neopinone, oripavine, northebaine, nororipavine or morphinone) and related compounds (such as heroin, morphine, codeine, thebaine, oripavine, oxycodone, hydrocodone, hydromorphone, oxymorphone, buprenorphine, naltrexone, naloxone or nalbuphine), wherein the microbial (such as fungal) host cell is heterologously expressing at least one
(Continued)

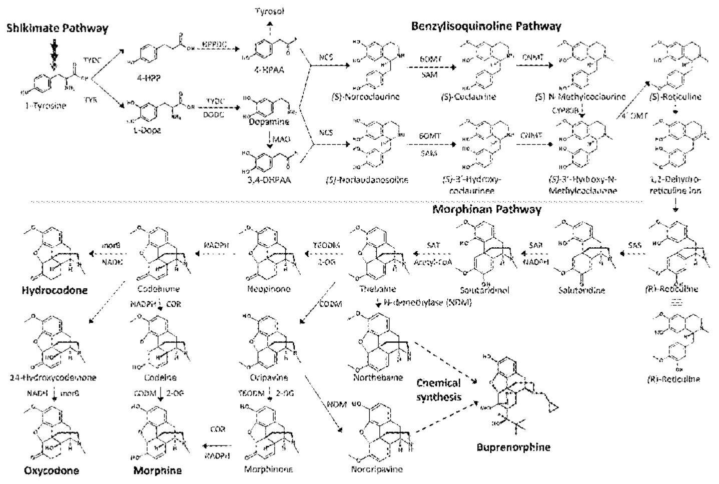

functional transporter protein capable of transporting reticuline or a derivative thereof (such as thebaine and/or oripavine) and a heterologously expressed enzyme capable of acting upon reticuline or a derivative thereof. The invention also relates to uses of the microbial host cells and methods of making an opioid compound and/or opioid precursor compound and/or opioid derivative of interest.

14 Claims, 1 Drawing Sheet

Specification includes a Sequence Listing.

(51) Int. Cl.
*C12P 17/18* (2006.01)
*C12R 1/66* (2006.01)
*C12R 1/865* (2006.01)

(52) U.S. Cl.
CPC . *C12R 2001/865* (2021.05); *C12Y 114/11031* (2013.01)

(58) Field of Classification Search
CPC .. C12Y 114/11031; C12P 17/18; C12P 17/04; C12R 2001/66; C12R 2001/865
See application file for complete search history.

(56) References Cited

U.S. PATENT DOCUMENTS

2019/0194269 A1 6/2019 Facchini et al.
2020/0325509 A1 10/2020 Enquist-Newman et al.

OTHER PUBLICATIONS

Winkler et al. Berberine bridge enzyme catalyzes the six electron oxidation of (S)-reticuline to dehydroscoulerine. Phytochemistry (2009), 70, 1092-1097. (Year: 2009).*
Galanie et al. Complete biosynthesis of opioids in yeast. Science (2005), 349(6252), 1095-1100 plus appended supplemental material. (Year: 2005).*
Nakagawa et.al. Total biosynthesis of opiates by stepwise fermentation using engineered *Escherichia coli*. Nature Communications (2016), 7(10390), 8 pages plus appended supplemental material. (Year: 2016).*
Khow et al. Strategies for production of active eukaryotic proteins in bacterial expression system. Asian Pac J Trop Biomed (2012), 2(2), 159-162 (Year: 2012).*
Marton et al. Studies on the Synthesis of [3-Thevinone Derivatives. Tetrahedron (1998), 54, 9143-9452. (Year: 1998).*
Brohee et al., "YTPdb: A wiki database of yeast membrane transporters" Biochimica Et Biophysica Acta (BBA)—Biomembranes 1798(10):1908-1912 (Oct. 2010).
Galanie et al., "Complete biosynthesis of opioids in yeast" Science 349(6252):1095-110 (Sep. 2015).
Hawkins et al., "Production of benzylisoquinoline alkaloids in *Saccharomyces cerevisiae*" Nature Chemical Biology 4(9):564-73 (Aug. 2008).
Murphy & Lin, "Vertebroplasty: a simple solution to a difficult problem" J Clin Densitom. 4(3):189-97 (Oct. 2001).
Schlager & Drager, "Exploiting plant alkaloids" Current Opinions in Biotechnology 37:155-164 (Jan. 2016).
Shitan et al., "Alkaloid transporters in plants." Plant Biotechnology 31(5):453-463 (Dec. 2014).
The International Search Report for International Application No. PCT/EP2019/077548; dated Nov. 18, 2019, pp. 1-6.

* cited by examiner

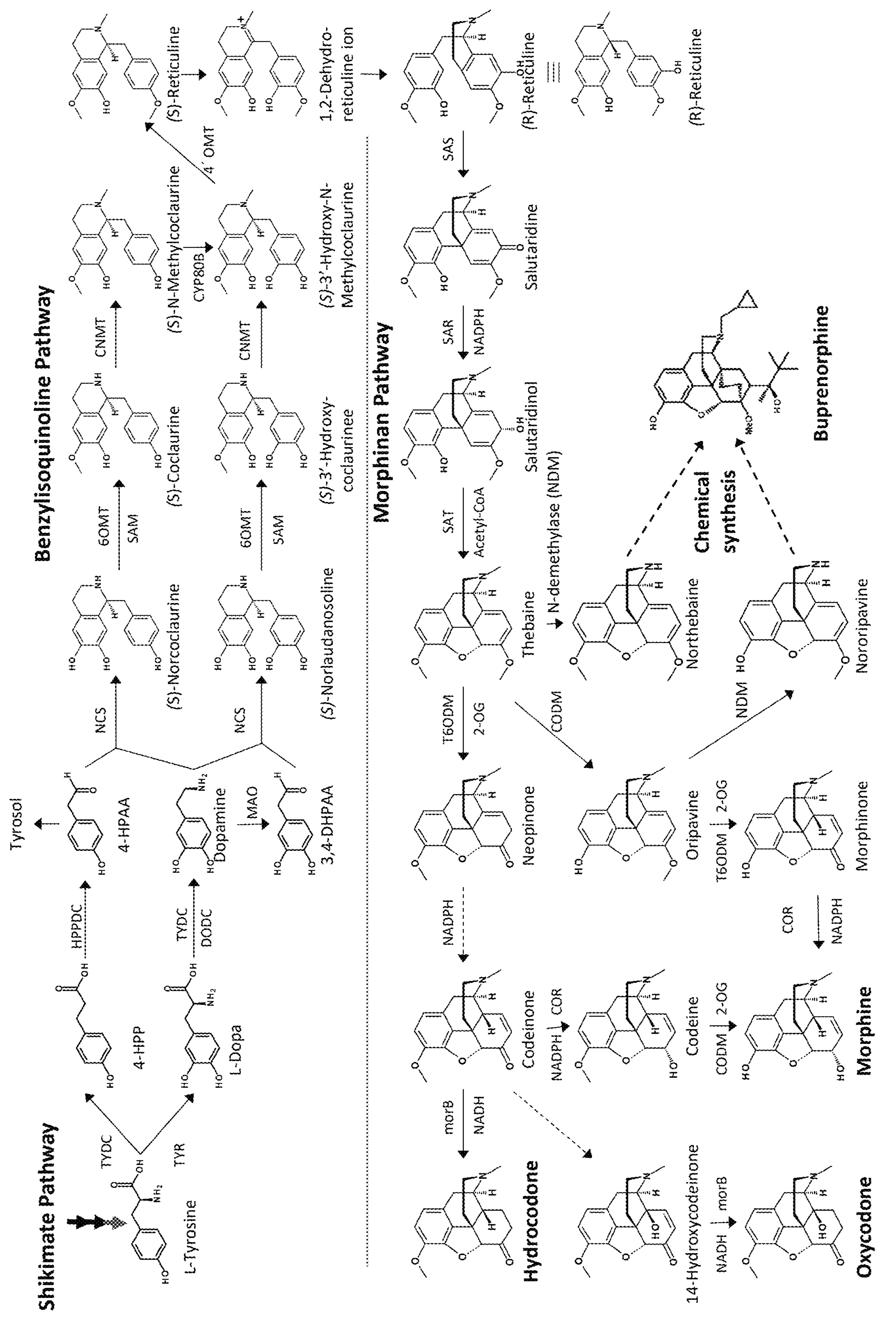
Shikimate Pathway
L-Tyrosine
TYDC
TYR
4-HPP
L-Dopa
HPPDC
TYDC
DODC
Tyrosol
4-HPAA
Dopamine
MAO
3,4-DHPAA
Benzylisoquinoline Pathway
NCS
NCS
(S)-Norcoclaurine
(S)-Norlaudanosoline
6OMT
SAM
6OMT
SAM
(S)-Coclaurine
(S)-3'-Hydroxy-coclaurinee
CNMT
CNMT
(S)-N-Methylcoclaurine
CYP80B
(S)-3'-Hydroxy-N-Methylcoclaurine
4'OMT
(S)-Reticuline
1,2-Dehydro-reticuline ion
(R)-Reticuline
(R)-Reticuline
Morphinan Pathway
SAS
Salutaridine
SAR
NADPH
Salutaridinol
SAT
Acetyl-CoA
Thebaine
N-demethylase (NDM)
Northebaine
Chemical synthesis
Buprenorphine
T6ODM
2-OG
Neopinone
CODM
Oripavine
NDM
Nororipavine
T6ODM
2-OG
Morphinone
NADPH
COR
NADPH
Codeinone
NADPH
COR
Codeine
CODM
2-OG
Morphine
morB
NADH
Hydrocodone
14-Hydroxycodeinone
NADH
morB
Oxycodone

MICROBIAL CELL WITH IMPROVED IN VIVO CONVERSION OF THEBAINE/ORIPAVINE

CROSS REFERENCE

This application is a U.S. national phase application under 35 U.S.C. § 371 of International Application No. PCT/EP2019/077548, filed Oct. 10, 2019, which claims the benefit of European Patent Application No. 18200911.8, filed Oct. 17, 2018, and European Patent Application No. 19197480.7, filed Sep. 16, 2019, the disclosures of each of which are explicitly incorporated by reference herein in their entirety.

REFERENCE TO AN ELECTRONIC SEQUENCE LISTING

The instant application contains a Sequence Listing which has been submitted electronically in ASCII format, and is incorporated into this application by reference in its entirety. The Sequence Listing is contained in the file created on Apr. 12, 2021, having the file name "P19-012PCTPCT_ST25.txt" and is 495 kb in size.

FIELD OF THE INVENTION

The present invention relates to a recombinant microbial host cell having improved in vivo conversion of thebaine and/or oripavine to relevant downstream opioid related compounds, wherein the microbial host cell heterologously expresses at least one functional transporter protein. The invention also relates to use of the microbial host cell to make an opioid compound, opioid pathway intermediate, opioid derivative or opioid precursor compound of interest.

BACKGROUND ART

Opioids are alkaloid narcotics, natural or synthetic, that act on opioid receptors to produce morphine-like effects. Opioid receptors are found principally in the central and peripheral nervous system and the gastrointestinal tract. The medical uses of various opioids includes pain relief, including anesthesia, as diarrhea suppressors, as cough suppressors, and in replacement therapy for opioid use disorder.

An opiate is a narcotic drug derived from opium. Morphine, the prototypical opiate was first isolated from the flowering opium poppy plant, *Papaver somniferum*. Other examples of natural opiates also isolated from *P. somniferum*, include morphine, codeine, thebaine and oripavine. The term opioid is a broader term for alkaloids that includes opiates and refers to any substance, natural or synthetic, that binds to the brain's opioid receptors.

Today commercially available synthetic opioid medical drug products (e.g. oxycodone, hydrocodone, hydromorphone, oxymorphone, buprenorphine, naltrexone, naloxone, nalbuphine) are obtained by chemical modification of natural opiates (e.g. thebaine) as starting precursor compounds.

For instance, the semi-synthetic opioids buprenorphine, naltrexone, naloxone and/or nalbuphine may be obtained by so-called semi-synthesis from e.g. the natural opiates thebaine or oripavine (Tomas Hudlicky; "Recent advances in process development for opiate-derived pharmaceutical agents"; Can. J. Chem. 93:492-501 (2015)). As discussed in Hudlicky et al., the natural opiates morphine and codeine are also potential starting materials for semi-synthesis of synthetic opioid medical drug products.

FIG. 1 herein shows the known synthesis pathway for different opioid compounds. It illustrates that, for example, buprenorphine may be obtained by a combination of biological and chemical synthesis steps starting from natural opiates such as thebaine and/or oripavine.

Today commercially available natural and synthetic opioid medical drug products are dependent on industrial opium poppy farming that is susceptible to environmental factors such as pests, disease, and climate, and to geopolitical factors, any of which can introduce instability and variability into this supply chain.

It is therefore desirable to establish a microbial-based manufacturing process for opioids or opioid precursors, as such a controlled, sustainable and scalable system could have the potential to address many of the current challenges associated with the opium poppy plant-based supply chain used to date.

The publication of Galanie et al. ("Complete biosynthesis of opioids in yeast"; Science. 2015 Sep. 4; 349 (6252): 1095-1100) describes a complete biosynthesis in engineered yeast of the opioids thebaine and hydrocodone starting from sugar.

WO2018/075670A1 describes biosynthesis in yeast of a number of the herein relevant opioids or opioid precursors, as reproduced here in FIG. 1.

Dastmalchi et al. 2019 employs a P450 only as a reductase partner to SalSyn acting on (R)-reticuline. Indeed, Dastmalchi 2019 teaches it is preferable to engineer an alternative pathway (In90-99), rather than use a P450 because it is "a perceived bottleneck".

As known to those skilled in the art, the term "P450", also known as "cytochrome P450" or simply "CYP", refers to a broad class of over 50,000 so far identified proteins that function as monooxygenases using heme groups as co-factors tethered by a cysteine-thiolate ligand. Of particular relevance to the current invention are cytochrome P450 enzymes capable of demethylating a reticuline derivative. In some aspects, preferred reticuline derivates include thebaine and oripavine. Individual P450 enzymes in this class may be capable of N-demethylation and/or O-demethylation. Non-limiting examples of activities of P450s capable of demethylating reticuline derivatives include thebaine 6-O-demethylase, thebaine O-demethylase, thebaine N-demethylase, oripavine N-demethylase, oripavine 6-O-demethylase and/or codeine O-demethylase. In some embodiments, a P450 capable of demethylating reticuline derivatives possesses more than one of these activities. The P450s are typically membrane-associated P450s.

FIG. 1 illustrates that thebaine may be converted variously into neopinone, oripavine or northebaine, and examples of suitable enzymes for doing this in vivo in yeast include:

- thebaine to neopinone: thebaine 6-O-demethylase (e.g. T6ODM gene)—see e.g. of WO2018/075670A1;
- thebaine to oripavine: Codeine O-demethylase (e.g. CODM gene)—see e.g. of WO2018/075670A1
- thebaine to northebaine: N-demethylase (e.g. *Bacillus* BM3 gene)—see e.g. and FIG. 24 of WO2018/075670A1.

Also illustrated in FIG. 1 herein, oripavine may be converted into nororipavine or morphinone, and examples of suitable enzymes for doing this in vivo in yeast include:

- oripavine into nororipavine: N-demethylase (e.g. *Bacillus* BM3 gene)—see e.g. and FIG. 24 of WO2018/075670A1;
- oripavine into morphinone: thebaine 6-O-demethylase (e.g. T6ODM gene)—see e.g. of WO2018/075670A1.

As discussed in Galanie et al. the overall yield of opioids from engineered microbial-based (e.g. yeast based) manufacturing process for opioids in the art remains inadequate to the extent that such microbial-based processes are to date not the preferred options for industrial commercial production of opioids (such as e.g. buprenorphine).

As used herein, the term "membrane transport protein" (or simply "transporter") is a membrane-bound or membrane-spanning protein involved in the movement of ions, small molecules, or macromolecules, such as peptides, across a biological membrane. A variety of transporters have evolved to move the hundreds of thousands of different substrates found in nature across suitable membranes. Of particular relevance to the current invention are transporters capable of transporting opiods and/or opioid pathway intermediates and/or opioid derivatives. An introduction to the topic can be found in Jørgensen et al. ("Origin and evolution of transporter substrate specificity within the NPF family"; eLife 2017; 6: e19466. DOI: 10.7554/eLife. 19466).

Without being limited by theory, the present inventors believe that none of the transporter proteins characterized to date are described be capable of transporting opiates like thebaine and/or oripavine into a microbial cell, such as e.g. a yeast cell.

SUMMARY OF THE INVENTION

The present invention provides an improved micorbial-based manufacturing process for the production of opioids and/or opioid precursors and/or opioid derivatives.

As discussed above and without being limited by theory, the present inventors believe that none of the transporter proteins characterized to date are described as being capable of transporting opiates like thebaine and/or oripavine into a microbial cell, such as e.g. a yeast cell.

The present inventors tested recombinant expression in *Saccharomyces cerevisiae* of a number of different transporter proteins to determine whether any of them could have a positive influence on the yield of any of several opioids. The chosen test system was the in vivo bioconversion of thebaine and/or oripavine to relevant downstream opioid biosynthesis compounds and intermediates.

As discussed within the working Examples herein, the inventors identified that a number of transporter proteins had no positive effect on the yields of in vivo bioconversions of thebaine and/or oripavine.

However, the inventors continued their investigations and found that a number of specific transporter proteins could give a surprisingly high improvement in the yield of in vivo bioconversion of thebaine and/or oripavine.

For instance, as discussed in e.g. the Conclusions of Examples 4 and 5 herein, expression of one or more of the transporter genes T14_PsoNPF3_GA, T1_CjaMDR1_GA, T4_EsaGTR_GA, T7_PtrPOT_GA or T97_ScaT14_GA in a yeast strain engineered to be capable of the relevant catalysis, resulted in improved bioconversion of thebaine to northebaine in the range of 22-63% in comparison to the control strain without such transporters. Also, as discussed in e.g. the Conclusion of Example 6, expression of one or more of the transporter genes T65_IjaNPF_GA, T94_EcrPOT_GA and T97_ScaT14_GA resulted in improved bioconversion of thebaine to northebaine in the range of 21.8% to 31.9%. Such increases in yield are objectively a significant improvement.

The work described herein is believed to be the first time this positive "thebaine and/or oripavine improved bioconversion yield" effect has been demonstrated for a transporter protein.

There are no objective technical reasons to believe that the herein discussed membrane transporter proteins as should directly influence the in vivo bioconversion of thebaine and/or oripavine enzymatic reactions.

Accordingly and without being limited by theory, the improved positive bioconversion yield first demonstrated herein may be related to the herein described transporter proteins increasing the intracellular concentration of thebaine and/or oripavine (i.e. in vivo) in the host microbial cell.

In the working Examples described herein, the inventors noted the positive effect of improvement of the yield of in vivo bioconversion of thebaine and/or oripavine demonstrated for the in vivo conversion of thebaine into northebaine, and for oripavine into nororipavine, and for thevinone into northevinone.

However, since an objectively plausible theory of this identified positive in vivo conversion yield effect relates to "an increased uptake of thebaine and/or oripavine into the host cell and therefore an increased amount of thebaine and/or oripavine present in vivo as such"—there is no reason to believe that this positive yield effect would also not be relevant for the in vivo conversion of thebaine and/or oripavine into other products such as e.g. neopinone or oripavine (see FIG. 1 herein).

Further, since thebaine and oripavine are structurally very similar (see e.g. FIG. 1 herein) it is believed to be plausible that herein discussed membrane transporter proteins could also have a similar positive effect on oripavine as such—i.e. "increased amount of oripavine present in vivo as such".

In working Examples herein, this is illustrated for e.g. T14 (se Example 4) and T97 (Example 5) that are both demonstrated to have a positive in vivo conversion effect for both thebaine and oripavine.

In many of the working Examples disclosed herein, the positive yield effect was demonstrated using *Saccharomyces cerevisiae* (*S. cerevisiae*) as host cell.

However, the herein discussed membrane transporter proteins are not from yeast (see table below). Many are from plants and fungi, and there is objectively no technical reason to believe that they should be optimized to only work positively in *S. cerevisiae*—to the contrary it is believed that the fact that a positive effect has herein been demonstrated for *S. cerevisiae* makes it plausible that a similar positive effect would be present for substantially all yeast host cells and many other microbial host cells.

Further, as discussed herein a number of the positively identified transporter are from fungi cells (more precisely from filamentous fungi cells). Prima facie there is no objective reason to believe that these fungi transporter should not work in a fungus cell in general—i.e. the host cell may be a fungus cell, such as e.g. a yeast cell or e.g. a filamentous fungus cell.

As discussed above, downstream to thebaine (i.e. starting from thebaine) may thebaine be converted into neopinone, oripavine or northebaine (see e.g. FIG. 1 herein) and suitable enzymes for doing this in vivo in yeast are known in the art—for instance:

- thebaine to neopinone: thebaine 6-O-demethylase (e.g. T6ODM gene)—see e.g. of WO2018/075670A1;
- thebaine to oripavine: Codeine O-demethylase (e.g. CODM gene)—se e.g. of WO2018/075670A1 thebaine to northebaine: N-demethylase (e.g. *Bacillus* BM3 gene)—see e.g. and FIG. 24 of WO2018/075670A1.

As shown in FIG. 1 herein, downstream to oripavine (i.e. starting from oripavine) may oripavine be converted into nororipavine or morphinone and suitable enzymes for doing this in vivo in yeast are also known in the art—for instance:

oripavine into nororipavine: N-demethylase (e.g. *Bacillus* BM3 gene)—see e.g. and FIG. 24 of WO2018/075670A1;

oripavine into morphinone: thebaine 6-O-demethylase (e.g. T6ODM gene)—see e.g. of WO2018/075670A1.

In working examples herein, fungal N-demethylase genes/enzymes were used that are different from the bacterial N-demethylase (e.g. *Bacillus* BM3 gene) described in WO2018/075670A1. As discussed in e.g. WO2018/075670A1 and PCT/EP2018/066155 the "conversion of thebaine/oripavine" may also function in fungus host cells in general, such as e.g. a yeast cell or e.g. a filamentous fungus cell.

The PCT/EP2018/066155 application also describes a number of different fungal O-demethylases that are suitable for the thebaine to oripavine conversion. However, PCT/EP2018/066155 does not disclose a microbial host cell, wherein the host cell expresses a P450 capable of demethylase activity on reticuline or its derivatives in combination with heterologous expression of an functional transporter protein.

In short, based on the technical disclosure herein and the prior art knowledge of the skilled person, it is routine work for the skilled person to make a recombinant fungus host cell capable of:

(1): in vivo conversion of thebaine into neopinone due to the in vivo presence of heterologously expressed thebaine 6-O-demethylase; or (2): in vivo conversion of thebaine into oripavine due to the in vivo presence of heterologously expressed O-demethylase; or (3): in vivo conversion of thebaine into northebaine due to the in vivo presence of heterologously expressed N-demethylase; or (4): in vivo conversion of oripavine into nororipavine due to the in vivo presence of heterologously expressed N-demethylase; or (5): in vivo conversion of oripavine into morphinone due to the in vivo presence of heterologously expressed thebaine 6-O-demethylase.

The table below provides both DNA and amino acids sequences of the positive transporter proteins discussed herein—i.e. that in working Examples herein have been recombinantly expressed in *Saccharomyces cerevisiae* and shown to have a positive influence on the yield of in vivo bioconversion of thebaine to relevant downstream opioid biosynthesis compounds.

| Transporter gene Code | Latin name of source organism | DNA SEQ ID NO: | Amino acid SEQ ID NO: |
|---|---|---|---|
| T14_PsoNPF3_GA | *Papaver somniferum* | 1 | 2 |
| T1_CjaMDR1_GA | *Camellia japonica* | 3 | 4 |
| T4_EsaGTR_GA | *Eutrema salsugineum* | 5 | 6 |
| T7_PtrPOT_GA | *Populus trichocarpa* | 7 | 8 |
| T60_AmeNPF2_GA | *Argemone mexican* | 9 | 10 |
| T57_AcoNPF_GA | *Aquilegia coerulea* | 11 | 12 |
| T52_BmePTR2_GA | *Basidiobolus meristosporus* | 13 | 14 |

-continued

| Transporter gene Code | Latin name of source organism | DNA SEQ ID NO: | Amino acid SEQ ID NO: |
|---|---|---|---|
| T38_ScuPTR2_GA | *Smittium culicis* | 15 | 16 |
| T11_AthGTR1_GA | *Arabidopsis thaliana* | 17 | 18 |
| T19_RmiPTR2_GA | *Rhizopus microsporus* | 19 | 20 |
| T70_CmaNPF_GA | *Chelidonium majus* | 21 | 22 |
| T54_MelPOT_GA | *Mortierella elongate* | 23 | 24 |
| T65_ljaNPF_GA | *Lonicera japonica* | 26 | 27 |
| T94_EcrPOT_GA | *Emmonsia crescens* | 28 | 29 |
| T97_ScaT14_GA | *Sanguinaria canadensis* | 30 | 31 |
| T101_McoPUP3_1 | *Macleaya cordata* | 33 | 32 |
| T102_PsoPUP3_1 | *Papaver somniferum* | 35 | 34 |
| T103_PsoPUP3_2 | *Papaver somniferum* | 37 | 36 |
| T104_PsoPUP3_3 | *Papaver somniferum* | 39 | 38 |
| T105_PsoPUP-L | *Papaver somniferum* | 41 | 40 |
| T109_GflPUP3_83 | *Glaucium Flavum* | 43 | 42 |
| T113_PsoPUP3_32 | *Papaver somniferum* | 45 | 44 |
| T114_TorPUP3_40 | *Trema orientale* | 47 | 46 |
| T115_CsaPUP3_48 | *Cucumis sativus* | 49 | 48 |
| T116_HanPUP3_56 | *Helianthus annuus* | 51 | 50 |
| T117_MacPUP3_64 | *Musa acuminata* subsp. *malaccensis* | 53 | 52 |
| T121_NnuPUP3_9 | *Nelumbo nucifera* | 55 | 54 |
| T122_PsoPUP3_17 | *Papaver somniferum* | 57 | 56 |
| T123_PsoPUP3_25 | *Papaver somniferum* | 59 | 58 |
| T124_PsoPUP3_33 | *Papaver somniferum* | 61 | 60 |
| T125_JcuPUP3_41 | *Jatropha curcas* | 63 | 62 |
| T126_CpePUP3_49 | *Cucurbita pepo* subsp. *pepo* | 65 | 64 |
| T127_LsaPUP3_57 | *Lactuca sativa* | 67 | 66 |
| T128_PsoPUP3_65 | *Papaver somniferum* | 69 | 68 |
| T129_PsoPUP3_73 | *Papaver somniferum* | 71 | 70 |
| T130_NdoPUP3_89 | *Nandina domestica* | 73 | 72 |
| T131_PbrPUP3_81 | *Papaver bracteatum* | 75 | 74 |
| T132_CmiPUP3_10 | *Cinnamomum micranthum* f. *kanehirae* | 77 | 76 |
| T133_PsoPUP3_18 | *Papaver somniferum* | 79 | 78 |
| T135_PsoPUP_34 | *Papaver somniferum* | 81 | 80 |
| T136_RchPUP3_42 | *Rosa chinensis* | 83 | 82 |
| T137_EguPUP3_50 | *Erythranthe guttata* | 85 | 84 |
| T138_AduPUP3_58 | *Arachis duranensis* | 87 | 86 |
| T139_PsoPUP3_66 | *Papaver somniferum* | 89 | 88 |
| T140_PalPUP3_74 | *Papaver alpinum* | 91 | 90 |
| T141_EcaPUP3_88 | *Eschscholzia californica* | 93 | 92 |
| T142_McoPUP3_4 | *Macleaya cordata* | 95 | 94 |
| T143_CmiPUP3_11 | *Cinnamomum micranthum* f. *kanehirae* | 97 | 96 |
| T144_PsoPUP3_19 | *Papaver somniferum* | 99 | 98 |
| T146_PsoPUP_35 | *Papaver somniferum* | 101 | 100 |
| T147_MesPUP3_43 | *Manihot esculenta* | 103 | 102 |
| T148_HimPUP3_51 | *Handroanthus impetiginosus* | 105 | 104 |
| T149_AcoPUP3_59 | *Aquilegia coerulea* | 107 | 106 |
| T150_PsoPUP3_67 | *Papaver somniferum* | 109 | 108 |
| T151_PatPUP3_75 | *Papaver atlanticum* | 111 | 110 |
| T152_GflPUP3_87 | *Glaucium Flavum* | 113 | 112 |
| T153_PsoPUP3_5 | *Papaver somniferum* | 115 | 114 |
| T154_CmiPUP3_12 | *Cinnamomum micranthum* f. *kanehirae* | 117 | 116 |
| T156_PsoPUP3_28 | *Papaver somniferum* | 119 | 118 |
| T157_RchPUP_36 | *Rosa chinensis* | 121 | 120 |
| T158_DziPUP3_44 | *Durio zibethinus* | 123 | 122 |
| T159_OeuPUP3_52 | *Olea europaea* var. *sylvestris* | 125 | 124 |
| T160_CeuPUP3_60 | *Coffea eugenioides* | 127 | 126 |
| T161_PsoPUP3_68 | *Papaver somniferum* | 129 | 128 |
| T162_PmiPUP3_76 | *Papaver miyabeanum* | 131 | 130 |
| T163_PbrPUP3_86 | *Papaver bracteatum* | 133 | 132 |
| T164_PsoPUP3_78 | *Papaver somniferum* | 135 | 134 |
| T165_AcoPUP3_13 | *Aquilegia coerulea* | 137 | 136 |
| T166_PsoPUP3_21 | *Papaver somniferum* | 139 | 138 |
| T168_FvePUP3_37 | *Fragaria vesca* subsp. *vesca* | 141 | 140 |
| T169_ZjuPUP3_45 | *Ziziphus jujuba* | 143 | 142 |
| T170_LsaPUP3_53 | *Lactuca sativa* | 145 | 144 |
| T171_McoPUP3_61 | *Macleaya cordata* | 147 | 146 |
| T172_AcoPUP3_69 | *Aquilegia coerulea* | 149 | 148 |
| T173_PnuPUP3_77 | *Papaver nudicale* | 151 | 150 |
| T174_PbrPUP3_85 | *Papaver bracteatum* | 153 | 152 |
| T175_PsoPUP3_6 | *Papaver somniferum* | 155 | 154 |

-continued

| Transporter gene Code | Latin name of source organism | DNA SEQ ID NO: | Amino acid SEQ ID NO: |
|---|---|---|---|
| T176_AcoPUP3_14 | *Aquilegia coerulea* | 157 | 156 |
| T177_PsoPUP3_22 | *Papaver somniferum* | 159 | 158 |
| T178_PsoPUP3_30 | *Papaver somniferum* | 161 | 160 |
| T179_PyePUP3_38 | *Prunus yedoensis* var. *nudiflora* | 163 | 162 |
| T180_McoPUP3_46 | *Macleaya cordata* | 165 | 164 |
| T181_HanPUP3_54 | *Helianthus annuus* | 167 | 166 |
| T182_CpaPUP3_62 | *Carica papaya* | 169 | 168 |
| T184_PraPUP3_79 | *Papaver radicatum* | 171 | 170 |
| T186_ScaPUP3_84 | *Sanguinaria canadensis* | 173 | 172 |
| T188_AcoPUP3_15 | *Aquilegia coerulea* | 175 | 174 |
| T189_PsoPUP3_23 | *Papaver somniferum* | 177 | 176 |
| T191_MdoPUP3_39 | *Malus domestica* | 179 | 178 |
| T192_CmiPUP3_47 | *Cinnamomum micranthum* f. *kanehirae* | 181 | 180 |
| T193_AanPUP3_55 | *Artemisia annua* | 183 | 182 |
| T194_CchPUP3_63 | *Capsicum chinense* | 185 | 184 |
| T195_JcuPUP3_71 | *Jatropha curcas* | 187 | 186 |
| T196_PtrPUP3_80 | *Papaver trinifolium* | 189 | 188 |

With reference to gene nomenclature, the "Transporter gene Code" may be seen as an internal code (used in e.g. Examples herein) and in the table below example sequences are connected to public known transporter protein information.

| Transporter gene Code | Official entry code | Database | Database description |
|---|---|---|---|
| T14_PsoNPF3_GA | | | Relevant sequence identity to "T11_AthGTR1_GA" |
| T1_CjaMDR1_GA | Q94IH6_COPJA | UniProt | ABC transporter |
| T4_EsaGTR_GA | V4NHT1_EUTSA | UniProt | Transmembrane transporter |
| T7_PtrPOT_GA | B9I314_POPTR | UniProt | Transmembrane transporter activity |
| T60_AmeNPF2_GA | | PhytoMetaSyn | Relevant sequence identity to "T11_AthGTR1_GA" |
| T57_AcoNPF_GA | AQUCO_00200462v1 | UniProt | Transmembrane transporter activity |
| T52_BmePTR2_GA | K493DRAFT_340722 | UniProt | Transmembrane transporter activity |
| T38_ScuPTR2_GA | AYI70_g3621 | UniProt | Transmembrane transporter activity |
| T11_AthGTR1_GA | NPF2.10 | UniProt | Proton-dependent glucosinolate-specific transporter |
| T19_RmiPTR2_GA | BCV71DRAFT_38134 | UniProt | Transmembrane transporter activity |
| T70_CmaNPF_GA | | PhytoMetaSyn | Relevant sequence identity to "T11_AthGTR1_GA" |
| T54_MelPOT_GA | K457DRAFT_66042 | UniProt | Transmembrane transporter activity |
| T65_ljaNPF_GA | | PhytoMetaSyn | Relevant sequence identity to "T11_AthGTR1_GA" |
| T94_EcrPOT_GA | GX50_01424 | UniProt | Transmembrane transporter activity |
| T97_ScaT14_GA | | PhytoMetaSyn | Relevant sequence identity to "T14_PsoNPF3_GA" |

As indicated in the table, the fact that e.g. "T11_AthGTR1_GA" is known to be a transporter protein can be verified by use of the "NPF2.10" entry code in the public known UniProt (https://www.uniprot.org) database.

For instance, "T14_PsoNPF3_GA" does not have an official (e.g. UniProt) entry code, since it was identified by the present inventors to be a transporter due to e.g. relevant sequence identity to "T11_AthGTR1_GA" and herein presented experimental work.

Accordingly, a first aspect of the invention relates to a recombinant microbial host cell capable of:

(a): in vivo conversion of thebaine into a thebaine derivative due to the in vivo presence of heterologously expressed enzyme; or (b): in vivo conversion of oripavine into an oripavine derivative due to the in vivo presence of heterologously expressed enzyme; or (c): in vivo conversion of thevinone into a thevinone derivative due to the in vivo presence of heterologously expressed enzyme.

and wherein the host cell is heterologously expressing at least one functional transporter protein capable of transporting reticuline or its derivatives.

As understood by the skilled person in the present context, the term "functional" within the term "functional transporter protein" of the first aspect simply requires that the transporter protein is capable of functioning as a transporter protein within the host cell. In contrast, as known in the art, a protein of interest may be nonfunctional due to e.g. a frameshift mutation or e.g. the insertion of a stop codon, misfolding or immediate degradation in an inappropriate host cell, or for other reasons.

As understood by the skilled person in the present context—the term "thebaine derivative" relates to a compound that thebaine may be converted into, examples of which include but are not limited to neopinone, oripavine and/or northebaine.

Similarly, the term "oripavine derivative" relates to a compound that oripavine ma converted into, examples of which include but are not limited to nororipavine and/or morphinone.

As discussed herein, an embodiment of the first aspect relates to a recombinant microbial (such as a fungus) host cell capable of:

(1): in vivo conversion of thebaine into neopinone due to the in vivo presence of heterologously expressed thebaine 6-O-demethylase; or (2): in vivo conversion of thebaine into oripavine due to the in vivo presence of heterologously expressed O-demethylase; or (3): in vivo conversion of thebaine into northebaine due to the in vivo presence of heterologously expressed N-demethylase; or (4): in vivo conversion of oripavine into nororipavine due to the in vivo presence of heterologously expressed N-demethylase; or (5): in vivo conversion of oripavine into morphinone due to the in vivo presence of heterologously expressed thebaine 6-O-demethylase; or and wherein the host cell is heterologously expressing at least one functional transporter protein selected from the group consisting of:

a transporter protein comprising an amino acid sequence which has at least 70% (preferably at least 80%, more preferably at least 90%, even more preferably at least 95% and most preferably at least 99%) identity with amino acids 1 to 584 of SEQ ID NO:2 (T14_PsoNPF3_GA);

a transporter protein comprising an amino acid sequence which has at least 70% (preferably at least 80%, more preferably at least 90%, even more preferably at least 95% and most preferably at least 99%) identity with amino acids 1 to 1289 of SEQ ID NO:4 (T1_CjaMDR1_GA);

a transporter protein comprising an amino acid sequence which has at least 70% (preferably at least 80%, more preferably at least 90%, even more preferably at least 95% and most preferably at least 99%) identity with amino acids 1 to 654 of SEQ ID NO:6 (T4_EsaGTR_GA);

a transporter protein comprising an amino acid sequence which has at least 70% (preferably at least 80%, more preferably at least 90%, even more preferably at least 95% and most preferably at least 99%) identity with amino acids 1 to 607 of SEQ ID NO:8 (T7_PtrPOT_GA);

a transporter protein comprising an amino acid sequence which has at least 70% (preferably at least 80%, more preferably at least 90%, even more preferably at least 95% and most preferably at least 99%) identity with amino acids 1 to 583 of SEQ ID NO: 10 (T60_AmeNPF2_GA);

a transporter protein comprising an amino acid sequence which has at least 70% (preferably at least 80%, more preferably at least 90%, even more preferably at least 95% and most preferably at least 99%) identity with amino acids 1 to 594 of SEQ ID NO: 12 (T57_AcoNPF_GA);

a transporter protein comprising an amino acid sequence which has at least 70% (preferably at least 80%, more preferably at least 90%, even more preferably at least 95% and most preferably at least 99%) identity with amino acids 1 to 527 of SEQ ID NO: 14 (T52_BmePTR2_GA);

a transporter protein comprising an amino acid sequence which has at least 70% (preferably at least 80%, more preferably at least 90%, even more preferably at least 95% and most preferably at least 99%) identity with amino acids 1 to 512 of SEQ ID NO: 16 (T38_ScuPTR2_GA);

a transporter protein comprising an amino acid sequence which has at least 70% (preferably at least 80%, more preferably at least 90%, even more preferably at least 95% and most preferably at least 99%) identity with amino acids 1 to 636 of SEQ ID NO: 18 (T11_AthGTR1_GA);

a transporter protein comprising an amino acid sequence which has at least 70% (preferably at least 80%, more preferably at least 90%, even more preferably at least 95% and most preferably at least 99%) identity with amino acids 1 to 565 of SEQ ID NO:20 (T19_RmiPTR2_GA);

a transporter protein comprising an amino acid sequence which has at least 70% (preferably at least 80%, more preferably at least 90%, even more preferably at least 95% and most preferably at least 99%) identity with amino acids 1 to 598 of SEQ ID NO:22 (T70_CmaNPF_GA);

a transporter protein comprising an amino acid sequence which has at least 70% (preferably at least 80%, more preferably at least 90%, even more preferably at least 95% and most preferably at least 99%) identity with amino acids 1 to 515 of SEQ ID NO:24 (T54_MelPOT_GA);

a transporter protein comprising an amino acid sequence which has at least 70% (preferably at least 80%, more preferably at least 90%, even more preferably at least 95% and most preferably at least 99%) identity with amino acids 1 to 593 of SEQ ID NO:27 (T65_IjaNPF_GA);

a transporter protein comprising an amino acid sequence which has at least 70% (preferably at least 80%, more preferably at least 90%, even more preferably at least 95% and most preferably at least 99%) identity with amino acids 1 to 604 of SEQ ID NO:29 (T94_EcrPOT_GA); and a transporter protein comprising an amino acid sequence which has at least 70% (preferably at least 80%, more preferably at least 90%, even more preferably at least 95% and most preferably at least 99%) identity with amino acids 1 to 604 of SEQ ID NO:31 (T97_ScaT14_GA); and a transporter protein comprising an amino acid sequence which has at least 70% (preferably at least 80%, more preferably at least 90%, even more preferably at least 95% and most preferably at least 99%) identity with the amino acid sequence of SEQ ID NO:32 (T101_McoPUP3_1); and a transporter protein comprising an amino acid sequence which has at least 70% (preferably at least 80%, more preferably at least 90%, even more preferably at least 95% and most preferably at least 99%) identity with the amino acid sequence of SEQ ID NO:34 (T102_PsoPUP3_1); and a transporter protein comprising an amino acid sequence which has at least 70% (preferably at least 80%, more preferably at least 90%, even more preferably at least 95% and most preferably at least 99%) identity with the amino acid sequence of SEQ ID NO:36 (T103_PsoPUP3_2); and a transporter protein comprising an amino acid sequence which has at least 70% (preferably at least 80%, more preferably at least 90%, even more preferably at least 95% and most preferably at least 99%) identity with the amino acid sequence of SEQ ID NO:38 (T104_PsoPUP3_3); and a transporter protein comprising an amino acid sequence which has at least 70% (preferably at least 80%, more preferably at least 90%, even more preferably at least 95% and most preferably at least 99%) identity with the amino acid sequence of SEQ ID NO:40 (T105_PsoPUP-L); and a transporter protein comprising an amino acid sequence which has at least 70% (preferably at least 80%, more preferably at least 90%, even more preferably at least 95% and most preferably at least 99%) identity with the amino acid sequence of SEQ ID NO:42 (T109_GfIPUP3_83); and a transporter protein comprising an amino acid sequence which has at least 70% (preferably at least 80%, more preferably at least 90%, even more preferably at least 95% and most preferably at least 99%) identity with the amino acid sequence of SEQ ID NO:44 (T113_PsoPUP3_32); and a transporter protein comprising an amino acid sequence which has at least 70% (preferably at least 80%, more preferably at least 90%, even more preferably at least 95% and most preferably at least 99%) identity with the amino acid sequence of SEQ ID NO:46 (T114_TorPUP3_40); and a transporter protein comprising an amino acid sequence which has at least 70% (preferably at least 80%, more preferably at least 90%, even more preferably at least 95% and most preferably at least 99%) identity with the amino acid sequence of SEQ ID NO:48 (T115_CsaPUP3_48); and a transporter protein comprising an amino acid sequence which has at least 70% (preferably at least 80%, more preferably at least 90%, even more preferably at least 95% and most preferably at least 99%) identity with the amino acid sequence of SEQ ID NO:50 (T116_HanPUP3_56); and a transporter protein comprising an amino acid sequence which has at least 70% (preferably at least 80%, more preferably at least 90%, even more preferably at least 95% and most preferably at least 99%) identity with the amino acid sequence of SEQ ID NO:52 (T117_MacPUP3_64); and a transporter protein comprising an amino acid sequence which has at least 70% (preferably at least 80%, more preferably at least 90%, even more preferably at least 95% and most preferably at least 99%) identity with the amino acid sequence of SEQ ID NO:54 (T121_NnuPUP3_9); and a transporter protein comprising an amino acid sequence which has at least 70% (preferably at least 80%, more preferably at least 90%, even more preferably at least 95% and most preferably at least 99%) identity with the amino acid sequence of SEQ ID NO:56 (T122_PsoPUP3_17); and a transporter protein comprising an amino acid sequence which has at least 70% (preferably at least 80%, more preferably at least 90%, even more preferably at least 95% and most preferably at least 99%) identity with the amino acid sequence of SEQ ID NO:58 (T123_PsoPUP3_25); and a transporter protein comprising an amino acid sequence which has at least 70% (preferably at least 80%, more preferably at least 90%, even more preferably at least 95% and most preferably at least 99%) identity with the amino acid sequence of SEQ ID NO:60 (T124_PsoPUP3_33); and a transporter protein comprising an amino acid sequence which has at least 70% (preferably at least 80%, more preferably at least 90%, even more preferably at least 95% and most preferably at least 99%) identity with the amino acid sequence of SEQ ID NO:62 (T125_JcuPUP3_41); and a transporter protein comprising an amino acid sequence which has at least 70% (preferably at least 80%, more preferably at least 90%, even more preferably at least 95% and most preferably at least 99%) identity with the amino acid sequence of SEQ ID NO:64 (T126_CpePUP3_49); and a transporter protein comprising an amino acid sequence which has at least 70% (preferably at least 80%, more preferably at least 90%, even more preferably at least 95% and most preferably at least 99%) identity with the amino acid sequence of SEQ ID NO:66 (T127_LsaPUP3_57); and a transporter protein comprising an amino acid sequence which has at least 70% (preferably at least 80%, more preferably at least 90%, even more preferably at least 95% and most preferably at least 99%) identity with the amino acid sequence of SEQ ID NO:68 (T128_PsoPUP3_65); and a transporter protein comprising an amino acid sequence which has at least 70% (preferably at least 80%, more preferably at least 90%, even more preferably at least 95% and most preferably at least 99%) identity with the amino acid sequence of SEQ ID NO:70 (T129_PsoPUP3_73); and a transporter protein comprising an amino acid sequence which has at least 70% (preferably at least 80%, more preferably at least 90%, even more preferably at least 95% and most preferably at least 99%) identity with the amino acid sequence of SEQ ID NO:72 (T130_NdoPUP3_89); and a transporter protein comprising an amino acid sequence which has at least 70% (preferably at least 80%, more preferably at least 90%, even more preferably at least 95% and most preferably at least 99%) identity with the amino acid sequence of SEQ ID NO:74 (T131_PbrPUP3_81); and a transporter protein comprising an amino acid sequence which has at least 70% (preferably at least 80%, more preferably at least 90%, even more preferably at least 95% and most preferably at least 99%) identity with the amino acid sequence of SEQ ID NO:76 (T132_CmiPUP3_10); and a transporter protein comprising an amino acid sequence which has at least 70% (preferably at least 80%, more preferably at least 90%, even more preferably at least 95% and most preferably at least 99%) identity with the amino acid sequence of SEQ ID NO:78 (T133_PsoPUP3_18); and a transporter protein comprising an amino acid sequence which has at least 70% (preferably at least 80%, more preferably at least 90%, even more preferably at least 95% and most preferably at least 99%) identity with the amino acid sequence of SEQ ID NO:80 (T135_PsoPUP_34); and a transporter protein comprising an amino acid sequence which has at least 70% (preferably at least 80%, more preferably at least 90%, even more preferably at least 95% and most preferably at least 99%) identity with the amino acid sequence of SEQ ID NO:82 (T136_RchPUP3_42); and a transporter protein comprising an amino acid sequence which has at least 70% (preferably at least 80%, more preferably at least 90%, even more preferably at least 95% and most preferably at least 99%) identity with the amino acid sequence of SEQ ID NO:84 (T137_EguPUP3_50); and a transporter protein comprising an amino acid sequence which has at least 70% (preferably at least 80%, more preferably at least 90%, even more preferably at least 95% and most preferably at least 99%) identity with the amino acid sequence of SEQ ID NO:86 (T138_AduPUP3_58); and a transporter protein comprising an amino acid sequence which has at least 70% (preferably at least 80%, more preferably at least 90%, even more preferably at least 95% and most preferably at least 99%) identity with the amino acid sequence of SEQ ID NO:88 (T139_PsoPUP3_66); and a transporter protein comprising an amino acid sequence which has at least 70% (preferably at least 80%, more preferably at least 90%, even more preferably at least 95% and most preferably at least 99%) identity with the amino acid sequence of SEQ ID NO:90 (T140_PalPUP3_74); and a transporter protein comprising an amino acid sequence which has at least 70% (preferably at least 80%, more preferably at least 90%, even more preferably at least 95% and most preferably at least 99%) identity with the amino acid sequence of SEQ ID NO:92 (T141_EcaPUP3_88); and a transporter protein comprising an amino acid sequence which has at least 70% (preferably at least 80%, more preferably at least 90%, even more preferably at least 95% and most preferably at least 99%) identity with the amino acid sequence of SEQ ID NO:94 (T142_McoPUP3_4); and a transporter protein comprising an amino acid sequence which has at least 70% (preferably at least 80%, more preferably at least 90%, even more preferably at least 95% and most preferably at least 99%) identity with the amino acid sequence of SEQ ID NO:96 (T143_CmiPUP3_11); and a transporter protein comprising an amino acid sequence which has at least 70% (preferably at least 80%, more preferably at least 90%, even more preferably at least 95% and most preferably at least 99%) identity with the amino acid sequence of SEQ ID NO:98 (T144_PsoPUP3_19); and a transporter protein comprising an amino acid sequence which has at least 70% (preferably at least 80%, more preferably at least 90%, even more preferably at least 95% and most preferably at least 99%) identity with the amino acid sequence of SEQ ID NO: 100 (T146_PsoPUP_35); and a transporter protein comprising an amino acid sequence which has at least 70% (preferably at least 80%, more preferably at least 90%, even more preferably at least 95% and most preferably at least 99%) identity with the amino acid sequence of SEQ ID NO: 102 (T147_MesPUP3_43); and a transporter protein comprising an amino acid sequence which has at least 70% (preferably at least 80%, more preferably at least 90%, even more preferably at least 95% and most preferably at least 99%) identity with the amino acid sequence of SEQ ID NO: 104 (T148_HimPUP3_51); and a transporter protein comprising an amino acid sequence which has at least 70% (preferably at least 80%, more preferably at least 90%, even more preferably at least 95% and most preferably at least 99%) identity with the amino acid sequence of SEQ ID NO: 106 (T149_AcoPUP3_59); and a transporter protein comprising an amino acid sequence which has at least 70% (preferably at least 80%, more preferably at least 90%, even more preferably at least 95% and most preferably at least 99%) identity with the amino acid sequence of SEQ ID NO: 108 (T150_PsoPUP3_67); and a transporter protein comprising an amino acid sequence which has at least 70% (preferably at least 80%, more preferably at least 90%, even more preferably at least 95% and most preferably at least 99%) identity with the amino acid sequence of SEQ ID NO: 110 (T151_PatPUP3_75); and a transporter protein comprising an amino acid sequence which has at least 70% (preferably at least 80%, more preferably at least 90%, even more preferably at least 95% and most preferably at least 99%) identity with the amino acid sequence of SEQ ID NO: 112 (T152_GflPUP3_87); and a transporter protein comprising an amino acid sequence which has at least 70% (preferably at least 80%, more preferably at least 90%, even more preferably at least 95% and most preferably at least 99%) identity with the amino acid sequence of SEQ ID NO: 114 (T153_PsoPUP3_5); and a transporter protein comprising an amino acid sequence which has at least 70% (preferably at least 80%, more preferably at least 90%, even more preferably at least 95% and most preferably at least 99%) identity with the amino acid sequence of SEQ ID NO: 116 (T154_CmiPUP3_12); and a transporter protein comprising an amino acid sequence which has at least 70% (preferably at least 80%, more preferably at least 90%, even more preferably at least 95% and most preferably at least 99%) identity with the amino acid sequence of SEQ ID NO: 118 (T156_PsoPUP3_28); and a transporter protein comprising an amino acid sequence which has at least 70% (preferably at least 80%, more preferably at least 90%, even more preferably at least 95% and most preferably at least 99%) identity with the amino acid sequence of SEQ ID NO: 120 (T157_RchPUP_36); and a transporter protein comprising an amino acid sequence which has at least 70% (preferably at least 80%, more preferably at least 90%, even more preferably at least 95% and most preferably at least 99%) identity with the amino acid sequence of SEQ ID NO: 122 (T158_DziPUP3_44); and a transporter protein comprising an amino acid sequence which has at least 70% (preferably at least 80%, more preferably at least 90%, even more preferably at least 95% and most preferably at least 99%) identity with the amino acid sequence of SEQ ID NO: 124 (T159_OeuPUP3_52); and a transporter protein comprising an amino acid sequence which has at least 70% (preferably at least 80%, more preferably at least 90%, even more preferably at least 95% and most preferably at least 99%) identity with the amino acid sequence of SEQ ID NO: 126 (T160_CeuPUP3_60); and a transporter protein comprising an amino acid sequence which has at least 70% (preferably at least 80%, more preferably at least 90%, even more preferably at least 95% and most preferably at least 99%) identity with the amino acid sequence of SEQ ID NO: 128 (T161_PsoPUP3_68); and a transporter protein comprising an amino acid sequence which has at least 70% (preferably at least 80%, more preferably at least 90%, even more preferably at least 95% and most preferably at least 99%) identity with the amino acid sequence of SEQ ID NO: 130 (T162_PmiPUP3_76); and a transporter protein comprising an amino acid sequence which has at least 70% (preferably at least 80%, more preferably at least 90%, even more preferably at least 95% and most preferably at least 99%) identity with the amino acid sequence of SEQ ID NO: 132 (T163_PbrPUP3_86); and a transporter protein comprising an amino acid sequence which has at least 70% (preferably at least 80%, more preferably at least 90%, even more preferably at least 95% and most preferably at least 99%) identity with the amino acid sequence of SEQ ID NO: 134 (T164_PsoPUP3_78); and a transporter protein comprising an amino acid sequence which has at least 70% (preferably at least 80%, more preferably at least 90%, even more preferably at least 95% and most preferably at least 99%) identity with the amino acid sequence of SEQ ID NO: 136 (T165_AcoPUP3_13); and a transporter protein comprising an amino acid sequence which has at least 70% (preferably at least 80%, more preferably at least 90%, even more preferably at least 95% and most preferably at least 99%) identity with the amino acid sequence of SEQ ID NO: 138 (T166_PsoPUP3_21); and a transporter protein comprising an amino acid sequence which has at least 70% (preferably at least 80%, more preferably at least 90%, even more preferably at least 95% and most preferably at least 99%) identity with the amino acid sequence of SEQ ID NO: 140 (T168_FvePUP3_37); and a transporter protein comprising an amino acid sequence which has at least 70% (preferably at least 80%, more preferably at least 90%, even more preferably at least 95% and most preferably at least 99%) identity with the amino acid sequence of SEQ ID NO: 142 (T169_ZjuPUP3_45); and a transporter protein comprising an amino acid sequence which has at least 70% (preferably at least 80%, more preferably at least 90%, even more preferably at least 95% and most preferably at least 99%) identity with the amino acid sequence of SEQ ID NO: 144 (T170_LsaPUP3_53); and a transporter protein comprising an amino acid sequence which has at least 70% (preferably at least 80%, more preferably at least 90%, even more preferably at least 95% and most preferably at least 99%) identity with the amino acid sequence of SEQ ID NO: 146 (T171_McoPUP3_61); and a transporter protein comprising an amino acid sequence which has at least 70% (preferably at least 80%, more preferably at least 90%, even more preferably at least 95% and most preferably at least 99%) identity with the amino acid sequence of SEQ ID NO: 148 (T172_AcoPUP3_69); and a transporter protein comprising an amino acid sequence which has at least 70% (preferably at least 80%, more preferably at least 90%, even more preferably at least 95% and most preferably at least 99%) identity with the amino acid sequence of SEQ ID NO: 150 (T173_PnuPUP3_77); and a transporter protein comprising an amino acid sequence which has at least 70% (preferably at least 80%, more preferably at least 90%, even more preferably at least 95% and most preferably at least 99%) identity with the amino acid sequence of SEQ ID NO: 152 (T174_PbrPUP3_85); and a transporter protein comprising an amino acid sequence which has at least 70% (preferably at least 80%, more preferably at least 90%, even more preferably at least 95% and most preferably at least 99%) identity with the amino acid sequence of SEQ ID NO: 154 (T175_PsoPUP3_6); and a transporter protein comprising an amino acid sequence which has at least 70% (preferably at least 80%, more preferably at least 90%, even more preferably at least 95% and most preferably at least 99%) identity with the amino acid sequence of SEQ ID NO: 156 (T176_AcoPUP3_14); and a transporter protein comprising an amino acid sequence which has at least 70% (preferably at least 80%, more preferably at least 90%, even more preferably at least 95% and most preferably at least 99%) identity with the amino acid sequence of SEQ ID NO: 158 (T177_PsoPUP3_22); and a transporter protein comprising an amino acid sequence which has at least 70% (preferably at least 80%, more preferably at least 90%, even more preferably at least 95% and most preferably at least 99%) identity with the amino acid sequence of SEQ ID NO: 160 (T178_PsoPUP3_30); and a transporter protein comprising an amino acid sequence which has at least 70% (preferably at least 80%, more preferably at least 90%, even more preferably at least 95% and most preferably at least 99%) identity with the amino acid sequence of SEQ ID NO: 162 (T179_PyePUP3_38); and a transporter protein comprising an amino acid sequence which has at least 70% (preferably at least 80%, more preferably at least 90%, even more preferably at least 95% and most preferably at least 99%) identity with the amino acid sequence of SEQ ID NO: 164 (T180_McoPUP3_46); and a transporter protein comprising an amino acid sequence which has at least 70% (preferably at least 80%, more preferably at least 90%, even more preferably at least 95% and most preferably at least 99%) identity with the amino acid sequence of SEQ ID NO: 166 (T181_HanPUP3_54); and a transporter protein comprising an amino acid sequence which has at least 70% (preferably at least 80%, more preferably at least 90%, even more preferably at least 95% and most preferably at least 99%) identity with the amino acid sequence of SEQ ID NO: 168 (T182_CpaPUP3_62); and a transporter protein comprising an amino acid sequence which has at least 70% (preferably at least 80%, more preferably at least 90%, even more preferably at least 95% and most preferably at least 99%) identity with the amino acid sequence of SEQ ID NO: 170 (T184_PraPUP3_79); and a transporter protein comprising an amino acid sequence which has at least 70% (preferably at least 80%, more preferably at least 90%, even more preferably at least 95% and most preferably at least 99%) identity with the amino acid sequence of SEQ ID NO: 172 (T186_ScaPUP3_84); and a transporter protein comprising an amino acid sequence which has at least 70% (preferably at least 80%, more preferably at least 90%, even more preferably at least 95% and most preferably at least 99%) identity with the amino acid sequence of SEQ ID NO: 174 (T188_AcoPUP3_15); and a transporter protein comprising an amino acid sequence which has at least 70% (preferably at least 80%, more preferably at least 90%, even more preferably at least 95% and most preferably at least 99%) identity with the amino acid sequence of SEQ ID NO: 176 (T189_PsoPUP3_23); and a transporter protein comprising an amino acid sequence which has at least 70% (preferably at least 80%, more preferably at least 90%, even more preferably at least 95% and most preferably at least 99%) identity with the amino acid sequence of SEQ ID NO: 178 (T191_MdoPUP3_39); and a transporter protein comprising an amino acid sequence which has at least 70% (preferably at least 80%, more preferably at least 90%, even more preferably at least 95% and most preferably at least 99%) identity with the amino acid sequence of SEQ ID NO: 180 (T192_CmiPUP3_47); and a transporter protein comprising an amino acid sequence which has at least 70% (preferably at least 80%, more preferably at least 90%, even more preferably at least 95% and most preferably at least 99%) identity with the amino acid sequence of SEQ ID NO: 182 (T193_AanPUP3_55); and a transporter protein comprising an amino acid sequence which has at least 70% (preferably at least 80%, more preferably at least 90%, even more preferably at least 95% and most preferably at least 99%) identity with the amino acid sequence of SEQ ID NO: 184 (T194_CchPUP3_63); and a transporter protein comprising an amino acid sequence which has at least 70% (preferably at least 80%, more preferably at least 90%, even more preferably at least 95% and most preferably at least 99%) identity with the amino acid sequence of SEQ ID NO: 186 (T195_JcuPUP3_71); and a transporter protein comprising an amino acid sequence which has at least 70% (preferably at least 80%, more preferably at least 90%, even more preferably at least 95% and most preferably at least 99%) identity with the amino acid sequence of SEQ ID NO: 188 (T196_PtrPUP3_80).

A second aspect of the invention relates to a method of in vivo producing a thebaine derivative or an oripavine derivative in a cell culture, comprising culturing the host cell of the first aspect and/or herein relevant embodiments thereof in the cell culture, under conditions;

(A): in which at least one heterologously expressed enzyme capable of the "conversion of thebaine/oripavine" of item (i) of the first aspect and/or herein relevant embodiments thereof is expressed in the host cell; and (B): in which thebaine and/or oripavine is present in vivo in the host cell; and (C): wherein the thebaine or oripavine of item (B) in vivo is converted into a thebaine derivative or an oripavine derivative due to the presence of the heterologously expressed enzyme of item (A) in order to thereby get in vivo production a thebaine derivative or an oripavine derivative.

A third aspect of the invention relates to a method of producing an opioid compound of interest, comprising first performing in vivo production of a thebaine derivative or an oripavine derivative (such as e.g. neopinone, oripavine, northebaine, nororipavine or morphinone) according to the second aspect and/or herein relevant embodiments thereof, followed by suitable in vivo and/or in vitro synthesis steps on the resulting thebaine derivative or oripavine derivative, in order to obtain the opioid compound of interest.

Embodiments of the present invention are described below by way of examples only.

Definitions

All definitions of herein relevant terms are in accordance of what would be understood by the skilled person in relation to the herein relevant technical context.

As used herein, the term "opioid pathway" refers to the multi-step synthesis of opioids and/or their derivatives. The natural synthesis of morphine is performed by a series of sequential enzymatic reactions in the opium poppy. At each step in the pathway, the product of the previous ("upstream") reaction becomes a substrate for the next reaction. However, alternative opioid pathways can be created by substituting different enzymes to carry out a specific catalysis, or by replacing several reactions in the pathway with an alternative multi-step route to achieve the same end product opioid or opioid derivative. Since each reaction product in the pathway soon used as a substrate for the next reaction, all reaction products are known as pathway intermediates until the final opioid or opioid derivative is achieved.

As used herein, the term "opioid transporter" refers to a membrane-bound or membrane-spanning protein involved in the movement across host cell membranes of opioids and/or opioid pathway intermediates and/or opioid derivatives.

An introduction to the NPF family of transporters can be found in Jørgensen et al. ("Origin and evolution of transporter substrate specificity within the NPF family"; eLife 2017; 6: e19466. DOI: 10.7554/eLife. 19466).

As used herein, the term "reticuline or a derivative thereof" refers to precursors and intermediates in the production of opioids and opioid derivatives. In some aspects, preferred reticuline derivates of particular relevance to the transporters and enzyme activities disclosed herein include thebaine and/or oripavine.

The term "endogenous" gene refers to a gene that originates from and is produced or synthesized within a particular organism, tissue, or cell and is expressed in the same species, organism, tissue or cell for use in the technologies described herein. Therefore an endogenously expressed gene has the source organism as the host organism.

The term "heterologous" relates to a protein that is genetically engineered (such as through recombinant DNA technologies) into a cell that does not normally make (i.e., express) that protein. Therefore a heterologously expressed gene is present in a host organism that is different from the source organism for that gene.

The term "in vitro" (Latin: in glass) relates to studies that are conducted using components of an organism that have been isolated from their usual biological surroundings. Colloquially, these experiments are commonly called "test tube experiments". In contrast, in vivo studies are those that are conducted using living organisms in their normal intact state.

The term "in vivo" (Latin for "within the living") relates to experimentation using a whole living organism, as opposed to a partial or dead organism, or an in vitro ("within the glass", e.g., in a test tube) controlled environment.

The term "biosynthetic" refers to a means of producing a compound wherein at least one step in the production process for synthesizing the compound is carried out in a recombinant biological host. In some circumstances, preferably the entire synthesis of the desired molecule is carried out in a recombinant host i.e. the entire biosynthetic pathway is present and functional within the recombinant host. In other circumstances, part of the biosynthetic pathway may be present in one host, and another part of the biosynthetic pathway may be present in another host.

The term "biotransformation" refers to the addition of a substrate to isolated cells, such that at least one enzyme endogenously or heterologously expressed in the cells are able to catalyze at least one transformation from said substrate into at least one desired product or biosynthetic pathway intermediate.

The term "recombinant host cell" is a commonly used term in the art. Within the field of genetic engineering, recombinant polynucleotide (e.g. DNA) molecules are polynucleotide (e.g. DNA) molecules that may be formed by methods of genetic recombination (such as molecular cloning) to bring together genetic material from two or more sources, creating DNA sequences that are not naturally found in biological organisms.

The term "Sequence Identity" relates to the relatedness between two amino acid sequences or between two nucleotide sequences.

For purposes of the present invention, the degree of sequence identity between two amino acid sequences is determined using the Needleman-Wunsch algorithm (Needleman and Wunsch, 1970, *J. Mol. Biol.* 48:443-453) as implemented in the Needle program of the EMBOSS package (EMBOSS: The European Molecular Biology Open Software Suite, Rice et al., 2000, *Trends Genet.* 16:276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment).

For purposes of the present invention, the degree of sequence identity between two nucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment).

DRAWINGS

FIG. 1: Shows prior art known synthesis pathway for different opioid compounds

DETAILED DESCRIPTION OF THE INVENTION

A Microbial Host Cell

As broadly known in the art, a microbe is a microscopic organism capable of existing in a single-celled form or in a colony of cells. Typically, microbes are capable of rapidly dividing into a relatively homogenous population and may be cultured by those skilled in the art very effectively under relatively simple conditions to quickly produce high densities of cells. Microbial host cells are such microbes suitable for industrial application which may be engineered (e.g. using recombinant DNA technologies) to produce one or more products of interest (such as opioids, their intermediates or derivatives). Suitable microbial host cells may be eukaryotic or prokaryotic cells. Non-limiting examples of suitable eukaryotes for scalable production of opioids, their intermediates or derivatives, include fungi such as a filamentous fungus cell or a yeast cell. Non-limiting examples of suitable prokaryotes for scalable production of opioids, their intermediates or derivatives, include bacteria, such as *E. coli, Pseudomonas* sp. or *Bacillus subtilis*. Non-limiting examples of suitable yeast cells for scalable production of opioids, their intermediates or derivatives, include As broadly known in the art, a fungus host cell may e.g. be a yeast cell or e.g. a filamentous fungus cell.

In some circumstances, the fungus host cell is preferably a yeast cell.

The fungal host cell may e.g. be a filamentous fungus cell—such as e.g. an *Aspergillus* sp. cell, *Penicillium* sp. cell, *Trichoderma* sp. cell, *Talaromyces* sp. cell, *Asteromyces* sp. cell or *Neurospora* sp. cell.

A preferred filamentous fungus cell is an *Aspergillus* sp. cell.

For example, suitable filamentous fungus cell species can be *Aspergillus nidulans, Aspergillus sydowii, Aspergillus terreus, Aspergillus oryzae, Aspergillus caelatus, Aspergillus chevalieri, Aspergillus longivesica, Aspergillus parvulus, Aspergillus amylovorus, Aspergillus niger, Aspergillus aculeatus, Aspergillus ellipticus, Aspergillus violaceofuscus, Aspergillus brunneoviolaceus, Aspergillus japonicus, Aspergillus brasiliensis, Aspergillus aculeatinus, Aspergillus thermomutatus, Aspergillus implicatus, Aspergillus acristatus, Penicillium bilaiae, Penicillium rubens, Penicillium chrysogenum, Penicillium expansum, Penicillium antarcticum, Trichoderma reesei, Talaromycesatroroseus, Asteromyces* cruciatus, or *Neurospora crassa.*

The yeast cell may e.g. be *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous, Candida albicans, Rhodotorula* sp., or Rhodospiridium sp.

In some circumstances, the yeast cell is preferably a *Saccharomyces*, most preferably, a *Saccharomyces cerevisiae* cell.

The heterologously expressed enzyme capable of the "conversion of thebaine/oripavine" of item (i) of the first aspect Preferably, the enzyme capable of converting thebaine/oripavine" into derivatives thereof and/or further intermediates in a pathway for opioid production, is a demethylase.

As discussed above, based on the technical disclosure herein and the prior art knowledge of the skilled person, it is routine work for the skilled person to make a recombinant microbial host (e.g. yeast) capable of:

(1): in vivo conversion of thebaine into neopinone due to the in vivo presence of heterologously expressed thebaine 6-O-demethylase; or (2): in vivo conversion of thebaine into oripavine due to the in vivo presence of heterologously expressed O-demethylase; or (3): in vivo conversion of thebaine into northebaine due to the in vivo presence of heterologously expressed N-demethylase; or (4): in vivo conversion of oripavine into nororipavine due to the in vivo presence of heterologously expressed N-demethylase; or (5): in vivo conversion of oripavine into morphinone due to the in vivo presence of heterologously expressed thebaine 6-O-demethylase.

The skilled person knows from the prior art and/or the technical disclosure herein different suitable examples of an "enzyme capable of converting thebaine/oripavine" into derivatives thereof and/or further intermediates in a pathway for opioid production, which may be heterologously expressed as an enzyme of item (i) of the first aspect such as e.g. the ones explicitly discussed herein.

As discussed above and without being limited by theory, the improved positive yield effect demonstrated herein is probably related to a speculated ability of the herein relevant transporter proteins to transport more thebaine and/or oripavine into the host cell, thereby increasing the intracellular amount of thebaine and/or oripavine (i.e. in vivo) in the host cell.

Consequently, one may obtain the benefit (i.e. improved yield of derivatives "enzyme capable of converting thebaine/oripavine" into derivatives thereof and/or further intermediates in a pathway for opioid production, thereof and/or further intermediates in a pathway for opioid production) of the present invention independently of the specific "enzyme capable of converting thebaine/oripavine/thevinone" into, heterologously enzyme used—i.e. one may in principle use any suitable (e.g. prior art known) "conversion of thebaine/oripavine" heterologously enzyme of interest—i.e. this element of the present invention may be seen as an element based on prior art known knowledge for the skilled person.

Examples of suitable "conversion of thebaine/oripavine" heterologously enzyme may e.g. be:

thebaine to neopinone: thebaine 6-O-demethylase encoded by the T6ODM gene—see e.g. of WO2018/075670A1;

thebaine to oripavine: Codeine O-demethylase encoded by the CODM gene-se e.g. of WO2018/075670A1 thebaine to northebaine: N-demethylase encoded by the *Bacillus* BM3 gene—see e.g. and FIG. 24 of WO2018/075670A1.

oripavine into nororipavine: N-demethylase encoded by the *Bacillus* BM3 gene—see e.g. and FIG. 24 of WO2018/075670A1;

oripavine into morphinone: thebaine 6-O-demethylase encoded by the T6ODM gene—see e.g. of WO2018/075670A1.

In working examples herein were used fungal N-demethylase genes/enzymes that are different from the bacterial N-demethylase (e.g. *Bacillus* BM3 gene) described in WO2018/075670A1.

The fungal N-demethylase based genes/enzymes used in working Example herein are described in international PCT patent application with number PCT/EP2018/066155, which was filed 18 Jun. 2018 and not published at the filing/priority date of the present application.

The PCT/EP2018/066155 application also describes a number of different fungal O-demethylases that are suitable for the thebaine to oripavine conversion.

Accordingly, in a preferred embodiment the N-demethylase is a N-demethylase selected from the group consisting of:

a N-demethylase comprising an amino acid sequence which has at least 70% (preferably at least 80%, more preferably at least 90%, even more preferably at least 95% and most preferably at least 99%) identity with amino acids 1 to 522 of SEQ ID NO:25 (CYPDN8).

Preferably, the recombinant fungus host cell is capable of:

(1): in vivo conversion of thebaine into neopinone due to the in vivo presence of heterologously expressed thebaine 6-O-demethylase; or (2): in vivo conversion of thebaine into oripavine due to the in vivo presence of heterologously expressed O-demethylase; or (3): in vivo conversion of thebaine into northebaine due to the in vivo presence of heterologously expressed N-demethylase.

Most preferably, the recombinant fungus host cell is capable of:

(3): in vivo conversion of thebaine into northebaine due to the in vivo presence of heterologously expressed N-demethylase.

It may also be preferred that the recombinant fungus host cell is capable of:

(3): in vivo conversion of thebaine into northebaine due to the in vivo presence of heterologously expressed N-demethylase; or (4): in vivo conversion of oripavine into nororipavine due to the in vivo presence of heterologously expressed N-demethylase.

Heterologously Expressing at Least One Functional Transporter Protein Capable of Transporting Reticuline and/or its Derivatives—First Aspect It some embodiments it may be preferred that the transporter protein capable of transporting reticuline and/or its derivatives is a transporter protein belonging to the NRT1/PTR (NPF) transporter protein family.

The skilled person may routinely determine whether or not a transporter protein capable of transporting reticuline and/or its derivatives is an NPF transporter protein or not. The two articles:

Jørgensen et al. ("Origin and evolution of transporter substrate specificity within the NPF fami-ly"; eLife 2017; 6: e19466. DOI: 10.7554/eLife. 19466);

Jørgensen et al. ("A Functional EXXEK Motif is Essential for Proton Coupling and Active Glucosinolate Transport by NPF2.11"; Plant Cell Physiol. 56 (12): 2340-2350 (2015)) in detail describe the NPF transporter protein family and based on the definition/description of this NPF family in these articles may the skilled person routinely determine whether or not a transporter protein of interest is an NPF transporter protein or not.

As discussed in the dated 2015 article of Jørgensen—the Functional EXXEK Motif is essential for NPF—i.e. in accordance with the art, an NPF transporter protein is a protein comprising this EXXEK Motif.

It some embodiments it may be preferred that the transporter protein capable of transporting reticuline and/or its derivatives is a transporter protein belonging to the Purine Uptake Permease (PUP) transporter protein family. The PUP transporters are believed to be a distinct group of a superfamily of drug and metabolite transporters that evolved in terrestrial plant species. Jelesko J. G. 2012 ("An expanding role for purine uptake permease-like transporters in plant secondary metabolism", Front Pnat Sci 2012; 3:78. As used herein, the term "capable of PUP activity" refers to purine nucleoside transmembrane transporter activity. As used herein, the term PUP transporters refers to uptake transporters capable of enhancing in-vivo concentration of purine nucleobase substrates in the host, and with particular reference to the specific reactions exemplified herein, to increase the uptake of reticuline derivatives, most preferably of thebaine and/or oripavine.

As discussed above, the recombinant host cell of an embodiment of the first aspect is a microbial host cell (such as a yeast cell), wherein the microbial host cell is heterologously expressing at least one functional transporter protein capable of transporting reticuline and/or its derivatives selected from the group consisting of:

- a transporter protein comprising an amino acid sequence which has at least 70% (preferably at least 80%, more preferably at least 90%, even more preferably at least 95% and most preferably at least 99%) identity with amino acids 1 to 584 of SEQ ID NO:2 (T14_PsoNPF3_GA);
- a transporter protein comprising an amino acid sequence which has at least 70% (preferably at least 80%, more preferably at least 90%, even more preferably at least 95% and most preferably at least 99%) identity with amino acids 1 to 1289 of SEQ ID NO:4 (T1_CjaMDR1_GA);
- a transporter protein comprising an amino acid sequence which has at least 70% (preferably at least 80%, more preferably at least 90%, even more preferably at least 95% and most preferably at least 99%) identity with amino acids 1 to 654 of SEQ ID NO:6 (T4_EsaGTR_GA);
- a transporter protein comprising an amino acid sequence which has at least 70% (preferably at least 80%, more preferably at least 90%, even more preferably at least 95% and most preferably at least 99%) identity with amino acids 1 to 607 of SEQ ID NO:8 (T7_PtrPOT_GA);
- a transporter protein comprising an amino acid sequence which has at least 70% (preferably at least 80%, more preferably at least 90%, even more preferably at least 95% and most preferably at least 99%) identity with amino acids 1 to 583 of SEQ ID NO: 10 (T60_AmeNPF2_GA);
- a transporter protein comprising an amino acid sequence which has at least 70% (preferably at least 80%, more preferably at least 90%, even more preferably at least 95% and most preferably at least 99%) identity with amino acids 1 to 594 of SEQ ID NO: 12 (T57_AcoNPF_GA);
- a transporter protein comprising an amino acid sequence which has at least 70% (preferably at least 80%, more preferably at least 90%, even more preferably at least 95% and most preferably at least 99%) identity with amino acids 1 to 527 of SEQ ID NO: 14 (T52_BmePTR2_GA);
- a transporter protein comprising an amino acid sequence which has at least 70% (preferably at least 80%, more preferably at least 90%, even more preferably at least 95% and most preferably at least 99%) identity with amino acids 1 to 512 of SEQ ID NO: 16 (T38_ScuPTR2_GA);
- a transporter protein comprising an amino acid sequence which has at least 70% (preferably at least 80%, more preferably at least 90%, even more preferably at least 95% and most preferably at least 99%) identity with amino acids 1 to 636 of SEQ ID NO: 18 (T11_AthGTR1_GA);
- a transporter protein comprising an amino acid sequence which has at least 70% (preferably at least 80%, more preferably at least 90%, even more preferably at least 95% and most preferably at least 99%) identity with amino acids 1 to 565 of SEQ ID NO:20 (T19_RmiPTR2_GA);
- a transporter protein comprising an amino acid sequence which has at least 70% (preferably at least 80%, more preferably at least 90%, even more preferably at least 95% and most preferably at least 99%) identity with amino acids 1 to 598 of SEQ ID NO:22 (T70_CmaNPF_GA);
- a transporter protein comprising an amino acid sequence which has at least 70% (preferably at least 80%, more preferably at least 90%, even more preferably at least 95% and most preferably at least 99%) identity with amino acids 1 to 515 of SEQ ID NO:24 (T54_MelPOT_GA);
- a transporter protein comprising an amino acid sequence which has at least 70% (preferably at least 80%, more preferably at least 90%, even more preferably at least 95% and most preferably at least 99%) identity with amino acids 1 to 593 of SEQ ID NO:27 (T65_ljaNPF_GA);
- a transporter protein comprising an amino acid sequence which has at least 70% (preferably at least 80%, more preferably at least 90%, even more preferably at least 95% and most preferably at least 99%) identity with amino acids 1 to 604 of SEQ ID NO:29 (T94_EcrPOT_GA); and
- a transporter protein comprising an amino acid sequence which has at least 70% (preferably at least 80%, more preferably at least 90%, even more preferably at least 95% and most preferably at least 99%) identity with amino acids 1 to 604 of SEQ ID NO:31 (T97_ScaT14_GA); and
- a transporter protein comprising an amino acid sequence which has at least 70% (preferably at least 80%, more preferably at least 90%, even more preferably at least 95% and most preferably at least 99%) identity with the amino acid sequence of SEQ ID NO:32 (T101_McoPUP3_1); and
- a transporter protein comprising an amino acid sequence which has at least 70% (preferably at least 80%, more preferably at least 90%, even more preferably at least 95% and most preferably at least 99%) identity with the amino acid sequence of SEQ ID NO:34 (T102_PsoPUP3_1); and
- a transporter protein comprising an amino acid sequence which has at least 70% (preferably at least 80%, more preferably at least 90%, even more preferably at least 95% and most preferably at least 99%) identity with the amino acid sequence of SEQ ID NO:36 (T103_PsoPUP3_2); and a transporter protein comprising an amino acid sequence which has at least 70% (preferably at least 80%, more preferably at least 90%, even more preferably at least 95% and most preferably at least 99%) identity with the amino acid sequence of SEQ ID NO:38 (T104_PsoPUP3_3); and a transporter protein comprising an amino acid sequence which has at least 70% (preferably at least 80%, more preferably at least 90%, even more preferably at least 95% and most preferably at least 99%) identity with the amino acid sequence of SEQ ID NO:40 (T105_PsoPUP-L); and a transporter protein comprising an amino acid sequence which has at least 70% (preferably at least 80%, more preferably at least 90%, even more preferably at least 95% and most preferably at least 99%) identity with the amino acid sequence of SEQ ID NO:42 (T109_GflPUP3_83); and a transporter protein comprising an amino acid sequence which has at least 70% (preferably at least 80%, more preferably at least 90%, even more preferably at least 95% and most preferably at least 99%) identity with the amino acid sequence of SEQ ID NO:44 (T113_PsoPUP3_32); and a transporter protein comprising an amino acid sequence which has at least 70% (preferably at least 80%, more preferably at least 90%, even more preferably at least 95% and most preferably at least 99%) identity with the amino acid sequence of SEQ ID NO:46 (T114_TorPUP3_40); and a transporter protein comprising an amino acid sequence which has at least 70% (preferably at least 80%, more preferably at least 90%, even more preferably at least 95% and most preferably at least 99%) identity with the amino acid sequence of SEQ ID NO:48 (T115_CsaPUP3_48); and a transporter protein comprising an amino acid sequence which has at least 70% (preferably at least 80%, more preferably at least 90%, even more preferably at least 95% and most preferably at least 99%) identity with the amino acid sequence of SEQ ID NO:50 (T116_HanPUP3_56); and a transporter protein comprising an amino acid sequence which has at least 70% (preferably at least 80%, more preferably at least 90%, even more preferably at least 95% and most preferably at least 99%) identity with the amino acid sequence of SEQ ID NO:52 (T117_MacPUP3_64); and a transporter protein comprising an amino acid sequence which has at least 70% (preferably at least 80%, more preferably at least 90%, even more preferably at least 95% and most preferably at least 99%) identity with the amino acid sequence of SEQ ID NO:54 (T121_NnuPUP3_9); and a transporter protein comprising an amino acid sequence which has at least 70% (preferably at least 80%, more preferably at least 90%, even more preferably at least 95% and most preferably at least 99%) identity with the amino acid sequence of SEQ ID NO:56 (T122_PsoPUP3_17); and a transporter protein comprising an amino acid sequence which has at least 70% (preferably at least 80%, more preferably at least 90%, even more preferably at least 95% and most preferably at least 99%) identity with the amino acid sequence of SEQ ID NO:58 (T123_PsoPUP3_25); and a transporter protein comprising an amino acid sequence which has at least 70% (preferably at least 80%, more preferably at least 90%, even more preferably at least 95% and most preferably at least 99%) identity with the amino acid sequence of SEQ ID NO:60 (T124_PsoPUP3_33); and a transporter protein comprising an amino acid sequence which has at least 70% (preferably at least 80%, more preferably at least 90%, even more preferably at least 95% and most preferably at least 99%) identity with the amino acid sequence of SEQ ID NO:62 (T125_JcuPUP3_41); and a transporter protein comprising an amino acid sequence which has at least 70% (preferably at least 80%, more preferably at least 90%, even more preferably at least 95% and most preferably at least 99%) identity with the amino acid sequence of SEQ ID NO:64 (T126_CpePUP3_49); and a transporter protein comprising an amino acid sequence which has at least 70% (preferably at least 80%, more preferably at least 90%, even more preferably at least 95% and most preferably at least 99%) identity with the amino acid sequence of SEQ ID NO:66 (T127_LsaPUP3_57); and a transporter protein comprising an amino acid sequence which has at least 70% (preferably at least 80%, more preferably at least 90%, even more preferably at least 95% and most preferably at least 99%) identity with the amino acid sequence of SEQ ID NO:68 (T128_PsoPUP3_65); and a transporter protein comprising an amino acid sequence which has at least 70% (preferably at least 80%, more preferably at least 90%, even more preferably at least 95% and most preferably at least 99%) identity with the amino acid sequence of SEQ ID NO:70 (T129_PsoPUP3_73); and a transporter protein comprising an amino acid sequence which has at least 70% (preferably at least 80%, more preferably at least 90%, even more preferably at least 95% and most preferably at least 99%) identity with the amino acid sequence of SEQ ID NO:72 (T130_NdoPUP3_89); and a transporter protein comprising an amino acid sequence which has at least 70% (preferably at least 80%, more preferably at least 90%, even more preferably at least 95% and most preferably at least 99%) identity with the amino acid sequence of SEQ ID NO:74 (T131_PbrPUP3_81); and a transporter protein comprising an amino acid sequence which has at least 70% (preferably at least 80%, more preferably at least 90%, even more preferably at least 95% and most preferably at least 99%) identity with the amino acid sequence of SEQ ID NO:76 (T132_CmiPUP3_10); and a transporter protein comprising an amino acid sequence which has at least 70% (preferably at least 80%, more preferably at least 90%, even more preferably at least 95% and most preferably at least 99%) identity with the amino acid sequence of SEQ ID NO:78 (T133_PsoPUP3_18); and a transporter protein comprising an amino acid sequence which has at least 70% (preferably at least 80%, more preferably at least 90%, even more preferably at least 95% and most preferably at least 99%) identity with the amino acid sequence of SEQ ID NO:80 (T135_PsoPUP_34); and a transporter protein comprising an amino acid sequence which has at least 70% (preferably at least 80%, more preferably at least 90%, even more preferably at least 95% and most preferably at least 99%) identity with the amino acid sequence of SEQ ID NO:82 (T136_RchPUP3_42); and a transporter protein comprising an amino acid sequence which has at least 70% (preferably at least 80%, more preferably at least 90%, even more preferably at least 95% and most preferably at least 99%) identity with the amino acid sequence of SEQ ID NO:84 (T137_EguPUP3_50); and a transporter protein comprising an amino acid sequence which has at least 70% (preferably at least 80%, more preferably at least 90%, even more preferably at least 95% and most preferably at least 99%) identity with the amino acid sequence of SEQ ID NO: 86 (T138_AduPUP3_58); and a transporter protein comprising an amino acid sequence which has at least 70% (preferably at least 80%, more preferably at least 90%, even more preferably at least 95% and most preferably at least 99%) identity with the amino acid sequence of SEQ ID NO:88 (T139_PsoPUP3_66); and a transporter protein comprising an amino acid sequence which has at least 70% (preferably at least 80%, more preferably at least 90%, even more preferably at least 95% and most preferably at least 99%) identity with the amino acid sequence of SEQ ID NO:90 (T140_PalPUP3_74); and a transporter protein comprising an amino acid sequence which has at least 70% (preferably at least 80%, more preferably at least 90%, even more preferably at least 95% and most preferably at least 99%) identity with the amino acid sequence of SEQ ID NO:92 (T141_EcaPUP3_88); and a transporter protein comprising an amino acid sequence which has at least 70% (preferably at least 80%, more preferably at least 90%, even more preferably at least 95% and most preferably at least 99%) identity with the amino acid sequence of SEQ ID NO:94 (T142_McoPUP3_4); and a transporter protein comprising an amino acid sequence which has at least 70% (preferably at least 80%, more preferably at least 90%, even more preferably at least 95% and most preferably at least 99%) identity with the amino acid sequence of SEQ ID NO:96 (T143_CmiPUP3_11); and a transporter protein comprising an amino acid sequence which has at least 70% (preferably at least 80%, more preferably at least 90%, even more preferably at least 95% and most preferably at least 99%) identity with the amino acid sequence of SEQ ID NO:98 (T144_PsoPUP3_19); and a transporter protein comprising an amino acid sequence which has at least 70% (preferably at least 80%, more preferably at least 90%, even more preferably at least 95% and most preferably at least 99%) identity with the amino acid sequence of SEQ ID NO: 100 (T146_PsoPUP_35); and a transporter protein comprising an amino acid sequence which has at least 70% (preferably at least 80%, more preferably at least 90%, even more preferably at least 95% and most preferably at least 99%) identity with the amino acid sequence of SEQ ID NO: 102 (T147_MesPUP3_43); and a transporter protein comprising an amino acid sequence which has at least 70% (preferably at least 80%, more preferably at least 90%, even more preferably at least 95% and most preferably at least 99%) identity with the amino acid sequence of SEQ ID NO: 104 (T148_HimPUP3_51); and a transporter protein comprising an amino acid sequence which has at least 70% (preferably at least 80%, more preferably at least 90%, even more preferably at least 95% and most preferably at least 99%) identity with the amino acid sequence of SEQ ID NO: 106 (T149_AcoPUP3_59); and a transporter protein comprising an amino acid sequence which has at least 70% (preferably at least 80%, more preferably at least 90%, even more preferably at least 95% and most preferably at least 99%) identity with the amino acid sequence of SEQ ID NO: 108 (T150_PsoPUP3_67); and a transporter protein comprising an amino acid sequence which has at least 70% (preferably at least 80%, more preferably at least 90%, even more preferably at least 95% and most preferably at least 99%) identity with the amino acid sequence of SEQ ID NO: 110 (T151_PatPUP3_75); and a transporter protein comprising an amino acid sequence which has at least 70% (preferably at least 80%, more preferably at least 90%, even more preferably at least 95% and most preferably at least 99%) identity with the amino acid sequence of SEQ ID NO: 112 (T152_GflPUP3_87); and a transporter protein comprising an amino acid sequence which has at least 70% (preferably at least 80%, more preferably at least 90%, even more preferably at least 95% and most preferably at least 99%) identity with the amino acid sequence of SEQ ID NO: 114 (T153_PsoPUP3_5); and a transporter protein comprising an amino acid sequence which has at least 70% (preferably at least 80%, more preferably at least 90%, even more preferably at least 95% and most preferably at least 99%) identity with the amino acid sequence of SEQ ID NO: 116 (T154_CmiPUP3_12); and a transporter protein comprising an amino acid sequence which has at least 70% (preferably at least 80%, more preferably at least 90%, even more preferably at least 95% and most preferably at least 99%) identity with the amino acid sequence of SEQ ID NO: 118 (T156_PsoPUP3_28); and a transporter protein comprising an amino acid sequence which has at least 70% (preferably at least 80%, more preferably at least 90%, even more preferably at least 95% and most preferably at least 99%) identity with the amino acid sequence of SEQ ID NO: 120 (T157_RchPUP_36); and a transporter protein comprising an amino acid sequence which has at least 70% (preferably at least 80%, more preferably at least 90%, even more preferably at least 95% and most preferably at least 99%) identity with the amino acid sequence of SEQ ID NO: 122 (T158_DziPUP3_44); and a transporter protein comprising an amino acid sequence which has at least 70% (preferably at least 80%, more preferably at least 90%, even more preferably at least 95% and most preferably at least 99%) identity with the amino acid sequence of SEQ ID NO: 124 (T159_OeuPUP3_52); and a transporter protein comprising an amino acid sequence which has at least 70% (preferably at least 80%, more preferably at least 90%, even more preferably at least 95% and most preferably at least 99%) identity with the amino acid sequence of SEQ ID NO: 126 (T160_CeuPUP3_60); and a transporter protein comprising an amino acid sequence which has at least 70% (preferably at least 80%, more preferably at least 90%, even more preferably at least 95% and most preferably at least 99%) identity with the amino acid sequence of SEQ ID NO: 128 (T161_PsoPUP3_68); and a transporter protein comprising an amino acid sequence which has at least 70% (preferably at least 80%, more preferably at least 90%, even more preferably at least 95% and most preferably at least 99%) identity with the amino acid sequence of SEQ ID NO: 130 (T162_PmiPUP3_76); and a transporter protein comprising an amino acid sequence which has at least 70% (preferably at least 80%, more preferably at least 90%, even more preferably at least 95% and most preferably at least 99%) identity with the amino acid sequence of SEQ ID NO: 132 (T163_PbrPUP3_86); and a transporter protein comprising an amino acid sequence which has at least 70% (preferably at least 80%, more preferably at least 90%, even more preferably at least 95% and most preferably at least 99%) identity with the amino acid sequence of SEQ ID NO: 134 (T164_PsoPUP3_78); and a transporter protein comprising an amino acid sequence which has at least 70% (preferably at least 80%, more preferably at least 90%, even more preferably at least 95% and most preferably at least 99%) identity with the amino acid sequence of SEQ ID NO: 136 (T165_AcoPUP3_13); and a transporter protein comprising an amino acid sequence which has at least 70% (preferably at least 80%, more preferably at least 90%, even more preferably at least 95% and most preferably at least 99%) identity with the amino acid sequence of SEQ ID NO: 138 (T166_PsoPUP3_21); and a transporter protein comprising an amino acid sequence which has at least 70% (preferably at least 80%, more preferably at least 90%, even more preferably at least 95% and most preferably at least 99%) identity with the amino acid sequence of SEQ ID NO: 140 (T168_FvePUP3_37); and a transporter protein comprising an amino acid sequence which has at least 70% (preferably at least 80%, more preferably at least 90%, even more preferably at least 95% and most preferably at least 99%) identity with the amino acid sequence of SEQ ID NO: 142 (T169_ZjuPUP3_45); and a transporter protein comprising an amino acid sequence which has at least 70% (preferably at least 80%, more preferably at least 90%, even more preferably at least 95% and most preferably at least 99%) identity with the amino acid sequence of SEQ ID NO: 144 (T170_LsaPUP3_53); and a transporter protein comprising an amino acid sequence which has at least 70% (preferably at least 80%, more preferably at least 90%, even more preferably at least 95% and most preferably at least 99%) identity with the amino acid sequence of SEQ ID NO: 146 (T171_McoPUP3_61); and a transporter protein comprising an amino acid sequence which has at least 70% (preferably at least 80%, more preferably at least 90%, even more preferably at least 95% and most preferably at least 99%) identity with the amino acid sequence of SEQ ID NO: 148 (T172_AcoPUP3_69); and a transporter protein comprising an amino acid sequence which has at least 70% (preferably at least 80%, more preferably at least 90%, even more preferably at least 95% and most preferably at least 99%) identity with the amino acid sequence of SEQ ID NO: 150 (T173_PnuPUP3_77); and a transporter protein comprising an amino acid sequence which has at least 70% (preferably at least 80%, more preferably at least 90%, even more preferably at least 95% and most preferably at least 99%) identity with the amino acid sequence of SEQ ID NO: 152 (T174_PbrPUP3_85); and a transporter protein comprising an amino acid sequence which has at least 70% (preferably at least 80%, more preferably at least 90%, even more preferably at least 95% and most preferably at least 99%) identity with the amino acid sequence of SEQ ID NO: 154 (T175_PsoPUP3_6); and a transporter protein comprising an amino acid sequence which has at least 70% (preferably at least 80%, more preferably at least 90%, even more preferably at least 95% and most preferably at least 99%) identity with the amino acid sequence of SEQ ID NO: 156 (T176_AcoPUP3_14); and a transporter protein comprising an amino acid sequence which has at least 70% (preferably at least 80%, more preferably at least 90%, even more preferably at least 95% and most preferably at least 99%) identity with the amino acid sequence of SEQ ID NO: 158 (T177_PsoPUP3_22); and a transporter protein comprising an amino acid sequence which has at least 70% (preferably at least 80%, more preferably at least 90%, even more preferably at least 95% and most preferably at least 99%) identity with the amino acid sequence of SEQ ID NO: 160 (T178_PsoPUP3_30); and a transporter protein comprising an amino acid sequence which has at least 70% (preferably at least 80%, more preferably at least 90%, even more preferably at least 95% and most preferably at least 99%) identity with the amino acid sequence of SEQ ID NO: 162 (T179_PyePUP3_38); and a transporter protein comprising an amino acid sequence which has at least 70% (preferably at least 80%, more preferably at least 90%, even more preferably at least 95% and most preferably at least 99%) identity with the amino acid sequence of SEQ ID NO: 164 (T180_McoPUP3_46); and a transporter protein comprising an amino acid sequence which has at least 70% (preferably at least 80%, more preferably at least 90%, even more preferably at least 95% and most preferably at least 99%) identity with the amino acid sequence of SEQ ID NO: 166 (T181_HanPUP3_54); and a transporter protein comprising an amino acid sequence which has at least 70% (preferably at least 80%, more preferably at least 90%, even more preferably at least 95% and most preferably at least 99%) identity with the amino acid sequence of SEQ ID NO: 168 (T182_CpaPUP3_62); and a transporter protein comprising an amino acid sequence which has at least 70% (preferably at least 80%, more preferably at least 90%, even more preferably at least 95% and most preferably at least 99%) identity with the amino acid sequence of SEQ ID NO: 170 (T184_PraPUP3_79); and a transporter protein comprising an amino acid sequence which has at least 70% (preferably at least 80%, more preferably at least 90%, even more preferably at least 95% and most preferably at least 99%) identity with the amino acid sequence of SEQ ID NO: 172 (T186_ScaPUP3_84); and a transporter protein comprising an amino acid sequence which has at least 70% (preferably at least 80%, more preferably at least 90%, even more preferably at least 95% and most preferably at least 99%) identity with the amino acid sequence of SEQ ID NO: 174 (T188_AcoPUP3_15); and a transporter protein comprising an amino acid sequence which has at least 70% (preferably at least 80%, more preferably at least 90%, even more preferably at least 95% and most preferably at least 99%) identity with the amino acid sequence of SEQ ID NO: 176 (T189_PsoPUP3_23); and a transporter protein comprising an amino acid sequence which has at least 70% (preferably at least 80%, more preferably at least 90%, even more preferably at least 95% and most preferably at least 99%) identity with the amino acid sequence of SEQ ID NO: 178 (T191_MdoPUP3_39); and a transporter protein comprising an amino acid sequence which has at least 70% (preferably at least 80%, more preferably at least 90%, even more preferably at least 95% and most preferably at least 99%) identity with the amino acid sequence of SEQ ID NO: 180 (T192_CmiPUP3_47); and a transporter protein comprising an amino acid sequence which has at least 70% (preferably at least 80%, more preferably at least 90%, even more preferably at least 95% and most preferably at least 99%) identity with the amino acid sequence of SEQ ID NO: 182 (T193_AanPUP3_55); and a transporter protein comprising an amino acid sequence which has at least 70% (preferably at least 80%, more preferably at least 90%, even more preferably at least 95% and most preferably at least 99%) identity with the amino acid sequence of SEQ ID NO: 184 (T194_CchPUP3_63); and a transporter protein comprising an amino acid sequence which has at least 70% (preferably at least 80%, more preferably at least 90%, even more preferably at least 95% and most preferably at least 99%) identity with the amino acid sequence of SEQ ID NO: 186 (T195_JcuPUP3_71); and a transporter protein comprising an amino acid sequence which has at least 70% (preferably at least 80%, more preferably at least 90%, even more preferably at least 95% and most preferably at least 99%) identity with the amino acid sequence of SEQ ID NO: 188 (T196_PtrPUP3_80).

It may be preferred that the host cell is a microbial host cell, wherein the microbial host cell is heterologously expressing at least two functional transporter proteins of the first aspect—for instance in working Example 5 the inventors discuss an example of a host cell that is heterologously expressing the six different functional transporter proteins SEQ ID NO:2 (T14_PsoNPF3_GA); SEQ ID NO: 4 (T1_CjaMDR1_GA); SEQ ID NO:10 (T60_AmeNPF2_GA); SEQ ID NO:14 (T52_BmePTR2_GA); SEQ ID NO: 18 (T11_AthGTR1_GA); SEQ ID NO:22 (T70_CmaNPF_GA).

As discussed in for example the Conclusions of Examples 4 and 5 herein, expression of one of the transporter genes T14_PsoNPF3_GA, T1_CjaMDR1_GA, T4_EsaGTR_GA, T7_PtrPOT_GA or T97_ScaT14_GA in combination with a P450 capable of demethylating reticuline and/or its derivatives in a yeast strain was shown to improve bioconversion of thebaine to northebaine in the range of 22-63% in comparison to the control strain. This is objectively a significant improvement.

Accordingly, preferably the recombinant host cell of the first aspect is a microbial host cell, wherein the microbial host cell (such as a yeast host cell) is heterologously expressing a P450 capable of demethylating reticuline and/or its derivatives and also heterologously expressing at least one functional transporter protein capable of transporting reticuline and/or its derivatives selected from the group consisting of:

a transporter protein comprising an amino acid sequence which has at least 70% (preferably at least 80%, more preferably at least 90%, even more preferably at least 95% and most preferably at least 99%) identity with amino acids 1 to 584 of SEQ ID NO:2 (T14_PsoNPF3_GA);

a transporter protein comprising an amino acid sequence which has at least 70% (preferably at least 80%, more preferably at least 90%, even more preferably at least 95% and most preferably at least 99%) identity with amino acids 1 to 1289 of SEQ ID NO:4 (T1_CjaMDR1_GA);

a transporter protein comprising an amino acid sequence which has at least 70% (preferably at least 80%, more preferably at least 90%, even more preferably at least 95% and most preferably at least 99%) identity with amino acids 1 to 654 of SEQ ID NO:6 (T4_EsaGTR_GA);

a transporter protein comprising an amino acid sequence which has at least 70% (preferably at least 80%, more preferably at least 90%, even more preferably at least 95% and most preferably at least 99%) identity with amino acids 1 to 607 of SEQ ID NO:8 (T7_PtrPOT_GA); and a transporter protein comprising an amino acid sequence which has at least 70% (preferably at least 80%, more preferably at least 90%, even more preferably at least 95% and most preferably at least 99%) identity with amino acids 1 to 604 of SEQ ID NO:31 (T97_ScaT14_GA); and a transporter protein comprising an amino acid sequence which has at least 70% (preferably at least 80%, more preferably at least 90%, even more preferably at least 95% and most preferably at least 99%) identity with the amino acid sequence of SEQ ID NO:32 (T101_McoPUP3_1); and a transporter protein comprising an amino acid sequence which has at least 70% (preferably at least 80%, more preferably at least 90%, even more preferably at least 95% and most preferably at least 99%) identity with the amino acid sequence of SEQ ID NO:34 (T102_PsoPUP3_1); and a transporter protein comprising an amino acid sequence which has at least 70% (preferably at least 80%, more preferably at least 90%, even more preferably at least 95% and most preferably at least 99%) identity with the amino acid sequence of SEQ ID NO:36 (T103_PsoPUP3_2); and a transporter protein comprising an amino acid sequence which has at least 70% (preferably at least 80%, more preferably at least 90%, even more preferably at least 95% and most preferably at least 99%) identity with the amino acid sequence of SEQ ID NO:38 (T104_PsoPUP3_3); and a transporter protein comprising an amino acid sequence which has at least 70% (preferably at least 80%, more preferably at least 90%, even more preferably at least 95% and most preferably at least 99%) identity with the amino acid sequence of SEQ ID NO:40 (T105_PsoPUP-L); and a transporter protein comprising an amino acid sequence which has at least 70% (preferably at least 80%, more preferably at least 90%, even more preferably at least 95% and most preferably at least 99%) identity with the amino acid sequence of SEQ ID NO:42 (T109_GflPUP3_83); and a transporter protein comprising an amino acid sequence which has at least 70% (preferably at least 80%, more preferably at least 90%, even more preferably at least 95% and most preferably at least 99%) identity with the amino acid sequence of SEQ ID NO:44 (T113_PsoPUP3_32); and a transporter protein comprising an amino acid sequence which has at least 70% (preferably at least 80%, more preferably at least 90%, even more preferably at least 95% and most preferably at least 99%) identity with the amino acid sequence of SEQ ID NO:46 (T114_TorPUP3_40); and a transporter protein comprising an amino acid sequence which has at least 70% (preferably at least 80%, more preferably at least 90%, even more preferably at least 95% and most preferably at least 99%) identity with the amino acid sequence of SEQ ID NO:48 (T115_CsaPUP3_48); and a transporter protein comprising an amino acid sequence which has at least 70% (preferably at least 80%, more preferably at least 90%, even more preferably at least 95% and most preferably at least 99%) identity with the amino acid sequence of SEQ ID NO:50 (T116_HanPUP3_56); and a transporter protein comprising an amino acid sequence which has at least 70% (preferably at least 80%, more preferably at least 90%, even more preferably at least 95% and most preferably at least 99%) identity with the amino acid sequence of SEQ ID NO:52 (T117_MacPUP3_64); and a transporter protein comprising an amino acid sequence which has at least 70% (preferably at least 80%, more preferably at least 90%, even more preferably at least 95% and most preferably at least 99%) identity with the amino acid sequence of SEQ ID NO:54 (T121_NnuPUP3_9); and a transporter protein comprising an amino acid sequence which has at least 70% (preferably at least 80%, more preferably at least 90%, even more preferably at least 95% and most preferably at least 99%) identity with the amino acid sequence of SEQ ID NO:56 (T122_PsoPUP3_17); and a transporter protein comprising an amino acid sequence which has at least 70% (preferably at least 80%, more preferably at least 90%, even more preferably at least 95% and most preferably at least 99%) identity with the amino acid sequence of SEQ ID NO:58 (T123_PsoPUP3_25); and a transporter protein comprising an amino acid sequence which has at least 70% (preferably at least 80%, more preferably at least 90%, even more preferably at least 95% and most preferably at least 99%) identity with the amino acid sequence of SEQ ID NO:60 (T124_PsoPUP3_33); and a transporter protein comprising an amino acid sequence which has at least 70% (preferably at least 80%, more preferably at least 90%, even more preferably at least 95% and most preferably at least 99%) identity with the amino acid sequence of SEQ ID NO:62 (T125_JcuPUP3_41); and a transporter protein comprising an amino acid sequence which has at least 70% (preferably at least 80%, more preferably at least 90%, even more preferably at least 95% and most preferably at least 99%) identity with the amino acid sequence of SEQ ID NO:64 (T126_CpePUP3_49); and a transporter protein comprising an amino acid sequence which has at least 70% (preferably at least 80%, more preferably at least 90%, even more preferably at least 95% and most preferably at least 99%) identity with the amino acid sequence of SEQ ID NO:66 (T127_LsaPUP3_57); and a transporter protein comprising an amino acid sequence which has at least 70% (preferably at least 80%, more preferably at least 90%, even more preferably at least 95% and most preferably at least 99%) identity with the amino acid sequence of SEQ ID NO:68 (T128_PsoPUP3_65); and a transporter protein comprising an amino acid sequence which has at least 70% (preferably at least 80%, more preferably at least 90%, even more preferably at least 95% and most preferably at least 99%) identity with the amino acid sequence of SEQ ID NO:70 (T129_PsoPUP3_73); and a transporter protein comprising an amino acid sequence which has at least 70% (preferably at least 80%, more preferably at least 90%, even more preferably at least 95% and most preferably at least 99%) identity with the amino acid sequence of SEQ ID NO:72 (T130_NdoPUP3_89); and a transporter protein comprising an amino acid sequence which has at least 70% (preferably at least 80%, more preferably at least 90%, even more preferably at least 95% and most preferably at least 99%) identity with the amino acid sequence of SEQ ID NO:74 (T131_PbrPUP3_81); and a transporter protein comprising an amino acid sequence which has at least 70% (preferably at least 80%, more preferably at least 90%, even more preferably at least 95% and most preferably at least 99%) identity with the amino acid sequence of SEQ ID NO:76 (T132_CmiPUP3_10); and a transporter protein comprising an amino acid sequence which has at least 70% (preferably at least 80%, more preferably at least 90%, even more preferably at least 95% and most preferably at least 99%) identity with the amino acid sequence of SEQ ID NO: 78 (T133_PsoPUP3_18); and a transporter protein comprising an amino acid sequence which has at least 70% (preferably at least 80%, more preferably at least 90%, even more preferably at least 95% and most preferably at least 99%) identity with the amino acid sequence of SEQ ID NO:80 (T135_PsoPUP_34); and a transporter protein comprising an amino acid sequence which has at least 70% (preferably at least 80%, more preferably at least 90%, even more preferably at least 95% and most preferably at least 99%) identity with the amino acid sequence of SEQ ID NO:82 (T136_RchPUP3_42); and a transporter protein comprising an amino acid sequence which has at least 70% (preferably at least 80%, more preferably at least 90%, even more preferably at least 95% and most preferably at least 99%) identity with the amino acid sequence of SEQ ID NO:84 (T137_EguPUP3_50); and a transporter protein comprising an amino acid sequence which has at least 70% (preferably at least 80%, more preferably at least 90%, even more preferably at least 95% and most preferably at least 99%) identity with the amino acid sequence of SEQ ID NO:86 (T138_AduPUP3_58); and a transporter protein comprising an amino acid sequence which has at least 70% (preferably at least 80%, more preferably at least 90%, even more preferably at least 95% and most preferably at least 99%) identity with the amino acid sequence of SEQ ID NO:88 (T139_PsoPUP3_66); and a transporter protein comprising an amino acid sequence which has at least 70% (preferably at least 80%, more preferably at least 90%, even more preferably at least 95% and most preferably at least 99%) identity with the amino acid sequence of SEQ ID NO:90 (T140_PalPUP3_74); and a transporter protein comprising an amino acid sequence which has at least 70% (preferably at least 80%, more preferably at least 90%, even more preferably at least 95% and most preferably at least 99%) identity with the amino acid sequence of SEQ ID NO:92 (T141_EcaPUP3_88); and a transporter protein comprising an amino acid sequence which has at least 70% (preferably at least 80%, more preferably at least 90%, even more preferably at least 95% and most preferably at least 99%) identity with the amino acid sequence of SEQ ID NO:94 (T142_McoPUP3_4); and a transporter protein comprising an amino acid sequence which has at least 70% (preferably at least 80%, more preferably at least 90%, even more preferably at least 95% and most preferably at least 99%) identity with the amino acid sequence of SEQ ID NO:96 (T143_CmiPUP3_11); and a transporter protein comprising an amino acid sequence which has at least 70% (preferably at least 80%, more preferably at least 90%, even more preferably at least 95% and most preferably at least 99%) identity with the amino acid sequence of SEQ ID NO:98 (T144_PsoPUP3_19); and a transporter protein comprising an amino acid sequence which has at least 70% (preferably at least 80%, more preferably at least 90%, even more preferably at least 95% and most preferably at least 99%) identity with the amino acid sequence of SEQ ID NO: 100 (T146_PsoPUP_35); and a transporter protein comprising an amino acid sequence which has at least 70% (preferably at least 80%, more preferably at least 90%, even more preferably at least 95% and most preferably at least 99%) identity with the amino acid sequence of SEQ ID NO: 102 (T147_MesPUP3_43); and a transporter protein comprising an amino acid sequence which has at least 70% (preferably at least 80%, more preferably at least 90%, even more preferably at least 95% and most preferably at least 99%) identity with the amino acid sequence of SEQ ID NO: 104 (T148_HimPUP3_51); and a transporter protein comprising an amino acid sequence which has at least 70% (preferably at least 80%, more preferably at least 90%, even more preferably at least 95% and most preferably at least 99%) identity with the amino acid sequence of SEQ ID NO: 106 (T149_AcoPUP3_59); and a transporter protein comprising an amino acid sequence which has at least 70% (preferably at least 80%, more preferably at least 90%, even more preferably at least 95% and most preferably at least 99%) identity with the amino acid sequence of SEQ ID NO: 108 (T150_PsoPUP3_67); and a transporter protein comprising an amino acid sequence which has at least 70% (preferably at least 80%, more preferably at least 90%, even more preferably at least 95% and most preferably at least 99%) identity with the amino acid sequence of SEQ ID NO: 110 (T151_PatPUP3_75); and a transporter protein comprising an amino acid sequence which has at least 70% (preferably at least 80%, more preferably at least 90%, even more preferably at least 95% and most preferably at least 99%) identity with the amino acid sequence of SEQ ID NO: 112 (T152_GflPUP3_87); and a transporter protein comprising an amino acid sequence which has at least 70% (preferably at least 80%, more preferably at least 90%, even more preferably at least 95% and most preferably at least 99%) identity with the amino acid sequence of SEQ ID NO: 114 (T153_PsoPUP3_5); and a transporter protein comprising an amino acid sequence which has at least 70% (preferably at least 80%, more preferably at least 90%, even more preferably at least 95% and most preferably at least 99%) identity with the amino acid sequence of SEQ ID NO: 116 (T154_CmiPUP3_12); and a transporter protein comprising an amino acid sequence which has at least 70% (preferably at least 80%, more preferably at least 90%, even more preferably at least 95% and most preferably at least 99%) identity with the amino acid sequence of SEQ ID NO: 118 (T156_PsoPUP3_28); and a transporter protein comprising an amino acid sequence which has at least 70% (preferably at least 80%, more preferably at least 90%, even more preferably at least 95% and most preferably at least 99%) identity with the amino acid sequence of SEQ ID NO: 120 (T157_RchPUP_36); and a transporter protein comprising an amino acid sequence which has at least 70% (preferably at least 80%, more preferably at least 90%, even more preferably at least 95% and most preferably at least 99%) identity with the amino acid sequence of SEQ ID NO: 122 (T158_DziPUP3_44); and a transporter protein comprising an amino acid sequence which has at least 70% (preferably at least 80%, more preferably at least 90%, even more preferably at least 95% and most preferably at least 99%) identity with the amino acid sequence of SEQ ID NO: 124 (T159_OeuPUP3_52); and a transporter protein comprising an amino acid sequence which has at least 70% (preferably at least 80%, more preferably at least 90%, even more preferably at least 95% and most preferably at least 99%) identity with the amino acid sequence of SEQ ID NO: 126 (T160_CeuPUP3_60); and a transporter protein comprising an amino acid sequence which has at least 70% (preferably at least 80%, more preferably at least 90%, even more preferably at least 95% and most preferably at least 99%) identity with the amino acid sequence of SEQ ID NO: 128 (T161_PsoPUP3_68); and a transporter protein comprising an amino acid sequence which has at least 70% (preferably at least 80%, more preferably at least 90%, even more preferably at least 95% and most preferably at least 99%) identity with the amino acid sequence of SEQ ID NO: 130 (T162_PmiPUP3_76); and a transporter protein comprising an amino acid sequence which has at least 70% (preferably at least 80%, more preferably at least 90%, even more preferably at least 95% and most preferably at least 99%) identity with the amino acid sequence of SEQ ID NO: 132 (T163_PbrPUP3_86); and a transporter protein comprising an amino acid sequence which has at least 70% (preferably at least 80%, more preferably at least 90%, even more preferably at least 95% and most preferably at least 99%) identity with the amino acid sequence of SEQ ID NO: 134 (T164_PsoPUP3_78); and a transporter protein comprising an amino acid sequence which has at least 70% (preferably at least 80%, more preferably at least 90%, even more preferably at least 95% and most preferably at least 99%) identity with the amino acid sequence of SEQ ID NO: 136 (T165_AcoPUP3_13); and a transporter protein comprising an amino acid sequence which has at least 70% (preferably at least 80%, more preferably at least 90%, even more preferably at least 95% and most preferably at least 99%) identity with the amino acid sequence of SEQ ID NO: 138 (T166_PsoPUP3_21); and a transporter protein comprising an amino acid sequence which has at least 70% (preferably at least 80%, more preferably at least 90%, even more preferably at least 95% and most preferably at least 99%) identity with the amino acid sequence of SEQ ID NO: 140 (T168_FvePUP3_37); and a transporter protein comprising an amino acid sequence which has at least 70% (preferably at least 80%, more preferably at least 90%, even more preferably at least 95% and most preferably at least 99%) identity with the amino acid sequence of SEQ ID NO: 142 (T169_ZjuPUP3_45); and a transporter protein comprising an amino acid sequence which has at least 70% (preferably at least 80%, more preferably at least 90%, even more preferably at least 95% and most preferably at least 99%) identity with the amino acid sequence of SEQ ID NO: 144 (T170_LsaPUP3_53); and a transporter protein comprising an amino acid sequence which has at least 70% (preferably at least 80%, more preferably at least 90%, even more preferably at least 95% and most preferably at least 99%) identity with the amino acid sequence of SEQ ID NO: 146 (T171_McoPUP3_61); and a transporter protein comprising an amino acid sequence which has at least 70% (preferably at least 80%, more preferably at least 90%, even more preferably at least 95% and most preferably at least 99%) identity with the amino acid sequence of SEQ ID NO: 148 (T172_AcoPUP3_69); and a transporter protein comprising an amino acid sequence which has at least 70% (preferably at least 80%, more preferably at least 90%, even more preferably at least 95% and most preferably at least 99%) identity with the amino acid sequence of SEQ ID NO: 150 (T173_PnuPUP3_77); and a transporter protein comprising an amino acid sequence which has at least 70% (preferably at least 80%, more preferably at least 90%, even more preferably at least 95% and most preferably at least 99%) identity with the amino acid sequence of SEQ ID NO: 152 (T174_PbrPUP3_85); and a transporter protein comprising an amino acid sequence which has at least 70% (preferably at least 80%, more preferably at least 90%, even more preferably at least 95% and most preferably at least 99%) identity with the amino acid sequence of SEQ ID NO: 154 (T175_PsoPUP3_6); and a transporter protein comprising an amino acid sequence which has at least 70% (preferably at least 80%, more preferably at least 90%, even more preferably at least 95% and most preferably at least 99%) identity with the amino acid sequence of SEQ ID NO: 156 (T176_AcoPUP3_14); and a transporter protein comprising an amino acid sequence which has at least 70% (preferably at least 80%, more preferably at least 90%, even more preferably at least 95% and most preferably at least 99%) identity with the amino acid sequence of SEQ ID NO: 158 (T177_PsoPUP3_22); and a transporter protein comprising an amino acid sequence which has at least 70% (preferably at least 80%, more preferably at least 90%, even more preferably at least 95% and most preferably at least 99%) identity with the amino acid sequence of SEQ ID NO: 160 (T178_PsoPUP3_30); and a transporter protein comprising an amino acid sequence which has at least 70% (preferably at least 80%, more preferably at least 90%, even more preferably at least 95% and most preferably at least 99%) identity with the amino acid sequence of SEQ ID NO: 162 (T179_PyePUP3_38); and a transporter protein comprising an amino acid sequence which has at least 70% (preferably at least 80%, more preferably at least 90%, even more preferably at least 95% and most preferably at least 99%) identity with the amino acid sequence of SEQ ID NO: 164 (T180_McoPUP3_46); and a transporter protein comprising an amino acid sequence which has at least 70% (preferably at least 80%, more preferably at least 90%, even more preferably at least 95% and most preferably at least 99%) identity with the amino acid sequence of SEQ ID NO: 166 (T181_HanPUP3_54); and a transporter protein comprising an amino acid sequence which has at least 70% (preferably at least 80%, more preferably at least 90%, even more preferably at least 95% and most preferably at least 99%) identity with the amino acid sequence of SEQ ID NO: 168 (T182_CpaPUP3_62); and a transporter protein comprising an amino acid sequence which has at least 70% (preferably at least 80%, more preferably at least 90%, even more preferably at least 95% and most preferably at least 99%) identity with the amino acid sequence of SEQ ID NO: 170 (T184_PraPUP3_79); and a transporter protein comprising an amino acid sequence which has at least 70% (preferably at least 80%, more preferably at least 90%, even more preferably at least 95% and most preferably at least 99%) identity with the amino acid sequence of SEQ ID NO: 172 (T186_ScaPUP3_84); and a transporter protein comprising an amino acid sequence which has at least 70% (preferably at least 80%, more preferably at least 90%, even more preferably at least 95% and most preferably at least 99%) identity with the amino acid sequence of SEQ ID NO: 174 (T188_AcoPUP3_15); and a transporter protein comprising an amino acid sequence which has at least 70% (preferably at least 80%, more preferably at least 90%, even more preferably at least 95% and most preferably at least 99%) identity with the amino acid sequence of SEQ ID NO: 176 (T189_PsoPUP3_23); and a transporter protein comprising an amino acid sequence which has at least 70% (preferably at least 80%, more preferably at least 90%, even more preferably at least 95% and most preferably at least 99%) identity with the amino acid sequence of SEQ ID NO: 178 (T191_MdoPUP3_39); and a transporter protein comprising an amino acid sequence which has at least 70% (preferably at least 80%, more preferably at least 90%, even more preferably at least 95% and most preferably at least 99%) identity with the amino acid sequence of SEQ ID NO: 180 (T192_CmiPUP3_47); and a transporter protein comprising an amino acid sequence which has at least 70% (preferably at least 80%, more preferably at least 90%, even more preferably at least 95% and most preferably at least 99%) identity with the amino acid sequence of SEQ ID NO: 182 (T193_AanPUP3_55); and a transporter protein comprising an amino acid sequence which has at least 70% (preferably at least 80%, more preferably at least 90%, even more preferably at least 95% and most preferably at least 99%) identity with the amino acid sequence of SEQ ID NO: 184 (T194_CchPUP3_63); and a transporter protein comprising an amino acid sequence which has at least 70% (preferably at least 80%, more preferably at least 90%, even more preferably at least 95% and most preferably at least 99%) identity with the amino acid sequence of SEQ ID NO: 186 (T195_JcuPUP3_71); and a transporter protein comprising an amino acid sequence which has at least 70% (preferably at least 80%, more preferably at least 90%, even more preferably at least 95% and most preferably at least 99%) identity with the amino acid sequence of SEQ ID NO: 188 (T196_PtrPUP3_80).

As discussed above and in working examples 4 and 5 herein, "T14_PsoNPF3_GA" and T97_ScaT14_GA are demonstrated to have a positive in vivo conversion effect for both thebaine and oripavine.

Accordingly, in some embodiments, the recombinant microbial host cell of the first aspect is a microbial cell, wherein the microbial host cell (such as yeast host cell) is heterologously expressing at least one functional transporter protein selected from the group consisting of:

a transporter protein comprising an amino acid sequence which has at least 70% (preferably at least 80%, more preferably at least 90%, even more preferably at least 95% and most preferably at least 99%) identity with amino acids 1 to 584 of SEQ ID NO:2 (T14_PsoNPF3_GA); and a transporter protein comprising an amino acid sequence which has at least 70% (preferably at least 80%, more preferably at least 90%, even more preferably at least 95% and most preferably at least 99%) identity with amino acids 1 to 604 of SEQ ID NO:31 (T97_ScaT14_GA).

A Method of In Vivo Producing a Thebaine Derivative or an Oripavine Derivative (Such as e.g. Neopinone, Oripavine, Northebaine, Nororipavine or Morphinone)—Second Aspect As discussed above, a second aspect of the invention relates to a method of in vivo producing a thebaine derivative or an oripavine derivative in a cell culture, comprising culturing the microbial host cell of the first aspect and/or herein relevant embodiments thereof in the cell culture, under conditions;

(A): in which at least one of the heterologously expressed enzyme capable of "conversion of thebaine and/or oripavine" of the first aspect herein relevant embodiments thereof is thereby present in vivo in the host cell; and (B): in which thebaine and/or oripavine is present in vivo in the host cell; and (C): wherein the thebaine or oripavine of item (B) in vivo is converted into a thebaine derivative or an oripavine derivative due to the presence of the heterologously expressed enzyme of item (A) in order to thereby get in vivo production a thebaine derivative or an oripavine derivative.

A preferred embodiment of the second aspect relates to a method of in vivo producing neopinone, oripavine, northebaine, nororipavine or morphinone in a cell culture, comprising culturing the host cell of the first aspect and/or herein relevant embodiments thereof in the cell culture, under conditions;

(A): in which at least one of the "conversion of thebaine/oripavine" heterologously enzyme of item (1-5) of an embodiment of the first aspect and/or herein relevant embodiments thereof is expressed and thereby present in vivo in the host cell; and (B): in which thebaine and/or oripavine is present in vivo in the host cell; and (C): wherein the thebaine and/or oripavine of item (B) in vivo is converted into neopinone, oripavine, northebaine, nororipavine or morphinone due to the presence of the heterologously expressed enzyme of item (A) in order to thereby get in vivo production of neopinone, oripavine, northebaine, nororipavine or morphinone.

In relation to item (B)—thebaine and/or oripavine may be present in vivo in the host cell via e.g.:

thebaine and/or oripavine in vivo biosynthesis within the host cell; and/or thebaine and/or oripavine may be present in a cell culture medium or reaction medium and then taken up by the host cell in order for the thebaine and/or oripavine to be present in vivo in the host cell for biotransformation.

As discussed herein-thebaine and/or oripavine in vivo biosynthesis within a microbial host cell (such as a yeast host cell) is well known in the art.

It is also well known (see e.g. working examples herein) how to prepare thebaine and/or oripavine supplemented cell culture medium or reaction medium to be taken up by the yeast host cell in order for the thebaine and/or oripavine to be present in vivo in the microbial host cell.

As discussed above, the improved positive yield effect demonstrated herein is probably related to that the herein relevant transporter proteins increase the intracellular amount of thebaine and/or oripavine (i.e. in vivo) in the fungus host cell because more thebaine and/or oripavine is transported into the host yeast cell. This advantageous effect is also relevant in relation to in vivo biosynthesis within the host cell of thebaine/oripavine, since some of the thebaine/oripavine may be exported out of the host cell and herein relevant transporter proteins can then transport the thebaine/oripavine back into the host cell again.

Using methods known in the art, the in item (C) produced neopinone, oripavine, northebaine, nororipavine or morphinone may be isolated in order to get a substantially pure (e.g. at least 20%, 30%, 50%, 60% or at least 90% pure w/w) composition of the compound(s). Alternatively, they may e.g. in vivo be converted to further herein relevant downstream compounds (see e.g. FIG. 1 herein and the Third Aspect, below).

In short, based on the technical disclosure herein and the prior art knowledge of the skilled person—it is routine work for the skilled person to perform the method of the second aspect and/or herein relevant embodiments thereof.

In relation to the second aspect—it may be preferred that it is a method for producing neopinone, oripavine or northebaine, wherein (A): at least one of the "conversion of thebaine" heterologously enzyme of item (1), (2) or (3) of the first aspect and/or herein relevant embodiments thereof is expressed and thereby present in vivo in the host cell; and (B): in which thebaine is present in vivo in the host cell; and (C): wherein the thebaine of item (B) in vivo is converted into neopinone, oripavine or northebaine due to the presence of the heterologously expressed enzyme of item (A) in order to thereby get in vivo production of neopinone, oripavine or northebaine.

In relation to the second aspect—it may be preferred that it is a method for producing oripavine or northebaine, wherein (A): at least one of the "conversion of thebaine" heterologously enzyme of item (2) or (3) of the first aspect and/or herein relevant embodiments thereof is expressed and thereby present in vivo in the host cell; and (B): in which thebaine is present in vivo in the host cell; and (C): wherein the thebaine of item (B) in vivo is converted into oripavine or northebaine due to the presence of the heterologously expressed enzyme of item (A) in order to thereby get in vivo production of oripavine or northebaine.

Most preferably is a method for producing northebaine, wherein (A): at least one of the "conversion of thebaine" heterologously enzyme of item (3) of the first aspect and/or herein relevant embodiments thereof is expressed and thereby present in vivo in the host cell; and (B): in which thebaine is present in vivo in the host cell; and (C): wherein the thebaine of item (B) in vivo is converted into northebaine due to the presence of the heterologously expressed enzyme of item (A) in order to thereby get in vivo production of northebaine.

Further, and in relation to the second aspect, it may be preferred that it is a method for producing oripavine, northebaine or nororipavine, wherein (A): at least one of the "conversion of thebaine" heterologously enzyme of item (2), (3) or (4) of the first aspect and/or herein relevant embodiments thereof is expressed and thereby present in vivo in the host cell; and (B): in which thebaine and/or oripavine is present in vivo in the host cell; and (C): wherein the thebaine of item (B) in vivo is converted into oripavine or northebaine or the oripavine of item (B) in vivo is converted into nororipavine due to the presence of the heterologously expressed enzyme of item (A) in order to thereby get in vivo production of oripavine, northebaine or nororipavine.

Preferably, the method of the second aspect and/or herein relevant embodiments thereof is a method, wherein there in item (C) of the second aspect is an increased in vivo conversion of thebaine and/or oripavine due to that the cultured host cell is heterologously expressing at least one functional transporter protein (e.g. T14_PsoNPF3_GA) of the first aspect and/or herein relevant embodiments thereof; and wherein the "increased in vivo conversion of thebaine and/or oripavine" is understood to be relative to an otherwise identical performed method using an otherwise identical control host cell that is not heterologously expressing at least one functional transporter protein (e.g. T14_PsoNPF3_GA) of the first aspect and/or herein relevant embodiments thereof.

The "increased in vivo conversion of thebaine and/or oripavine" is understood to be relative to an otherwise identical control host cell, which is not heterologously expressing at least one functional transporter protein (e.g. T14_PsoNPF3_GA) of the first aspect.

The skilled person knows or can easily identify (by e.g. routine genome sequencing) an "otherwise identical control host cell" with no heterologously expressing of at least one functional transporter protein (e.g. T14_PsoNPF3_GA) of the first aspect.

If for instance the yeast host cell is heterologously expressing e.g. T14_PsoNPF3_GA-then is the method of the second aspect and/or herein relevant embodiments thereof simply performed with the host cell heterologously expressing T14_PsoNPF3_GA and the otherwise identical control host cell with no expressing of T14_PsoNPF3_GA and the amount of in vivo conversion of thebaine and/or oripavine is then measured (e.g. by LC-MS)-if the use of the host cell with expressing of T14_PsoNPF3_GA is giving increased in vivo conversion as compared to the control host cell then it is understood that there is an increased in vivo conversion of thebaine and/or oripavine due to that the host cell is heterologously expressing T14_PsoNPF3_GA.

A Method of Producing an Opioid Compound of Interest—Third Aspect

As discussed above, a third aspect of the invention relates to a method of producing an opioid compound of interest, comprising first performing in vivo production of a thebaine derivative or an oripavine derivative (such as e.g. neopinone, oripavine, northebaine, nororipavine or morphinone) according to the second aspect and/or herein relevant embodiments thereof followed by suitable in vivo and/or in vitro synthesis steps in order to obtain the opioid compound of interest.

A preferred embodiment of the third aspect relates to a method of producing an opioid compound of interest, comprising first performing in vivo production of neopinone, oripavine, northebaine, nororipavine or morphinone according to the second aspect and/or herein relevant embodiments thereof followed by suitable in vivo and/or in vitro synthesis steps in order to obtain the opioid compound of interest.

In short, based on the technical disclosure herein and the prior art knowledge of the skilled person—it is routine work for the skilled person to perform the method of the third aspect and/or herein relevant embodiments thereof.

As discussed herein, starting from neopinone, oripavine, northebaine, nororipavine or morphinone-suitable in vivo and/or in vitro synthesis steps in order to obtain the opioid compound of interest are well known in the art. See for example WO2018/211331 and Sipos et al. (2009).

As understood—the term "in vitro synthesis steps" may e.g. relate to suitable chemical synthesis steps as e.g. illustrated for buprenorphine in FIG. 1 herein.

Preferably, the opioid compound of interest is heroin, morphine, codeine, thebaine, oripavine, oxycodone, hydrocodone, hydromorphone, oxymorphone, buprenorphine, naltrexone, naloxone, nalmefene, noroxymorphone or nalbuphine. In some embodiments, most preferably the opioid compound of interest is buprenorphine, nalmefene or noroxymorphone.

EXAMPLES

As discussed above, the amino acid sequence for P450 CYPDN8 N-demethylase from *Rhizopus* microspores is shown as SEQ ID NO. 9 herein and discussed in international PCT patent application with number PCT/EP2018/066155, which was filed 18 Jun. 2018.

PCT patent application with number PCT/EP2018/066155 also describes other herein relevant technical details such as e.g. further details in relation to herein referred pOD75 and pOD13 plasmids. Accordingly, based on the technical disclosure herein and the technical disclosure of PCT patent application with number PCT/EP2018/066155—the skilled person can routinely carry out the relevant technical matter of the present invention-such as e.g. the relevant working Examples herein.

Example 1: Strain Engineering

*Saccharomyces cerevisiae* yeast strains were constructed in strain background EVST25898 (genotype MATalpha his3Δ0 leu2Δ0 ura3Δ0 aro3Δ::pTEF1-ARO4 (K229L)-tCYC1::pPGK1-ARO7(T266L)-tADH1::KI CAT5-91Met GAL2 ho MIP1-661Thr SAL1-1 YORWΔ22::npBIO1nt20npBIO6nt).

The EVST25898 with the genotype above corresponds to S288C (genotype MATalpha his3Δ0 leu2Δ0 ura3Δ0). S288C is a publicly available widely used laboratory strain (see the *Saccharomyces* Genome Database (SGD)). As is known from other works, one would get similar results by use of EVST25898 with genotype above or by use of S288C (genotype MATalpha his3Δ0 leu2Δ0 ura3Δ0) as background/control strains, since these two host phenotypes are substantially identical.

Plasmid Based Gene Expression

Strain was transformed with relevant plasmids using the lithium acetate method (Gietz et al. 2002. Methods Enzymol. Vol 350, p 87-96).

For testing the impact of possible transporter proteins on the bioconversion of Thebaine to Northebaine, the host yeast strain was transformed with a plasmid containing cytochrome P450 gene CYPDN8 N-demethylase from *Rhizopus microspores* (pOD75) along with a plasmid containing Cel_CPR (co) from *Cunninghamella elegans* (pOD13) in combination with the various possible transporter proteins. Genes were inserted and expressed using either P413TEF, P415TEF or p416TEF, all described by Mumberg et al., 1995. Gene. April 14; 156 (1): 119-22.

The control strain was constructed by transforming strain EVST25898 with pOD75, pOD13 as well as an empty plasmid: p416TEF.

Table 1 describes the plasmids that were expressed with the yeast strains. Transformants were selected in synthetic complete (SC) agar plates lacking histidine, leucine and uracil. Transformation plates were incubated for 3-4 days at 30° C. until visible colonies were obtained.

TABLE 1

Plasmids expressed in the corresponding yeast strains

| Vector name | Backbone | Promoter-Gene-Terminator | Yeast Selection Marker | Description |
|---|---|---|---|---|
| pOD13 | P413TEF | pTEF1-Cel_CPR_co-tCYC1 | HIS3 | Cel_CPR (co) from *Cunninghamella elegans* |
| pOD75 | P415TEF | pTEF1-CYPDN8-tCYC1 | LEU2 | A0A0C7AZL4 (co) from *Rhizopus microsporus* |
| P416TEF | | No gene inserted | URA3 | Mumberg et al., 1995. Gene. Apr 14; 156(1): 119-22 |

Gene Expression by Integration.

Strain EVST25898 was modified by genomic integration using the *Saccharomyces cerevisiae* gene integration and expression system developed by Mikkelsen, M D et al. (Metab. Eng. 14, Issue 2, 104-111 (2012)). The cytochrome P450 gene CYPDN8, N-demethylase from *Rhizopus* microspores was expressed using the well-known *Saccha-* romyces cerevisiae TEF1 promoter, and the Cel_CPR (co) from *Cunninghamella elegans* was expressed using the *Saccharomyces cerevisiae* PGK1 promoter. The expression cassette was integrated in site XII-5 using the *Kluyveromyces lactis* URA3 marker as selection marker for growth on media lacking uracil (described by Mikkelsen, M D et al. (Metab. Eng. 14, Issue 2, 104-111 (2012)). Subsequently, the transporter genes T11_AthGTR1_GA (SEQ ID NO: 17), T52_BmePTR2_GA (SEQ ID NO: 13), T14_PsoNPF3_GA (SEQ ID NO: 1), T60_AmeNPF2_GA (SEQ ID NO: 9), T1_CjaMDR1_GA (SEQ ID NO: 3) and T70_CmaNPF_GA (SEQ ID NO: 21) were integrated into the site XI-5 of the *Saccharomyces cerevisiae* strain using the *Saccharomyces cerevisiae* TEF1, PGK1, TEF2, TDH3, TPI1, and PDC1 promoters respectively. Selection for transformants was done using the well-known *Kluyveromyces lactis* LEU2 marker available e.g. from EUROSCARF and growth on media lacking leucine. After that, plasmid pOD13 (see Table 1) was transformed with the resulting strain in order to make the strain prototrophic by selecting on media lacking histidine. Transformation plates were incubated for 3-4 days at 30° C. until visible colonies were obtained.

Example 2. Cultivation and Harvest of Yeast Strains

Cultivation. Yeast strains were cultivated in 96-deep-well-plate (DWP) format. Cells were grown in 0.5 ml SC-His-Leu-Ura medium at 30° C. with shaking at 250 rpm in ISF1-X Kuhner shaker for 20-24 hours and utilized as precultures for in vivo bioconversion assays.

50 μl of the overnight cell cultures were grown in 450 μl Synthetic complete (SC)-His-Leu-Ura medium (pH 7) or DELFT minimal medium (pH 7) containing 0.5 mM thebaine or oripavine. Both media contain 0.1 M potassium phosphate buffer.

Thebaine (or Oripavine) were added via a 25 mM stock solution in DMSO. Cells were grown for 72 hours with shaking at 250 rpm.

Harvest. 50 μl of cell cultures were transferred to a new 96-deep-well-plate containing 50 μl of MilliQ water. The harvested 96 well plate was incubated at 80° C. for 10 minutes. Plate was then centrifugated for 10 minutes at 4000 rpm. The supernatants were then diluted in MilliQ water to reach a final dilution of 1:100. Thebaine, northebaine, oripavine and nororipavine contents were analyzed by LC-MS.

Example 3. LC-MS Procedures

For all compounds (Thebaine, Northebaine, Oripavine and Nororipavine) stock solutions were prepared in DMSO at a concentration of 10 mM. Standard solutions were prepared at concentrations of 6 μM, 4 μM, 2 μM, 1 μM, 500 nM, 200 nM, 100 nM, 50 nM, 20 nM and 10 nM from the stock solutions. Samples were injected into the Agilent 1290 UPLC coupled to an Ultivo Triple Quadrupole. The LC-MS method was as follows: Mobile Phase A. $H_2O$+0.1% Formic acid; Mobile Phase B: Acetonitrile+0.1% Formic acid; Column: Phenomenex Kinetex 1.7 μm XB-C18 100 Å, 2.1×100 mm. The elution gradient is shown in Table 2 and the LC-MS conditions are given in Table 3. Table 4 shows the mass spectrometer source and detector parameters and Table 5 shows the target compounds, their retention times, their parent ion, transition ions (MRM) as well as dwell times, cone voltages and collision energies used.

TABLE 2

Gradient for LC-MS

| Time (min) | % B |
|---|---|
| 0 | 2 |
| 0.30 | 2 |
| 4.00 | 30 |
| 4.40 | 100 |
| 4.90 | 100 |
| 5 | 2 |
| 6 | 2 |

TABLE 3

LC-MS conditions

| Parameter | Value |
|---|---|
| Injection volume | 2 μl |
| Column Temperature | 30° C. ± 4° C. |
| Injection method | Flow through needle |
| Flow | 0.4 ml/min |
| Auto sampler temperature | 10° C. ± 2° C. |
| Reconditioning wash | 2% Acetonitrile (in $H_2O$), 5 sec |
| Weak wash | 20% Methanol (in $H_2O$), 5 sec |
| Strong wash | 30% Acetonitrile, 30% Methanol, 30% 2-Propanol, 10% $H_2O$, 10 sec |
| Seal wash | 20% 2-Propanol (in $H_2O$) |

TABLE 4

Mass spectrometer source and detector parameters (Ultivo Triple Quadrupole)

| Source Parameter | Value |
|---|---|
| Ion Source | Electrospray Positive Mode (ESI+) |
| Capillary Voltage | 3.5 kV |
| Nozzle Voltage | 500 V |
| Source Gas Temperature | 290° C. |
| Source Gas Flow | 12 L/min |
| Source Sheath Gas Temperature | 380° C. |
| Source Sheath Gas Flow | 12 L/min |
| Nebulizer | 30 psi |
| Mode | MS/MS |
| Collision | See Table 4 |

TABLE 5

Multiple reaction monitoring targets and conditions (ESI+)

| Target compound | Retention time (min) | Parent ion (m/z) | Daughter ion (m/z) | Dwell time (ms) | Fragmentor voltage (V) | Collision energy (V) |
|---|---|---|---|---|---|---|
| Northebaine | 3.53 | 298 | 249 | 55.03 | 100 | 20 |
| Thebaine | 3.6 | 312 | 58 | 61.53 | 110 | 10 |
| Oripavine | 2.59 | 298 | 237 | 64.05 | 110 | 5 |
| Nororipavine | 2.54 | 284 | 218 | 70.30 | 110 | 10 |

Example 4. Identification of Transporters Capable of Improving Bioconversion of Thebaine and/or Derivatives Thereof Bioconversion. Expression of transporter genes in a strain containing cytochrome P450 gene CYPDN8 and cytochrome P450 reductase Cel_CPR (co) gave remarkable improvement in bioconversion of thebaine to northebaine for some of the transporter genes, where some exhibited a significant improved bioconversion when strains were grown in presence of 0.5 mM thebaine.

TABLE 6

Bioconversion of thebaine to northebaine in strains expressing different possible transporter enzymes and improvement in the bioconversion as compared to control strain not expressing any heterologous transporter genes.

| Transporter genes | Percentage bioconversion of Thebaine to Northebaine (%) | Improvement in Thebaine to Northebaine bioconversion (%) | Growth medium |
|---|---|---|---|
| T1_CjaMDR1_GA | 12.0 | 45 | SC-his-leu-ura |
| T3_NcaNPF_GA | 6.7 | −19 | SC-his-leu-ura |
| T4_EsaGTR_GA | 11.3 | 36 | SC-his-leu-ura |
| T5_AlyPOT_GA | 6.1 | −27 | SC-his-leu-ura |
| T6_CruGTR_GA | 6.4 | −23 | SC-his-leu-ura |
| T7_PtrPOT_GA | 13.5 | 63 | SC-his-leu-ura |
| T8_BnaMFS_GA | 4.2 | −49 | SC-his-leu-ura |
| T10_BolGTR_GA | 6.0 | −28 | SC-his-leu-ura |
| T11_AthGTR1_GA | 9.7 | 17 | SC-his-leu-ura |
| T12_PSoNPF1_GA | 6.7 | −19 | SC-his-leu-ura |
| T14_PSoNPF3_GA | 10.3 | 24 | SC-his-leu-ura |
| T17_PSoNPF6_GA | 5.1 | −39 | SC-his-leu-ura |
| Control SC-his-leu-ura | 8.3 | 0.0 | SC-his-leu-ura |
| T18_PsoNPF7_GA | *10.0* | *2* | DELFT minimal medium |
| T19_RmiPTR2_GA | 9.5 | 13 | DELFT minimal medium |
| T20_RmiPTR2_v2_GA | 7.9 | −6 | DELFT minimal medium |
| T21_RalPTR2_GA | 7.3 | −13 | DELFT minimal medium |
| T22_CanPOT_GA | 4.4 | −48 | DELFT minimal medium |
| T23_ArePOT_GA | 4.6 | −45 | DELFT minimal medium |
| T24_SlyPTR2_GA | 4.0 | −52 | DELFT minimal medium |
| T25_AorPOT_GA | 4.1 | −51 | DELFT minimal medium |
| T26_NfuPOT_GA | 4.0 | −52 | DELFT minimal medium |
| T28_MciPOT_GA | 4.2 | −50 | DELFT minimal medium |
| T29_AcaPOT_GA | 5.1 | −39 | DELFT minimal medium |
| T30_MlyPOT_GA | 5.6 | −33 | DELFT minimal medium |
| T31_TgaPOT_GA | 4.4 | −48 | DELFT minimal medium |
| T32_AarPOT_GA | 5.1 | −39 | DELFT minimal medium |
| T33_CcuPTR2_GA | 4.6 | −45 | DELFT minimal medium |
| T34_HvePOT_GA | 5.5 | −35 | DELFT minimal medium |
| T35_EcuPOT_GA | 7.8 | −7 | DELFT minimal medium |
| T36_RnePOT_GA | 4.3 | −49 | DELFT minimal medium |
| T37_OcoPOT_GA | 4.8 | −45 | DELFT minimal medium |
| T38_ScuPTR2_GA | 9.9 | 18 | DELFT minimal medium |
| T39_CgrPOT_GA | 5.6 | −33 | DELFT minimal medium |
| T40_EdePOT_GA | 6.1 | −27 | DELFT minimal medium |
| T41_CalPTR2_GA | 5.7 | −32 | DELFT minimal medium |
| T44_CcaMFS_GA | 4.4 | −48 | DELFT minimal medium |
| T45_PanPOT_GA | *9.8* | *0* | DELFT minimal medium |
| T46_RchPOT_GA | 8.1 | −4 | DELFT minimal medium |
| T47_PbeNPF_GA | 4.6 | −45 | DELFT minimal medium |
| T48_CcaPOT_GA | *9.7* | *−1* | DELFT minimal medium |
| T49_HanPOT_GA | 7.7 | −8 | DELFT minimal medium |
| T51_TorPOT_GA | 5.5 | −35 | DELFT minimal medium |
| T52_BmePTR2_GA | *11.7* | *19* | DELFT minimal medium |
| T53_EhePOT_GA | 7.3 | −13 | DELFT minimal medium |
| T54_MelPOT_GA | *10.9* | *11* | DELFT minimal medium |
| T55_NsyNPF_GA | 3.2 | −62 | DELFT minimal medium |
| T56_CanNPF_GA | 8.4 | 0 | DELFT minimal medium |
| T57_AcoNPF_GA | *11.7* | *19* | DELFT minimal medium |
| T59_AmeNPF1_GA | 5.3 | −37 | DELFT minimal medium |
| T60_AmeNPF2_GA | *11.9* | *21* | DELFT minimal medium |
| T61_TwiNPF_GA | 8.1 | −4 | DELFT minimal medium |
| T62_SmaNPF_GA | 7.5 | −11 | DELFT minimal medium |
| T63_CfoNPF_GA | 7.4 | −12 | DELFT minimal medium |
| T64_XsiNPF_GA | 6.9 | −18 | DELFT minimal medium |
| T66_TelNPF_GA | 8.3 | −1 | DELFT minimal medium |
| T69_PhoNPF_GA | 5.4 | −36 | DELFT minimal medium |
| T70_CmaNPF_GA | 9.1 | 8 | DELFT minimal medium |
| T72_TcoNPF_GA | 8.4 | 0 | DELFT minimal medium |
| T73_PbrNPF1_GA | 5.8 | −31 | DELFT minimal medium |
| T74_PbrNPF2_GA | 6.6 | −21 | DELFT minimal medium |
| T75_PbrNPF3_GA | 7.7 | −8 | DELFT minimal medium |
| T76_AhuNPF_GA | 4.9 | −42 | DELFT minimal medium |
| T77_PocNPF_GA | 5.5 | −35 | DELFT minimal medium |

TABLE 6-continued

Bioconversion of thebaine to northebaine in strains expressing different possible transporter enzymes and improvement in the bioconversion as compared to control strain not expressing any heterologous transporter genes.

| Transporter genes | Percentage bioconversion of Thebaine to Northebaine (%) | Improvement in Thebaine to Northebaine bioconversion (%) | Growth medium |
|---|---|---|---|
| T78_VofNPF_GA | 8.5 | 1 | DELFT minimal medium |
| T79_EcaNPF_GA | 7.6 | −10 | DELFT minimal medium |
| T80_CroNPF_GA | *9.8* | *0* | DELFT minimal medium |
| T82_NsaNPF_GA | *8.8* | *−10* | DELFT minimal medium |
| Control DELFT | 8.4 | 0.0 | DELFT minimal medium |
| *Control DELFT* | *9.8* | *0.0* | *DELFT minimal medium* |

Numbers in Italic are relative to Control DELFT of 9.8.

Improvement of Bioconversion:

Expression of one of the transporter genes T14_PsoNPF3_GA, T1_CjaMDR1_GA, T4_EsaGTR_GA or T7_PtrPOT_GA in a yeast strain that contains cytochrome P450 gene CYPDN8 and cytochrome P450 reductase Cel_CPR (co), results in improved bioconversion of thebaine to northebaine in the range of 24-63% in comparison to the control strain.

Further, significant improvement was also seen for the transporter genes T60_AmeNPF2_GA, T57_AcoNPF_GA, T52_BmePTR2_GA, T38_ScuPTR2_GA, T11_AthGTR1_GA, T19_RmiPTR2_GA, T70_CmaNPF_GA or T54_MelPOT_GA.

Conclusions

The results of this Example demonstrate expression of one of the transporter genes T14_PsoNPF3_GA, T1_CjaMDR1_GA, T4_EsaGTR_GA or T7_PtrPOT_GA in a yeast strain that contains cytochrome P450 gene CYPDN8 and cytochrome P450 reductase Cel_CPR (co), results in improved bioconversion of thebaine to northebaine in the range of 24-63% in comparison to the control strain.

Further, significant improvement was also seen for the transporter genes T60_AmeNPF2_GA, T57_AcoNPF_GA, T52_BmePTR2_GA, T38_ScuPTR2_GA, T11_AthGTR1_GA, T19_RmiPTR2_GA, T70_CmaNPF_GA or T54_MelPOT_GA.

Further, Transporters were Tested for Improvement in Conversion of the Thebaine Derivative Oripavine to Nororipavine Bioconversion. Expression of transporter gene T14_PsoNPF3_GA from *Papaver somniferum* in a strain containing cytochrome P450 gene CYPDN8 and cytochrome P450 reductase Cel_CPR (co) showed remarkable improvement in bioconversion of oripavine to nororipavine. In an assay where a strain was grown in presence of 0.5 mM oripavine, the strain containing T14_PsoNPF3_GA exhibited 2.3% bioconversion of the oripavine to nororipavine, which corresponds to an improvement in bioconversion of oripavine to nororipavine by 64% in comparison to the control strain.

TABLE 7

Bioconversion and improvement in oripavine to nororipavine bioconversion compared to the control strain, observed when growing strains expressing different possible transporter proteins.

| Transporter genes | Bioconversion of oripavine to nororipavine (%) | Improvement of oripavine to nororipavine bioconversion as compared to control (%) |
|---|---|---|
| T14_PsoNPF3_GA | 2.3 | 64 |
| Control | 1.4 | 0 |

Conclusions

The result of this Example demonstrate that expression of transporter gene T14_PsoNPF3_GA gave around 64% more bioconversion of oripavine to nororipavine-which is a remarkable yield improvement.

Example 5. Identification of Further Transporters Capable of Improving Bioconversion of Thebaine and/or Derivatives Thereof This Example 5 discusses transporter genes that are not explicitly mentioned in corresponding Example 4 above.

Bioconversion. In bioconversion experiments similar to Example 4 above-3 additional transporters have shown to improve bioconversion of thebaine to northebaine.

As shown in Table 8 below, T65_IjaNPF_GA, T94_EcrPOT_GA and T97_ScaT14_GA are able to improve bioconversion of thebaine to northebaine by 29.9%, 31.9% and 21.8%, respectively, when compared to a control strain.

Table 8 also shows a yeast strain which genes CYPDN8 from *Rhizopus* microspores and Cel_CPR_co from *Cunninghamella elegans* have been integrated into host strain EVST25898 (Example 1) at Chromosome XII-5 with URA3 from *Kluyveromyces lactis* as selection marker. Subsequently, 6 different transporters T11_AthGTR1_GA, T52_BmePTR2_GA, T14_PsoNPF3_GA, T60_AmeNPF2_GA, T1_CjaMDR1_GA, and T70_CmaNPF_GA were expressed in the same strain at Chromosome XI-5 with LEU2 from *Kluyveromyces lactis* as selection marker. Plasmid pOD13 (Table 1) was also expressed in the same strain to make the strain prototrophic. An indication of improvement in the bioconversion of thebaine to northebaine when multiple copies of various transporters were expressed in the same strain.

TABLE 8

Bioconversion of thebaine to northebaine in strains expressing different possible transporter enzymes and improvement in the bioconversion as compared to control strain not expressing any heterologous transporter genes.

| Transporter genes | Percentage bioconversion of Thebaine to Northebaine (%) | Improvement in Thebaine to Northebaine bioconversion (%) | Growth medium |
|---|---|---|---|
| T65_ljaNPF_GA | 10.9 | 29.9 | DELFT minimal medium |
| T94_EcrPOT_GA | 11.1 | 31.9 | DELFT minimal medium |
| T97_ScaT14_GA | 10.2 | 21.8 | DELFT minimal medium |
| T11_AthGTR1_GA + T52_BmePTR2_GA + T14_PsoNPF3_GA + T60_AmeNPF2_GA + T1_CjaMDR1_GA + T70_CmaNPF_GA | 11.3 | 34.6 | DELFT minimal medium |
| Control DELFT | 8.4 | | DELFT minimal medium |

When multiple of different genes were expressed in the yeast cell, it is referred to as gene1+gene2, etc.

Conclusions

In bioconversion experiments similar to Example 4 above—the results of this Example demonstrate that three additional transporters have shown to improve bioconversion of thebaine to northebaine.

As shown in Table 8, T65_ljaNPF_GA, T94_EcrPOT_GA and T97_ScaT14_GA are able to improve bioconversion of thebaine to northebaine by 29.9%, 31.9% and 21.8%, respectively, when compared to a control strain.

Further, a strain comprising a combination of 6 transporter proteins discussed in Example 4 gave a very good improvement of thebaine to northebaine.

Further, Transporters were Tested for Improvement in Conversion of the Thebaine Derivative Oripavine to Nororipavine Bioconversion. In bioconversion experiments similar to Example 4 above—an additional transporter that is able to help improving bioconversion of oripavine to nororipavine has been identified. As shown in Table 9 below, T97_ScaT14_GA from *Sanguinaria canadensis* is able to convert close to 5% of oripavine to nororipavine when fed with 0.5 mM oripavine. In comparison to the control strain, expression of T97_ScaT14_GA improves the bioconversion of oripavine to nororipavine by 254.4%.

TABLE 9

Bioconversion and improvement in oripavine to nororipavine bioconversion compared to the control strain.

| Transporter genes | Bioconversion of oripavine to nororipavine (%) | Improvement of oripavine to nororipavine bioconversion as compared to control (%) |
|---|---|---|
| T97_ScaT14_GA | 4.96 | 254.4 |
| Control | 1.4 | 0 |

Conclusions

In bioconversion experiments similar to Example 4 above, the results of this Example demonstrate an additional transporter able to help in improving bioconversion of oripavine to nororipavine has been identified.

As shown in Table 9, T97_ScaT14_GA from *Sanguinaria canadensis* is able to convert close to 5% of oripavine to nororipavine when fed with 0.5 mM oripavine. In comparison to the control strain, expression of T97_ScaT14_GA improves the bioconversion of oripavine to nororipavine by 254.4%.

Example 6. Identification of Purine Uptake Permease (PUP) Transporters Capable of Improving Bioconversion of Thebaine Bioconversion. The impact of purine uptake permease transporter proteins on bioconversion of thebaine to northebaine was studied by transforming yeast strain with a plasmid containing a cytochrome P450 comparable to the above examples that was capable of acting on reticuline derivatives such as thebaine and/or oripavine using the backbone plasmid p415TEF. A plasmid containing cytochrome P450 reductase (pOD13 from Example 1) was also expressed in combination with various candidate transporter proteins. Yeast strain construction and method of screening for PUP transporters were as previously described in Example 1. Table 10 shows the result of percentage bioconversion from thebaine to northebaine with the expression of various PUP transporters. Table 10 also presents the percentage improvement in the bioconversion when normalized for a control strain expressing P450 but not expressing any heterologous transporter.

TABLE 10

Percentage P450-mediated bioconversion from Thebaine to Northebaine with the expression of various transporters and percentage improvements in the bioconversion as compared to a control strains not expressing any heterologous transporters.

| PUP Transporters | Percentage bioconversion of Thebaine to Northebaine (%) | Percentage Improvement in Thebaine to Northebalne bioconversion (%) |
|---|---|---|
| T101_McoPUP3_1 | 7.0 | 6.7 |
| T102_PsoPUP3_1 | 8.6 | 29.8 |
| T103_PsoPUP3_2 | 7.1 | 7.9 |

TABLE 10-continued

Percentage P450-mediated bioconversion from Thebaine to Northebaine with the expression of various transporters and percentage improvements in the bioconversion as compared to a control strains not expressing any heterologous transporters.

| PUP Transporters | Percentage bioconversion of Thebaine to Northebaine (%) | Percentage Improvement in Thebaine to Northebalne bioconversion (%) |
|---|---|---|
| T104_PsoPUP3_3 | 7.4 | 11.4 |
| T105_PsoPUP-L | 9.2 | 39.8 |
| Control 1 | 6.6 | — |
| T109_GflPUP3_83 | 6.4 | 55.0 |
| T122_PsoPUP3_17 | 6.1 | 48.4 |
| T130_NdoPUP3_89 | 4.9 | 19.9 |
| T131_PbrPUP3_81 | 4.9 | 20.4 |
| T132_CmiPUP3_10 | 6.6 | 60.2 |
| T133_PsoPUP3_18 | 5.9 | 42.7 |
| T136_RchPUP3_42 | 4.6 | 11.1 |
| T137_EguPUP3_50 | 5.1 | 24.7 |
| T138_AduPUP3_58 | 4.6 | 11.7 |
| T139_PsoPUP3_66 | 4.9 | 19.5 |
| T140_PalPUP3_74 | 5.4 | 30.5 |
| T141_EcaPUP3_88 | 6.8 | 64.7 |
| T142_McoPUP3_4 | 7.7 | 88.9 |
| T143_CmiPUP3_11 | 5.8 | 41.8 |
| T144_PsoPUP3_19 | 7.7 | 87.1 |
| T146_PsoPUP_35 | 4.6 | 13.4 |
| T147_MesPUP3_43 | 6.1 | 49.8 |
| T148_HimPUP3_51 | 5.0 | 21.4 |
| T149_AcoPUP3_59 | 6.9 | 69.1 |
| T150_PsoPUP3_67 | 5.9 | 43.6 |
| T151_PatPUP3_75 | 5.7 | 39.1 |
| T152_GflPUP3_87 | 8.0 | 94.0 |
| T153_PsoPUP3_5 | 4.9 | 19.1 |
| T154_CmiPUP3_12 | 7.1 | 74.2 |
| T157_RchPUP_36 | 5.8 | 42.1 |
| T159_OeuPUP3_52 | 5.8 | 41.8 |
| T160_CeuPUP3_60 | 5.4 | 30.9 |
| T161_PsoPUP3_68 | 6.2 | 51.9 |
| T162_PmiPUP3_76 | 6.4 | 56.1 |
| T163_PbrPUP3_86 | 5.1 | 24.8 |
| T164_PsoPUP3_78 | 5.2 | 27.2 |
| T165_AcoPUP3_13 | 6.5 | 57.9 |
| T166_PsoPUP3_21 | 6.6 | 61.9 |
| T168_FvePUP3_37 | 6.4 | 56.5 |
| T169_ZjuPUP3_45 | 6.6 | 60.6 |
| T170_LsaPUP3_53 | 6.7 | 62.6 |
| T171_McoPUP3_61 | 5.5 | 33.8 |
| T172_AcoPUP3_69 | 6.6 | 60.2 |
| T174_PbrPUP3_85 | 5.3 | 29.4 |
| T175_PsoPUP3_6 | 6.7 | 63.9 |
| T176_AcoPUP3_14 | 5.8 | 41.5 |
| T177_PsoPUP3_22 | 6.5 | 57.4 |
| T178_PsoPUP3_30 | 6.1 | 47.6 |
| T180_McoPUP3_46 | 5.5 | 35.0 |
| T181_HanPUP3_54 | 5.3 | 30.1 |
| T182_CpaPUP3_62 | 6.9 | 67.8 |
| T184_PraPUP3_79 | 5.2 | 27.9 |
| T186_ScaPUP3_84 | 7.0 | 69.8 |
| T188_AcoPUP3_15 | 4.7 | 14.7 |
| T189_PsoPUP3_23 | 4.7 | 14.8 |
| T191_MdoPUP3_39 | 5.2 | 26.5 |
| T192_CmiPUP3_47 | 5.5 | 35.0 |
| T193_AanPUP3_55 | 6.2 | 51.9 |
| T194_CchPUP3_63 | 5.7 | 39.1 |
| T195_JcuPUP3_71 | 5.3 | 29.8 |
| T196_PtrPUP3_80 | 5.7 | 39.1 |
| Control 2 | 4.1 | — |

Note:
Control 1 is used as the control for T101_McoPUP3_1, T102_PsoPUP3_1, T103_PsoPUP3_2, T104_PsoPUP3_3 and T105_PsoPUP-L. Control 2 is used as control for the rest of the PUP transporters. This was done to compensate for any slight variations that may arise between different runs of LC-MS analysis.

Improvement of bioconversion. When compared to a control strain without a heterologous transporter, several strains engineered with PUP transporters exhibited at least 50% greater bioconversion of the 0.5 mM thebaine fed in this assay. Amongst the PUP transporters examined, PUP transporters T152_GflPUP3_87, T149_AcoPUP3_59, T109_GflPUP3_83, T142_McoPUP3_4, T144_PsoPUP3_19, T141_EcaPUP3_88, T182_CpaPUP3_62, T193_AanPUP3_55 and T122_PsoPUP3_17 exhibited improvements in bioconversion of thebaine to northebaine in the range of 48-94% in comparison to the control strain without a heterologous transporter (Table 10). Expression of some PUP transporters, such as T152_GflPUP3_87 from Glaucium flavum, T149_AcoPUP3_59 from Aquilegia *coerulea*, and T142_McoPUP3_4 from Macleaya *cordata*, gave remarkable improvements in the P450-mediated bioconversion of thebaine to northebaine.

TABLE 11

Purine Uptake Permease transporters which have been demonstrated herein to provide especially large improvements in the P450-mediated bioconversion from Thebaine to Northebaine.

| PUP Transporters | Latin Name for Origin of Sourced Genes |
|---|---|
| T152_GflPUP3_87 | *Glaucium flavum* |
| T142_McoPUP3_4 | *Macleaya cordata* |
| T144_PsoPUP3_19 | *Papaver somniferum* |
| T149_AcoPUP3_59 | *Aquilegia coerulea* |
| T109_GflPUP3_83 | *Glaucium flavum* |
| T141_EcaPUP3_88 | *Eschscholzia californica* |
| T182_CpaPUP3_62 | *Carica papaya* |
| T193_AanPUP3_55 | *Artemisia annua* |
| T132_CmiPUP3_10 | *Cinnamomum micranthum* f. *kanehirae* |
| T186_ScaPUP3_84 | *Sanguinaria canadensis* |
| T175_PsoPUP3_6 | *Papaver somniferum* |
| T122_PsoPUP3_17 | *Papaver somniferum* |

Conclusions

Table 11 shows some of the PUP transporters that have been herein demonstrated for the first time to shown very considerable improvements in the bioconversion from Thebaine to Northebaine by P450s. In particular, the results of this Example demonstrate that expression of PUP transporters T152_GflPUP3_87 from Glaucium flavum, T149_AcoPUP3_59 from Aquilegia *coerulea*, T109_GflPUP3_83 from Glaucium flavum, T142_McoPUP3_4 from Macleaya *cordata*, T144_PsoPUP3_19 from *Papaver somniferum*, T141_EcaPUP3_88 from *Eschscholzia californica*, T182_CpaPUP3_62 from *Carica papaya*, T193_AanPUP3_55 from *Artemisia annua*, *T*132_CmiPUP3_10 from *Cinnamomum micranthum* f. *kanehirae*, T186_ScaPUP3_84 from *Sanguinaria canadensis*, T175_PsoPUP3_6 from *Papaver somniferum* and T122_PsoPUP3_17 from *Papaver somniferum*, each stimulated somewhere in the range of 48-94% more bioconversion of thebaine to northebaine. The improvements in yield shown herein are both unexpected and highly valuable given the nature of the opioid-related compounds produced.

Example 7. Identification of Purine Uptake Permease (PUP) Transporters Capable of Improving Bioconversion of Oripavine to Nororipavine Bioconversion. The impact of purine uptake permease transporter proteins on bioconversion of oripavine to nororipavine was studied by transforming yeast with a plasmid containing a comparable cytochrome P450 that was capable of acting on reticuline derivatives such as thebaine and/or oripavine using the backbone plasmid p415TEF. A plasmid containing cytochrome P450 reductase (pOD13 from Example 1) was also expressed in combination with various possible transporter proteins. Yeast strain construction and method of screening for PUP transporters were as previously described in Example 1. Table 12 shows the result of percentage bioconversion from oripavine to nororipavine with the expression of various PUP transporters. Table 12 also presents the percentage improvement in the bioconversion when normalized for a control strain expressing P450 but not expressing any heterologous transporter.

Improvement of bioconversion. The percentage bioconversion of strains displayed by several PUP transporters exhibited as high as 1600% and greater bioconversion of the 0.5 mM oripavine fed to the assay when compared to a control strain expressing P450 but not expressing transporter. Amongst the transporters examined in this example, PUP transporters T149_AcoPUP3_59, T168_FvePUP3_37, T116_HanPUP3_56, T192_CmiPUP3_47, T109_GflPUP3_83, T180_McoPUP3_46, T193_AanPUP3_55, T165_AcoPUP3_13, T195_JcuPUP3_71 and T143_CmiPUP3_11 exhibited improvements in the P450-mediated bioconversion of oripavine to nororipavine in the range of 1400-1662% in comparison to the control strain expressing P450 but not expressing a heterologous transporter (Table 12). Expression of some PUP transporters, such as T149_AcoPUP3_59 from Aquilegia *coerulea*, T168_FvePUP3_37 from Fragaria *vesca* subsp. *vesca*, and T116_HanPUP3_56 from *Helianthus annuus* gave particularly remarkable improvements in the P450-mediated bioconversion of oripavine to nororipavine.

TABLE 12

Percentage of P450-mediated bioconversion from Oripavine to Nororipavine with the expression of various transporters and the percentage improvement in the bioconversion as compared to a control strains not expressing any heterologous transporters.

| PUP Transporters | Percentage Bioconversion of Oripavine to Nororipavine (%) | Percentage Improvement in Oripavine to Nororipavine bioconversion (%) |
|---|---|---|
| T101_McoPUP3_1 | 3.5 | 147.7 |
| T102_PsoPUP3_1 | 10.1 | 621.4 |
| T103_PsoPUP3_2 | 1.7 | 21.9 |
| T104_PsoPUP3_3 | 8.0 | 474.8 |
| T105_PsoPUP-L | 12.2 | 771.1 |
| Control 1 | 1.4 | — |
| T109_GflPUP3_83 | 15.5 | 1447.6 |
| T113_PsoPUP3_32 | 10.1 | 912.6 |
| T114_TorPUP3_40 | 5.9 | 486.0 |
| T115_CsaPUP3_48 | 11.7 | 1065.5 |
| T116_HanPUP3_56 | 17.5 | 1653.1 |
| T117_MacPUP3_64 | 4.2 | 317.4 |
| T121_NnuPUP3_9 | 1.5 | 47.1 |
| T122_PsoPUP3_17 | 12.5 | 1149.3 |
| T123_PsoPUP3_25 | 1.3 | 32.4 |
| T124_PsoPUP3_33 | 4.9 | 393.9 |
| T125_JcuPUP3_41 | 14.5 | 1346.2 |
| T126_CpePUP3_49 | 11.8 | 1077.1 |
| T127_LsaPUP3_57 | 5.4 | 441.7 |
| T128_PsoPUP3_65 | 4.8 | 383.9 |
| T129_PsoPUP3_73 | 6.3 | 532.3 |
| T130_NdoPUP3_89 | 14.2 | 1315.0 |
| T131_PbrPUP3_81 | 5.0 | 399.4 |
| T132_CmiPUP3_10 | 14.8 | 1383.1 |
| T133_PsoPUP3_18 | 14.5 | 1349.6 |
| T135_PsoPUP_34 | 1.7 | 73.4 |

TABLE 12-continued

Percentage of P450-mediated bioconversion from Oripavine to Nororipavine with the expression of various transporters and the percentage improvement in the bioconversion as compared to a control strains not expressing any heterologous transporters.

| PUP Transporters | Percentage Bioconversion of Oripavine to Nororipavine (%) | Percentage Improvement in Oripavine to Nororipavine bioconversion (%) |
|---|---|---|
| T136_RchPUP3_42 | 13.0 | 1197.8 |
| T137_EguPUP3_50 | 8.4 | 744.8 |
| T138_AduPUP3_58 | 14.5 | 1348.7 |
| T139_PsoPUP3_66 | 4.4 | 341.0 |
| T140_PalPUP3_74 | 3.6 | 264.7 |
| T141_EcaPUP3_88 | 11.3 | 1030.8 |
| T142_McoPUP3_4 | 15.4 | 1438.8 |
| T143_CmiPUP3_11 | 15.8 | 1483.1 |
| T144_PsoPUP3_19 | 15.1 | 1408.2 |
| T146_PsoPUP_35 | 5.8 | 478.0 |
| T147_MesPUP3_43 | 10.5 | 954.4 |
| T148_HimPUP3_51 | 7.7 | 674.8 |
| T149_AcoPUP3_59 | 17.4 | 1639.5 |
| T150_PsoPUP3_67 | 13.4 | 1240.3 |
| T151_PatPUP3_75 | 13.2 | 1223.8 |
| T152_GflPUP3_87 | 14.9 | 1394.9 |
| T153_PsoPUP3_5 | 6.8 | 583.2 |
| T154_CmiPUP3_12 | 11.4 | 1039.5 |
| T156_PsoPUP3_28 | 6.9 | 589.7 |
| T157_RchPUP_36 | 12.2 | 1123.8 |
| T158_DziPUP3_44 | 7.7 | 673.2 |
| T159_OeuPUP3_52 | 10.0 | 902.7 |
| T160_CeuPUP3_60 | 4.0 | 304.6 |
| T161_PsoPUP3_68 | 13.4 | 1237.9 |
| T162_PmiPUP3_76 | 14.1 | 1314.8 |
| T163_PbrPUP3_86 | 3.8 | 280.2 |
| T164_PsoPUP3_78 | 5.5 | 448.3 |
| T165_AcoPUP3_13 | 15.3 | 1429.8 |
| T166_PsoPUP3_21 | 10.3 | 931.0 |
| T168_FvePUP3_37 | 17.6 | 1662.4 |
| T169_ZjuPUP3_45 | 14.1 | 1310.9 |
| T170_LsaPUP3_53 | 14.7 | 1372.2 |
| T171_McoPUP3_61 | 3.5 | 251.3 |
| T172_AcoPUP3_69 | 12.3 | 1126.4 |
| T173_PnuPUP3_77 | 1.9 | 94.1 |
| T174_PbrPUP3_85 | 5.5 | 452.5 |
| T175_PsoPUP3_6 | 8.7 | 769.9 |
| T176_AcoPUP3_14 | 7.4 | 636.2 |
| T177_PsoPUP3_22 | 11.3 | 1029.5 |
| T178_PsoPUP3_30 | 15.0 | 1396.5 |
| T179_PyePUP3_38 | 4.4 | 344.5 |
| T180_McoPUP3_46 | 16.8 | 1580.6 |
| T181_HanPUP3_54 | 12.6 | 1160.4 |
| T182_CpaPUP3_62 | 14.5 | 1349.5 |
| T184_PraPUP3_79 | 3.3 | 234.2 |
| T186_ScaPUP3_84 | 10.6 | 962.2 |
| T188_AcoPUP3_15 | 3.0 | 197.8 |
| T189_PsoPUP3_23 | 8.3 | 729.7 |
| T191_MdoPUP3_39 | 9.5 | 849.2 |
| T192_CmiPUP3_47 | 17.2 | 1618.5 |
| T193_AanPUP3_55 | 15.5 | 1454.4 |
| T194_CchPUP3_63 | 2.1 | 110.0 |
| T195_JcuPUP3_71 | 15.1 | 1413.6 |
| T196_PtrPUP3_80 | 10.9 | 986.6 |
| Control 2 | 1.0 | — |

Note:
Control 1 is used as the control for T101_McoPUP3_1, T102_PsoPUP3_1, T103_PsoPUP3_2, T104_PsoPUP3_3 and T105_PsoPUP-L. Control 2 is used as control for the rest of the PUP transporters. This is was done to account for any slight variations that may arise from different runs of LC-MS analysis.

TABLE 13

Purine Uptake Permease transporters which have demonstrated herein to provide especially large improvements in the P450-mediated bioconversion of Oripavine to Nororipavine.

| Transporter Genes | Latin Name for Origin of Sourced Genes |
|---|---|
| T149_AcoPUP3_59 | *Aquilegia coerulea* |
| T168_FvePUP3_37 | *Fragaria vesca* subsp. *vesca* |
| T116_HanPUP3_56 | *Helianthus annuus* |
| T192_CmiPUP3_47 | *Cinnamomum micranthum* f. *kanehirae* |
| T109_GflPUP3_83 | *Glaucium Flavum* |
| T180_McoPUP3_46 | *Macleaya cordata* |
| T193_AanPUP3_55 | *Artemisia annua* |
| T165_AcoPUP3_13 | *Aquilegia coerulea* |
| T195_JcuPUP3_71 | *Jatropha curcas* |
| T143_CmiPUP3_11 | *Cinnamomum micranthum* f. *kanehirae* |

Conclusions

Table 13 shows some of the PUP transporters that have been demonstrated herein for the first time to shown particularly high improvements in the P450-mediated bioconversion of oripavine to nororipavine. Amongst the transporters examined in this example, PUP transporters T149_AcoPUP3_59 from Aquilegia *coerulea*, T168_FvePUP3_37 from Fragaria *vesca* subsp. *vesca*, T116_HanPUP3_56 from *Helianthus annuus*, T192_CmiPUP3_47 from *Cinnamomum micranthum* f. *kanehirae*, T109_GflPUP3_83 from Glaucium flavum, T180_McoPUP3_46 from Macleaya *cordata*, T193_AanPUP3_55 from *Artemisia annua*, T165_AcoPUP3_13 from Aquilegia *coerulea*, T195_JcuPUP3_71 from Jatropha curcas and T143_CmiPUP3_11 from *Cinnamomum micranthum* f. *kanehirae*, exhibited improvements in the range of 1400-1662% more P450-mediated bioconversion of thebaine to northebaine in comparison to the control strain expressing P450 but not expressing a heterologous transporter. Such improvements in yield are particularly remarkable and represent a significant step forward towards a sustainable, secure, and scalable biosynthetic means of producing these compounds.

REFERENCES

1: Tomas Hudlicky; "Recent advances in process development for opiate-derived pharmaceutical agents"; Can. J. Chem. 93:492-501 (2015)

2: Galanie et al. ("Complete biosynthesis of opioids in yeast"; Science. 2015 Sep. 4; 349 (6252): 1095-1100)

3: WO2018/075670A1

4: Jørgensen et al. ("Origin and evolution of transporter substrate specificity within the NPF fami-ly"; eLife 2017; 6: e19466. DOI: 10.7554/eLife. 19466)

5: Jørgensen et al. ("A Functional EXXEK Motif is Essential for Proton Coupling and Active Glu-cosinolate Transport by NPF2.11"; Plant Cell Physiol. 56 (12): 2340-2350 (2015))

6: Sipos et al. ("First Synthesis and Utilization of Oripavidine—a concise and Efficient Route to Important Morphinans and Apomorphines"; Helvetica Chimica Acta. Vol. 92:1359-1365 (2009))

7: WO2018/211331

8: Dastmalchi et al. ("Purine permease-type benzylisquinoline alkaloid transporters in opium poppy"; Plant Physiology Preview. DOI: 10.1104/pp. 19.00565 (2019))

The invention claimed is:

1. A recombinant yeast cell heterologously expressing a transporter protein, wherein the transporter protein:

(i) comprises an amino acid sequence having at least 70% identity with an amino acid sequence selected from the group consisting of SEQ ID NOs: 112, 42, 56, 76, 78, 92, 94, 96, 98, 102, 106, 108, 116, 120, 124, 128, 130, 136, 138, 140, 142, 144, 148, 154, 156, 158, 160, 168, 172, 182, amino acids 1 to 607 of SEQ ID NO: 8, amino acids 1 to 1289 of SEQ ID NO:4, amino acids 1 to 654 of SEQ ID NO: 6, and amino acids 1 to 583 of SEQ ID NO: 10; and/or (ii) comprises an amino acid sequence having at least 70% identity with an amino acid sequence selected from the group consisting of SEQ ID NOs: 182, 186, 42, 44, 48, 50, 56, 62, 64, 72, 76, 78, 82, 86, 92, 94, 96, 98, 102, 106, 108, 110, 112, 116, 120, 124, 128, 130, 136, 138, 140, 142, 144, 148, 154, 158, 160, 164, 166, 168, 172, 178, 180, and amino acids 1 to 604 of SEQ ID NO: 31; and wherein heterologous expression of the transporter protein improves the recombinant yeast cell uptake of thebaine or oripavine for in vivo conversion.

2. The recombinant yeast cell of claim 1, wherein:

(a) the transporter protein improves the yeast cell uptake of thebaine and comprises an amino acid sequence having at least 90% identity with an amino acid sequence selected from the group consisting of SEQ ID NOs: 112, 42, 56, 76, 78, 92, 94, 96, 98, 102, 106, 108, 116, 120, 124, 128, 130, 136, 138, 140, 142, 144, 148, 154, 156, 158, 160, 168, 172, 182, amino acids 1 to 607 of SEQ ID NO:8, amino acids 1 to 1289 of SEQ ID NO:4, amino acids 1 to 654 of SEQ ID NO:6, and amino acids 1 to 583 of SEQ ID NO: 10; and (b) the transporter protein improves the yeast cell uptake of oripavine and comprises an amino acid sequence having at least 90% identity with an amino acid sequence selected from the group consisting of SEQ ID NOs: 182, 186, 42, 44, 48, 50, 56, 62, 64, 72, 76, 78, 82, 86, 92, 94, 96, 98, 102, 106, 108, 110, 112, 116, 120, 124, 128, 130, 136, 138, 140, 142, 144, 148, 154, 158, 160, 164, 166, 168, 172, 178, 180, and amino acids 1 to 604 of SEQ ID NO: 31.

3. The recombinant yeast cell of claim 1, which further converts thebaine and/or oripavine into an opioid compound of interest due to the in vivo presence of a heterologously expressed demethylase enzyme.

4. The recombinant yeast cell of claim 3, wherein the heterologously expressed demethylase enzyme is a P450 capable of demethylase activity on thebaine and/or oripavine, and wherein the recombinant yeast cell:

(1) converts thebaine into neopinone by in vivo heterologous expression of thebaine 6-O-demethylase; or (2) converts thebaine into oripavine by in vivo heterologous expression of O-demethylase; or (3) converts thebaine into northebaine by in vivo heterologous expression of N-demethylase; or (4) converts oripavine into nororipavine by in vivo heterologous expression of heterologously expressed N-demethylase; or (5) converts oripavine into morphinone by in vivo heterologous expression of oripavine 6-O-demethylase.

5. The recombinant yeast cell of claim 1, wherein the transporter protein comprises an amino acid sequence having at least 70% identity with an amino acid sequence selected from the group consisting of SEQ ID NOs: 2, 10, 12, 14, 16, 20, 22, 27, and 31.

6. The recombinant yeast cell of claim 1, wherein the transporter protein comprises an amino acid sequence having at least 70% identity with an amino acid sequence selected from the group consisting of SEQ ID NOs: 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, and 188.

7. The recombinant yeast cell of claim 1, wherein the transporter protein comprises an amino acid sequence having at least 70% identity with an amino acid sequence selected from the group consisting of SEQ ID NOs: 42, 50, 96, 106, 136, 140, 164, 180, 182, and 186.

8. The recombinant yeast cell of claim 1, wherein the transporter protein comprises an amino acid sequence having at least 70% identity with an amino acid sequence selected from the group consisting of SEQ ID NOs: 42, 56, 76, 78, 92, 94, 96, 98, 102, 106, 112, 154, 168, 172, and 182.

9. The recombinant yeast cell of claim 1, wherein the transporter protein comprises an amino acid sequence having at least 70% identity with an amino acid sequence selected from the group consisting of SEQ ID NOs: 42, 106, 182, and 186.

10. The recombinant yeast cell of claim 1, wherein the recombinant yeast cell is a *Saccharomyces cerevisiae* cell.

11. A method of producing in vivo a thebaine derivative or an oripavine derivative in a cell culture, comprising culturing the recombinant yeast cell of claim 1 in the cell culture.

12. The method of claim 11, wherein the method further comprises in vivo producing neopinone, oripavine, northebaine, nororipavine or morphinone in the cell culture.

13. The method of claim 11, wherein in vivo production a thebaine derivative or an oripavine derivative is increased compared to a control host yeast cell that is not heterologously expressing the transporter protein.

14. The recombinant yeast cell of claim 3, wherein the opioid compound of interest is neopinone, oripavine, northebaine, nororipavine, or morphinone.

* * * * *

SEQUENCE LISTING

```
<160> NUMBER OF SEQ ID NOS: 189

<210> SEQ ID NO 1
<211> LENGTH: 1755
<212> TYPE: DNA
<213> ORGANISM: Papaver somniferum

<400> SEQUENCE: 1

atggccaaga acatcaacga caagccaaac ttgcatatct tggatgatga agaacctacc      60

gaagcttctt ctactcatgg tggtagaaaa agaggtggtt ggattacttt cccattcatt     120

actgctgcta ttttggctat ccaagttggt tcttctggtt ggtctgctaa tttgaccgtt     180

tttttgatcg gtcagttcaa cttcatgtcc attaaggctg ctcaagttgg taatatcgtt     240

gctggtactt cttccttctt gccaattttt ggtgcaattt tggccgattc tttcttcggt     300

aacttctccg ttattgccgt ttcttctttg ttctctttga tgggcttgat cttgttcatg     360

ttcactgtta ccgttccatc cttaagacca caacaatgtg ctgctaatgt tactggttct     420

tcagctggta tgtgtgaacc agcttctact ttacaaattg ctgtcttgta cacctccatt     480

accttgtctg ctttaggttt aggtggttct agattcactg ttgctactat gggtgctgat     540

caatttgaaa agccaaagga tcaagagtgc ttcttcaatt ggcatttctt caacttctac     600

gtcggtttga tgattggtgt tgttggtatc gtttacatcc aagacaatat cggttgggat     660

agaggtgttg gtatttgttt ggccgttaac atcttgggtt tagttacttt tttggccggt     720

aagaggtatt acagacaagt taagactcaa ggcaacccct acaaatcttt ggctagagtt     780
```

```
gttgttgcta ccatcttgaa gagaaacctg tctatttctt ctgcctctga aactttctac    840

catggttttt ctgatggcgt gtccatgaag tctttatctt ctccaacatc ctccttcaga    900

ttcttgaata gagctgcttt gaaagttgat ggtgacacta atgaagatgg ttccgttgct    960

aaagaatggc gtttgtgtac tgttcaacaa gttgaggatt tcaagaccgt cattagaatt   1020

atcccactgt ggttctcttc gttctttttg tctactccaa tcggtatcca atcttctttg   1080

gctgttttac aagccttgag aatggataga catatcggta ctcataactt caagattcca   1140

gctggttctt tcttggtttt cactttggtt gctaccgcta tttccttgac cttgatcgat   1200

agatttttgg tcccaaccta ccaaaagttg attagaaggc cattgactcc attgcaaaga   1260

attggtgtag gtcacgtttt gacggttatt tctatggctg cttctgctat cgttgaaaga   1320

aagagattgt ctatcgtttg gtctgatggt ttgacctctt ctactacttc tgttactatg   1380

tcagctttgt ggttggttat cccattggtt ttggttggtg ttggtgaagc ttttcatttt   1440

ccaggtcaag ttgccttgta ctaccaagaa tttccagttt ccttgcattc tacctccact   1500

gctatgattt ctttgttagt tgctgtcggc ttttacttgt ctactgccat gattgatttg   1560

gtccaaagaa ttactggttg gctgccaaac aatattaacc agggtagatt ggacaacatg   1620

ttctggttgt tggttgttat cggtgttatc aacttcggtt acttcatcgt ctgttccttg   1680

ttgtacaagt accaaaactt caacgatcaa aacccaacta aggttgacga taagccaaga   1740

caaggtcaga attga                                                    1755
```

```
<210> SEQ ID NO 2
<211> LENGTH: 584
<212> TYPE: PRT
<213> ORGANISM: Papaver somniferum

<400> SEQUENCE: 2

Met Ala Lys Asn Ile Asn Asp Lys Pro Asn Leu His Ile Leu Asp Asp
1               5                   10                  15

Glu Glu Pro Thr Glu Ala Ser Ser Thr His Gly Gly Arg Lys Arg Gly
            20                  25                  30

Gly Trp Ile Thr Phe Pro Phe Ile Thr Ala Ala Ile Leu Ala Ile Gln
        35                  40                  45

Val Gly Ser Ser Gly Trp Ser Ala Asn Leu Thr Val Phe Leu Ile Gly
    50                  55                  60

Gln Phe Asn Phe Met Ser Ile Lys Ala Ala Gln Val Gly Asn Ile Val
65                  70                  75                  80

Ala Gly Thr Ser Ser Phe Leu Pro Ile Phe Gly Ala Ile Leu Ala Asp
                85                  90                  95

Ser Phe Phe Gly Asn Phe Ser Val Ile Ala Val Ser Ser Leu Phe Ser
            100                 105                 110

Leu Met Gly Leu Ile Leu Phe Met Phe Thr Val Thr Val Pro Ser Leu
        115                 120                 125

Arg Pro Gln Gln Cys Ala Ala Asn Val Thr Gly Ser Ser Ala Gly Met
    130                 135                 140

Cys Glu Pro Ala Ser Thr Leu Gln Ile Ala Val Leu Tyr Thr Ser Ile
145                 150                 155                 160

Thr Leu Ser Ala Leu Gly Leu Gly Gly Ser Arg Phe Thr Val Ala Thr
                165                 170                 175

Met Gly Ala Asp Gln Phe Glu Lys Pro Lys Asp Gln Glu Cys Phe Phe
            180                 185                 190

Asn Trp His Phe Phe Asn Phe Tyr Val Gly Leu Met Ile Gly Val Val
```

```
        195                 200                 205

Gly Ile Val Tyr Ile Gln Asp Asn Ile Gly Trp Asp Arg Gly Val Gly
    210                 215                 220

Ile Cys Leu Ala Val Asn Ile Leu Gly Leu Val Thr Phe Leu Ala Gly
225                 230                 235                 240

Lys Arg Tyr Tyr Arg Gln Val Lys Thr Gln Gly Asn Pro Tyr Lys Ser
                245                 250                 255

Leu Ala Arg Val Val Val Ala Thr Ile Leu Lys Arg Asn Leu Ser Ile
            260                 265                 270

Ser Ser Ala Ser Glu Thr Phe Tyr His Gly Phe Ser Asp Gly Val Ser
        275                 280                 285

Met Lys Ser Leu Ser Ser Pro Thr Ser Ser Phe Arg Phe Leu Asn Arg
    290                 295                 300

Ala Ala Leu Lys Val Asp Gly Asp Thr Asn Glu Asp Gly Ser Val Ala
305                 310                 315                 320

Lys Glu Trp Arg Leu Cys Thr Val Gln Gln Val Glu Asp Phe Lys Thr
                325                 330                 335

Val Ile Arg Ile Ile Pro Leu Trp Phe Ser Ser Phe Phe Leu Ser Thr
            340                 345                 350

Pro Ile Gly Ile Gln Ser Ser Leu Ala Val Leu Gln Ala Leu Arg Met
        355                 360                 365

Asp Arg His Ile Gly Thr His Asn Phe Lys Ile Pro Ala Gly Ser Phe
    370                 375                 380

Leu Val Phe Thr Leu Val Ala Thr Ala Ile Ser Leu Thr Leu Ile Asp
385                 390                 395                 400

Arg Phe Leu Val Pro Thr Tyr Gln Lys Leu Ile Arg Arg Pro Leu Thr
                405                 410                 415

Pro Leu Gln Arg Ile Gly Val Gly His Val Leu Thr Val Ile Ser Met
            420                 425                 430

Ala Ala Ser Ala Ile Val Glu Arg Lys Arg Leu Ser Ile Val Trp Ser
        435                 440                 445

Asp Gly Leu Thr Ser Ser Thr Thr Ser Val Thr Met Ser Ala Leu Trp
    450                 455                 460

Leu Val Ile Pro Leu Val Leu Val Gly Val Gly Glu Ala Phe His Phe
465                 470                 475                 480

Pro Gly Gln Val Ala Leu Tyr Tyr Gln Glu Phe Pro Val Ser Leu His
                485                 490                 495

Ser Thr Ser Thr Ala Met Ile Ser Leu Leu Val Ala Val Gly Phe Tyr
            500                 505                 510

Leu Ser Thr Ala Met Ile Asp Leu Val Gln Arg Ile Thr Gly Trp Leu
        515                 520                 525

Pro Asn Asn Ile Asn Gln Gly Arg Leu Asp Asn Met Phe Trp Leu Leu
    530                 535                 540

Val Val Ile Gly Val Ile Asn Phe Gly Tyr Phe Ile Val Cys Ser Leu
545                 550                 555                 560

Leu Tyr Lys Tyr Gln Asn Phe Asn Asp Gln Asn Pro Thr Lys Val Asp
                565                 570                 575

Asp Lys Pro Arg Gln Gly Gln Asn
            580


<210> SEQ ID NO 3
<211> LENGTH: 3870
<212> TYPE: DNA
<213> ORGANISM: Camellia japonica
```

<400> SEQUENCE: 3

```
atggccgagg agaacggttt ggatggtgat ttgaacaacc atcaagctac tgcttctact     60
tctaactctc cagttcaagg tgctaatggt acttctgaaa caaaaggtgc tcaagagaag    120
tccgaaaagt ccaaagaaga agaaaagatc ggtcaatccg ttccttacta caagttgttg    180
tctttcgctg attccaagga tgttttgttg atggttattg gtactattgc tgctgttgca    240
aatggtgctt ctatgccagt tatgactttg ttgttgggtg acttgattaa cgcttttggt    300
caaaacgcta acaacaccga tactttgaga gttgtttcta aggttgcctt gaagttcgtc    360
tacttgtcta ttggtgctgg tgttgcttca tttttccaag ttgcttgctg gatggttact    420
ggtgaaagac aagctgctag aatcagatcc ttgtacttga aaaccatctt gagacaagat    480
gttgccttct tcgacaaaga aactaacact ggtgaagttg tcggtagaat gtctggtgat    540
actgttttga ttcaagatgc catcggtgaa aaggtcggta agttcattca actgttctct    600
acctttatcg gtggtttctt gattgctttt gtcaaaggtt ggttgttgac cttggttatg    660
ttgacttcta ttccaccatt ggttttctgt ggtgctttga tgactattac catttccaag    720
atggcttcca gaggtcaagt tgcatattct caagctggta tcgttgtcga acaaaccatt    780
ggtagtatta gaaccgttgc ttctttcaca ggtgaaaaac atgctgttac ccagtacgaa    840
aagtacttga acaaagctta cttggccggt attcatgaag gtttggcttc aggtgttggt    900
ttgggttctg ttttgttagt tatcttctgc tcctactctt tggctgtttg gtttggtggt    960
aagatgatta tcgaaaaggg ttacaatggt ggcaacgtca ttaacattat cgttgctgtt   1020
ttgaccggct ctatgtcttt gggtcaagct tctccatgtt tgggtgcttt tgctgctggt   1080
caagctgctg catacaaaat gttggaaacc attaagagga agccagagat cgattcttat   1140
gatacttctg gtcacaagtc cgatgatatc agaggtgata ttgaattgag ggatgtctct   1200
tttacttacc cagctagacc agatgaacaa atctttaacg gtttctcctt gttcatccca   1260
tctggtacta catctgcttt ggttggtcaa tctggttctg gtaagtctac cgttatctcc   1320
ttgattgaaa gattctacga tccacaagcc ggtgaagttt taattgatgg tgttaacttg   1380
aaggacttcc agttgagatg gattagaggt aaaatcggct tggtttctca agaaccagtt   1440
ttgttcgctt cctccatcag agataatatt gcttacggta aagatggtgc caccgttgaa   1500
gaaatcaaag ctgctactga aagagctaac gcctctaaat tcattgacaa attgccacaa   1560
ggtttggata ccttggttgg tgaacatggt actcaattgt ctggtggtca aaagcaaaga   1620
attgctattg ctagagccat tttgaaggac cccaagaatct tgttgttaga tgaagctact   1680
tcagctttgg atgccgaatc tgaacatata gttcaagaag ccttggacag aatcatggtt   1740
aacagaacta ctgttattgt cgcccataga ttgtccactg ttagaaatgc tgataccatt   1800
gccgttatcc atagaggtaa gattgtcgaa aaaggttccc acttggactt gttgttgaat   1860
ccagatggtg cttactgcca attgatcaga ttgcaagaaa tcggtagatc cgaagttgat   1920
aaggctgaaa atgttgagtc tggcttgaac tcttctcaac aacattctat cggtaggtct   1980
atctctagag gttctagtgg tgttggtaac tcttctagac attccttctc tgtttctttc   2040
ggtttcccca ccggccacat ctacgagacc actgctggtt tggaatctac ttctccagct   2100
ccaattggtc aaactcaaga agttccattg agaagattgg ctactttgaa caagccagaa   2160
attccagtct tgctgttggg tgttatttct gctatggtta acggtgttat cttcccaatt   2220
ttcggtgtct tgttgtcctc tgttattaag actttctatg aacccgagga caagttgaga   2280
```

```
aaggatacca gattttgggc tttcatgttc attattttgg gtgttgcctc ttttgttgct   2340

gctccagcta cagcttactt ttttgctgtt gctggttgca gattgatcca aagaattaga   2400

tctatgtgct tcagaaccgt cgctcatatg gaaattgatt ggtttgatga accagaacat   2460

gcctctggtg caattggtgc taaattgtct gctgatgctt ctacagttag aggtttggtc   2520

ggtgatgctt tggctttgtt ggttcaaaat gctgctacag ctgtttgcgg tttggttatt   2580

gcatttgttg ctaattggac cttggccttg attatcttgg ttttgatccc tttgattggt   2640

gtcaacggtt acgttcaaat gaagtttatg aagggttttt ccgctgatgc caagatgatg   2700

tatgaagaag cttcacaagt tgctaacgat gccgttggtt ctataagaac tgttgcatct   2760

ttttgcgctg aagaaaaggt tatgcagctg tacaagaaaa agtgtgaagg tcctatgaag   2820

accggtatca gacaaggttt aatttccggt attggtttcg gtatctcctt cttcttgtta   2880

ttcaacgttt acgccacttc tttttacgct ggtgctagat tggttgatgc tggtaaaact   2940

actttctccg atgtgttcag agttttcttt gccttgacta tggctgcttt gggtatttct   3000

caatcttctt cattggctcc agattcctct aaggctaaat cttctaccgc ttccattttc   3060

ggtattctgg acagaaagtc caagatcgat agttctgatg aatccggtat gactgttgaa   3120

aacgttaagg gtgaaatcga gttgagacac atctctttta agtatccaac cagaccagac   3180

atccaaatct tcagagattt gtccttggct attcactctg gtaagactgt tgctttagtt   3240

ggtgaaagtg gtagcggtaa gtcaactgtt attagcttgt tgcagagatt ttacgaccca   3300

gattcaggtc atattacctt ggatggtatc gagatccaaa agttccaact aagatggttg   3360

agattgcaga tgggtttagt tagtcaagag cctgtcttgt tcaacgaaac tattagagct   3420

aacattgcct atggcaaaga aggtgacgct acagaaactg aaattttggc tgctgctgaa   3480

ttggctaatg ctcataagtt tatttccggc ttgcaacaag gttacgatac tgttgtaggt   3540

gaaagaggta ttcaactatc aggtggacaa aaacagagag ttgcaatcgc aagagcaatg   3600

gttaaggctc caaagatttt gttattggat gaagccacat ctgcattgga cgctgaatca   3660

gaaagagttg ttcaagacgc tttggataag gttatggtca atagaactac agtttgggtt   3720

gctcacagat tgtctactat taagaacgct gatgttatcg ccgttgttaa gaatggtgtt   3780

attgctgaaa agggtaagca caacgatttg atcaatgtta aggacggtgt ttacgcttct   3840

ttagttgcat tgcatacctc cgcctcctaa                                    3870
```

<210> SEQ ID NO 4
<211> LENGTH: 1289
<212> TYPE: PRT
<213> ORGANISM: Camellia japonica

<400> SEQUENCE: 4

```
Met Ala Glu Glu Asn Gly Leu Asp Gly Asp Leu Asn Asn His Gln Ala
1               5                   10                  15

Thr Ala Ser Thr Ser Asn Ser Pro Val Gln Gly Ala Asn Gly Thr Ser
            20                  25                  30

Glu Thr Lys Gly Ala Gln Glu Lys Ser Glu Lys Ser Lys Glu Glu Glu
        35                  40                  45

Lys Ile Gly Gln Ser Val Pro Tyr Tyr Lys Leu Leu Ser Phe Ala Asp
    50                  55                  60

Ser Lys Asp Val Leu Leu Met Val Ile Gly Thr Ile Ala Ala Val Ala
65                  70                  75                  80

Asn Gly Ala Ser Met Pro Val Met Thr Leu Leu Leu Gly Asp Leu Ile
                85                  90                  95
```

```
Asn Ala Phe Gly Gln Asn Ala Asn Asn Thr Asp Thr Leu Arg Val Val
            100                 105                 110

Ser Lys Val Ala Leu Lys Phe Val Tyr Leu Ser Ile Gly Ala Gly Val
        115                 120                 125

Ala Ser Phe Phe Gln Val Ala Cys Trp Met Val Thr Gly Glu Arg Gln
    130                 135                 140

Ala Ala Arg Ile Arg Ser Leu Tyr Leu Lys Thr Ile Leu Arg Gln Asp
145                 150                 155                 160

Val Ala Phe Phe Asp Lys Glu Thr Asn Thr Gly Glu Val Val Gly Arg
                165                 170                 175

Met Ser Gly Asp Thr Val Leu Ile Gln Asp Ala Ile Gly Glu Lys Val
            180                 185                 190

Gly Lys Phe Ile Gln Leu Phe Ser Thr Phe Ile Gly Gly Phe Leu Ile
        195                 200                 205

Ala Phe Val Lys Gly Trp Leu Leu Thr Leu Val Met Leu Thr Ser Ile
    210                 215                 220

Pro Pro Leu Val Phe Cys Gly Ala Leu Met Thr Ile Thr Ile Ser Lys
225                 230                 235                 240

Met Ala Ser Arg Gly Gln Val Ala Tyr Ser Gln Ala Gly Ile Val Val
                245                 250                 255

Glu Gln Thr Ile Gly Ser Ile Arg Thr Val Ala Ser Phe Thr Gly Glu
            260                 265                 270

Lys His Ala Val Thr Gln Tyr Glu Lys Tyr Leu Asn Lys Ala Tyr Leu
        275                 280                 285

Ala Gly Ile His Glu Gly Leu Ala Ser Gly Val Gly Leu Gly Ser Val
    290                 295                 300

Leu Leu Val Ile Phe Cys Ser Tyr Ser Leu Ala Val Trp Phe Gly Gly
305                 310                 315                 320

Lys Met Ile Ile Glu Lys Gly Tyr Asn Gly Gly Asn Val Ile Asn Ile
                325                 330                 335

Ile Val Ala Val Leu Thr Gly Ser Met Ser Leu Gly Gln Ala Ser Pro
            340                 345                 350

Cys Leu Gly Ala Phe Ala Ala Gly Gln Ala Ala Ala Tyr Lys Met Leu
        355                 360                 365

Glu Thr Ile Lys Arg Lys Pro Glu Ile Asp Ser Tyr Asp Thr Ser Gly
    370                 375                 380

His Lys Ser Asp Asp Ile Arg Gly Asp Ile Glu Leu Arg Asp Val Ser
385                 390                 395                 400

Phe Thr Tyr Pro Ala Arg Pro Asp Glu Gln Ile Phe Asn Gly Phe Ser
                405                 410                 415

Leu Phe Ile Pro Ser Gly Thr Thr Ser Ala Leu Val Gly Gln Ser Gly
            420                 425                 430

Ser Gly Lys Ser Thr Val Ile Ser Leu Ile Glu Arg Phe Tyr Asp Pro
        435                 440                 445

Gln Ala Gly Glu Val Leu Ile Asp Gly Val Asn Leu Lys Asp Phe Gln
    450                 455                 460

Leu Arg Trp Ile Arg Gly Lys Ile Gly Leu Val Ser Gln Glu Pro Val
465                 470                 475                 480

Leu Phe Ala Ser Ser Ile Arg Asp Asn Ile Ala Tyr Gly Lys Asp Gly
                485                 490                 495

Ala Thr Val Glu Glu Ile Lys Ala Ala Thr Glu Arg Ala Asn Ala Ser
            500                 505                 510
```

```
Lys Phe Ile Asp Lys Leu Pro Gln Gly Leu Asp Thr Leu Val Gly Glu
        515                 520                 525

His Gly Thr Gln Leu Ser Gly Gly Gln Lys Gln Arg Ile Ala Ile Ala
    530                 535                 540

Arg Ala Ile Leu Lys Asp Pro Arg Ile Leu Leu Leu Asp Glu Ala Thr
545                 550                 555                 560

Ser Ala Leu Asp Ala Glu Ser Glu His Ile Val Gln Glu Ala Leu Asp
                565                 570                 575

Arg Ile Met Val Asn Arg Thr Thr Val Ile Val Ala His Arg Leu Ser
            580                 585                 590

Thr Val Arg Asn Ala Asp Thr Ile Ala Val Ile His Arg Gly Lys Ile
        595                 600                 605

Val Glu Lys Gly Ser His Leu Asp Leu Leu Leu Asn Pro Asp Gly Ala
    610                 615                 620

Tyr Cys Gln Leu Ile Arg Leu Gln Glu Ile Gly Arg Ser Glu Val Asp
625                 630                 635                 640

Lys Ala Glu Asn Val Glu Ser Gly Leu Asn Ser Ser Gln Gln His Ser
                645                 650                 655

Ile Gly Arg Ser Ile Ser Arg Gly Ser Ser Gly Val Gly Asn Ser Ser
            660                 665                 670

Arg His Ser Phe Ser Val Ser Phe Gly Leu Pro Thr Gly His Ile Tyr
        675                 680                 685

Glu Thr Thr Ala Gly Leu Glu Ser Thr Ser Pro Ala Pro Ile Gly Gln
    690                 695                 700

Thr Gln Glu Val Pro Leu Arg Arg Leu Ala Thr Leu Asn Lys Pro Glu
705                 710                 715                 720

Ile Pro Val Leu Leu Leu Gly Val Ile Ser Ala Met Val Asn Gly Val
                725                 730                 735

Ile Phe Pro Ile Phe Gly Val Leu Leu Ser Ser Val Ile Lys Thr Phe
            740                 745                 750

Tyr Glu Pro Glu Asp Lys Leu Arg Lys Asp Thr Arg Phe Trp Ala Phe
        755                 760                 765

Met Phe Ile Ile Leu Gly Val Ala Ser Phe Val Ala Ala Pro Ala Thr
    770                 775                 780

Ala Tyr Phe Phe Ala Val Ala Gly Cys Arg Leu Ile Gln Arg Ile Arg
785                 790                 795                 800

Ser Met Cys Phe Arg Thr Val Ala His Met Glu Ile Asp Trp Phe Asp
                805                 810                 815

Glu Pro Glu His Ala Ser Gly Ala Ile Gly Ala Lys Leu Ser Ala Asp
            820                 825                 830

Ala Ser Thr Val Arg Gly Leu Val Gly Asp Ala Leu Ala Leu Leu Val
        835                 840                 845

Gln Asn Ala Ala Thr Ala Val Cys Gly Leu Val Ile Ala Phe Val Ala
    850                 855                 860

Asn Trp Thr Leu Ala Leu Ile Ile Leu Val Leu Ile Pro Leu Ile Gly
865                 870                 875                 880

Val Asn Gly Tyr Val Gln Met Lys Phe Met Lys Gly Phe Ser Ala Asp
                885                 890                 895

Ala Lys Met Met Tyr Glu Glu Ala Ser Gln Val Ala Asn Asp Ala Val
            900                 905                 910

Gly Ser Ile Arg Thr Val Ala Ser Phe Cys Ala Glu Glu Lys Val Met
        915                 920                 925

Gln Leu Tyr Lys Lys Lys Cys Glu Gly Pro Met Lys Thr Gly Ile Arg
```

```
    930                 935                 940

Gln Gly Leu Ile Ser Gly Ile Gly Phe Gly Ile Ser Phe Phe Leu Leu
945                 950                 955                 960

Phe Asn Val Tyr Ala Thr Ser Phe Tyr Ala Gly Ala Arg Leu Val Asp
                965                 970                 975

Ala Gly Lys Thr Thr Phe Ser Asp Val Phe Arg Val Phe Phe Ala Leu
            980                 985                 990

Thr Met Ala Ala Leu Gly Ile Ser  Gln Ser Ser Ser Leu  Ala Pro Asp
        995                 1000                1005

Ser Ser  Lys Ala Lys Ser Ser  Thr Ala Ser Ile Phe  Gly Ile Leu
    1010                1015                1020

Asp Arg  Lys Ser Lys Ile Asp  Ser Ser Asp Glu Ser  Gly Met Thr
    1025                1030                1035

Val Glu  Asn Val Lys Gly Glu  Ile Glu Leu Arg His  Ile Ser Phe
    1040                1045                1050

Lys Tyr  Pro Thr Arg Pro Asp  Ile Gln Ile Phe Arg  Asp Leu Ser
    1055                1060                1065

Leu Ala  Ile His Ser Gly Lys  Thr Val Ala Leu Val  Gly Glu Ser
    1070                1075                1080

Gly Ser  Gly Lys Ser Thr Val  Ile Ser Leu Leu Gln  Arg Phe Tyr
    1085                1090                1095

Asp Pro  Asp Ser Gly His Ile  Thr Leu Asp Gly Ile  Glu Ile Gln
    1100                1105                1110

Lys Phe  Gln Leu Arg Trp Leu  Arg Leu Gln Met Gly  Leu Val Ser
    1115                1120                1125

Gln Glu  Pro Val Leu Phe Asn  Glu Thr Ile Arg Ala  Asn Ile Ala
    1130                1135                1140

Tyr Gly  Lys Glu Gly Asp Ala  Thr Glu Thr Glu Ile  Leu Ala Ala
    1145                1150                1155

Ala Glu  Leu Ala Asn Ala His  Lys Phe Ile Ser Gly  Leu Gln Gln
    1160                1165                1170

Gly Tyr  Asp Thr Val Val Gly  Glu Arg Gly Ile Gln  Leu Ser Gly
    1175                1180                1185

Gly Gln  Lys Gln Arg Val Ala  Ile Ala Arg Ala Met  Val Lys Ala
    1190                1195                1200

Pro Lys  Ile Leu Leu Leu Asp  Glu Ala Thr Ser Ala  Leu Asp Ala
    1205                1210                1215

Glu Ser  Glu Arg Val Val Gln  Asp Ala Leu Asp Lys  Val Met Val
    1220                1225                1230

Asn Arg  Thr Thr Val Trp Val  Ala His Arg Leu Ser  Thr Ile Lys
    1235                1240                1245

Asn Ala  Asp Val Ile Ala Val  Val Lys Asn Gly Val  Ile Ala Glu
    1250                1255                1260

Lys Gly  Lys His Asn Asp Leu  Ile Asn Val Lys Asp  Gly Val Tyr
    1265                1270                1275

Ala Ser  Leu Val Ala Leu His  Thr Ser Ala Ser
    1280                1285
```

<210> SEQ ID NO 5
<211> LENGTH: 1965
<212> TYPE: DNA
<213> ORGANISM: Eutrema salsugineum

<400> SEQUENCE: 5

```
atgaagtccc gcgtcatcct ctcccaccgc gagcgccgcg acaacatcaa caacaaccgc      60
gactccttct gcaactacac ccagatcgac accatggagc gcaagccctt cgaggtcgag     120
accaccacca ccaccaccgc caccgaggac cacaagccct actccgccgt cgacggcggc     180
ggctccgacc tcacctccac cgtcgactcc ttcgacgacg agcagaagaa gctcgtctac     240
cgcggctgga aggtcatgcc cttcatcatc ggcaacgaga ccttcgagaa gatcggcatc     300
atcggcaccc tctccaacct cctcgtctac ctcacccagg tcttcaacct caagtccgtc     360
accgccgcca ccatcatcaa cgccttctcc ggcaccatca acttcggcac cttcgtcgcc     420
gccttcctct gcgacaccta cttcggccgc tacaagaccc tctccgtcgc cgtcatcgcc     480
tgcttcctcg gctccttcgt catcctcatg accgccgccg tccccggcct ccaccccacc     540
ccctgcggca ccaagtcctt ctgccagggc ccctccggcg gccagatcgc cttcctcctc     600
atgggcctcg ccctcctcgt cgtcggcgcc ggcggcatcc gcccctgcaa cctcgccttc     660
ggcgccgacc agttcaaccc caagtccgag tccggcaaga agggcatcaa ctccttcttc     720
aactggtact tcttcacctt caccttcgcc cagatcatct ccctcaccct cgtcgtctac     780
atccagtcca acgtctcctg gaccatcggc ctctccatcc ccgtcggcct catgttcctc     840
gcctgcgtca tcttcttcgc cggcgacaag ctctacgtca aggtcaaggc ctccggctcc     900
cccctcgcct ccatcggcca cgtcatcgtc gccgccatca agaagcgcgg cctcaagccc     960
gtcaagcagc cctggctcga gctctacaac cacatcccca tcaactaccc caacaccacc    1020
ctcaagtaca ccgaccagtt ccgcttcctc gacaaggccg ccatcatgac ccccgaggac    1080
aagctcaagt ccgacggcgc cgcctccgac ccctggaagc tctgcaccat gcagcacgtc    1140
gaggaggtca agtgcatcgt ccgcgtcatc cccatctggt tcgcctgcgc catctactac    1200
ctcgccatct ccatgcagat gacctacccc gtcttccagg ccttccaggg cgaccgccgc    1260
ctcggctccg gcggcttcaa gatccccgcc gccacctacg tcgtcttcct catgaccggc    1320
atgaccgtct tcatcatctt ctacgaccgc gtcctcgtcc cctccctccg ccgcgtcacc    1380
cgcctcgaca ccggcatcac cctcctccag cgcatcggcg ccggcatctt cttcgccgtc    1440
ctctccctcc tcgtctccgc cttcatcgag gagcgccgcc gcaacttcgc cctcacccgc    1500
cccaccctcg gcatcgagcc ccgccgcggc gagatctcct ccatgtccgc catgtggctc    1560
atcccccagc tcctcctcgc cggcgtcgcc gaggccttcg ccgccatcgg ccagatggag    1620
ttctactaca agcagttccc cgagaacatg aagtccttcg ccggctccat cttctacgtc    1680
ggcgccggcg tctcctccta cctctcctcc ttcctcatct ccaccgtcca ccgcatgacc    1740
gagcactccc cctccggcaa ctggctcgcc gaggacctca acaagggcaa gctcgactac    1800
ttctacttca tgctcaccgg cctcatggtc gtcaacatgg tctacttcct cctcgtcgcc    1860
aagtggtacc gctacaaggg ctccaacgac gaggacaagc ccgtcatcga gaccaacgag    1920
gaggagaaga agcagcacca gcagctcgac aagaactccg tctaa                    1965
```

<210> SEQ ID NO 6
<211> LENGTH: 654
<212> TYPE: PRT
<213> ORGANISM: Eutrema salsugineum

<400> SEQUENCE: 6

```
Met Lys Ser Arg Val Ile Leu Ser His Arg Glu Arg Arg Asp Asn Ile
1               5                   10                  15

Asn Asn Asn Arg Asp Ser Phe Cys Asn Tyr Thr Gln Ile Asp Thr Met
            20                  25                  30
```

```
Glu Arg Lys Pro Phe Glu Val Glu Thr Thr Thr Thr Thr Thr Ala Thr
        35                  40                  45

Glu Asp His Lys Pro Tyr Ser Ala Val Asp Gly Gly Gly Ser Asp Leu
    50                  55                  60

Thr Ser Thr Val Asp Ser Phe Asp Asp Glu Gln Lys Lys Leu Val Tyr
65                  70                  75                  80

Arg Gly Trp Lys Val Met Pro Phe Ile Ile Gly Asn Glu Thr Phe Glu
                85                  90                  95

Lys Ile Gly Ile Ile Gly Thr Leu Ser Asn Leu Leu Val Tyr Leu Thr
            100                 105                 110

Gln Val Phe Asn Leu Lys Ser Val Thr Ala Ala Thr Ile Ile Asn Ala
        115                 120                 125

Phe Ser Gly Thr Ile Asn Phe Gly Thr Phe Val Ala Ala Phe Leu Cys
    130                 135                 140

Asp Thr Tyr Phe Gly Arg Tyr Lys Thr Leu Ser Val Ala Val Ile Ala
145                 150                 155                 160

Cys Phe Leu Gly Ser Phe Val Ile Leu Met Thr Ala Ala Val Pro Gly
                165                 170                 175

Leu His Pro Thr Pro Cys Gly Thr Lys Ser Phe Cys Gln Gly Pro Ser
            180                 185                 190

Gly Gly Gln Ile Ala Phe Leu Leu Met Gly Leu Ala Leu Leu Val Val
        195                 200                 205

Gly Ala Gly Gly Ile Arg Pro Cys Asn Leu Ala Phe Gly Ala Asp Gln
    210                 215                 220

Phe Asn Pro Lys Ser Glu Ser Gly Lys Lys Gly Ile Asn Ser Phe Phe
225                 230                 235                 240

Asn Trp Tyr Phe Phe Thr Phe Thr Phe Ala Gln Ile Ile Ser Leu Thr
                245                 250                 255

Leu Val Val Tyr Ile Gln Ser Asn Val Ser Trp Thr Ile Gly Leu Ser
            260                 265                 270

Ile Pro Val Gly Leu Met Phe Leu Ala Cys Val Ile Phe Phe Ala Gly
        275                 280                 285

Asp Lys Leu Tyr Val Lys Val Lys Ala Ser Gly Ser Pro Leu Ala Ser
    290                 295                 300

Ile Gly His Val Ile Val Ala Ala Ile Lys Lys Arg Gly Leu Lys Pro
305                 310                 315                 320

Val Lys Gln Pro Trp Leu Glu Leu Tyr Asn His Ile Pro Ile Asn Tyr
                325                 330                 335

Pro Asn Thr Thr Leu Lys Tyr Thr Asp Gln Phe Arg Phe Leu Asp Lys
            340                 345                 350

Ala Ala Ile Met Thr Pro Glu Asp Lys Leu Lys Ser Asp Gly Ala Ala
        355                 360                 365

Ser Asp Pro Trp Lys Leu Cys Thr Met Gln His Val Glu Glu Val Lys
    370                 375                 380

Cys Ile Val Arg Val Ile Pro Ile Trp Phe Ala Cys Ala Ile Tyr Tyr
385                 390                 395                 400

Leu Ala Ile Ser Met Gln Met Thr Tyr Pro Val Phe Gln Ala Phe Gln
                405                 410                 415

Gly Asp Arg Arg Leu Gly Ser Gly Gly Phe Lys Ile Pro Ala Ala Thr
            420                 425                 430

Tyr Val Val Phe Leu Met Thr Gly Met Thr Val Phe Ile Ile Phe Tyr
        435                 440                 445
```

```
Asp Arg Val Leu Val Pro Ser Leu Arg Arg Val Thr Arg Leu Asp Thr
    450                 455                 460

Gly Ile Thr Leu Leu Gln Arg Ile Gly Ala Gly Ile Phe Phe Ala Val
465                 470                 475                 480

Leu Ser Leu Leu Val Ser Ala Phe Ile Glu Glu Arg Arg Arg Asn Phe
                485                 490                 495

Ala Leu Thr Arg Pro Thr Leu Gly Ile Glu Pro Arg Arg Gly Glu Ile
            500                 505                 510

Ser Ser Met Ser Ala Met Trp Leu Ile Pro Gln Leu Leu Leu Ala Gly
        515                 520                 525

Val Ala Glu Ala Phe Ala Ala Ile Gly Gln Met Glu Phe Tyr Tyr Lys
    530                 535                 540

Gln Phe Pro Glu Asn Met Lys Ser Phe Ala Gly Ser Ile Phe Tyr Val
545                 550                 555                 560

Gly Ala Gly Val Ser Ser Tyr Leu Ser Ser Phe Leu Ile Ser Thr Val
                565                 570                 575

His Arg Met Thr Glu His Ser Pro Ser Gly Asn Trp Leu Ala Glu Asp
            580                 585                 590

Leu Asn Lys Gly Lys Leu Asp Tyr Phe Tyr Phe Met Leu Thr Gly Leu
        595                 600                 605

Met Val Val Asn Met Val Tyr Phe Leu Leu Val Ala Lys Trp Tyr Arg
    610                 615                 620

Tyr Lys Gly Ser Asn Asp Glu Asp Lys Pro Val Ile Glu Thr Asn Glu
625                 630                 635                 640

Glu Glu Lys Lys Gln His Gln Gln Leu Asp Lys Asn Ser Val
                645                 650
```

```
<210> SEQ ID NO 7
<211> LENGTH: 1824
<212> TYPE: DNA
<213> ORGANISM: Populus trichocarpa

<400> SEQUENCE: 7

atggaaaaga gagatgagag gggttccatt ggtgaagaaa atggtaaaga atccgtccag      60

aacgacttga aagaaactat gggtaattct ggtgaggacg agactaattc taagccaaaa     120

gttatctaca gaggctggaa agttatgcca ttcattattg gtaacgaaac cttcgagaag     180

ttgggtacta ttggtacttt gtccaacctg ttgatctact tgactaccgt tttcaacatg     240

aagtctatta ccgctgctac cattatcact gtttttaacg gtactgctaa cttgggtact     300

ttgattggtg ctttcttgtg tgatacttac ttcggtagat acaagaccat tggttttgct     360

actgttgctt ctttcttggg tttgttggct attcaattga ctgctgccat ttctaaattg     420

catccaccac attgtgccaa agaatccatt acttgtattg gtccaactgg tggtcaaatt     480

gctttttgt tagccggttt catcctgatg attattggtg ctggtggtat tagaccatgt     540

aatttggctt ttggtgccga tcaatttgat ccagaaactg aatctggtaa gagaggtgtt     600

aactctttct tcaactggta cttcttcact ttcaccttcg ctcaaatgat ctctttgacc     660

ttgatcgttt acgtccagtc taatgtttct tggccaattg gtttgggtat tccagctatt     720

ttgatgctga tttcctgctt ggtttactac atgggtacta agttgtacgt taaggttaag     780

gctactggtt ctccaatgac ttctgttgct agagttatag ttgttgccgt caagaagaga     840

aagttgaagc cagttgatca gccatggttg tctttgttta attacatccc accaaagtcc     900

atcaactcca agttgtctta tactgaccag ttcagattct tggataaggc tgctattatg     960
```

-continued acccaccaag atcaagttaa tccagatggt tcaccagcta atccatggaa attgtgttca 1020
ttgcaacaag tcgaagaggt caagtgtttg ttcagagtta ttccagtttg gactgccgct 1080
attatctatt acgttgctgt tgtccaacaa cacacctacg ttgtttttca agctgtccaa 1140
tctaacagaa ggttgggtaa ctctaatttt gctattccag cagcctctta catcgtgttt 1200
ttgatgttgt ccatgtccat cttcatccca atctacgata gaattttggt cccattcttg 1260
agaaggatca caggtaaaga agctggtatt accatcttgc aaagaatcgg tgttggtatc 1320
tttttgacca tcgttaccat gttggtttcc ggtttagtcg aagaaaagag aagaactatt 1380
gctttgacta agccaacttt gggtaatgct ccaagaaaag gtgctatctc ttctatgtct 1440
gctttgtggt tgattcccca attgtcattg tctggtattg ctgaagcttt cggttctatt 1500
ggtcaagtcg aattctacta caagcagttc ccagaaaaca tgagatctat tggtggttct 1560
ttgttctact gtggtatggc tgcttcttct tacttctcat ctttgttgat caccgttgtt 1620
catcaaacta ctaatggtgc tgctactggt aattggttgt ctgaagattt gaacaagggc 1680
agattggatt actactacta catgattgct gccttgggtg ttttgaatat gggttacttt 1740
ttgttgtgcg ccagatggta taagtacaaa ggtggtaaag atgacgcctt gttggaattg 1800
tgtggtggtg aaaaaaccat ctaa 1824

<210> SEQ ID NO 8
<211> LENGTH: 607
<212> TYPE: PRT
<213> ORGANISM: Populus trichocarpa

<400> SEQUENCE: 8

Met Glu Lys Arg Asp Glu Arg Gly Ser Ile Gly Glu Glu Asn Gly Lys
1 5 10 15

Glu Ser Val Gln Asn Asp Leu Lys Glu Thr Met Gly Asn Ser Gly Glu
20 25 30

Asp Glu Thr Asn Ser Lys Pro Lys Val Ile Tyr Arg Gly Trp Lys Val
35 40 45

Met Pro Phe Ile Ile Gly Asn Glu Thr Phe Glu Lys Leu Gly Thr Ile
50 55 60

Gly Thr Leu Ser Asn Leu Leu Ile Tyr Leu Thr Thr Val Phe Asn Met
65 70 75 80

Lys Ser Ile Thr Ala Ala Thr Ile Ile Thr Val Phe Asn Gly Thr Ala
85 90 95

Asn Leu Gly Thr Leu Ile Gly Ala Phe Leu Cys Asp Thr Tyr Phe Gly
100 105 110

Arg Tyr Lys Thr Ile Gly Phe Ala Thr Val Ala Ser Phe Leu Gly Leu
115 120 125

Leu Ala Ile Gln Leu Thr Ala Ala Ile Ser Lys Leu His Pro Pro His
130 135 140

Cys Ala Lys Glu Ser Ile Thr Cys Ile Gly Pro Thr Gly Gly Gln Ile
145 150 155 160

Ala Phe Leu Leu Ala Gly Phe Ile Leu Met Ile Ile Gly Ala Gly Gly
165 170 175

Ile Arg Pro Cys Asn Leu Ala Phe Gly Ala Asp Gln Phe Asp Pro Glu
180 185 190

Thr Glu Ser Gly Lys Arg Gly Val Asn Ser Phe Phe Asn Trp Tyr Phe
195 200 205

Phe Thr Phe Thr Phe Ala Gln Met Ile Ser Leu Thr Leu Ile Val Tyr
210 215 220

```
Val Gln Ser Asn Val Ser Trp Pro Ile Gly Leu Gly Ile Pro Ala Ile
225                 230                 235                 240

Leu Met Leu Ile Ser Cys Leu Val Tyr Tyr Met Gly Thr Lys Leu Tyr
                245                 250                 255

Val Lys Val Lys Ala Thr Gly Ser Pro Met Thr Ser Val Ala Arg Val
            260                 265                 270

Ile Val Val Ala Val Lys Lys Arg Lys Leu Lys Pro Val Asp Gln Pro
        275                 280                 285

Trp Leu Ser Leu Phe Asn Tyr Ile Pro Pro Lys Ser Ile Asn Ser Lys
    290                 295                 300

Leu Ser Tyr Thr Asp Gln Phe Arg Phe Leu Asp Lys Ala Ala Ile Met
305                 310                 315                 320

Thr His Gln Asp Gln Val Asn Pro Asp Gly Ser Pro Ala Asn Pro Trp
                325                 330                 335

Lys Leu Cys Ser Leu Gln Gln Val Glu Glu Val Lys Cys Leu Phe Arg
            340                 345                 350

Val Ile Pro Val Trp Thr Ala Ala Ile Ile Tyr Tyr Val Ala Val Val
        355                 360                 365

Gln Gln His Thr Tyr Val Val Phe Gln Ala Val Gln Ser Asn Arg Arg
    370                 375                 380

Leu Gly Asn Ser Asn Phe Ala Ile Pro Ala Ala Ser Tyr Ile Val Phe
385                 390                 395                 400

Leu Met Leu Ser Met Ser Ile Phe Ile Pro Ile Tyr Asp Arg Ile Leu
                405                 410                 415

Val Pro Phe Leu Arg Arg Ile Thr Gly Lys Glu Ala Gly Ile Thr Ile
            420                 425                 430

Leu Gln Arg Ile Gly Val Gly Ile Phe Leu Thr Ile Val Thr Met Leu
        435                 440                 445

Val Ser Gly Leu Val Glu Glu Lys Arg Arg Thr Ile Ala Leu Thr Lys
    450                 455                 460

Pro Thr Leu Gly Asn Ala Pro Arg Lys Gly Ala Ile Ser Ser Met Ser
465                 470                 475                 480

Ala Leu Trp Leu Ile Pro Gln Leu Ser Leu Ser Gly Ile Ala Glu Ala
                485                 490                 495

Phe Gly Ser Ile Gly Gln Val Glu Phe Tyr Tyr Lys Gln Phe Pro Glu
            500                 505                 510

Asn Met Arg Ser Ile Gly Gly Ser Leu Phe Tyr Cys Gly Met Ala Ala
        515                 520                 525

Ser Ser Tyr Phe Ser Ser Leu Leu Ile Thr Val Val His Gln Thr Thr
    530                 535                 540

Asn Gly Ala Ala Thr Gly Asn Trp Leu Ser Glu Asp Leu Asn Lys Gly
545                 550                 555                 560

Arg Leu Asp Tyr Tyr Tyr Tyr Met Ile Ala Ala Leu Gly Val Leu Asn
                565                 570                 575

Met Gly Tyr Phe Leu Leu Cys Ala Arg Trp Tyr Lys Tyr Lys Gly Gly
            580                 585                 590

Lys Asp Asp Ala Leu Leu Glu Leu Cys Gly Gly Glu Lys Thr Ile
        595                 600                 605
```

<210> SEQ ID NO 9
<211> LENGTH: 1752
<212> TYPE: DNA
<213> ORGANISM: Argemone mexicana

<400> SEQUENCE: 9

```
atggtcctgg ttgaatcctc tggtgataag gattcttctg gtttggttga ttttcaaggt     60
aacccagttg ataactctag aactggtggt tggttggctg ctggtttgat tttgggtact    120
gaattgtctg aaagaatctg cgttatgggc atctctatga acatggttac ttacttggtt    180
ggtgacatgc acttgtcctc ttctaaatct gctaacatcg ttaccaactt catgggcact    240
ttgaacatct tgggtttgtt aggtggtttt ttggctgatg ctaaattggg tagatacttg    300
actgttgcta ccttcgcttc tattactgct ttgggtgttg ctttgttgac cgtttctact    360
tccatttctg gtttaagacc accaccatgt gatgactcaa gaaagaatac ttgtgttcaa    420
gccaacggtt ctcaattggc tatgttgtat ttgtccttgt acattatcgc tttaggtggt    480
ggtggcatta agtctaatgt ttcaggtttt ggttccgatc aattcgatgc ttctaacccc    540
aaagaacaaa aggctatggt ttacttcttc aacaggttct acttctgcat ctctttgggt    600
tctttgttct ccgttactat cttggtttac atccaagata acgttggtag aggttggggt    660
tatggtattt ctgctggtac tatgattatt gccgttgccg ttttcttagg tggtactaag    720
ttgtacagat tcagaaagcc acaaggttct ccattgacta ctatttggag agttgtttac    780
ttggcctgga agaagagaaa tttgtctttc ccatctcacg actcgttctt gaatgaatgt    840
aacacttcta aggttgctca cacccagaga ttgagatgtt tggatagagc tgctattttg    900
gatgacaagg ttgtttcttc aggcaacact aacaatccat ggttggtttc tactgtcatg    960
gaagttgaag aggttaagat ggtcttgcaa ttgattccaa tttggtctac ctgcattttg   1020
ttctggacta tctactctca aatgaacacc ttcaccattg aacaagctac cttcatgaac   1080
agaaacatcg gttcttttga agttccagct ggttctttct ctgtgttctt gtttttgacg   1140
atcctgttgt tcacctcctt gaacgaaaag ttgtttgttc caatggccag aaagatcacc   1200
agaaaacctc aaggtttgac ttccttgcaa agagttggta tcggtttggt tttttctgtt   1260
gctggtatga ctgcttctgc tatcgttgaa aaaagacgta gacaaatggc cgtccaagaa   1320
aacaatcaaa ttaccgcttt ttggttggtc ccacaatttt tcatagttgg tgctggtgaa   1380
gcttttgctt atgttggtca attggaattc ttcatcagag aagctccaga aaggatgaag   1440
tctatgtcta caggtttgtt cttgtctact ttggctatgg gtttcttcgt gtcatctttg   1500
ttggttacat tggttgttgc tgctactggt aaatcttggt tgagaaacaa tttgaacaag   1560
ggcaagttgg agaacttcta ttggatgttg gctgttttgg gtgtgattaa cttcttggtg   1620
tttttggcct ttgctaggaa tcatcagtac aaggttcaaa agtctgaagg tccagctaac   1680
gaccaagaaa aagaattgac tcattggcaa ggtgaagcca tcgttgatat tgaaaaaaag   1740
gctgtctgct aa                                                        1752
```

<210> SEQ ID NO 10
<211> LENGTH: 583
<212> TYPE: PRT
<213> ORGANISM: Argemone mexicana

<400> SEQUENCE: 10

```
Met Val Leu Val Glu Ser Ser Gly Asp Lys Asp Ser Ser Gly Leu Val
1               5                   10                  15

Asp Phe Gln Gly Asn Pro Val Asp Asn Ser Arg Thr Gly Gly Trp Leu
            20                  25                  30

Ala Ala Gly Leu Ile Leu Gly Thr Glu Leu Ser Glu Arg Ile Cys Val
        35                  40                  45
```

```
Met Gly Ile Ser Met Asn Met Val Thr Tyr Leu Val Gly Asp Met His
    50                  55                  60

Leu Ser Ser Ser Lys Ser Ala Asn Ile Val Thr Asn Phe Met Gly Thr
65                  70                  75                  80

Leu Asn Ile Leu Gly Leu Leu Gly Gly Phe Leu Ala Asp Ala Lys Leu
                85                  90                  95

Gly Arg Tyr Leu Thr Val Ala Thr Phe Ala Ser Ile Thr Ala Leu Gly
            100                 105                 110

Val Ala Leu Leu Thr Val Ser Thr Ser Ile Ser Gly Leu Arg Pro Pro
        115                 120                 125

Pro Cys Asp Asp Ser Arg Lys Asn Thr Cys Val Gln Ala Asn Gly Ser
    130                 135                 140

Gln Leu Ala Met Leu Tyr Leu Ser Leu Tyr Ile Ile Ala Leu Gly Gly
145                 150                 155                 160

Gly Gly Ile Lys Ser Asn Val Ser Gly Phe Gly Ser Asp Gln Phe Asp
                165                 170                 175

Ala Ser Asn Pro Lys Glu Gln Lys Ala Met Val Tyr Phe Phe Asn Arg
            180                 185                 190

Phe Tyr Phe Cys Ile Ser Leu Gly Ser Leu Phe Ser Val Thr Ile Leu
        195                 200                 205

Val Tyr Ile Gln Asp Asn Val Gly Arg Gly Trp Gly Tyr Gly Ile Ser
    210                 215                 220

Ala Gly Thr Met Ile Ile Ala Val Ala Val Phe Leu Gly Gly Thr Lys
225                 230                 235                 240

Leu Tyr Arg Phe Arg Lys Pro Gln Gly Ser Pro Leu Thr Thr Ile Trp
                245                 250                 255

Arg Val Val Tyr Leu Ala Trp Lys Lys Arg Asn Leu Ser Phe Pro Ser
            260                 265                 270

His Asp Ser Phe Leu Asn Glu Cys Asn Thr Ser Lys Val Ala His Thr
        275                 280                 285

Gln Arg Leu Arg Cys Leu Asp Arg Ala Ala Ile Leu Asp Asp Lys Val
    290                 295                 300

Val Ser Ser Gly Asn Thr Asn Asn Pro Trp Leu Val Ser Thr Val Met
305                 310                 315                 320

Glu Val Glu Glu Val Lys Met Val Leu Gln Leu Ile Pro Ile Trp Ser
                325                 330                 335

Thr Cys Ile Leu Phe Trp Thr Ile Tyr Ser Gln Met Asn Thr Phe Thr
            340                 345                 350

Ile Glu Gln Ala Thr Phe Met Asn Arg Asn Ile Gly Ser Phe Glu Val
        355                 360                 365

Pro Ala Gly Ser Phe Ser Val Phe Leu Phe Leu Thr Ile Leu Leu Phe
    370                 375                 380

Thr Ser Leu Asn Glu Lys Leu Phe Val Pro Met Ala Arg Lys Ile Thr
385                 390                 395                 400

Arg Lys Pro Gln Gly Leu Thr Ser Leu Gln Arg Val Gly Ile Gly Leu
                405                 410                 415

Val Phe Ser Val Ala Gly Met Thr Ala Ser Ala Ile Val Glu Lys Arg
            420                 425                 430

Arg Arg Gln Met Ala Val Gln Glu Asn Asn Gln Ile Thr Ala Phe Trp
        435                 440                 445

Leu Val Pro Gln Phe Phe Ile Val Gly Ala Gly Glu Ala Phe Ala Tyr
    450                 455                 460

Val Gly Gln Leu Glu Phe Phe Ile Arg Glu Ala Pro Glu Arg Met Lys
```

```
465                 470                 475                 480

Ser Met Ser Thr Gly Leu Phe Leu Ser Thr Leu Ala Met Gly Phe Phe
                485                 490                 495

Val Ser Ser Leu Leu Val Thr Leu Val Val Ala Ala Thr Gly Lys Ser
            500                 505                 510

Trp Leu Arg Asn Asn Leu Asn Lys Gly Lys Leu Glu Asn Phe Tyr Trp
        515                 520                 525

Met Leu Ala Val Leu Gly Val Ile Asn Phe Leu Val Phe Leu Ala Phe
    530                 535                 540

Ala Arg Asn His Gln Tyr Lys Val Gln Lys Ser Glu Gly Pro Ala Asn
545                 550                 555                 560

Asp Gln Glu Lys Glu Leu Thr His Trp Gln Gly Glu Ala Ile Val Asp
                565                 570                 575

Ile Glu Lys Lys Ala Val Cys
            580


<210> SEQ ID NO 11
<211> LENGTH: 1785
<212> TYPE: DNA
<213> ORGANISM: Aquilegia coerulea

<400> SEQUENCE: 11

atggaaaaga acgacgacga caagaaggtt catcacgata ttgaagatca cgtcgacaag     60

caaaagatca attacagagg tgttaaggcc atgccttaca ttattggtaa cgaaaccttt    120

gaaaagctgg gtactattgg cacttcttcc aatatggttg tttacttgac taccgtgttc    180

aacatgaagt ctgcttcagc tactactttg gtcaatgttt tcaatggcac taccaatttc    240

gctccattga ttggtgcttt tttgtccgat gcttacttcg gtagatacaa gactttgggt    300

ttcgcctcta tttcttcttt gactggtatg ttcgttatca tgttgactgc tgctattacc    360

aaattgcatc caccacattg tggtactaag gatactggtc attgcattgg tccaactaca    420

ttgcaatttg ctttcttgtt gttgggcttc gccttttttgg ttgttggtgc tggtggtatt    480

agaccatgta atttggcttt tggtgccgat caattcaacc caaatactga atctggtaag    540

aggggtatca actctttttt caactggtac tacttcactt tcaccttcgc tatgatggtt    600

tctgttacct tgatcgttta cgtccaatcc gatattaact gggctattgg tttggctatt    660

cctacctttt tgatgttctt gtcttgtgcc acttacttcg ttggttctag aatctacgtt    720

aaggttaagc cagaaggttc tccattgggt agagttgttc aagtttttgt tgctgccaag    780

aagaagagaa gattgaagtt gccagaaaac ccacacttgt ctttgttttc ttatcaacct    840

accggttcta tcaacgcttc tttgccatat acagaccagt ttagattctt ggataaggcc    900

gctattatta ccccagaaga ttctatcaaa ccagatggtt ctgctgttga tccttggaga    960

ttgtgtggta tgcaacaagt tgaagaggtt aagtgcatca tgagagttat tccaatttgg   1020

gcctctggta ttatctacta cactgctata gttcagatgc acacttacgt tgttttacaa   1080

gccttgcagt ccgatagaag attaggtggt tctggttttg aagttccagc tgcttcttat   1140

atcgttttcg ctatggttgg tttgaccttc tggattccaa tctacgatag aattatcgtc   1200

ccaaccttga gaaagttcac tggtaaagaa ggtggtatca ccttgttgca aagaatgggt   1260

attggtatcg ttttgtccat taccaccatg ttggtttcag ctgttgttga agttagaaga   1320

agaaactacg ctttgactag accaactttg ggtattgcta aatctggtgg tgctatttca   1380

tctatgccag gtttgtggtt gtctccacaa ttgctattgg ctggtttgtc tgaagctttt   1440
```

-continued gattccgttg gtcaaatcga gttctactac aaacaattcc cagagaacat gagatccatt 1500
gccggttctt tctttttctt gactatggct ggtgctaact acttgtctgg ttttttggtt 1560
tccttgatcc atagagttac tgctaattct ccaactggta attggttgcc agatgatttg 1620
aacaaaggca gattggacta cttctactac ttgtttgctg ccttgggtat tttgaacttc 1680
ggttactttt tagtttgcgc cagatggtac agatacaaag gtactggtgg tgttactatt 1740
gaattggcta atgaatctac cccaaccgaa aagcacatcg tttaa 1785

<210> SEQ ID NO 12
<211> LENGTH: 594
<212> TYPE: PRT
<213> ORGANISM: Aquilegia coerulea

<400> SEQUENCE: 12

Met Glu Lys Asn Asp Asp Asp Lys Lys Val His His Asp Ile Glu Asp
1 5 10 15

His Val Asp Lys Gln Lys Ile Asn Tyr Arg Gly Val Lys Ala Met Pro
20 25 30

Tyr Ile Ile Gly Asn Glu Thr Phe Glu Lys Leu Gly Thr Ile Gly Thr
35 40 45

Ser Ser Asn Met Val Val Tyr Leu Thr Thr Val Phe Asn Met Lys Ser
50 55 60

Ala Ser Ala Thr Thr Leu Val Asn Val Phe Asn Gly Thr Thr Asn Phe
65 70 75 80

Ala Pro Leu Ile Gly Ala Phe Leu Ser Asp Ala Tyr Phe Gly Arg Tyr
85 90 95

Lys Thr Leu Gly Phe Ala Ser Ile Ser Ser Leu Thr Gly Met Phe Val
100 105 110

Ile Met Leu Thr Ala Ala Ile Thr Lys Leu His Pro Pro His Cys Gly
115 120 125

Thr Lys Asp Thr Gly His Cys Ile Gly Pro Thr Thr Leu Gln Phe Ala
130 135 140

Phe Leu Leu Leu Gly Phe Ala Phe Leu Val Val Gly Ala Gly Gly Ile
145 150 155 160

Arg Pro Cys Asn Leu Ala Phe Gly Ala Asp Gln Phe Asn Pro Asn Thr
165 170 175

Glu Ser Gly Lys Arg Gly Ile Asn Ser Phe Phe Asn Trp Tyr Tyr Phe
180 185 190

Thr Phe Thr Phe Ala Met Met Val Ser Val Thr Leu Ile Val Tyr Val
195 200 205

Gln Ser Asp Ile Asn Trp Ala Ile Gly Leu Ala Ile Pro Thr Phe Leu
210 215 220

Met Phe Leu Ser Cys Ala Thr Tyr Phe Val Gly Ser Arg Ile Tyr Val
225 230 235 240

Lys Val Lys Pro Glu Gly Ser Pro Leu Gly Arg Val Val Gln Val Phe
245 250 255

Val Ala Ala Lys Lys Lys Arg Arg Leu Lys Leu Pro Glu Asn Pro His
260 265 270

Leu Ser Leu Phe Ser Tyr Gln Pro Thr Gly Ser Ile Asn Ala Ser Leu
275 280 285

Pro Tyr Thr Asp Gln Phe Arg Phe Leu Asp Lys Ala Ala Ile Ile Thr
290 295 300

Pro Glu Asp Ser Ile Lys Pro Asp Gly Ser Ala Val Asp Pro Trp Arg
305 310 315 320

```
Leu Cys Gly Met Gln Gln Val Glu Glu Val Lys Cys Ile Met Arg Val
                325                 330                 335

Ile Pro Ile Trp Ala Ser Gly Ile Ile Tyr Tyr Thr Ala Ile Val Gln
            340                 345                 350

Met His Thr Tyr Val Val Leu Gln Ala Leu Gln Ser Asp Arg Arg Leu
        355                 360                 365

Gly Gly Ser Gly Phe Glu Val Pro Ala Ala Ser Tyr Ile Val Phe Ala
    370                 375                 380

Met Val Gly Leu Thr Phe Trp Ile Pro Ile Tyr Asp Arg Ile Ile Val
385                 390                 395                 400

Pro Thr Leu Arg Lys Phe Thr Gly Lys Glu Gly Gly Ile Thr Leu Leu
                405                 410                 415

Gln Arg Met Gly Ile Gly Ile Val Leu Ser Ile Thr Thr Met Leu Val
            420                 425                 430

Ser Ala Val Val Glu Val Arg Arg Arg Asn Tyr Ala Leu Thr Arg Pro
        435                 440                 445

Thr Leu Gly Ile Ala Lys Ser Gly Gly Ala Ile Ser Ser Met Pro Gly
    450                 455                 460

Leu Trp Leu Ser Pro Gln Leu Leu Leu Ala Gly Leu Ser Glu Ala Phe
465                 470                 475                 480

Asp Ser Val Gly Gln Ile Glu Phe Tyr Tyr Lys Gln Phe Pro Glu Asn
                485                 490                 495

Met Arg Ser Ile Ala Gly Ser Phe Phe Phe Leu Thr Met Ala Gly Ala
            500                 505                 510

Asn Tyr Leu Ser Gly Phe Leu Val Ser Leu Ile His Arg Val Thr Ala
        515                 520                 525

Asn Ser Pro Thr Gly Asn Trp Leu Pro Asp Asp Leu Asn Lys Gly Arg
    530                 535                 540

Leu Asp Tyr Phe Tyr Tyr Leu Phe Ala Ala Leu Gly Ile Leu Asn Phe
545                 550                 555                 560

Gly Tyr Phe Leu Val Cys Ala Arg Trp Tyr Arg Tyr Lys Gly Thr Gly
                565                 570                 575

Gly Val Thr Ile Glu Leu Ala Asn Glu Ser Thr Pro Thr Glu Lys His
            580                 585                 590

Ile Val


<210> SEQ ID NO 13
<211> LENGTH: 1584
<212> TYPE: DNA
<213> ORGANISM: Basidiobolus meristosporus

<400> SEQUENCE: 13

atgtccaacg aaaagccaga ccacgacaaa gaagttaatt acgttgacga caagatcgag      60

gaacaaccta atccagatga tatcgaaaaa agagttgctg gtaaagttcc attggctgcc     120

tggtttatta tcattaccga attgtgtgaa aggttcgctt tttacggtgc ttctttgatg     180

ttccaacctt acatgttgaa gatgttgggt ttctctaaag gtactgctac cgctgttaat     240

agaggttttc aattcttggc ttacttcacc actattttgg gtgctgttgt tgctgataga     300

tacgtcggta aattcaagac catcgtcatc ttcagcttgt tctacatgat tggcttgatt     360

atcttggctt tgtctgcttt gccatcttct ttggaaggtt cctttggtat tatcggtttc     420

attattgcct tgtacgcctt catttctttt ggtactggtg gtatcaagtc caacgtttct     480

tcttttgctg ccgaacaaat caaagagggt attttcccaa caaaaacccc aggtgtttac     540
```

atcgattctc aattgaccgt tgaaaggatc tttaggtttt tctactgggc cattaactgt 600
ggtgctttgt tgggtcaatt catttgtcca atcgttgcca atgattacgg ttcttaccca 660
ttggcttatt ccttgccagc tatcatgttt gttttgggtt tagtcatttt cgtgtccgct 720
aaaaggttgt actatgttaa gccaccatct ggtactgttt tgtctaagac ttactcctgc 780
attaagtacg ccttgtctca tagaaaagct ccattggata atgctaagac caatggtcca 840
atagaacact ggttggatta cgctaaagtt gatggttttg aatgggatga ctccttcgtt 900
gaggatttga aaaaaacctt gagagcctcc ttggtgtttt tgttttatcc atttttattgg 960 gccctgtact acaacatgtc tgacaacttt attaacatgg gcttgaccat gcaaaggcca 1020
tcttttattt ctggtccaga acagttgaac ctgatcaact ctttggtttt ggttgttgcc 1080
attccaatct tcgataccat catcttccca ctgttgagaa aaatgggttg tagattgggt 1140
ccaattacca gaattactat cggttttacc attgctacct tggcctttgt ttacgttacc 1200
atattgcaag accaagtcta caagactggt ccttactaca atttcactga cttgtctggt 1260
ttacctgctg gtgaacaacc agttaacgat attactattt ggtggcaaat catccccttc 1320
attggtattg ccatttccga aattttcgct tctgttaccg gtttggaatt cgcttttaga 1380
caagctgctc ctgaattgaa gtctgttgtt actgctttgt tcctgtttac caattgtggt 1440
ggttcattga tcggtttgat tttggctatt tggtccaacg atccaaactt cgtttacgtt 1500
ttcggtatcc aaactggttt gatgggtgtt atgaccatta tcttctattg gctgttcaga 1560
aagtacgatg ccattgattg ctga 1584

<210> SEQ ID NO 14
<211> LENGTH: 527
<212> TYPE: PRT
<213> ORGANISM: Basidiobolus meristosporus

<400> SEQUENCE: 14

Met Ser Asn Glu Lys Pro Asp His Asp Lys Glu Val Asn Tyr Val Asp
1 5 10 15

Asp Lys Ile Glu Glu Gln Pro Asn Pro Asp Asp Ile Glu Lys Arg Val
20 25 30

Ala Gly Lys Val Pro Leu Ala Ala Trp Phe Ile Ile Ile Thr Glu Leu
35 40 45

Cys Glu Arg Phe Ala Phe Tyr Gly Ala Ser Leu Met Phe Gln Pro Tyr
50 55 60

Met Leu Lys Met Leu Gly Phe Ser Lys Gly Thr Ala Thr Ala Val Asn
65 70 75 80

Arg Gly Phe Gln Phe Leu Ala Tyr Phe Thr Thr Ile Leu Gly Ala Val
85 90 95

Val Ala Asp Arg Tyr Val Gly Lys Phe Lys Thr Ile Val Ile Phe Ser
100 105 110

Leu Phe Tyr Met Ile Gly Leu Ile Ile Leu Ala Leu Ser Ala Leu Pro
115 120 125

Ser Ser Leu Glu Gly Ser Phe Gly Ile Ile Gly Phe Ile Ile Ala Leu
130 135 140

Tyr Ala Phe Ile Ser Phe Gly Thr Gly Gly Ile Lys Ser Asn Val Ser
145 150 155 160

Ser Phe Ala Ala Glu Gln Ile Lys Glu Gly Ile Phe Pro Thr Lys Thr
165 170 175

Pro Gly Val Tyr Ile Asp Ser Gln Leu Thr Val Glu Arg Ile Phe Arg

```
            180                 185                 190

Phe Phe Tyr Trp Ala Ile Asn Cys Gly Ala Leu Leu Gly Gln Phe Ile
        195                 200                 205

Cys Pro Ile Val Ala Asn Asp Tyr Gly Ser Tyr Pro Leu Ala Tyr Ser
    210                 215                 220

Leu Pro Ala Ile Met Phe Val Leu Gly Leu Val Ile Phe Val Ser Ala
225                 230                 235                 240

Lys Arg Leu Tyr Tyr Val Lys Pro Pro Ser Gly Thr Val Leu Ser Lys
                245                 250                 255

Thr Tyr Ser Cys Ile Lys Tyr Ala Leu Ser His Arg Lys Ala Pro Leu
            260                 265                 270

Asp Asn Ala Lys Thr Asn Gly Pro Ile Glu His Trp Leu Asp Tyr Ala
        275                 280                 285

Lys Val Asp Gly Phe Glu Trp Asp Asp Ser Phe Val Glu Asp Leu Lys
    290                 295                 300

Lys Thr Leu Arg Ala Ser Leu Val Phe Leu Phe Tyr Pro Phe Tyr Trp
305                 310                 315                 320

Ala Leu Tyr Tyr Asn Met Ser Asp Asn Phe Ile Asn Met Gly Leu Thr
                325                 330                 335

Met Gln Arg Pro Ser Phe Ile Ser Gly Pro Glu Gln Leu Asn Leu Ile
            340                 345                 350

Asn Ser Leu Val Leu Val Val Ala Ile Pro Ile Phe Asp Thr Ile Ile
        355                 360                 365

Phe Pro Leu Leu Arg Lys Met Gly Cys Arg Leu Gly Pro Ile Thr Arg
    370                 375                 380

Ile Thr Ile Gly Phe Thr Ile Ala Thr Leu Ala Phe Val Tyr Val Thr
385                 390                 395                 400

Ile Leu Gln Asp Gln Val Tyr Lys Thr Gly Pro Tyr Tyr Asn Phe Thr
                405                 410                 415

Asp Leu Ser Gly Leu Pro Ala Gly Glu Gln Pro Val Asn Asp Ile Thr
            420                 425                 430

Ile Trp Trp Gln Ile Ile Pro Phe Ile Gly Ile Ala Ile Ser Glu Ile
        435                 440                 445

Phe Ala Ser Val Thr Gly Leu Glu Phe Ala Phe Arg Gln Ala Ala Pro
    450                 455                 460

Glu Leu Lys Ser Val Val Thr Ala Leu Phe Leu Phe Thr Asn Cys Gly
465                 470                 475                 480

Gly Ser Leu Ile Gly Leu Ile Leu Ala Ile Trp Ser Asn Asp Pro Asn
                485                 490                 495

Phe Val Tyr Val Phe Gly Ile Gln Thr Gly Leu Met Gly Val Met Thr
            500                 505                 510

Ile Ile Phe Tyr Trp Leu Phe Arg Lys Tyr Asp Ala Ile Asp Cys
        515                 520                 525


<210> SEQ ID NO 15
<211> LENGTH: 1539
<212> TYPE: DNA
<213> ORGANISM: Smittium culicis

<400> SEQUENCE: 15

atgagggtca aagaattcaa gccagaaact gctacttcta acgaattcac cgaagaacac      60

tcttacacca ttccaaagga ttaccaaaaa ggtatcccag gcaatttgaa gttggcttct     120

aaattggtta tcgtcaccga attgtgtgaa aggtttacct tctacggtat ctctgttatg     180
```

```
ttgccctctt acttgattga cgttttcggt ttgtcatcct ctgaaactgt ttttagagct    240

aaggcctttt ccttcttggc ttactttttt actatcgttg gtgctatcgt tgccgatgaa    300

tggtttggta aattcaagac cgttatgatc ttctccatct ggtactttgt tggtactgtt    360

atcttgtccg ttacctccat ggatttcttg tctgtttctg gtaagaacgt tggtttcatc    420

gttgctatct acgcttttat tgcttttggt actggtggta ttaaggccaa cgtttcttct    480

tttgttgccg aacaagttga ccccgttttc aaaaaaacaa agaacccagg tatctacatc    540

gatccaaagt tggctattga aagatgctac agatacttct actgggctat taacaccggt    600

gctattttgg gtttagctgt ttgtccacaa ttggctaaaa gagctggtta cgcttctggt    660

tattggtcta ctgctgctgt taattttgtt ggcttcggta tattcttcct gggcagatct    720

aagtacaaga tggttaatcc atcagagtcc gctttgaaga aggtttacag agttatttcc    780

tacgccagaa agaacaaaaa gaccgattct gatcattggt tggatgctgc taaaggtgtt    840

aattctccac aatggaatga tgaattcgtc gaaggtttga agggttctat taaggctgtt    900

aagatcttgt gcttcttgcc aatctattgg atgttgtaca tgaacgttac cgacaacttt    960

atcttgcagg ctagaagaat gaaggaacct tcttggattt cctccgacca attgatcttg   1020

ttggttcaat tgaccttggt tatcttgatc cccttgtacg attacttctt catcccattc   1080

ttgaggttcc gtaacattaa gtttggtcca atcaagagaa tcaccatcgg tttcgttttg   1140

attaccttgg gtttcatcta caccatcatc acccaaaaga gaatctataa ctctccacca   1200

tacttcaact ttactgctcc aggttctaac ttggatcaga agaacaatat ttccttgtgg   1260

tggcaaatcc cctcctttat tttcttgggt tcctcagaaa ttttcgcctc tgttacctct   1320

ttggaaattg ccttttcatt gtctccacca gagttgaagt ctctgttgaa ctctttgtct   1380

ttgttcacca tttgcttggg taacttgttg ggtatgtctc tgtctaagtt gtcttacgat   1440

ccaatcatct tgaacgtcta cattggtgaa gcttgtgcta tgatcgttac caccatcata   1500

ttctttttct gcttccgttc tttcgacaag acctactaa                          1539
```

<210> SEQ ID NO 16
<211> LENGTH: 512
<212> TYPE: PRT
<213> ORGANISM: Smittium culicis

<400> SEQUENCE: 16

```
Met Arg Val Lys Glu Phe Lys Pro Glu Thr Ala Thr Ser Asn Glu Phe
1               5                   10                  15

Thr Glu Glu His Ser Tyr Thr Ile Pro Lys Asp Tyr Gln Lys Gly Ile
            20                  25                  30

Pro Gly Asn Leu Lys Leu Ala Ser Lys Leu Val Ile Val Thr Glu Leu
        35                  40                  45

Cys Glu Arg Phe Thr Phe Tyr Gly Ile Ser Val Met Leu Pro Ser Tyr
    50                  55                  60

Leu Ile Asp Val Phe Gly Leu Ser Ser Ser Glu Thr Val Phe Arg Ala
65                  70                  75                  80

Lys Ala Phe Ser Phe Leu Ala Tyr Phe Phe Thr Ile Val Gly Ala Ile
                85                  90                  95

Val Ala Asp Glu Trp Phe Gly Lys Phe Lys Thr Val Met Ile Phe Ser
            100                 105                 110

Ile Trp Tyr Phe Val Gly Thr Val Ile Leu Ser Val Thr Ser Met Asp
        115                 120                 125

Phe Leu Ser Val Ser Gly Lys Asn Val Gly Phe Ile Val Ala Ile Tyr
```

```
    130                 135                 140

Ala Phe Ile Ala Phe Gly Thr Gly Gly Ile Lys Ala Asn Val Ser Ser
145                 150                 155                 160

Phe Val Ala Glu Gln Val Asp Pro Val Phe Lys Lys Thr Lys Asn Pro
                165                 170                 175

Gly Ile Tyr Ile Asp Pro Lys Leu Ala Ile Glu Arg Cys Tyr Arg Tyr
            180                 185                 190

Phe Tyr Trp Ala Ile Asn Thr Gly Ala Ile Leu Gly Leu Ala Val Cys
        195                 200                 205

Pro Gln Leu Ala Lys Arg Ala Gly Tyr Ala Ser Gly Tyr Trp Ser Thr
    210                 215                 220

Ala Ala Val Asn Phe Val Gly Phe Gly Ile Phe Phe Leu Gly Arg Ser
225                 230                 235                 240

Lys Tyr Lys Met Val Asn Pro Ser Glu Ser Ala Leu Lys Lys Val Tyr
                245                 250                 255

Arg Val Ile Ser Tyr Ala Arg Lys Asn Lys Lys Thr Asp Ser Asp His
            260                 265                 270

Trp Leu Asp Ala Ala Lys Gly Val Asn Ser Pro Gln Trp Asn Asp Glu
        275                 280                 285

Phe Val Glu Gly Leu Lys Gly Ser Ile Lys Ala Val Lys Ile Leu Cys
    290                 295                 300

Phe Leu Pro Ile Tyr Trp Met Leu Tyr Met Asn Val Thr Asp Asn Phe
305                 310                 315                 320

Ile Leu Gln Ala Arg Arg Met Lys Glu Pro Ser Trp Ile Ser Ser Asp
                325                 330                 335

Gln Leu Ile Leu Leu Val Gln Leu Thr Leu Val Ile Leu Ile Pro Leu
            340                 345                 350

Tyr Asp Tyr Phe Phe Ile Pro Phe Leu Arg Phe Arg Asn Ile Lys Phe
        355                 360                 365

Gly Pro Ile Lys Arg Ile Thr Ile Gly Phe Val Leu Ile Thr Leu Gly
    370                 375                 380

Phe Ile Tyr Thr Ile Ile Thr Gln Lys Arg Ile Tyr Asn Ser Pro Pro
385                 390                 395                 400

Tyr Phe Asn Phe Thr Ala Pro Gly Ser Asn Leu Asp Gln Lys Asn Asn
                405                 410                 415

Ile Ser Leu Trp Trp Gln Ile Pro Ser Phe Ile Phe Leu Gly Ser Ser
            420                 425                 430

Glu Ile Phe Ala Ser Val Thr Ser Leu Glu Ile Ala Phe Ser Leu Ser
        435                 440                 445

Pro Pro Glu Leu Lys Ser Leu Leu Asn Ser Leu Ser Leu Phe Thr Ile
    450                 455                 460

Cys Leu Gly Asn Leu Leu Gly Met Ser Leu Ser Lys Leu Ser Tyr Asp
465                 470                 475                 480

Pro Ile Ile Leu Asn Val Tyr Ile Gly Glu Ala Cys Ala Met Ile Val
                485                 490                 495

Thr Thr Ile Ile Phe Phe Phe Cys Phe Arg Ser Phe Asp Lys Thr Tyr
            500                 505                 510
```

<210> SEQ ID NO 17
<211> LENGTH: 1911
<212> TYPE: DNA
<213> ORGANISM: Arabidopsis thaliana

<400> SEQUENCE: 17

```
atgaagtcca gggttatctt gaaccacaga gatagaagag ataagaacca taacaacaac      60
aataccaacc actacaccca agttgatacc atggaaagaa aaccattgga agttgaacca     120
tctactacta ccactaacac cgatgttgtt gactcattcg aagaagaaca acgtaagatc     180
gtttacagag gttggaaagt tatgccattc atcattggta acgaaacctt cgaaaagttg     240
ggtatcatag gcactttgtc caacttgttg gtttacttga cttccgtgtt caacttgaag     300
tcttatactg ctgccaccat tattaacgct ttctccggta ctattaactt cggtactttt     360
attgctgcct tcttgtgtga tacttacttc ggtagataca agaccttgtc cgttgctgtt     420
attgcttgtt ttttgggttc cttcgttatt ttgttgaccg ctgctattcc atcattgcat     480
ccagttgctt gtggtaacaa gatttcttgt gaaggtccat ccgttggtca gattttgttt     540
ttgttgatgg gtttgggttt cttggttgtt ggtgctggtg gtattagacc atgtaatttg     600
gcttttggtg ccgatcaatt caacccaaaa tcagaatctg gtaagaaggg catcaactca     660
tttttcaact ggtacttttt caccttcacc ttcgctcaaa ttatctcctt gactgccgtt     720
gtttacatcc agtctaatgt ttcttggacc atcggtttga ttattccagt tgccttgatg     780
ttcttggcct gcgttatttt ctttgccggt gatagattat acgttaaggt taaggcttct     840
ggttctccat tggctggtat tgctagagtt attgcagctg ctattaagaa gagaggtttg     900
aagccagtta agcaaccatg ggttaacttg tacaaccaca ttccatctaa ctacgctaac     960
actactttga agtacaccga ccaattcaga ttcttggata aggctgcaat tatgacccca    1020
gaagaaaagt tgaattctga tggtactgct tctgatccat ggaagttgtg tactttacaa    1080
caagtcgaag aggttaagtg catcgttaga gttatcccaa tttggttcgc ttccaccatc    1140
tattacttgg ccattactat ccaaatgacg tacccagttt tccaagcctt gcaatctgat    1200
agaagattag gttcaggtgg tttcagaatt ccagctgcta cttatgttgt tttcttgatg    1260
actggtatga ccgtgttcat catcttctac gatagagttt tggtcccatc cttgagaaga    1320
gttactggtt tggaaactgg tatctctttg ttgcaaagaa ttggtgccgg tttcactttc    1380
gctattatgt ctttgttagt ctccggtttc atcgaagaga gaagaagaaa tttcgctttg    1440
accaagccaa ctttaggtat ggctccaaga actggtgaaa tctcttcaat gtctgctttg    1500
tggttgattc cacaattgac tttagcaggt attgctgaag cttttgctgc tattggtcaa    1560
atggaattct actacaagca gttcccagag aacatgaagt catttgctgg ttccattttt    1620
tacgttggag ctggtgtttc ttcttacttg gcttctttct tgatctccac tgttcataga    1680
actactgctc attctccatc tggtaattgg ttggctgaag atttgaacaa ggctaagttg    1740
gactacttct actttatgtt gaccggtttg atggttgtca atatggctta cttcttgtta    1800
atggctagat ggtacagata caaaggtggt aacgatgaag atatcaccga aatcgaaact    1860
aacgaggaag aaactaagca acaacagttg caagacaaga actccgtttg a             1911
```

<210> SEQ ID NO 18
<211> LENGTH: 636
<212> TYPE: PRT
<213> ORGANISM: Arabidopsis thaliana

<400> SEQUENCE: 18

```
Met Lys Ser Arg Val Ile Leu Asn His Arg Asp Arg Arg Asp Lys Asn
1               5                   10                  15

His Asn Asn Asn Asn Thr Asn His Tyr Thr Gln Val Asp Thr Met Glu
            20                  25                  30

Arg Lys Pro Leu Glu Val Glu Pro Ser Thr Thr Thr Thr Asn Thr Asp
```

```
        35                  40                  45

Val Val Asp Ser Phe Glu Glu Glu Gln Arg Lys Ile Val Tyr Arg Gly
    50                  55                  60

Trp Lys Val Met Pro Phe Ile Ile Gly Asn Glu Thr Phe Glu Lys Leu
65                  70                  75                  80

Gly Ile Ile Gly Thr Leu Ser Asn Leu Leu Val Tyr Leu Thr Ser Val
                85                  90                  95

Phe Asn Leu Lys Ser Tyr Thr Ala Ala Thr Ile Ile Asn Ala Phe Ser
            100                 105                 110

Gly Thr Ile Asn Phe Gly Thr Phe Ile Ala Ala Phe Leu Cys Asp Thr
        115                 120                 125

Tyr Phe Gly Arg Tyr Lys Thr Leu Ser Val Ala Val Ile Ala Cys Phe
    130                 135                 140

Leu Gly Ser Phe Val Ile Leu Leu Thr Ala Ala Ile Pro Ser Leu His
145                 150                 155                 160

Pro Val Ala Cys Gly Asn Lys Ile Ser Cys Glu Gly Pro Ser Val Gly
                165                 170                 175

Gln Ile Leu Phe Leu Leu Met Gly Leu Gly Phe Leu Val Val Gly Ala
            180                 185                 190

Gly Gly Ile Arg Pro Cys Asn Leu Ala Phe Gly Ala Asp Gln Phe Asn
        195                 200                 205

Pro Lys Ser Glu Ser Gly Lys Lys Gly Ile Asn Ser Phe Phe Asn Trp
    210                 215                 220

Tyr Phe Phe Thr Phe Thr Phe Ala Gln Ile Ile Ser Leu Thr Ala Val
225                 230                 235                 240

Val Tyr Ile Gln Ser Asn Val Ser Trp Thr Ile Gly Leu Ile Ile Pro
                245                 250                 255

Val Ala Leu Met Phe Leu Ala Cys Val Ile Phe Phe Ala Gly Asp Arg
            260                 265                 270

Leu Tyr Val Lys Val Lys Ala Ser Gly Ser Pro Leu Ala Gly Ile Ala
        275                 280                 285

Arg Val Ile Ala Ala Ala Ile Lys Lys Arg Gly Leu Lys Pro Val Lys
    290                 295                 300

Gln Pro Trp Val Asn Leu Tyr Asn His Ile Pro Ser Asn Tyr Ala Asn
305                 310                 315                 320

Thr Thr Leu Lys Tyr Thr Asp Gln Phe Arg Phe Leu Asp Lys Ala Ala
                325                 330                 335

Ile Met Thr Pro Glu Glu Lys Leu Asn Ser Asp Gly Thr Ala Ser Asp
            340                 345                 350

Pro Trp Lys Leu Cys Thr Leu Gln Gln Val Glu Glu Val Lys Cys Ile
        355                 360                 365

Val Arg Val Ile Pro Ile Trp Phe Ala Ser Thr Ile Tyr Tyr Leu Ala
    370                 375                 380

Ile Thr Ile Gln Met Thr Tyr Pro Val Phe Gln Ala Leu Gln Ser Asp
385                 390                 395                 400

Arg Arg Leu Gly Ser Gly Gly Phe Arg Ile Pro Ala Ala Thr Tyr Val
                405                 410                 415

Val Phe Leu Met Thr Gly Met Thr Val Phe Ile Ile Phe Tyr Asp Arg
            420                 425                 430

Val Leu Val Pro Ser Leu Arg Arg Val Thr Gly Leu Glu Thr Gly Ile
        435                 440                 445

Ser Leu Leu Gln Arg Ile Gly Ala Gly Phe Thr Phe Ala Ile Met Ser
    450                 455                 460
```

```
Leu Leu Val Ser Gly Phe Ile Glu Glu Arg Arg Arg Asn Phe Ala Leu
465                 470                 475                 480

Thr Lys Pro Thr Leu Gly Met Ala Pro Arg Thr Gly Glu Ile Ser Ser
                485                 490                 495

Met Ser Ala Leu Trp Leu Ile Pro Gln Leu Thr Leu Ala Gly Ile Ala
            500                 505                 510

Glu Ala Phe Ala Ala Ile Gly Gln Met Glu Phe Tyr Tyr Lys Gln Phe
        515                 520                 525

Pro Glu Asn Met Lys Ser Phe Ala Gly Ser Ile Phe Tyr Val Gly Ala
    530                 535                 540

Gly Val Ser Ser Tyr Leu Ala Ser Phe Leu Ile Ser Thr Val His Arg
545                 550                 555                 560

Thr Thr Ala His Ser Pro Ser Gly Asn Trp Leu Ala Glu Asp Leu Asn
                565                 570                 575

Lys Ala Lys Leu Asp Tyr Phe Tyr Phe Met Leu Thr Gly Leu Met Val
            580                 585                 590

Val Asn Met Ala Tyr Phe Leu Leu Met Ala Arg Trp Tyr Arg Tyr Lys
        595                 600                 605

Gly Gly Asn Asp Glu Asp Ile Thr Glu Ile Glu Thr Asn Glu Glu Glu
    610                 615                 620

Thr Lys Gln Gln Gln Leu Gln Asp Lys Asn Ser Val
625                 630                 635


<210> SEQ ID NO 19
<211> LENGTH: 1698
<212> TYPE: DNA
<213> ORGANISM: Rhizopus microsporus

<400> SEQUENCE: 19

atgaacgaag agaagcagga ctccatcatc gaaactaact ctaagcacaa caatttcttc     60

gaaacctaca acgaagaata cccagaacct actgaagaag attggaaatc tttgccagaa    120

gtttctgacg ctattccaaa agctgctttc ttggttatct tgatcgaatt ctgtgaaagg    180

ttcacctact atggtttgtc tggtccattc caaaactaca ttcaaaatcc accacctcca    240

tcttatccag cttcattgcc aggtgctatg ggtaaaggtc aacaaactgc tactgctttg    300

aacacctttt tcactttctg gtgttacatc accccaattt tgggtgctgt tattgctgat    360

caattctggg gtaagtacag aaccattctg gttttctcca ttatctactt gttgggttta    420

gccattttga ccttgacttc tattccacca gctattgctt caggtgcttc ttttcctggt    480

tatatcgttg ccattatcat cgtcggttta ggtactggtg gtatcaagtc taatgtttca    540

ccattggttg ctgaacagta cagatctaaa tctgcttacg ttaagacctt gaagaacggt    600

aagagagtta tcgttactcc acaagctacc taccaaaaga tcttcaactt tttctactgg    660

ggcatcaaca tcggttcttt gtctgctatt gctactaccg aattggaaaa gaatgttggt    720

ttttggccag ctttcgtttt gccaactttg atgtttattc cctgcatcat catcgtcatc    780

ttgggtagaa atcagtacat tcagaaccca cctagaggtt ctgtttttgt tgaagctggt    840

agactgtttt ggttgtcttg gaaagtaaaa ggtggtttgg atgcttgtaa gccatctaat    900

ttggctagag aatatccaga atacgctatt aaggctacct gggatgatgt tttcgttgac    960

gaattgaaga gaaccttgaa ggcttgtgtt atcttctgtt ggtatccaat ctactggttg   1020

tgctattctc aaatgaccaa caacttggtt tctatggctg gtactatgtt gactggtaat   1080

gttccaaacg acatcatgca aaacattgat ccaattgcct tgattatcat catccccatc   1140
```

atggattcta tcgtttatcc aggtttgaga aggttaggtt tgccaatgag gccaattgct 1200
agaattactt gtggtttttt ctttgctgct gctgcaatgg gttatactgc tggtattcaa 1260
tccatggttt acaagtctgc tccttactat gatcatccag aaggtagaca aaactggatt 1320
tctgctgctt atttgatccc atcctacgtt ttgattgcca tctctgaaat tttcgcctct 1380
attaccggta tggaatacgc ttacaaaaag gctccacaat ccatgaagtc tatcgttatg 1440
gctttgttct tgttgaccaa ctgcttcgct tctattttgg cttttgcttt ggtttccgtt 1500
gctgttgatc caaagttaga atggatgtac acaggtattt ccgctgctat gttcttctgt 1560
accattatgt tctacatctg ccatcataag gctgatgata ctgatgtaga agaagatgcc 1620
atcgttagag ataacatggc tcaaaaagct accgatgacg aaatcgttac tgaatacgaa 1680
ttggagaaaa acaggtaa 1698

<210> SEQ ID NO 20
<211> LENGTH: 565
<212> TYPE: PRT
<213> ORGANISM: Rhizopus microsporus

<400> SEQUENCE: 20

Met Asn Glu Glu Lys Gln Asp Ser Ile Ile Glu Thr Asn Ser Lys His
1 5 10 15

Asn Asn Phe Phe Glu Thr Tyr Asn Glu Glu Tyr Pro Glu Pro Thr Glu
20 25 30

Glu Asp Trp Lys Ser Leu Pro Glu Val Ser Asp Ala Ile Pro Lys Ala
35 40 45

Ala Phe Leu Val Ile Leu Ile Glu Phe Cys Glu Arg Phe Thr Tyr Tyr
50 55 60

Gly Leu Ser Gly Pro Phe Gln Asn Tyr Ile Gln Asn Pro Pro Pro Pro
65 70 75 80

Ser Tyr Pro Ala Ser Leu Pro Gly Ala Met Gly Lys Gly Gln Gln Thr
85 90 95

Ala Thr Ala Leu Asn Thr Phe Phe Thr Phe Trp Cys Tyr Ile Thr Pro
100 105 110

Ile Leu Gly Ala Val Ile Ala Asp Gln Phe Trp Gly Lys Tyr Arg Thr
115 120 125

Ile Leu Val Phe Ser Ile Ile Tyr Leu Leu Gly Leu Ala Ile Leu Thr
130 135 140

Leu Thr Ser Ile Pro Pro Ala Ile Ala Ser Gly Ala Ser Phe Pro Gly
145 150 155 160

Tyr Ile Val Ala Ile Ile Ile Val Gly Leu Gly Thr Gly Gly Ile Lys
165 170 175

Ser Asn Val Ser Pro Leu Val Ala Glu Gln Tyr Arg Ser Lys Ser Ala
180 185 190

Tyr Val Lys Thr Leu Lys Asn Gly Lys Arg Val Ile Val Thr Pro Gln
195 200 205

Ala Thr Tyr Gln Lys Ile Phe Asn Phe Phe Tyr Trp Gly Ile Asn Ile
210 215 220

Gly Ser Leu Ser Ala Ile Ala Thr Thr Glu Leu Glu Lys Asn Val Gly
225 230 235 240

Phe Trp Pro Ala Phe Val Leu Pro Thr Leu Met Phe Ile Pro Cys Ile
245 250 255

Ile Ile Val Ile Leu Gly Arg Asn Gln Tyr Ile Gln Asn Pro Pro Arg
260 265 270

```
Gly Ser Val Phe Val Glu Ala Gly Arg Leu Phe Trp Leu Ser Trp Lys
        275                 280                 285

Val Lys Gly Gly Leu Asp Ala Cys Lys Pro Ser Asn Leu Ala Arg Glu
    290                 295                 300

Tyr Pro Glu Tyr Ala Ile Lys Ala Thr Trp Asp Asp Val Phe Val Asp
305                 310                 315                 320

Glu Leu Lys Arg Thr Leu Lys Ala Cys Val Ile Phe Cys Trp Tyr Pro
                325                 330                 335

Ile Tyr Trp Leu Cys Tyr Ser Gln Met Thr Asn Asn Leu Val Ser Met
            340                 345                 350

Ala Gly Thr Met Leu Thr Gly Asn Val Pro Asn Asp Ile Met Gln Asn
        355                 360                 365

Ile Asp Pro Ile Ala Leu Ile Ile Ile Ile Pro Ile Met Asp Ser Ile
    370                 375                 380

Val Tyr Pro Gly Leu Arg Arg Leu Gly Leu Pro Met Arg Pro Ile Ala
385                 390                 395                 400

Arg Ile Thr Cys Gly Phe Phe Phe Ala Ala Ala Met Gly Tyr Thr
                405                 410                 415

Ala Gly Ile Gln Ser Met Val Tyr Lys Ser Ala Pro Tyr Tyr Asp His
            420                 425                 430

Pro Glu Gly Arg Gln Asn Trp Ile Ser Ala Ala Tyr Leu Ile Pro Ser
        435                 440                 445

Tyr Val Leu Ile Ala Ile Ser Glu Ile Phe Ala Ser Ile Thr Gly Met
    450                 455                 460

Glu Tyr Ala Tyr Lys Lys Ala Pro Gln Ser Met Lys Ser Ile Val Met
465                 470                 475                 480

Ala Leu Phe Leu Leu Thr Asn Cys Phe Ala Ser Ile Leu Ala Phe Ala
                485                 490                 495

Leu Val Ser Val Ala Val Asp Pro Lys Leu Glu Trp Met Tyr Thr Gly
            500                 505                 510

Ile Ser Ala Ala Met Phe Phe Cys Thr Ile Met Phe Tyr Ile Cys His
        515                 520                 525

His Lys Ala Asp Asp Thr Asp Val Glu Glu Asp Ala Ile Val Arg Asp
    530                 535                 540

Asn Met Ala Gln Lys Ala Thr Asp Asp Glu Ile Val Thr Glu Tyr Glu
545                 550                 555                 560

Leu Glu Lys Asn Arg
                565
```

<210> SEQ ID NO 21
<211> LENGTH: 1797
<212> TYPE: DNA
<213> ORGANISM: Chelidonium majus

<400> SEQUENCE: 21

```
atggaaatgg aaaaagagaa gcaaaagtcc gaagatatgg gtgctgatta tgatgaacct      60

aacaagaaga tcatcaacta cagaggtgtt aaggtcatgc cattcattat tggtaacgaa     120

accttcgaga agttgggtac tattggtact tctaccaact tgatggttta cttgactacc     180

gtgttcaaca tgaagtctgt ttctgctgct actctgatga atatgttcaa tggcactact     240

aatttggccc ctttgtttgg tgcttttttg tctgatgctt atttcggtag gtacatcact     300

ttgggtttcg cctctatttc ttctttcttg ggtatgttcg ttttgacttt gaccgctgct     360

atttctaaat tgcatccacc acattgtggt actaaggata ctgctatgtg tattggtcca     420
```

actgttggtc agttgacttt tttgttgact ggtttcgctt tcttgatagt tggtgctggt 480
ggtattagac catgtaattt ggcttttggt gccgatcaat tcaacccaaa aactgaatct 540
ggtaagaagg gcatcaactc atttttcaac tggtactact tcactttcac cttcgctatg 600
atggtttctt tgaccttgat cgtttacgtc cagtctaata tcaattgggc tttaggtttg 660
gccattccaa tgttcttgat gtttttatcc ggtgccttgt tcttcatggg cactagaatg 720
tatgttatcg ttaagccaga aggctctcca ttgaaatctg ttgctcaagt tatggttgct 780
gctacgaaga aaagaagatt gaagttgcca gaaaacaacc ccgaattgtc tttgtttaat 840
tacttgccag ccaactccat caactctaga ttgcctttta cagaccagtt cagattcttg 900
gataaggctg ctatcgttac aaacgacgat aagatcaatc aagatggttc agctgctaat 960
ccttggagat tgtgtagaat gcaacaaatc gaagaggtca agtgcttgat gagagttatt 1020
ccaatttggg cctctggtat cattttctac gttaccatag ttcaacaaca cacctttgct 1080
gtttttcaag ccttgcaatc tgatagaaga ttgggtgaat ctagctttca agttccagct 1140
gcttcttaca tcgttttcca aatgttgtct ttgaccatct ggatcccaat ctacgatcaa 1200
gttatagtcc catccttgag aaagttgaca ggtaaagaag gtggtatcac cttgttgcaa 1260
agaatgggta ttggtatcgt cttgtccatt atcaccatgt tggtttctgc tttggttgaa 1320
gaaaaaagaa gaggttttgc tttcaccaag ccaactttgg gtactgctag aggtggtggt 1380
gctatttcat ctatgtctgg tttgtggttg attgcccaac taactattgc tggtttatcc 1440
gaagctttca acttgattgg tcagatcgaa ttctactaca agcaattccc tgaaaacatg 1500
agatctattg ccggttcctt tttgttttgt ggtatggctg gtgctaacta cttgtcaggt 1560
tttatggttt ccatcgttca tagaactacc gagggttctt ctatgggtaa ttggttggat 1620
gaagatttga acaagggcaa gttggactac ttctactatg ttattgcagg tttgggtgtt 1680
ttgaacttcg gttacttttt agtttgcgct agatggtaca gatacaaggg tacaattgat 1740
ggtgacacta ttgaaatggc tatggaaact gaacaaaccg aaaagcacgt tgtctga 1797

<210> SEQ ID NO 22
<211> LENGTH: 598
<212> TYPE: PRT
<213> ORGANISM: Chelidonium majus

<400> SEQUENCE: 22

Met Glu Met Glu Lys Glu Lys Gln Lys Ser Glu Asp Met Gly Ala Asp
1 5 10 15

Tyr Asp Glu Pro Asn Lys Lys Ile Ile Asn Tyr Arg Gly Val Lys Val
20 25 30

Met Pro Phe Ile Ile Gly Asn Glu Thr Phe Glu Lys Leu Gly Thr Ile
35 40 45

Gly Thr Ser Thr Asn Leu Met Val Tyr Leu Thr Thr Val Phe Asn Met
50 55 60

Lys Ser Val Ser Ala Ala Thr Leu Met Asn Met Phe Asn Gly Thr Thr
65 70 75 80

Asn Leu Ala Pro Leu Phe Gly Ala Phe Leu Ser Asp Ala Tyr Phe Gly
85 90 95

Arg Tyr Ile Thr Leu Gly Phe Ala Ser Ile Ser Ser Phe Leu Gly Met
100 105 110

Phe Val Leu Thr Leu Thr Ala Ala Ile Ser Lys Leu His Pro Pro His
115 120 125

-continued

```
Cys Gly Thr Lys Asp Thr Ala Met Cys Ile Gly Pro Thr Val Gly Gln
    130                 135                 140

Leu Thr Phe Leu Leu Thr Gly Phe Ala Phe Leu Ile Val Gly Ala Gly
145                 150                 155                 160

Gly Ile Arg Pro Cys Asn Leu Ala Phe Gly Ala Asp Gln Phe Asn Pro
                165                 170                 175

Lys Thr Glu Ser Gly Lys Lys Gly Ile Asn Ser Phe Phe Asn Trp Tyr
            180                 185                 190

Tyr Phe Thr Phe Thr Phe Ala Met Met Val Ser Leu Thr Leu Ile Val
        195                 200                 205

Tyr Val Gln Ser Asn Ile Asn Trp Ala Leu Gly Leu Ala Ile Pro Met
    210                 215                 220

Phe Leu Met Phe Leu Ser Gly Ala Leu Phe Phe Met Gly Thr Arg Met
225                 230                 235                 240

Tyr Val Ile Val Lys Pro Glu Gly Ser Pro Leu Lys Ser Val Ala Gln
                245                 250                 255

Val Met Val Ala Ala Thr Lys Lys Arg Arg Leu Lys Leu Pro Glu Asn
            260                 265                 270

Asn Pro Glu Leu Ser Leu Phe Asn Tyr Leu Pro Ala Asn Ser Ile Asn
        275                 280                 285

Ser Arg Leu Pro Phe Thr Asp Gln Phe Arg Phe Leu Asp Lys Ala Ala
    290                 295                 300

Ile Val Thr Asn Asp Asp Lys Ile Asn Gln Asp Gly Ser Ala Ala Asn
305                 310                 315                 320

Pro Trp Arg Leu Cys Arg Met Gln Gln Ile Glu Glu Val Lys Cys Leu
                325                 330                 335

Met Arg Val Ile Pro Ile Trp Ala Ser Gly Ile Ile Phe Tyr Val Thr
            340                 345                 350

Ile Val Gln Gln His Thr Phe Ala Val Phe Gln Ala Leu Gln Ser Asp
        355                 360                 365

Arg Arg Leu Gly Glu Ser Ser Phe Gln Val Pro Ala Ala Ser Tyr Ile
    370                 375                 380

Val Phe Gln Met Leu Ser Leu Thr Ile Trp Ile Pro Ile Tyr Asp Gln
385                 390                 395                 400

Val Ile Val Pro Ser Leu Arg Lys Leu Thr Gly Lys Glu Gly Gly Ile
                405                 410                 415

Thr Leu Leu Gln Arg Met Gly Ile Gly Ile Val Leu Ser Ile Ile Thr
            420                 425                 430

Met Leu Val Ser Ala Leu Val Glu Glu Lys Arg Arg Gly Phe Ala Phe
        435                 440                 445

Thr Lys Pro Thr Leu Gly Thr Ala Arg Gly Gly Gly Ala Ile Ser Ser
    450                 455                 460

Met Ser Gly Leu Trp Leu Ile Ala Gln Leu Thr Ile Ala Gly Leu Ser
465                 470                 475                 480

Glu Ala Phe Asn Leu Ile Gly Gln Ile Glu Phe Tyr Tyr Lys Gln Phe
                485                 490                 495

Pro Glu Asn Met Arg Ser Ile Ala Gly Ser Phe Leu Phe Cys Gly Met
            500                 505                 510

Ala Gly Ala Asn Tyr Leu Ser Gly Phe Met Val Ser Ile Val His Arg
        515                 520                 525

Thr Thr Glu Gly Ser Ser Met Gly Asn Trp Leu Asp Glu Asp Leu Asn
    530                 535                 540

Lys Gly Lys Leu Asp Tyr Phe Tyr Tyr Val Ile Ala Gly Leu Gly Val
```

545 550 555 560

Leu Asn Phe Gly Tyr Phe Leu Val Cys Ala Arg Trp Tyr Arg Tyr Lys
565 570 575

Gly Thr Ile Asp Gly Asp Thr Ile Glu Met Ala Met Glu Thr Glu Gln
580 585 590

Thr Glu Lys His Val Val
595

<210> SEQ ID NO 23
<211> LENGTH: 1548
<212> TYPE: DNA
<213> ORGANISM: Mortierella elongata

<400> SEQUENCE: 23
atgccaaagg cctgctactt cattttgcca aacgaatttg gtgaaaggtt ctgctattat 60
ggtgttcagc caaacttgaa caagtacttc caattgatta ccggtatgaa cccaactaac 120
gctaaggttt attctactgc tttcaccatg ttggcctact tttttccatt gattggtgct 180
gctttgtccg actctttttt aggtaaatgg tggaccatta tcggtttctc taccgtttat 240
ttgatcggta tgatcatggt taccgttttc gctatcccaa atttgattgg tccaatcggt 300
caagtctcta acttcttgac ttttttgccc atgttggtta ttgccattgg tactggtggt 360
attaagccat gtgtttcttc tcatggtggt gatcaatatt tgccatctca agaagctggt 420
aaggacttgt tcttcaacat cttctacgtt tccattaacg ttggtgcttt gttgacccaa 480
ttcatcgttc caaaaatgac cgaattgaag tgctacggtc aagatacttg ttatgctggt 540 gctttttgt tgccaactgt tgtttttgct ttggccttcg ctatttttg tgctggtcat 600 aagttctaca gaatcgttcc accattgggt gaatttttgc cattgaaagc tgttcaagct 660
tctttgttgg ctgctagaag gcatagagct gcttctccac aagaaagagc tgctaaaggt 720
cattggttga actttgctga agctgaatat ggtggtgtgt tcattgaaga agtcagagat 780
tttggtttgg ttttggttcc agttgttatc ccatttgctt tctgttggat gctgtacaat 840
cagaactcta acgaatgggc taatcagtac tatttgatgt ctggtgcatt attcggtggt 900
aatgacgaaa ctgcttctta tgttcaaggt gctatgttcg gtaacgttaa caccattttg 960
atcatcttgt gggttccatt cttggctact tttgtttacc cattctgtac taagagaggc 1020
tggaattttt caccacaaag aagaatgggt ttgggtttct tggttgttgt tatttccttt 1080
gctgtttcag ctgctttggc tccatctgtt gaaaaagctt atttggaatc cggtaggttg 1140
atgaaggatg ctgctaaata tgatggcaag tactgtgaaa agtgttactc tgcttggtgg 1200
caattaccac aatggatttt gttgtctttg ggtgaagctt tgttttctcc aactggtgtt 1260
caattcacct acattgaagc aggtagacaa ttcagagctg tttctacttc tttctggtta 1320
ttggctacct ccttcggttc tatcttgatt atgattttcg aaccagtttt cgccggctac 1380
aatttgtcat ctggtacaaa aggttgggcc tattctggta ttggtttgtt cggtttcttg 1440
ctgtactgtg ttacttccta ttactacgtt ccaagaaagg tcagaccatc tattaacgaa 1500
gctgctagat tggctaaaaa ggctgaatac gctattacct cctactaa 1548

<210> SEQ ID NO 24
<211> LENGTH: 515
<212> TYPE: PRT
<213> ORGANISM: Mortierella elongata

<400> SEQUENCE: 24

```
Met Pro Lys Ala Cys Tyr Phe Ile Leu Pro Asn Glu Phe Gly Glu Arg
1               5                   10                  15

Phe Cys Tyr Tyr Gly Val Gln Pro Asn Leu Asn Lys Tyr Phe Gln Leu
            20                  25                  30

Ile Thr Gly Met Asn Pro Thr Asn Ala Lys Val Tyr Ser Thr Ala Phe
        35                  40                  45

Thr Met Leu Ala Tyr Phe Phe Pro Leu Ile Gly Ala Ala Leu Ser Asp
    50                  55                  60

Ser Phe Leu Gly Lys Trp Trp Thr Ile Ile Gly Phe Ser Thr Val Tyr
65                  70                  75                  80

Leu Ile Gly Met Ile Met Val Thr Val Phe Ala Ile Pro Asn Leu Ile
                85                  90                  95

Gly Pro Ile Gly Gln Val Ser Asn Phe Leu Thr Phe Leu Pro Met Leu
            100                 105                 110

Val Ile Ala Ile Gly Thr Gly Gly Ile Lys Pro Cys Val Ser Ser His
        115                 120                 125

Gly Gly Asp Gln Tyr Leu Pro Ser Gln Glu Ala Gly Lys Asp Leu Phe
    130                 135                 140

Phe Asn Ile Phe Tyr Val Ser Ile Asn Val Gly Ala Leu Leu Thr Gln
145                 150                 155                 160

Phe Ile Val Pro Lys Met Thr Glu Leu Lys Cys Tyr Gly Gln Asp Thr
                165                 170                 175

Cys Tyr Ala Gly Ala Phe Leu Leu Pro Thr Val Val Phe Ala Leu Ala
            180                 185                 190

Phe Ala Ile Phe Cys Ala Gly His Lys Phe Tyr Arg Ile Val Pro Pro
        195                 200                 205

Leu Gly Glu Phe Leu Pro Leu Lys Ala Val Gln Ala Ser Leu Leu Ala
    210                 215                 220

Ala Arg Arg His Arg Ala Ala Ser Pro Gln Glu Arg Ala Ala Lys Gly
225                 230                 235                 240

His Trp Leu Asn Phe Ala Glu Ala Glu Tyr Gly Gly Val Phe Ile Glu
                245                 250                 255

Glu Val Arg Asp Phe Gly Leu Val Leu Val Pro Val Val Ile Pro Phe
            260                 265                 270

Ala Phe Cys Trp Met Leu Tyr Asn Gln Asn Ser Asn Glu Trp Ala Asn
        275                 280                 285

Gln Tyr Tyr Leu Met Ser Gly Ala Leu Phe Gly Gly Asn Asp Glu Thr
    290                 295                 300

Ala Ser Tyr Val Gln Gly Ala Met Phe Gly Asn Val Asn Thr Ile Leu
305                 310                 315                 320

Ile Ile Leu Trp Val Pro Phe Leu Ala Thr Phe Val Tyr Pro Phe Cys
                325                 330                 335

Thr Lys Arg Gly Trp Asn Phe Ser Pro Gln Arg Arg Met Gly Leu Gly
            340                 345                 350

Phe Leu Val Val Val Ile Ser Phe Ala Val Ser Ala Ala Leu Ala Pro
        355                 360                 365

Ser Val Glu Lys Ala Tyr Leu Glu Ser Gly Arg Leu Met Lys Asp Ala
    370                 375                 380

Ala Lys Tyr Asp Gly Lys Tyr Cys Glu Lys Cys Tyr Ser Ala Trp Trp
385                 390                 395                 400

Gln Leu Pro Gln Trp Ile Leu Leu Ser Leu Gly Glu Ala Leu Phe Ser
                405                 410                 415

Pro Thr Gly Val Gln Phe Thr Tyr Ile Glu Ala Gly Arg Gln Phe Arg
```

```
            420                 425                 430

Ala Val Ser Thr Ser Phe Trp Leu Leu Ala Thr Ser Phe Gly Ser Ile
        435                 440                 445

Leu Ile Met Ile Phe Glu Pro Val Phe Ala Gly Tyr Asn Leu Ser Ser
    450                 455                 460

Gly Thr Lys Gly Trp Ala Tyr Ser Gly Ile Gly Leu Phe Gly Phe Leu
465                 470                 475                 480

Leu Tyr Cys Val Thr Ser Tyr Tyr Tyr Val Pro Arg Lys Val Arg Pro
                485                 490                 495

Ser Ile Asn Glu Ala Ala Arg Leu Ala Lys Lys Ala Glu Tyr Ala Ile
            500                 505                 510

Thr Ser Tyr
        515


<210> SEQ ID NO 25
<211> LENGTH: 522
<212> TYPE: PRT
<213> ORGANISM: Rhizopus microsporus

<400> SEQUENCE: 25

Met Asp His Leu Ile Gln Val Tyr Asn Ser Ser Thr Gln Val Leu Ile
1               5                   10                  15

Pro Val Leu Gln Lys Arg Ser Lys Ala Ser Tyr Ile Thr Ala Ala Ile
            20                  25                  30

Ala Leu Ile Ile Ala Gln Arg Leu Tyr Ser Tyr Phe Arg Val Pro Lys
        35                  40                  45

His Leu Arg Gly Phe Pro Lys Leu Pro Tyr Phe Gly Ile Ala Lys Ser
    50                  55                  60

Phe Phe Ala Lys Glu Ser Pro Arg Glu Arg Val Lys Lys Tyr Ile Leu
65                  70                  75                  80

Pro Ile Ile Asn Glu Arg Asp Gly Phe Tyr Ile Ser Asn Ile Pro Phe
                85                  90                  95

Gly Trp Met Leu Tyr Val Thr Asn Pro Ile Ala Ala Lys Gln Ile Leu
            100                 105                 110

Leu Lys Ser Asn Gly Phe Pro Lys Asn His Gly Leu Leu Glu Asp Met
        115                 120                 125

Gly Glu Asn Leu Phe Ile Glu Phe Ile Gly Lys Asp Asn Val Val Leu
    130                 135                 140

Thr Asn Gly Asp Thr Trp Lys Arg Gln Arg Lys Val Met Asn Pro Ala
145                 150                 155                 160

Phe His His Ser Leu Pro Ile Lys Thr Met Ser Asn Val Val Phe Ser
                165                 170                 175

Leu Ile Ser Val Ile Asp Gln Ala Asn Gly Thr Val Pro Val Ala Ser
            180                 185                 190

Thr Met Gln Asn Phe Thr Leu Asp Thr Leu Gly Leu Ala Ile Phe Gly
        195                 200                 205

Phe Asp Phe Lys Ala Leu Gln Gly Asp Gly Asp Glu Trp Thr Lys Thr
    210                 215                 220

Tyr Arg Leu Val Ser Asp Cys Leu Phe Asp Pro Ile Ile Asn Val Phe
225                 230                 235                 240

Ser Ser Tyr Ser Phe Ile Phe Asp Arg Ile Tyr Pro Arg Arg Arg Arg
                245                 250                 255

Gly Ala Met Ala Thr Arg Lys Leu Gly Glu Lys Phe Leu Glu Ile Ala
            260                 265                 270
```

```
Gln Gln Lys Arg Met Glu Ile Lys Ser Gly Ala Phe Ala Asp Val Pro
        275                 280                 285

Asp Asn Glu Lys Asp Leu Leu Thr Leu Met Leu Glu Ala Glu Glu Lys
    290                 295                 300

Gly Asp Val Trp Thr Ser Glu Asp Glu Leu Arg His Asn Ile Ala Val
305                 310                 315                 320

Leu Phe Leu Ala Gly His Asp Thr Thr Ala His Ala Leu Ser Phe Cys
                325                 330                 335

Phe Tyr His Leu Ala Lys Asn Lys Asp Ile Gln Gln Lys Leu Arg Lys
            340                 345                 350

Glu Val Leu Asp Leu Leu Gly Asp Glu Pro Val Asp Val Val Pro Thr
        355                 360                 365

Val Glu Gln Leu Lys Asp Met Gln Tyr Leu Asn Met Val Ile Lys Glu
    370                 375                 380

Asn Leu Arg Met Asn Ser Pro Ala Asp Met Leu Phe Ser Arg Asp Val
385                 390                 395                 400

Gln Glu Asp Ile Val Leu Ala Asn Thr Phe Ile Pro Lys Gly Thr Val
                405                 410                 415

Ile Ser Ile Asn Ile Glu Ala Leu His Cys Asn Pro Lys Leu Trp His
            420                 425                 430

Asn Pro Asp Gln Phe Asp Pro Glu Arg Phe Ala Pro Gly Gly Glu His
        435                 440                 445

Glu Gln His Glu Gly Met Thr Trp Leu Pro Phe Ser Asn Gly Thr Arg
    450                 455                 460

Gln Cys Leu Gly Met Asn Phe Ser Leu Phe Glu Gln Arg Leu Val Ile
465                 470                 475                 480

Ala Met Ile Leu Lys Lys Tyr Glu Ile Ser Ile Pro Glu Asp Ser Ile
                485                 490                 495

His Arg Asn His Ile Ile Asn Asp Met Pro Phe Asn Val Ala Pro Lys
            500                 505                 510

Ser Leu Glu Leu Thr Phe Thr Lys Arg Tyr
        515                 520


<210> SEQ ID NO 26
<211> LENGTH: 1782
<212> TYPE: DNA
<213> ORGANISM: Lonicera japonica

<400> SEQUENCE: 26

atggaaaaga acgagaaaga atccatggaa aacgacgaaa agatcttgac taatgacgaa      60

ccagaaatca actacagagg tgttaaggct atgccattga ttattggtaa cgaaaccttc     120

gaaaagttgg gtgctattgg tactttgtcc aacttgttgg tttacttgac taccgtgttc     180

aacatgaagt ctattactgc taccaccatc ctgaatgttt tcaatggtac taccaacttc     240

tctactttgt tgggtgcatt cttgtctgat acttacttcg gtagatacaa gactttgggt     300

ttcgcttcta ttgcttcttt cttgggtttg ttggttattg atttgaccgc cattatcaag     360

tggttgcatc cacctcattg tggtgctgaa actacaaaat gtattggtcc aactccatgg     420

cagatggttt ttttgtttac tggtttcggt ttgatggtca ttggtgctgc tggtattaga     480

ccatgtaatt tggcttttgg tgccgatcaa ttcaacccaa atactgattc tggtaagaag     540

ggcatcaact cattcttcaa ctggtacttt ttcaccatca ccttcgctca aatggtttct     600

ttgactttgg ttgtctacat ccagtctgat gtttcttggg ctattggttt gggtattcca     660

accattttca tgttggtgtc ttgcgtcttg tttttcatgg gtactaagat ctacgttaag     720
```

```
gtcaaaccag aaggttctcc attcacatct attgctcaag ttatggctgt tgctgctaag    780

aagagaagat tgaaattgcc agaacaaccc tggttgtctt tgttttctta tgctccatct    840

aagtccatca actccaaatt gccacatact gaccaattca gattcttgga taaggctgct    900

atagttactc cagaagatca aatcaacttg gatggttctg ctactgatcc ttggagattg    960

tgttctatgc aacaagtcga agaaatgaag tgcgttttga gagttattcc aatttgggct   1020

tccgctatca tctactacgt tgccattatt caacaacagc agtacgttgt tttccaagcc   1080

ttgcaatcta atagacactt cggtaactcc aagttccaaa ttccagctgc ttcttacact   1140

gtgttctcta tgttgtcctt gaccttgttc attccaatct acgatagaat cttggtccca   1200

cagttgagaa agttgactgg taaagaaggt ggtatcacct tgttacaaag aatgggtgtt   1260

ggtatcatct tgaccgtttt gtcatctttg gttgctgccc aagttgaaaa gagaagaaga   1320

aatttggcat tgaccagacc aacattgggt atacaaccac atagaggtgg tatttcttct   1380

atgtctggtt tgtggttggt tccacaattg gctattacag gtttggctga agctttcact   1440

aacatcggtc aagttgaatt ctactacaag cagttcccag aaaacatgag atctgttgct   1500

ggttcttttt tcttctgtgg tatggctgct tcctcttact tgaactcttt cttagttacc   1560

gttgttcaca gaactactga aggtgctgct actggtaatt ggttgccaga agatttgaac   1620

aaaggcagat tggactactt ttactacatg gttaccggtt tgggtgttgt caattctatg   1680

tacttttgt tgtgcgctaa gtggtacagg tacaaaggta ctggtggttc tgttgttggt   1740

gttgaaatgc aaacaaaaga agtcgataag caggtcgtct ga                       1782
```

<210> SEQ ID NO 27
<211> LENGTH: 593
<212> TYPE: PRT
<213> ORGANISM: Lonicera japonica

<400> SEQUENCE: 27

```
Met Glu Lys Asn Glu Lys Glu Ser Met Glu Asn Asp Glu Lys Ile Leu
1               5                   10                  15

Thr Asn Asp Glu Pro Glu Ile Asn Tyr Arg Gly Val Lys Ala Met Pro
            20                  25                  30

Leu Ile Ile Gly Asn Glu Thr Phe Glu Lys Leu Gly Ala Ile Gly Thr
        35                  40                  45

Leu Ser Asn Leu Leu Val Tyr Leu Thr Thr Val Phe Asn Met Lys Ser
    50                  55                  60

Ile Thr Ala Thr Thr Ile Leu Asn Val Phe Asn Gly Thr Thr Asn Phe
65                  70                  75                  80

Ser Thr Leu Leu Gly Ala Phe Leu Ser Asp Thr Tyr Phe Gly Arg Tyr
                85                  90                  95

Lys Thr Leu Gly Phe Ala Ser Ile Ala Ser Phe Leu Gly Leu Leu Val
            100                 105                 110

Ile Asp Leu Thr Ala Ile Ile Lys Trp Leu His Pro Pro His Cys Gly
        115                 120                 125

Ala Glu Thr Thr Lys Cys Ile Gly Pro Thr Pro Trp Gln Met Val Phe
    130                 135                 140

Leu Phe Thr Gly Phe Gly Leu Met Val Ile Gly Ala Ala Gly Ile Arg
145                 150                 155                 160

Pro Cys Asn Leu Ala Phe Gly Ala Asp Gln Phe Asn Pro Asn Thr Asp
                165                 170                 175

Ser Gly Lys Lys Gly Ile Asn Ser Phe Phe Asn Trp Tyr Phe Phe Thr
```

```
            180                 185                 190

Ile Thr Phe Ala Gln Met Val Ser Leu Thr Leu Val Val Tyr Ile Gln
        195                 200                 205

Ser Asp Val Ser Trp Ala Ile Gly Leu Gly Ile Pro Thr Ile Phe Met
    210                 215                 220

Leu Val Ser Cys Val Leu Phe Phe Met Gly Thr Lys Ile Tyr Val Lys
225                 230                 235                 240

Val Lys Pro Glu Gly Ser Pro Phe Thr Ser Ile Ala Gln Val Met Ala
                245                 250                 255

Val Ala Ala Lys Lys Arg Arg Leu Lys Leu Pro Glu Gln Pro Trp Leu
            260                 265                 270

Ser Leu Phe Ser Tyr Ala Pro Ser Lys Ser Ile Asn Ser Lys Leu Pro
        275                 280                 285

His Thr Asp Gln Phe Arg Phe Leu Asp Lys Ala Ala Ile Val Thr Pro
    290                 295                 300

Glu Asp Gln Ile Asn Leu Asp Gly Ser Ala Thr Asp Pro Trp Arg Leu
305                 310                 315                 320

Cys Ser Met Gln Gln Val Glu Glu Met Lys Cys Val Leu Arg Val Ile
                325                 330                 335

Pro Ile Trp Ala Ser Ala Ile Ile Tyr Tyr Val Ala Ile Ile Gln Gln
            340                 345                 350

Gln Gln Tyr Val Val Phe Gln Ala Leu Gln Ser Asn Arg His Phe Gly
        355                 360                 365

Asn Ser Lys Phe Gln Ile Pro Ala Ala Ser Tyr Thr Val Phe Ser Met
    370                 375                 380

Leu Ser Leu Thr Leu Phe Ile Pro Ile Tyr Asp Arg Ile Leu Val Pro
385                 390                 395                 400

Gln Leu Arg Lys Leu Thr Gly Lys Glu Gly Gly Ile Thr Leu Leu Gln
                405                 410                 415

Arg Met Gly Val Gly Ile Ile Leu Thr Val Leu Ser Ser Leu Val Ala
            420                 425                 430

Ala Gln Val Glu Lys Arg Arg Arg Asn Leu Ala Leu Thr Arg Pro Thr
        435                 440                 445

Leu Gly Ile Gln Pro His Arg Gly Gly Ile Ser Ser Met Ser Gly Leu
    450                 455                 460

Trp Leu Val Pro Gln Leu Ala Ile Thr Gly Leu Ala Glu Ala Phe Thr
465                 470                 475                 480

Asn Ile Gly Gln Val Glu Phe Tyr Tyr Lys Gln Phe Pro Glu Asn Met
                485                 490                 495

Arg Ser Val Ala Gly Ser Phe Phe Phe Cys Gly Met Ala Ala Ser Ser
            500                 505                 510

Tyr Leu Asn Ser Phe Leu Val Thr Val Val His Arg Thr Thr Glu Gly
        515                 520                 525

Ala Ala Thr Gly Asn Trp Leu Pro Glu Asp Leu Asn Lys Gly Arg Leu
    530                 535                 540

Asp Tyr Phe Tyr Tyr Met Val Thr Gly Leu Gly Val Val Asn Ser Met
545                 550                 555                 560

Tyr Phe Leu Leu Cys Ala Lys Trp Tyr Arg Tyr Lys Gly Thr Gly Gly
                565                 570                 575

Ser Val Val Gly Val Glu Met Gln Thr Lys Glu Val Asp Lys Gln Val
            580                 585                 590

Val
```

<210> SEQ ID NO 28
<211> LENGTH: 1815
<212> TYPE: DNA
<213> ORGANISM: Emmonsia crescens

<400> SEQUENCE: 28
atggccacct ctcaagaagt tgaagttcaa agagctgctg attcttctgc tccagaaaaa 60
gttccagttg gtatggacga aaaatctgtt ggtgctgctg tttacaattc ctctcatggt 120
tctttggaca acattaacag acaagctcca actatggaag agttgacttc cttgagaaga 180
attccaggta agattccatg gattgctttc tccattgctt tcgttgaatt gtgcgaaagg 240
ttttcctatt acggtactac catcgttttc gtcaactaca tccaaagaga attgccacca 300
ggttctacta ctggtgcttc tggtactaat ggtactccag gtgctttagg tttgggtcaa 360
agagcatcta ctggtttgac tttgtttaac aacttctggt cctacatcat gccattggtt 420
ggtgcttatg ttgctgatga acatttgggt agattcaaca ccatcatgta ctctattgct 480
atcgctttgg ttggtcatac catcttgatt atttctgcca ttccaccagt tctgaagaat 540
ccaaatggtg ctgttgcttg ttttgccgtt ggtattatca ttatgggtat tggtactggt 600
ggcttcaagt ctaatatctc tccattgatt gctgaacagt acaccgaaga gtatatgttc 660
attgaaacta ccaaggacgg tgaaagagtt atagttgatc cagctgctac catctctaga 720
atctaccatt acttctacct gatgattaac atcggtgctt tgttgggtca gatctctatg 780
gtttatgccg aaaagtatgt cggcttctac ttgtcttttt tgttgccaac ttgtttgttc 840
acgttgtgtc cattggtctt gtatgttttg agacacaagt actccagaca aagacctgtt 900
ggttctgttt atggtaaagc ttggaaagtt tggagattgg ctacaaaggg tcaagtttct 960
tggaatccag ctactactta cagaaacttc catgatccag atatgtggga aagagctaag 1020
ccatctaata ttgctaacaa gccagtttgg atgacctttg atgatgcttg ggttgatgaa 1080
gttagaagag gtttgagagc ttgcgctgtt tttttgtggt atcctttgtt ttggctgtcc 1140
tacaatcaga tgttgaacaa cttgacttct caagccgcta ctatggaatt gaatggtgtt 1200
ccaaacgatg tcatctctaa cttgaatcca ttcaccttga tcatcttcat ccctttgttg 1260
gacagattct tctacccaac tttgaggaaa ttgggtatca atttgacccc agttaagaga 1320
atcgctatcg gttttgttgt tgctggttgt tctatggttg ctgctgcagt tactcaacat 1380
tacatctaca aattgggtcc atgtggtaag ttcgctaatg attgtgctgc tgataatatt 1440
ccagctccaa tttctgtttg ggttcaaact gttccatacg tcttaggtgg tatctctgaa 1500
attttcgctt ctgtcacttc tttggaatac gcttttacaa aggcccctaa gaacatgaga 1560
tctttggttc aagcagttgc tttgttcacc aatgctattt ctgctgcatt gggtcaagct 1620
ttggtttctt tatctgaaga tccactgttg gaatggaact atgctgttac tgctattttg 1680
gcttttgttg gtgcagcagg tttttggatt tctaatagag gtactgacaa ggacgaagat 1740
gccttgaaca atttgccagc tggtgattgt gaatctggtg ctaatgatat tgagaacaag 1800
ttgaccgaga actaa 1815

<210> SEQ ID NO 29
<211> LENGTH: 604
<212> TYPE: PRT
<213> ORGANISM: Emmonsia crescens

<400> SEQUENCE: 29

Met Ala Thr Ser Gln Glu Val Glu Val Gln Arg Ala Ala Asp Ser Ser

-continued

```
1               5                   10                  15

Ala Pro Glu Lys Val Pro Val Gly Met Asp Glu Lys Ser Val Gly Ala
            20                  25                  30

Ala Val Tyr Asn Ser Ser His Gly Ser Leu Asp Asn Ile Asn Arg Gln
        35                  40                  45

Ala Pro Thr Met Glu Glu Leu Thr Ser Leu Arg Arg Ile Pro Gly Lys
    50                  55                  60

Ile Pro Trp Ile Ala Phe Ser Ile Ala Phe Val Glu Leu Cys Glu Arg
65                  70                  75                  80

Phe Ser Tyr Tyr Gly Thr Thr Ile Val Phe Val Asn Tyr Ile Gln Arg
                85                  90                  95

Glu Leu Pro Pro Gly Ser Thr Thr Gly Ala Ser Gly Thr Asn Gly Thr
            100                 105                 110

Pro Gly Ala Leu Gly Leu Gly Gln Arg Ala Ser Thr Gly Leu Thr Leu
        115                 120                 125

Phe Asn Asn Phe Trp Ser Tyr Ile Met Pro Leu Val Gly Ala Tyr Val
    130                 135                 140

Ala Asp Glu His Leu Gly Arg Phe Asn Thr Ile Met Tyr Ser Ile Ala
145                 150                 155                 160

Ile Ala Leu Val Gly His Thr Ile Leu Ile Ile Ser Ala Ile Pro Pro
                165                 170                 175

Val Leu Lys Asn Pro Asn Gly Ala Val Ala Cys Phe Ala Val Gly Ile
            180                 185                 190

Ile Ile Met Gly Ile Gly Thr Gly Gly Phe Lys Ser Asn Ile Ser Pro
        195                 200                 205

Leu Ile Ala Glu Gln Tyr Thr Glu Glu Tyr Met Phe Ile Glu Thr Thr
    210                 215                 220

Lys Asp Gly Glu Arg Val Ile Val Asp Pro Ala Ala Thr Ile Ser Arg
225                 230                 235                 240

Ile Tyr His Tyr Phe Tyr Leu Met Ile Asn Ile Gly Ala Leu Leu Gly
                245                 250                 255

Gln Ile Ser Met Val Tyr Ala Glu Lys Tyr Val Gly Phe Tyr Leu Ser
            260                 265                 270

Phe Leu Leu Pro Thr Cys Leu Phe Thr Leu Cys Pro Leu Val Leu Tyr
        275                 280                 285

Val Leu Arg His Lys Tyr Ser Arg Gln Arg Pro Val Gly Ser Val Tyr
    290                 295                 300

Gly Lys Ala Trp Lys Val Trp Arg Leu Ala Thr Lys Gly Gln Val Ser
305                 310                 315                 320

Trp Asn Pro Ala Thr Thr Tyr Arg Asn Phe His Asp Pro Asp Met Trp
                325                 330                 335

Glu Arg Ala Lys Pro Ser Asn Ile Ala Asn Lys Pro Val Trp Met Thr
            340                 345                 350

Phe Asp Asp Ala Trp Val Asp Glu Val Arg Arg Gly Leu Arg Ala Cys
        355                 360                 365

Ala Val Phe Leu Trp Tyr Pro Leu Phe Trp Leu Ser Tyr Asn Gln Met
    370                 375                 380

Leu Asn Asn Leu Thr Ser Gln Ala Ala Thr Met Glu Leu Asn Gly Val
385                 390                 395                 400

Pro Asn Asp Val Ile Ser Asn Leu Asn Pro Phe Thr Leu Ile Ile Phe
                405                 410                 415

Ile Pro Leu Leu Asp Arg Phe Phe Tyr Pro Thr Leu Arg Lys Leu Gly
            420                 425                 430
```

```
Ile Asn Leu Thr Pro Val Lys Arg Ile Ala Ile Gly Phe Val Val Ala
        435                 440                 445

Gly Cys Ser Met Val Ala Ala Ala Val Thr Gln His Tyr Ile Tyr Lys
    450                 455                 460

Leu Gly Pro Cys Gly Lys Phe Ala Asn Asp Cys Ala Ala Asp Asn Ile
465                 470                 475                 480

Pro Ala Pro Ile Ser Val Trp Val Gln Thr Val Pro Tyr Val Leu Gly
                485                 490                 495

Gly Ile Ser Glu Ile Phe Ala Ser Val Thr Ser Leu Glu Tyr Ala Phe
            500                 505                 510

Thr Lys Ala Pro Lys Asn Met Arg Ser Leu Val Gln Ala Val Ala Leu
        515                 520                 525

Phe Thr Asn Ala Ile Ser Ala Ala Leu Gly Gln Ala Leu Val Ser Leu
    530                 535                 540

Ser Glu Asp Pro Leu Leu Glu Trp Asn Tyr Ala Val Thr Ala Ile Leu
545                 550                 555                 560

Ala Phe Val Gly Ala Ala Gly Phe Trp Ile Ser Asn Arg Gly Thr Asp
                565                 570                 575

Lys Asp Glu Asp Ala Leu Asn Asn Leu Pro Ala Gly Asp Cys Glu Ser
            580                 585                 590

Gly Ala Asn Asp Ile Glu Asn Lys Leu Thr Glu Asn
        595                 600


<210> SEQ ID NO 30
<211> LENGTH: 1815
<212> TYPE: DNA
<213> ORGANISM: Sanguinaria canadensis

<400> SEQUENCE: 30

atggctgcta ctaagttgca acccaagttg ttgaatcaaa ccttgatgat ctcccaagac     60

cagttgattt tggatgaaga agctgctgct ccatcttcta ctcatgttgg tagacaaaga    120

ggtggttgga ttactttgcc attcgttact gtttctttgt tgggtttgac tgttgctgct    180

tctggttggg gttctaacat tatcgttttt ttgatcggcc agttcaacat caagtctatt    240

gaagctgctc agatctccaa cattatttct ggtactacca acttcttgcc aattttggct    300

gctattattg ccgattcttt cttcggttct ttctccgttg ttgctgtttc ctctttcatt    360

tctttcatgg gcttgatctt gttgactttg acagttaccg tcagatcctt aagaccatct    420

tctcaatgtg ttgataacga taccttggct tgtgaaacta ctccatctgg ttctacattg    480

caatttgctg tcttgtacac tgctttgacc ttgacctctt taggtttagg tggtactaga    540

ttcactattg ctactatggg tgctgatcaa ttcgataagc caaaggatca agcctctttt    600

ttcaactggt acttcgtcac cttgtacatt gcatctacta ttggtgttgt tggtgtcgtt    660

tacatccaag ataacgttgg ttgggattgg ggttttggta tttctttagc tgctaatgct    720

gttggcttga tcgttttctt ggctggtaaa agatattaca gacacgttaa gccagatggc    780

tctccattca aatctttggc tagagttgtt gttgccacca ttagaaaaag aaagatgtcc    840

gtttcttccg aagctaagac ttattactac ggttattcta ctggtggtgc taccattgaa    900

ccttgtccat ctccaacttc atctttcaga tttttgaaca gagctgcctt gaaaaccgaa    960

ggtgattctc atgaagatgg ttctgttgct aaaccttgga gattgtgtac tgttcaacaa   1020

gtcgaggatc taaagacctt gattagaatt ttcccactgt ggtccacctc catttttttg   1080

tctactccaa ttggtatcca gatctctttg gctgttttac aagctttgac catggataga   1140
```

catattggta gaccaggtca ttttaaagtt ccagccggtt cttttctggt tttctctttg 1200
acttctaccg ctatcacttt gactttgttc gacagattct tgttgccaac ctaccaaaga 1260
gttactagaa ggccattgac tccattgcaa cgtgttggta ttggtcatgt cttgaacatt 1320
ttaggtatgg ctgcttcagc tttggttgaa tggcgtagat tgcatgttgc tagatctcat 1380
caattgacct ccagttcttc atcttcttct actatcgttc caatgtccgc tttttggttg 1440
gttattccat tggctatcgt tggtgttggt gaagcttttc attttccagg tcaagttgcc 1500
ttgtattacc aagaatttcc agcctcattg cattctacat ccactgctat gattagcttg 1560
ttgattgctg ttggtttcta cttgtctacc gccatgattg atttggttca aagagtaact 1620
ggttggctgc caaacaatat taacgaaggt agattggaca acatgttctg gttgttggtt 1680
gttatcggtg ttatcaactt cggttactac ttgacttgtt ccgtcttgta cgaataccag 1740
aacttggacg atcagtacca aaagtccatt aaggttgatg atgatgacga tcagccaaga 1800
caagaacaaa actga 1815

<210> SEQ ID NO 31
<211> LENGTH: 604
<212> TYPE: PRT
<213> ORGANISM: Sanguinaria canadensis

<400> SEQUENCE: 31

Met Ala Ala Thr Lys Leu Gln Pro Lys Leu Leu Asn Gln Thr Leu Met
1 5 10 15

Ile Ser Gln Asp Gln Leu Ile Leu Asp Glu Glu Ala Ala Ala Pro Ser
20 25 30

Ser Thr His Val Gly Arg Gln Arg Gly Gly Trp Ile Thr Leu Pro Phe
35 40 45

Val Thr Val Ser Leu Leu Gly Leu Thr Val Ala Ala Ser Gly Trp Gly
50 55 60

Ser Asn Ile Ile Val Phe Leu Ile Gly Gln Phe Asn Ile Lys Ser Ile
65 70 75 80

Glu Ala Ala Gln Ile Ser Asn Ile Ile Ser Gly Thr Thr Asn Phe Leu
85 90 95

Pro Ile Leu Ala Ala Ile Ile Ala Asp Ser Phe Phe Gly Ser Phe Ser
100 105 110

Val Val Ala Val Ser Ser Phe Ile Ser Phe Met Gly Leu Ile Leu Leu
115 120 125

Thr Leu Thr Val Thr Val Arg Ser Leu Arg Pro Ser Ser Gln Cys Val
130 135 140

Asp Asn Asp Thr Leu Ala Cys Glu Thr Thr Pro Ser Gly Ser Thr Leu
145 150 155 160

Gln Phe Ala Val Leu Tyr Thr Ala Leu Thr Leu Thr Ser Leu Gly Leu
165 170 175

Gly Gly Thr Arg Phe Thr Ile Ala Thr Met Gly Ala Asp Gln Phe Asp
180 185 190

Lys Pro Lys Asp Gln Ala Ser Phe Phe Asn Trp Tyr Phe Val Thr Leu
195 200 205

Tyr Ile Ala Ser Thr Ile Gly Val Val Gly Val Val Tyr Ile Gln Asp
210 215 220

Asn Val Gly Trp Asp Trp Gly Phe Gly Ile Ser Leu Ala Ala Asn Ala
225 230 235 240

Val Gly Leu Ile Val Phe Leu Ala Gly Lys Arg Tyr Tyr Arg His Val

```
                245                 250                 255

Lys Pro Asp Gly Ser Pro Phe Lys Ser Leu Ala Arg Val Val Val Ala
            260                 265                 270

Thr Ile Arg Lys Arg Lys Met Ser Val Ser Ser Glu Ala Lys Thr Tyr
        275                 280                 285

Tyr Tyr Gly Tyr Ser Thr Gly Gly Ala Thr Ile Glu Pro Cys Pro Ser
    290                 295                 300

Pro Thr Ser Ser Phe Arg Phe Leu Asn Arg Ala Ala Leu Lys Thr Glu
305                 310                 315                 320

Gly Asp Ser His Glu Asp Gly Ser Val Ala Lys Pro Trp Arg Leu Cys
                325                 330                 335

Thr Val Gln Gln Val Glu Asp Leu Lys Thr Leu Ile Arg Ile Phe Pro
            340                 345                 350

Leu Trp Ser Thr Ser Ile Phe Leu Ser Thr Pro Ile Gly Ile Gln Ile
        355                 360                 365

Ser Leu Ala Val Leu Gln Ala Leu Thr Met Asp Arg His Ile Gly Arg
    370                 375                 380

Pro Gly His Phe Lys Val Pro Ala Gly Ser Phe Leu Val Phe Ser Leu
385                 390                 395                 400

Thr Ser Thr Ala Ile Thr Leu Thr Leu Phe Asp Arg Phe Leu Leu Pro
                405                 410                 415

Thr Tyr Gln Arg Val Thr Arg Arg Pro Leu Thr Pro Leu Gln Arg Val
            420                 425                 430

Gly Ile Gly His Val Leu Asn Ile Leu Gly Met Ala Ala Ser Ala Leu
        435                 440                 445

Val Glu Trp Arg Arg Leu His Val Ala Arg Ser His Gln Leu Thr Ser
    450                 455                 460

Ser Ser Ser Ser Ser Ser Thr Ile Val Pro Met Ser Ala Phe Trp Leu
465                 470                 475                 480

Val Ile Pro Leu Ala Ile Val Gly Val Gly Glu Ala Phe His Phe Pro
                485                 490                 495

Gly Gln Val Ala Leu Tyr Tyr Gln Glu Phe Pro Ala Ser Leu His Ser
            500                 505                 510

Thr Ser Thr Ala Met Ile Ser Leu Leu Ile Ala Val Gly Phe Tyr Leu
        515                 520                 525

Ser Thr Ala Met Ile Asp Leu Val Gln Arg Val Thr Gly Trp Leu Pro
    530                 535                 540

Asn Asn Ile Asn Glu Gly Arg Leu Asp Asn Met Phe Trp Leu Leu Val
545                 550                 555                 560

Val Ile Gly Val Ile Asn Phe Gly Tyr Tyr Leu Thr Cys Ser Val Leu
                565                 570                 575

Tyr Glu Tyr Gln Asn Leu Asp Asp Gln Tyr Gln Lys Ser Ile Lys Val
            580                 585                 590

Asp Asp Asp Asp Asp Gln Pro Arg Gln Glu Gln Asn
        595                 600


<210> SEQ ID NO 32
<211> LENGTH: 481
<212> TYPE: PRT
<213> ORGANISM: Macleaya cordata

<400> SEQUENCE: 32

Met Ala Met Asn Ile Glu Met Ile Glu Glu Gly Val Ile Asn His Gln
1               5                   10                  15
```

-continued

```
Ala Glu Thr Asn Gln Asn Lys Leu Ser Ala Gly His His Gly Asp Tyr
            20                  25                  30

Glu His His Glu Asp Tyr Ser Lys Lys Ser Leu Met Glu Lys Trp Gly
        35                  40                  45

Leu Leu Phe Leu Tyr Cys Ile Cys Ser Ala Val Gly Thr Ile Gly Gly
    50                  55                  60

Pro Leu Leu Leu Arg Leu Tyr Phe Leu His Gly Gly Asn Arg Lys Trp
65                  70                  75                  80

Leu Ser Ser Gly Leu Gln Thr Ala Gly Phe Pro Ile Leu Val Ile Pro
                85                  90                  95

Leu Ala Ile Leu Tyr Phe Lys Arg Asp Arg Thr Pro Cys Ser Val Gln
            100                 105                 110

Phe Phe Ala Ser Pro Lys Leu Leu Leu Ser Ser Ile Ile Ile Gly Ile
        115                 120                 125

Leu Leu Gly Val Asn Asn Phe Met Tyr Ser Tyr Gly Leu Ser Phe Leu
    130                 135                 140

Pro Val Ser Thr Ser Ser Ile Leu Ile Ser Thr Gln Leu Ile Phe Thr
145                 150                 155                 160

Ala Leu Phe Ala Phe Ile Met Val Arg Gln Lys Phe Ser Pro Tyr Ser
                165                 170                 175

Ile Asn Ser Ile Val Val Met Thr Leu Gly Ser Val Leu Leu Gly Phe
            180                 185                 190

Gly Lys Ser Gly Asp Arg Pro Glu Gly Val Ser Ser Ser Gln Tyr Leu
        195                 200                 205

Leu Gly Phe Ile Leu Ser Ile Gly Ala Ala Ala Leu Gly Gly Phe Val
    210                 215                 220

Leu Pro Cys Thr Glu Val Ala Tyr Ala Lys Ala Ser Lys Val Leu Thr
225                 230                 235                 240

Tyr Pro Ile Val Leu Gln Phe Gln Phe Cys Met Ala Leu Ser Ala Thr
                245                 250                 255

Ile Phe Cys Ile Ile Gly Met Leu Val Asn Lys Asp Phe Ser Ala Met
            260                 265                 270

Gln Arg Glu Ala Asn Glu Tyr Glu Leu Gly Ala Met Lys Tyr Tyr Leu
        275                 280                 285

Val Leu Val Ser Ser Ala Val Val Trp Gln Val Met Tyr Ile Gly Thr
    290                 295                 300

Leu Gly Ile Ile Phe Cys Thr Thr Ser Leu Phe Ala Gly Ile Ile Ser
305                 310                 315                 320

Ala Val Leu Leu Pro Leu Thr Glu Ile Ala Ala Val Ile Val Phe His
                325                 330                 335

Glu Lys Phe Thr Gly Glu Lys Gly Met Ala Leu Ala Leu Gly Leu Trp
            340                 345                 350

Gly Phe Ser Ser Tyr Phe Tyr Gly Ser Tyr Arg Glu Ser Lys Lys Gln
        355                 360                 365

Thr Lys Thr Pro His Glu Ile Asp Asp Thr Ser Lys Thr Lys Leu Arg
    370                 375                 380

Ala Val Asn Gly Tyr Ser Lys Ile Arg Ile Arg Phe Glu Ser Ile Thr
385                 390                 395                 400

Leu Ser Glu Ser Pro Arg Gln Leu Gln Ala Pro Ser Arg Ser Glu Ala
                405                 410                 415

Ser Leu Gln Tyr Cys Ser Val Gln Ile Cys Lys Gly Leu Val Leu Leu
            420                 425                 430

Cys Pro Asp Leu Leu Asn Leu Phe Glu Arg Leu Leu Ile Arg Pro Asp
```

435 440 445

Leu Gln Gly Arg Glu Lys Val Ala Gly Leu Lys Lys Lys Gly Leu Leu
450 455 460

Val Lys Asp Asp Leu Pro Trp Pro Asp Leu Ala Leu His Val Leu Ser
465 470 475 480

Trp

<210> SEQ ID NO 33
<211> LENGTH: 1446
<212> TYPE: DNA
<213> ORGANISM: Macleaya cordata

<400> SEQUENCE: 33
atggccatga acatcgaaat gatcgaagaa ggtgttatca accatcaggc tgaaactaat 60
cagaacaaat tgtctgctgg tcatcacggt gattacgaac atcatgaaga ttactccaaa 120
aagtccctga tggaaaaatg ggtttgttg ttcttgtact gcatttgttc agccgttggt 180
actattggtg gtcctttgtt gttgaggttg tatttcttgc atggtggtaa cagaaagtgg 240
ttatcctctg gtttacaaac tgctggtttc ccaattttgg ttattccatt ggctatcctg 300
tacttcaaga gagatagaac tccttgctct gttcaatttt tcgcttctcc aaagctgctg 360
ttgtcctcta ttatcattgg tatcttgttg ggcgtcaaca acttcatgta ttcttacggt 420
ttgtccttct tgccagtttc cacttcctct attttgatct ctacccaatt gattttcacc 480
gctttgttcg ccttcattat ggtcagacaa aagttctctc catactccat caactccatc 540
gttgttatga ctttgggttc cgttttgtta ggtttcggta aatctggtga tagacctgaa 600
ggtgtttctt cctctcaata tttgttgggc ttcatcttgt ctattggtgc tgctgcttta 660
ggtggttttg ttttgccatg tactgaagtt gcttacgcta aagcttctaa ggttttgacc 720
tatccaatcg tcttgcaatt ccaattctgt atggctttgt ctgctaccat tttctgcatt 780
atcggtatgt tggttaacaa ggatttctcc gctatgcaaa gggaagctaa tgaatatgaa 840
ttgggtgcca tgaagtacta cttggtcttg gtttcttcag ctgttgtttg gcaagttatg 900
tacattggta ctctgggtat tatcttctgt accacctctt tgtttgccgg tattatttca 960
gcagttttgt tgccattgac cgaaattgct gctgttatcg tttttcacga aaagttcact 1020
ggtgaaaaag gtatggcatt ggctttaggt ttgtggggtt tttcttctta cttctacggt 1080
tcctacaggg aatctaagaa gcaaacaaaa actccacacg aaatcgatga tacctccaag 1140
actaagttga gagctgttaa tggttactcc aagatcagaa tcaggttcga atctatcacc 1200
ttgtctgaat ctccaagaca attgcaagct ccttctagat ctgaagcctc tttacaatac 1260
tgttccgtcc aaatctgtaa gggtttagtt ttgttatgcc ccgacttgtt gaatttgttc 1320
gaaaggttgt tgatcagacc agacttgcaa ggtagagaaa aagttgctgg tttgaagaaa 1380
aaaggcttgt tggtcaaaga tgatttgcca tggccagatt tggctttaca tgttttgtct 1440
tggtaa 1446

<210> SEQ ID NO 34
<211> LENGTH: 384
<212> TYPE: PRT
<213> ORGANISM: Papaver somniferum

<400> SEQUENCE: 34

Met Ser Ile Glu Thr Pro Glu Thr Leu Gly Pro Asn Gln Asn Gly Asn
1 5 10 15

```
Pro Lys Thr Asn Ile Glu Lys Pro Ile Lys Thr Arg Asn Trp Leu Leu
            20                  25                  30

Ile Val Ile Asn Cys Ala Leu Val Ala Cys Gly Ala Ile Gly Gly Pro
        35                  40                  45

Leu Leu Met Arg Leu Tyr Tyr Leu His Gly Gly Ser Arg Lys Trp Leu
    50                  55                  60

Ser Ser Cys Leu Gln Thr Ala Gly Phe Pro Ile Leu Ile Phe Pro Leu
65                  70                  75                  80

Ile Phe Leu Tyr Ile Lys Ser Lys Leu Ser Lys Thr Asn Lys Asp Gln
                85                  90                  95

Thr Ser Ser Phe Tyr Ile Glu Pro Lys Leu Phe Val Ser Ala Ile Ala
            100                 105                 110

Ile Gly Ile Leu Phe Gly Phe Ala Asn Phe Met Tyr Ala Leu Gly Leu
        115                 120                 125

Ser Tyr Leu Pro Val Ser Thr Ser Ser Ile Leu Phe Ala Thr Gln Leu
    130                 135                 140

Cys Phe Thr Ala Phe Phe Ala Trp Leu Ile Val Lys Gln Lys Phe Thr
145                 150                 155                 160

Ala Phe Ile Ile Asn Ala Val Val Val Met Thr Leu Gly Ser Val Leu
                165                 170                 175

Leu Gly Ile Asn Thr Asn Gly Asp Arg Pro Ile Gly Val Ser Lys Ala
            180                 185                 190

Gln Tyr Leu Met Gly Phe Leu Met Thr Leu Ala Ala Ala Ala Leu Thr
        195                 200                 205

Gly Leu Val Met Pro Leu Ile Glu Leu Thr Phe Ser Lys Ala Thr Arg
    210                 215                 220

Arg Val Thr Tyr Ser Thr Leu Leu Gln Leu Gln Phe Thr Tyr Ser Leu
225                 230                 235                 240

Phe Ala Thr Gly Leu Asn Val Ile Gly Met Leu Ile Asn Lys Asp Phe
                245                 250                 255

Gln Ala Ile Pro Arg Glu Ala Asp Glu Phe Glu Phe Gly Lys His Lys
            260                 265                 270

Tyr Tyr Met Ile Ile Val Leu Thr Ala Ile Thr Trp Gln Leu Ala Thr
        275                 280                 285

Leu Gly Phe Phe Gly Leu Ile Leu Tyr Thr Ser Ala Leu Phe Asn Gly
    290                 295                 300

Ile Tyr Gly Ser Leu Leu Phe Pro Phe Thr Gly Val Ala Ala Val Ile
305                 310                 315                 320

Val Tyr His Glu Asn Phe Thr Gly Leu Lys Gly Met Ala Leu Ala Leu
                325                 330                 335

Cys Leu Trp Gly Phe Phe Ser Tyr Phe Tyr Gly Glu Tyr Lys Met Met
            340                 345                 350

Lys Lys Val Gly Asn Asn Glu Arg His Gly Lys Val Glu Glu Val Glu
        355                 360                 365

Asn Gln Pro Lys Arg Leu Asp Asp Gln Glu Pro Pro Tyr Arg Leu Val
    370                 375                 380
```

<210> SEQ ID NO 35
<211> LENGTH: 1155
<212> TYPE: DNA
<213> ORGANISM: Papaver somniferum

<400> SEQUENCE: 35
atgtccattg aaactccaga aaccttgggt ccaaatcaaa atggtaatcc aaagaccaac     60

```
atcgagaagc caatcaagac tagaaattgg ttgttgatcg ttatcaactg cgctttggtt    120

gcttgtggtg ctattggtgg tccattattg atgaggttgt attacttgca tggtggttcc    180

agaaaatggt tgtcctcttg tttacaaact gctggtttcc caattctgat cttcccattg    240

attttcttgt acatcaagtc caagctgtcc aagactaaca aggatcaaac ttcctcattc    300

tacatcgagc caaagttgtt cgtttccgct attgcaattg gtatcttgtt tggtttcgcc    360

aactttatgt atgccttggg tttgtcttat ttgccagttt ccacttcctc tattttgttc    420

gctactcaat tgtgtttcac cgcttttttt gcttggttga tcgtcaagca aaagttcact    480

gccttcatta ttaacgccgt tgttgttatg actttgggct ctgttttgtt gggtattaac    540

actaatggtg acagaccaat cggtgtttct aaagctcaat acttgatggg tttcttgatg    600

actttagctg ctgctgcttt gactggtttg gttatgccat tgattgaact gactttctct    660

aaggctacta gaagagttac ttactccacc ttgttgcagt tgcaattcac ctattctttg    720

tttgctaccg gtttgaacgt tatcggcatg ttgattaaca aagacttcca agccattcca    780

agagaagctg acgaatttga attcggtaaa cacaagtact acatgatcat cgttttgacc    840

gctattactt ggcaattggc tactttgggt tttttcggtt tgatcttgta cacctctgct    900

ttgtttaatg gtatctacgg ctctttgttg ttcccattca ctggtgttgc tgctgttata    960

gtttaccacg aaaatttcac tggcttgaaa ggtatggctt tggctttgtg tttgtggggt   1020

ttttttctt acttctacgg cgagtacaag atgatgaaga aagttggtaa caacgaaaga   1080

cacggtaagg ttgaagaagt tgaaaaccag ccaaaaagat tggatgatca agaaccacct   1140

tacaggttgg tttga                                                    1155
```

```
<210> SEQ ID NO 36
<211> LENGTH: 391
<212> TYPE: PRT
<213> ORGANISM: Papaver somniferum

<400> SEQUENCE: 36

Met Ala Thr Ser Thr Met Asn Ile Glu Thr Pro Glu Thr Leu Gly Pro
1               5                   10                  15

His Gln Asn Gly Asn Ser Lys Pro His Ile Glu Glu Thr Ile Glu Ala
            20                  25                  30

Lys Asn Trp Leu Leu Leu Ile Ile Asn Cys Ala Leu Val Phe Cys Gly
        35                  40                  45

Val Ile Gly Cys Pro Leu Leu Met Arg Leu Tyr Tyr Leu His Gly Gly
    50                  55                  60

Ser Arg Lys Trp Leu Thr Ala Ser Leu Glu Ala Ala Gly Phe Pro Val
65                  70                  75                  80

Leu Ile Phe Pro Leu Ile Phe Leu Tyr Ile Lys Ser Lys Ser Ser Thr
                85                  90                  95

Gln Asn Asn Asp Gln Ser Thr Ser Phe Cys Met Glu Pro Lys Leu Phe
            100                 105                 110

Leu Trp Ser Ala Ile Val Gly Ile Gly Tyr Gly Val Ala His Phe Met
        115                 120                 125

Tyr Ala Trp Gly Phe Ser Tyr Leu Pro Val Ser Thr Ser Thr Ile Leu
    130                 135                 140

Ser Ala Thr Gln Leu Cys Phe Thr Ala Phe Phe Ala Trp Leu Ile Val
145                 150                 155                 160

Lys Gln Lys Ile Thr Ala Phe Ile Ile Asn Ala Val Val Val Met Thr
                165                 170                 175
```

```
Leu Gly Ser Val Leu Leu Gly Ile Asn Thr Asn Gly Asp Arg Pro Ile
            180                 185                 190

Gly Val Ser Lys Ala Arg Tyr Leu Gln Gly Phe Leu Leu Thr Leu Ala
        195                 200                 205

Ala Ser Val Leu Cys Gly Ser Met Met Pro Leu Ile Glu Leu Ala Tyr
    210                 215                 220

Ser Lys Ala Thr Arg Asn Val Thr Tyr Ala Thr Leu Leu Gln Phe Gln
225                 230                 235                 240

Ile Thr Leu Ser Leu Val Ala Thr Gly Leu Asp Val Ile Gly Met Leu
                245                 250                 255

Ile Asn Lys Asp Phe Gln Ala Ile His Arg Glu Ala Asp Glu Phe Gly
            260                 265                 270

Leu Gly Lys Ser Lys Tyr Tyr Met Ile Ile Ile Phe Thr Ala Leu Thr
        275                 280                 285

Ser Gln Leu Ala Ser Ile Gly Phe Leu Gly Val Ile Leu Tyr Thr Asn
    290                 295                 300

Ala Leu Phe Ile Gly Ile Tyr Gly Ser Val Leu Leu Pro Phe Ile Glu
305                 310                 315                 320

Val Ala Gly Val Ile Phe Phe His Glu Ser Phe Thr Gly Leu Lys Gly
                325                 330                 335

Met Ala Leu Ala Leu Cys Leu Trp Gly Phe Ser Ser Tyr Phe Tyr Gly
            340                 345                 350

Glu Tyr Lys Leu Met Asn Lys Ala Gly Asn Asn Lys Ser Ala Val Glu
        355                 360                 365

Lys Ile Asp Glu Lys Val Glu Asn Glu Pro Lys Lys Leu Asp Asp Gln
    370                 375                 380

Glu Pro Pro Tyr Asn Thr Val
385                 390
```

<210> SEQ ID NO 37
<211> LENGTH: 1176
<212> TYPE: DNA
<213> ORGANISM: Papaver somniferum

<400> SEQUENCE: 37

```
atggctactt ccaccatgaa cattgaaact ccagaaactt tgggtccaca tcaaaatggt     60

aattccaagc cacatatcga agaaaccatt gaagctaaga actggctgtt gttgattatt    120

aactgcgctt tggttttctg cggtgttatt ggttgtccat tattgatgag gttgtactac    180

ttgcatggtg gttctagaaa atggttgact gcttctttgg aagctgctgg ttttccagtt    240

ttgattttcc ctttgatctt cctgtacatc aagtccaaat cttctaccca aaacaacgac    300

caatctacct cattctgtat ggaacctaag ttgtttttgt ggtctgccat agttggtatt    360

ggttatggtg ttgctcattt catgtatgct tggggttttt cttacttgcc agtttctacc    420

tccactattt tgtctgctac tcaattgtgt ttcaccgctt tttttgcttg gttgatcgtc    480

aagcaaaaga ttaccgcctt cattattaac gccgttgttg ttatgacttt gggctctgtt    540

ttgttgggta ttaacactaa tggtgacaga ccaatcggtg tttctaaagc tagatacttg    600

caaggtttct tgttgacttt ggctgcttca gttttgtgtg gttctatgat gccattgatt    660

gaattggctt actctaaggc tactagaaac gttacttacg ctaccttgtt gcaattccaa    720

atcaccttgt ctttggttgc tactggtttg gatgttatcg gcatgttgat taacaaggac    780

ttccaagcta ttcacagaga agctgatgaa ttcggtttgg gcaaatctaa gtactacatg    840

atcattatct tcaccgcctt gacttctcaa ttggcttcta ttggtttctt gggtgttatc    900
```

```
ttgtacacca acgctttgtt cattggtatc tacggttctg tcttgttgcc attcatagaa    960

gttgctggtg ttatattctt ccacgaatct ttcactggtt tgaaaggtat ggctttggct   1020

ttgtgtttgt ggggtttctc ttcttacttt tacggtgagt acaagctaat gaacaaggct   1080

ggtaacaaca agtctgccgt tgaaaaaatt gacgaaaagg ttgaaaacga gccaaagaag   1140

ttggacgatc aagaaccacc ttacaacact gtttga                             1176


<210> SEQ ID NO 38
<211> LENGTH: 413
<212> TYPE: PRT
<213> ORGANISM: Papaver somniferum

<400> SEQUENCE: 38

Met Asp Ile Glu Ala Val Ser Thr Asn Glu Gly Ala Ala Thr Asn Tyr
1               5                   10                  15

Asn His Gly Gly Asn His Gln Ser Asn Leu Ile Val Pro Asn Asn His
            20                  25                  30

Glu Asp Asp Leu Gln Ser Thr Ala Asn Pro Ile Thr Gln Asn Arg Val
        35                  40                  45

Ile Lys Trp Lys Leu Leu Ile Val Phe Cys Phe Phe Ser Ala Phe Gly
    50                  55                  60

Tyr Leu Gly Gly Pro Leu Leu Gln Arg Leu Tyr Tyr Thr His Gly Gly
65                  70                  75                  80

Gly Arg Lys Trp Leu Ser Ser Met Leu Gln Thr Ala Gly Phe Pro Val
                85                  90                  95

Leu Val Ala Pro Leu Ser Tyr Ile Tyr Ile Lys Lys Val Asn Gly Pro
            100                 105                 110

Ser Tyr Asp Ser Ser Trp Val Phe Met Met Glu Pro Lys Leu Phe Ile
        115                 120                 125

Tyr Ser Ala Thr Met Gly Val Val Leu Gly Leu Asp Asn Tyr Met Tyr
    130                 135                 140

Ser Ala Gly Leu Phe Tyr Leu Pro Val Ser Thr Ser Ser Leu Leu Phe
145                 150                 155                 160

Ser Thr Gln Leu Ala Phe Thr Ala Val Phe Ala Phe Ile Ile Val Arg
                165                 170                 175

Gln Lys Phe Thr Phe Tyr Ser Phe Asn Ser Val Val Leu Met Thr Leu
            180                 185                 190

Gly Ala Val Val Leu Ala Leu Asn Thr Ser Ser Asp Lys Ser Pro Gly
        195                 200                 205

Thr Thr Gln Gln Gln Tyr Tyr Leu Gly Phe Phe Leu Thr Leu Ala Gly
    210                 215                 220

Ala Ala Leu Ala Gly Leu Cys Met Pro Leu Ile Glu Leu Ala Tyr Gly
225                 230                 235                 240

Lys Ser Ser Lys Pro Ile Thr Tyr Ser Val Val Met Gln Phe Gln Phe
                245                 250                 255

Val Leu Ser Leu Phe Ser Thr Leu Val Cys Met Ile Gly Met Ala Ile
            260                 265                 270

Asn Asn Asp Phe Lys Val Ile Pro Arg Glu Gly Arg Asn Phe Gly Leu
        275                 280                 285

Gly Glu Thr Lys Tyr Tyr Phe Leu Ile Val Ala Thr Ala Ile Val Tyr
    290                 295                 300

Gln Leu Phe Thr Ile Gly Phe Met Gly Ile Ile Tyr Cys Thr Ser Ser
305                 310                 315                 320
```

```
Leu Phe Ala Gly Ile Phe Thr Thr Cys Leu Leu Pro Phe Ser Gln Val
                325                 330                 335

Ala Ala Thr Ile Ala Phe His Glu Lys Phe Thr Gly Gln Lys Gly Met
            340                 345                 350

Ser Leu Ala Leu Cys Leu Trp Gly Phe Val Ser Tyr Phe Ile Gly Glu
        355                 360                 365

Tyr Lys Lys Thr Lys Lys Pro His Pro Ile Ala Tyr Asp Asn Lys Ala
    370                 375                 380

Glu Glu Leu Lys Glu Lys Leu Asp Gln Leu Thr Asp Ser Asn Thr Met
385                 390                 395                 400

Glu Gly Ser His Lys Ser Glu Ser Arg Phe Val His Pro
                405                 410


<210> SEQ ID NO 39
<211> LENGTH: 1242
<212> TYPE: DNA
<213> ORGANISM: Papaver somniferum

<400> SEQUENCE: 39

atggatatcg aagctgtttc taccaatgaa ggtgctgcta ctaattacaa tcatggtggt     60

aaccatcagt ccaacttgat cgttccaaac aatcatgaag atgacttgca atctactgct    120

aacccaatca ctcaaaacag agttatcaag tggaagctgt tgatcgtttt ctgtttcttt    180

tctgccttcg gttacttagg tggtccatta ttgcaaaggt tgtactatac acatggtggt    240

ggtagaaaat ggctgtcatc tatgttgcaa actgctggtt ttccagtttt ggttgctcca    300

ttgtcttaca tctacatcaa gaaagttaac ggtccctcct atgattcttc ttgggttttt    360

atgatggaac ccaagctgtt tatctactct gctactatgg gtgttgtttt gggtttagac    420

aactacatgt attccgctgg tttgttctat ttgccagttt ctacttcctc cttgttgttc    480

tctactcaat tggcttttac tgctgttttc gccttcatta tcgtcagaca aaagttcacc    540

ttctacagct tcaattccgt tgttttgatg actttgggtg ctgttgtttt agctttgaac    600

acctcttctg ataagtctcc aggtactact caacaacaat attacttggg tttcttcttg    660

actttggctg gtgctgcttt ggcaggtttg tgtatgccat tgattgaatt ggcttacggc    720

aaatcttcca agccaattac ttactccgtt gtcatgcaat tccaattcgt cttgtctttg    780

ttttctacct tggtctgcat gattggtatg gccattaaca acgatttcaa ggtcattcca    840

agagagggta gaaattttgg tttgggtgaa acgaagtact acttcttgat agttgctacc    900

gctatcgttt accagttgtt cactattggt ttcatgggta ttatctactg cacctcatct    960

ttgttcgctg gtattttcac tacttgcttg ttgccatttt cacaagttgc tgctaccatt   1020

gcttttcatg agaagtttac tggtcaaaag ggtatgtctt tggctttgtg tttgtggggt   1080

tttgtctcct actttattgg cgagtacaaa aagactaaga agccacatcc aattgcctac   1140

gataacaaag ccgaagaatt gaaagaaaag ttggaccaat tgaccgactc taacactatg   1200

gaaggttctc ataagtccga atccagattc gttcatccat ga                       1242


<210> SEQ ID NO 40
<211> LENGTH: 384
<212> TYPE: PRT
<213> ORGANISM: Papaver somniferum

<400> SEQUENCE: 40

Met Ile Ile Glu Thr Leu Asp Ile Leu Gly Pro Asn Gln Asn Gly Asn
1               5                   10                  15
```

```
Ser Gly Thr His Thr Gln Lys Pro Ile Lys Thr Arg Asn Trp Leu Leu
            20                  25                  30

Ile Ile Ile Asn Cys Ala Leu Val Phe Cys Gly Val Ile Gly Gly Pro
        35                  40                  45

Leu Leu Met Arg Leu Tyr Tyr Leu His Gly Gly Ser Arg Lys Trp Leu
    50                  55                  60

Ser Ser Phe Leu Gln Thr Ala Gly Phe Pro Val Leu Ile Phe Pro Leu
65                  70                  75                  80

Ile Phe Leu Tyr Ile Lys Pro Lys Leu Ser Thr Gln Asn Asn Asp Gln
                85                  90                  95

Ser Ser Ser Phe Phe Met Glu Pro Lys Leu Phe Leu Trp Ser Ala Ile
            100                 105                 110

Val Gly Ile Val Phe Gly Val Ser Asn Phe Met Tyr Ala Leu Gly Leu
        115                 120                 125

Ser Tyr Leu Pro Val Ser Thr Ser Thr Ile Leu Phe Ala Thr Gln Leu
    130                 135                 140

Cys Phe Thr Ala Ile Phe Ala Trp Leu Ile Val Lys Gln Lys Phe Thr
145                 150                 155                 160

Ala Phe Ile Ile Asn Ala Val Ile Val Met Thr Leu Gly Ser Ile Leu
                165                 170                 175

Leu Gly Ile Asn Thr Asn Gly Asp Arg Pro Ile Gly Val Ser Lys Thr
            180                 185                 190

Gln Tyr Leu Ile Gly Phe Leu Met Thr Leu Ala Ala Ala Ala Leu Thr
        195                 200                 205

Gly Leu Gly Thr Pro Phe Val Glu Leu Ser Phe Ile Lys Ala Thr Arg
    210                 215                 220

Asn Ile Thr Tyr Pro Thr Leu Leu Gln Phe Gln Val Ile Leu Cys Leu
225                 230                 235                 240

Phe Gly Thr Cys Leu Asn Val Ile Gly Met Leu Ile Asn Lys Asp Phe
                245                 250                 255

Gln Ala Ile Pro Arg Glu Ala Asp Met Phe Glu Leu Gly Lys Ser Lys
            260                 265                 270

Tyr Tyr Met Ile Ile Cys Leu Thr Ala Leu Thr Trp Gln Leu Ser Gly
        275                 280                 285

Ile Gly Leu Val Gly Leu Ile Leu Tyr Thr Asn Ala Leu Phe Asn Gly
    290                 295                 300

Ile Tyr Val Ser Val Leu Val Pro Phe Thr Glu Val Ala Ala Val Ile
305                 310                 315                 320

Phe Phe His Glu Lys Phe Thr Gly Leu Lys Gly Met Ala Leu Ala Leu
                325                 330                 335

Cys Leu Trp Gly Phe Ser Ser Tyr Phe Tyr Gly Glu Tyr Lys Met Met
            340                 345                 350

Asn Lys Val Gly Asp Asn Glu Thr His Glu Lys Ile Glu Glu Ala Glu
        355                 360                 365

Ser Glu Pro Lys Arg Leu Glu Asp Gln Gln Ala Pro Tyr Ser Thr Val
    370                 375                 380
```

<210> SEQ ID NO 41
<211> LENGTH: 1155
<212> TYPE: DNA
<213> ORGANISM: Papaver somniferum

<400> SEQUENCE: 41

```
atgatcatcg aaaccttgga tatcttgggt ccaaatcaaa atggtaactc tggtactcat      60
```

```
acccagaagc caatcaaaac tagaaactgg ttgctgatca ttatcaactg cgctttggtt    120

ttctgtggtg ttattggtgg tccattattg atgaggttgt actacttgca tggtggttct    180

agaaagtggc tatcttcttt cttgcaaact gctggttttc cagtcttgat tttccctttg    240

atcttcctgt acatcaagcc aaaattgtct acccaaaaca acgaccagtc ctcctcattt    300

ttcatggaac ctaagttgtt tttgtggtcc gctatagttg gtatcgtttt cggtgtttct    360

aacttcatgt atgccttggg tttgtcttac ttgccagttt ccacttccac tattttgttc    420

gctactcaat tgtgcttcac cgctattttt gcttggttga tcgttaagca aaagttcacc    480

gccttcatta ttaacgccgt tatcgttatg actctgggct caattttgtt gggtattaac    540

actaatggtg acagacctat tggtgtctct aagactcaat acttgatcgg tttcttgatg    600

actttggctg ctgctgcttt gactggtttg ggtactccat ttgttgaact gtctttcatt    660

aaggccacca gaaacattac ttacccaacc ttgttgcaat tccaagtcat tttgtgtttg    720

ttcggcacct gtttgaacgt tattggcatg ttgattaaca aggacttcca agccattcca    780

agagaagctg atatgttcga attgggcaaa tccaagtact acatgattat ttgcttgacc    840

gctttgacct ggcaattgtc tggtattggt ttggttggtt tgatcttgta cactaacgct    900

ttgttcaacg gcatctacgt ttctgttttg gttccattca ctgaagttgc tgccgttata    960

ttctttcatg agaagttcac tggtttgaaa ggtatggctt tggctttgtg tttatggggt   1020

ttttcctctt acttttacgg cgagtacaag atgatgaaca aagttggtga taacgaaacc   1080

cacgaaaaga ttgaagaagc tgaatctgaa cccaagagat tggaagatca gcaagctcca   1140

tattctaccg tttga                                                     1155
```

<210> SEQ ID NO 42
<211> LENGTH: 373
<212> TYPE: PRT
<213> ORGANISM: Glaucium Flavum

<400> SEQUENCE: 42

```
Met Asn Pro Asp Leu Asp Leu Gln Thr Tyr Thr Glu Tyr Pro Ala Lys
1               5                   10                  15

Thr Lys Asn Trp Pro Leu Ile Ile Leu Asn Thr Val Ile Met Thr Ile
            20                  25                  30

Gly Val Ile Gly Gly Pro Leu Leu Met Arg Leu Tyr Tyr Ile His Gly
        35                  40                  45

Gly Asn Arg Arg Trp Leu Ser Ser Cys Ile Gln Asn Ala Gly Phe Pro
    50                  55                  60

Ile Leu Leu Ile Pro Leu Thr Phe Leu Phe Phe Gln Tyr Ser Lys Thr
65                  70                  75                  80

Pro His Gln Glu Asn His His Leu Ser Ser Ser Pro Leu Ser Ser Lys
                85                  90                  95

Pro Ser Ser Phe Leu Met Glu Pro Lys Leu Phe Leu Ser Ser Ser Phe
            100                 105                 110

Val Gly Ile Leu Phe Gly Leu Asn Asn Phe Met Tyr Ser Leu Gly Leu
        115                 120                 125

Ser Tyr Ile Pro Ile Ser Thr Ser Ser Leu Leu Phe Ala Thr Gln Leu
    130                 135                 140

Ala Phe Val Ala Phe Phe Ala Trp Leu Ile Val Lys Gln Gln Phe Thr
145                 150                 155                 160

Ala Tyr Ser Ile Asn Ser Val Val Leu Met Thr Leu Gly Ser Ile Leu
                165                 170                 175
```

```
Leu Gly Val Lys Asn Asp Gly Asp Arg Pro Val Gly Val Thr Lys Ala
            180                 185                 190

Glu Tyr Met Leu Gly Phe Leu Leu Thr Leu Gly Ser Ala Ala Leu Val
        195                 200                 205

Gly Phe Ile Leu Pro Leu Val Glu Leu Ser Tyr Ser Lys Ala Thr Arg
    210                 215                 220

His Val Asn Tyr Thr Thr Ile Leu Gln Tyr Gln Leu Asn Leu Ala Leu
225                 230                 235                 240

Phe Ser Thr Ile Phe Asn Ser Ile Gly Met Val Ile Asn Lys Asp Phe
                245                 250                 255

Gln Ala Ile Pro Arg Glu Ala Ser Glu Phe Glu Leu Gly Lys Thr Met
            260                 265                 270

Tyr Tyr Thr Ile Leu Ile Thr Gly Ala Ile Ile Trp Gln Leu Ser Phe
        275                 280                 285

Ile Gly Gly Leu Gly Val Ile Leu Tyr Thr Ser Ser Leu Phe Ser Gly
    290                 295                 300

Ile Leu Thr Ser Val Leu Leu Pro Phe Thr Glu Ile Ala Ala Val Ile
305                 310                 315                 320

Val Tyr Arg Glu Ser Phe Thr Gly Leu Lys Gly Met Ala Leu Ala Leu
                325                 330                 335

Cys Leu Trp Gly Phe Thr Ser Tyr Phe Tyr Gly Glu Tyr Lys Met Met
            340                 345                 350

Lys Asn Met Lys Thr Lys Thr Ser Glu Lys Val Val Asp Asn Asp Glu
        355                 360                 365

Glu Pro Cys Thr Val
    370
```

<210> SEQ ID NO 43
<211> LENGTH: 1122
<212> TYPE: DNA
<213> ORGANISM: Glaucium Flavum

<400> SEQUENCE: 43

```
atgaacccag acttggactt gcaaacctat actgaatatc cagctaagac taagaactgg      60

ccattgatta ttttgaacac cgtcattatg accatcggtg ttattggtgg tccattattg     120

atgaggttgt actacattca tggtggtaac agaagatggt tgtcctcttg tattcaaaat     180

gctggtttcc ccattctgtt gatcccattg actttttttgt tcttccagta ctctaagacc     240

ccacatcaag aaaaccatca cttgtcatct tctccattgt cctctaagcc atcctcattt     300

ttgatggaac ctaagctgtt cctgtcctct tcttttgttg gtattttgtt cggcttgaac     360

aacttcatgt acagcttggg tttgagctat attccaatct ccacttcgtc tttgttgttc     420

gctactcaat tggcttttgt tgcttttttc gcttggttga tcgtcaagca acaattcact     480

gcttactcca tcaactccgt tgttttgatg actttgggtt ccattttgtt gggtgttaag     540

aacgatggtg atagaccagt tggtgttaca aaagctgagt acatgttggg tttcttgttg     600

actttaggtt ctgctgcttt ggttggtttc attttgccat tggttgagct gtcttactct     660

aaggctacta gacatgttaa ctacaccacc atcttgcaat accaattgaa cttggctttg     720

ttcagcacca tcttcaactc tattggtatg gttatcaaca aggacttcca agctattcca     780

agagaagcct ctgaatttga attgggtaag actatgtact acacgatctt gattaccggt     840

gccattattt ggcaattgtc tttcattggt ggtttgggcg ttatcttgta cacatcttct     900

ttgttctccg gtatcttgac ctctgttttg ttgccattca ctgaaattgc tgccgttatc     960
```

```
gtttacagag aatctttcac tggtttgaaa ggtatggctt tggctttatg tttgtggggt   1020

tttacctctt acttttacgg tgagtacaag atgatgaaga atatgaagac caagacctcc   1080

gaaaaggttg ttgacaacga tgaagaacca tgtaccgttt ga                      1122


<210> SEQ ID NO 44
<211> LENGTH: 383
<212> TYPE: PRT
<213> ORGANISM: Papaver somniferum

<400> SEQUENCE: 44

Met Ala Thr Ser Thr Pro Leu Asn Met Glu Ala Pro Glu Ile Leu Gly
1               5                   10                  15

Thr Thr Gln Asn Gly Asn Ser Lys Thr His Val Glu Lys Pro Thr Lys
            20                  25                  30

Thr Lys Asn Trp Leu Met Ile Ile Ile Asn Ser Ala Phe Val Thr Ile
        35                  40                  45

Gly Leu Val Gly Gly Pro Leu Leu Ile Arg Leu Tyr Tyr Leu His Gly
    50                  55                  60

Gly Asn Arg Lys Trp Leu Thr Ser Cys Leu Gln Ser Ala Gly Phe Pro
65                  70                  75                  80

Ile Leu Ile Phe Pro Leu Thr Phe Leu Phe Ile Gln Ser Lys Leu Ser
                85                  90                  95

Thr Glu Ser Pro Ser Phe Trp Leu Glu Pro Lys Leu Ser Leu Trp Ser
            100                 105                 110

Ala Ile Ile Gly Ile Leu Phe Gly Leu Ile Asn Phe Met Tyr Ser Ser
        115                 120                 125

Gly Leu Ser Tyr Ile Pro Val Ser Thr Ser Ser Leu Leu Leu Ala Thr
    130                 135                 140

Gln Leu Cys Phe Val Ala Phe Phe Ser Trp Leu Phe Val Lys Gln Lys
145                 150                 155                 160

Phe Thr Ala Phe Ile Ile Asn Ala Val Val Val Met Thr Leu Gly Ser
                165                 170                 175

Val Leu Leu Gly Ile Asn Thr Asp Gly Asp Arg Pro Val Gly Val Ser
            180                 185                 190

Lys Ala Gln Tyr Leu Thr Gly Phe Leu Thr Thr Leu Gly Ala Ala Ala
        195                 200                 205

Leu Ala Gly Leu Met Met Pro Leu Ile Glu Leu Gly Phe Ser Lys Ala
    210                 215                 220

Val Arg Asp Leu Asn Tyr Ser Ser Leu Leu Gln Phe Gln Phe Ile Phe
225                 230                 235                 240

Ser Ser Ser Ser Thr Ile Phe Cys Val Ile Gly Met Leu Val Asn Lys
                245                 250                 255

Asp Phe Gln Val Ile Pro Arg Glu Ala Asn Glu Phe Glu Leu Gly Lys
            260                 265                 270

Ala Met Tyr Tyr Ile Leu Met Val Leu Thr Ala Ile Thr Trp Gln Leu
        275                 280                 285

Leu Asn Val Gly Ile Val Gly Val Ile Ser Tyr Ala Ser Ala Leu Phe
    290                 295                 300

Tyr Gly Ile Leu Thr Ser Val Leu Val Pro Phe Thr Gly Val Ala Ala
305                 310                 315                 320

Val Ile Phe Tyr His Glu Ser Phe Thr Gly Leu Lys Gly Met Ala Leu
                325                 330                 335

Ala Leu Cys Leu Trp Gly Phe Cys Ser Tyr Phe Tyr Gly Glu Tyr Lys
            340                 345                 350
```

Met Met Ser Lys Lys Val Ile Asn Asn Gly Asn Pro Glu Thr Ile Glu
355 360 365

Lys Asp Glu Asn Glu Pro Lys Arg Leu Asp Asp Leu Gly Glu Pro
370 375 380

<210> SEQ ID NO 45
<211> LENGTH: 1152
<212> TYPE: DNA
<213> ORGANISM: Papaver somniferum

<400> SEQUENCE: 45
atggctactt ctaccccatt gaatatggaa gctccagaaa ttttgggtac aacccaaaat 60
ggtaactcta agacccatgt tgaaaagcca actaagacta agaactggct gatgatcatt 120
atcaactctg ccttcgttac cattggtttg gttggtggtc cattattgat taggttgtac 180
tacttgcatg gtggcaatag aaaatggttg acttcttgct tgcaatctgc tggtttccca 240
attttgattt tccctttgac cttcctgttc atccagtcta aattgtctac tgagtctcca 300
tctttttggt tggaacctaa gttgtctttg tggtccgcta ttattggtat cttgttcggt 360
ctgatcaact tcatgtattc ctctggtttg tcctatattc cagtctctac ttcctctttg 420
ttgttggcta ctcaattgtg tttcgttgct ttcttctctt ggttgttcgt caagcaaaag 480
ttcaccgcct ttattatcaa cgccgttgtt gttatgactt tgggttctgt tttgttgggt 540
attaacaccg atggtgatag accagttggt gtttctaaag ctcaatactt gactggtttc 600
ttgactactt tgggtgctgc tgctttggct ggtttgatga tgccattgat tgaattgggt 660
ttctccaagg ctgttagaga cttgaattac tcgtctttgt tgcagttcca gttcatcttc 720
tcttcatcct ctactatttt ctgcgtcatc ggtatgttgg ttaacaagga tttccaagtc 780
attcctagag aagccaatga attcgaacta ggtaaagcca tgtactacat cttgatggtt 840
ttgactgcta ttacctggca gttgttgaat gttggtatcg ttggtgttat ttcctacgct 900
tctgctttgt tctacggtat tttgacctct gttttggttc cattcactgg tgttgctgct 960
gttattttct accatgaatc tttcaccggt ttgaaaggta tggctttggc tttgtgtttg 1020
tggggttttt gttcttactt ttacggcgag tacaagatga tgtccaaaaa ggttattaac 1080
aacggcaacc cagaaaccat tgaaaaggac gaaaatgaac ctaagagatt ggatgatttg 1140
ggtgagccat aa 1152

<210> SEQ ID NO 46
<211> LENGTH: 372
<212> TYPE: PRT
<213> ORGANISM: Trema orientale

<400> SEQUENCE: 46

Met Glu Met Glu Met Glu Met Asp Gln Glu Asp His Asp Gln Ser Ala
1 5 10 15

Lys His Asn Arg Ser Leu Leu Ile Leu Asn Cys Ile Leu Leu Thr Ile
20 25 30

Gly Asn Cys Gly Gly Pro Leu Ile Met Arg Leu Tyr Phe Ile His Gly
35 40 45

Gly Lys Arg Val Trp Leu Ser Ser Trp Leu Glu Thr Gly Gly Cys Phe
50 55 60

Ile Ile Ile Ile Pro Leu Ala Ala Ala Tyr Phe Arg Arg Arg Arg Arg
65 70 75 80

Arg Arg Arg Leu Ala Ser Ala Arg Leu Val Gln Met Glu Pro Phe Leu

```
                85                  90                  95

Phe Leu Gly Ser Ala Val Ile Gly Leu Ala Thr Gly Phe Asp Asp Tyr
            100                 105                 110

Leu Tyr Ala Tyr Gly Val Ala Arg Leu Pro Val Ser Thr Ser Ser Leu
        115                 120                 125

Ile Ile Ala Ser Gln Leu Ala Phe Thr Ala Gly Phe Ala Phe Leu Leu
    130                 135                 140

Val Lys Gln Arg Phe Thr Ser Tyr Ser Val Asn Ala Val Val Leu Leu
145                 150                 155                 160

Thr Ile Gly Gly Ala Val Leu Ala Leu His Thr Arg Gly Asp Arg Pro
                165                 170                 175

Lys Gly Glu Ser Glu Lys Asp Tyr Val Val Gly Phe Leu Met Thr Val
            180                 185                 190

Ala Ala Ala Val Leu Tyr Gly Phe Ile Leu Pro Leu Val Glu Leu Met
        195                 200                 205

Tyr Lys Lys Ala Lys Gln Arg Ile Thr Tyr Ser Leu Val Leu Glu Ile
    210                 215                 220

Gln Phe Val Met Cys Phe Phe Ala Thr Leu Phe Cys Thr Val Gly Met
225                 230                 235                 240

Leu Ile Asn Lys Asp Phe Lys Ala Ile Pro Arg Glu Ala Arg Lys Phe
                245                 250                 255

Glu Leu Gly Glu Thr Thr Tyr Tyr Val Val Leu Val Leu Ser Ala Ile
            260                 265                 270

Ile Trp Gln Gly Phe Phe Leu Gly Ala Ile Gly Val Ile Phe Cys Ala
        275                 280                 285

Ser Ser Leu Leu Ser Gly Ile Val Ile Ala Val Leu Leu Pro Val Thr
    290                 295                 300

Glu Ile Leu Ala Val Ile Phe Tyr Lys Glu Asn Phe Gln Ala Glu Lys
305                 310                 315                 320

Gly Val Ser Leu Ala Leu Ser Leu Trp Gly Phe Val Ser Tyr Phe Tyr
                325                 330                 335

Gly Glu Ile Lys Gln Ser Lys Lys Ile Lys Lys Glu Arg Asp Asn Lys
            340                 345                 350

Gln Pro Thr Lys Ser Ser Ser Ser Thr Pro Ala Arg Glu Met Ser His
        355                 360                 365

Val Ala Ser Pro
    370
```

<210> SEQ ID NO 47
<211> LENGTH: 1119
<212> TYPE: DNA
<213> ORGANISM: Trema orientale

<400> SEQUENCE: 47

```
atggaaatgg agatggaaat ggatcaagaa gatcacgatc aatctgctaa gcacaacaga      60

tccttgttga ttttgaactg catcttgttg accattggta attgtggtgg tccattgatt     120

atgaggttgt actttattca cggtggtaag agagtttggt tgtcatcttg gttggaaact     180

ggtggttgct tcattattat cattccattg gctgctgctt acttcagaag aagaaggcgt     240

agaagaagat tggcttctgc tagattggtt caaatggaac catttttgtt cttgggttcc     300

gctgttattg gtttggctac tggttttgat gattacttgt atgcttacgg tgttgccaga     360

ttgccagttt ctacttcctc tttgattatc gcttctcaat tggcttttac tgctggtttt     420

gctttcttgt tggtcaagca aagattcacc tcttactctg ttaacgccgt tgttttgtta     480
```

```
actattggtg gtgctgtttt ggccttgcat acaagaggtg atagaccaaa aggtgaatcc    540

gaaaaggatt acgttgttgg tttcttgatg actgttgctg ctgctgtctt gtatggtttc    600

attttgccat tggtcgagct gatgtacaaa aaggctaagc aaagaattac ctactccttg    660

gtcttggaaa tccaattcgt tatgtgtttc ttcgctacct tgttctgtac tgttggcatg    720

ttgattaaca aggacttcaa ggctattcca agagaagcta gaaagttcga attgggtgaa    780

actacctatt acgtcgtttt ggttttgtcc gccattattt ggcaaggttt ctttttgggt    840

gctatcggtg ttattttctg cgcttcttct ttgttgtccg gtatcgttat tgctgtttta    900

ttgccagtca ccgaaatttt ggctgttatc ttctacaaag aaaacttcca agccgaaaag    960

ggtgtttctt tggctttgtc tttgtggggt ttcgtttctt acttttacgg tgaaatcaag   1020

cagtccaaga agattaagaa agagagagat aacaagcagc ccaccaaatc ttcatcttct   1080

actccagcta gagaaatgtc tcatgttgct tctccatga                          1119
```

<210> SEQ ID NO 48
<211> LENGTH: 363
<212> TYPE: PRT
<213> ORGANISM: Cucumis sativus

<400> SEQUENCE: 48

```
Met Asp Lys Glu Gln Gln Gln Gln Asn Thr Pro Ser Val Lys Arg Thr
1               5                   10                  15

Leu Leu Ile Phe Asn Cys Cys Leu Leu Ala Val Gly Asn Cys Gly Gly
            20                  25                  30

Pro Leu Ile Met Arg Leu Tyr Phe Val His Gly Gly Lys Arg Val Trp
        35                  40                  45

Leu Ser Ser Cys Leu Glu Thr Gly Gly Trp Pro Ile Ile Phe Ile Pro
    50                  55                  60

Leu Leu Ile Ser Tyr Ile His Arg Arg Arg Leu Ala Ala Leu Asp Pro
65                  70                  75                  80

Ser Gly Ser Pro Asn Ser Ala Gln Phe Ile Phe Met Lys Pro Arg Leu
                85                  90                  95

Phe Leu Ala Ser Ala Phe Ile Gly Ile Leu Thr Gly Phe Asp Asp Tyr
            100                 105                 110

Leu Tyr Ala Tyr Gly Val Ala Arg Leu Pro Val Ser Thr Ser Ala Leu
        115                 120                 125

Ile Ile Ala Cys Gln Leu Ala Phe Thr Ala Gly Phe Ala Phe Leu Leu
    130                 135                 140

Val Lys Gln Lys Phe Thr Ser Tyr Ser Ile Asn Ala Val Val Leu Leu
145                 150                 155                 160

Thr Ile Gly Gly Ala Val Leu Ala Leu His Thr Ser Gly Asp Arg Pro
                165                 170                 175

Ala Gly Glu Ser Asn Lys Asp Tyr Ile Ala Gly Phe Leu Met Thr Val
            180                 185                 190

Ala Ala Ala Val Val Tyr Gly Phe Val Leu Pro Leu Val Glu Leu Thr
        195                 200                 205

Tyr Lys Lys Ala Arg Gln Gln Ile Thr Tyr Thr Leu Val Leu Glu Phe
    210                 215                 220

Gln Leu Ile Met Ser Leu Phe Ala Thr Ile Val Cys Ala Ile Gly Met
225                 230                 235                 240

Leu Ile Asn Asn Asp Phe Gln Val Ile Pro Arg Glu Ala Glu Ala Phe
                245                 250                 255
```

```
Gly Leu Gly Lys Phe Arg Tyr Tyr Leu Val Leu Val Leu Ser Ala Ile
            260                 265                 270

Leu Trp Gln Gly Phe Phe Leu Gly Ala Ile Gly Val Ile Phe Ser Ser
        275                 280                 285

Ser Ser Leu Phe Ser Gly Ile Val Ile Ala Val Leu Leu Pro Val Thr
    290                 295                 300

Glu Ile Leu Ala Val Ile Ile Phe Asn Glu Arg Phe Gln Ala Glu Lys
305                 310                 315                 320

Gly Val Ser Leu Ala Leu Asn Leu Trp Gly Phe Leu Ser Tyr Phe Tyr
                325                 330                 335

Gly Glu Ile Lys His Asn Lys Arg Lys Lys Leu Glu Leu Gln Arg Tyr
            340                 345                 350

Glu Glu Thr Thr Ser Thr Gln Val Ala Asn Val
        355                 360


<210> SEQ ID NO 49
<211> LENGTH: 1092
<212> TYPE: DNA
<213> ORGANISM: Cucumis sativus

<400> SEQUENCE: 49

atggacaaag aacaacagca acagaacacc ccatctgtta agagaacttt gttgattttc      60

aactgctgct tgttggctgt tggtaattgt ggtggtccat tgattatgag gttgtacttt     120

gttcatggtg gtaagagagt ttggttgtcc tcttgtttgg aaactggtgg ttggccaatt     180

atcttcattc cactgttgat ctcttacatc cacagaagaa gattggctgc tttggatcca     240

tctggttctc caaattctgc tcagttcatt tttatgaagc ccaggttgtt tttggcctct     300

gcttttattg gtattttgac cggtttcgac gattacttgt atgcttatgg tgttgctaga     360

ttgccagttt ctacttccgc tttgattatt gcttgtcaat tggcttttac tgctggtttc     420

gctttcttgt tggttaagca aaagttcacc tcctactcca ttaacgctgt tgttttgttg     480

actattggtg gtgctgtttt ggcattgcat acttcaggtg atagacctgc tggtgaatct     540

aacaaagatt acattgccgg tttcttgatg actgttgctg ctgcagttgt ttacggtttt     600

gttttgccat tggttgagtt gacttacaag aaggccagac aacaaattac ctacaccttg     660

gtcttggagt tccaattgat catgtctttg ttcgctacta tcgtttgcgc tataggcatg     720

ttgattaaca acgatttcca agtcattcca agagaagctg aagcttttgg tttaggtaag     780

ttcaggtact acttggtgtt ggttttgtct gctattttgt ggcaaggttt tttcttgggt     840

gctatcggtg ttatcttctc ctcatcatct ttgttctccg gtatcgttat tgcagttttg     900

ttgccagtta ccgaaatttt ggccgttatc atcttcaacg aaagattcca agctgaaaag     960

ggtgtttctt tggctttgaa tttgtggggt ttcctgtctt acttttacgg tgaaatcaaa    1020

cacaacaagc gtaagaagtt ggaattgcag agatacgaag aaaccacttc tactcaagtt    1080

gccaacgttt ga                                                        1092


<210> SEQ ID NO 50
<211> LENGTH: 373
<212> TYPE: PRT
<213> ORGANISM: Helianthus annuus

<400> SEQUENCE: 50

Met Glu Asn Gln Lys Glu Thr Thr Ile Thr Ile Ser Lys Asp Thr Asn
1               5                   10                  15

Thr Thr Pro Met Thr Thr Glu Val Ser Leu Phe Ala Arg Lys Thr Leu
```

```
            20                  25                  30

Leu Ile Leu Asn Cys Leu Leu Leu Ser Ile Gly Thr Cys Gly Gly Pro
        35                  40                  45

Leu Ile Met Arg Leu Tyr Phe Val His Gly Gly Ser Arg Val Trp Leu
    50                  55                  60

Ser Ser Val Leu Gln Thr Ala Gly Phe Pro Phe Ile Ile Ala Val Ile
65                  70                  75                  80

Ile Ile Leu Tyr Phe Cys Arg Ser Ala Val Ala Lys Asn Gln Asn Asn
                85                  90                  95

Lys Thr Thr Lys Leu Phe Tyr Met Arg Pro Arg Leu Phe Leu Ala Ala
            100                 105                 110

Val Phe Ile Gly Leu Ile Thr Gly Leu Asp Asn Tyr Leu Tyr Ala Tyr
        115                 120                 125

Gly Val Ala Arg Leu Pro Val Ser Thr Ser Ser Leu Ile Ile Ala Phe
    130                 135                 140

Gln Leu Ala Phe Thr Ala Phe Phe Ala Tyr Leu Val Val Lys Leu Lys
145                 150                 155                 160

Phe Thr Pro Tyr Ser Val Asn Ala Val Val Leu Leu Thr Val Gly Ala
                165                 170                 175

Gly Val Leu Ala Leu His Ala Ser Ser Asp Arg Pro Glu Gly Glu Ser
            180                 185                 190

Lys Lys Glu Tyr Thr Met Gly Phe Val Met Thr Leu Met Ala Ala Leu
        195                 200                 205

Val Tyr Gly Phe Leu Leu Pro Leu Ile Glu Leu Thr Tyr Asn Lys Ala
    210                 215                 220

Gln Gln Glu Ile Thr Tyr Thr Leu Val Leu Glu Ile Gln Met Val Leu
225                 230                 235                 240

Ser Leu Phe Ala Thr Val Phe Cys Val Val Gly Met Ile Val Asn Asn
                245                 250                 255

Asp Phe Gln Val Ile Pro Arg Glu Ala Ser Lys Phe Glu Phe Gly Ala
            260                 265                 270

Thr Lys Tyr Tyr Ile Ile Leu Cys Ala Ser Ala Leu Ile Trp Gln Cys
        275                 280                 285

Tyr Phe Leu Gly Ala Ile Gly Val Ile Phe Cys Ser Ser Ala Leu Leu
    290                 295                 300

Ser Gly Ile Ile Ile Ser Val Leu Leu Pro Val Ile Glu Val Leu Ala
305                 310                 315                 320

Val Val Phe Tyr Lys Glu Lys Phe Gln Ala Glu Lys Gly Val Ser Leu
                325                 330                 335

Val Leu Ser Leu Trp Gly Phe Ala Ser Tyr Phe Tyr Gly Glu Tyr Lys
            340                 345                 350

Val Thr Lys Lys Ala Lys Arg Cys Asn Thr Phe Ser Ser Thr Ile Asn
        355                 360                 365

Gly Ala Cys Leu Ser
    370


<210> SEQ ID NO 51
<211> LENGTH: 1122
<212> TYPE: DNA
<213> ORGANISM: Helianthus annuus

<400> SEQUENCE: 51

atggaaaacc agaaagaaac caccatcacc atttctaagg ataccaacac tactccaatg      60

accactgaag tttctttgtt cgctagaaag accctgttga ttttgaactg cttgttgttg     120
```

```
tctattggta cttgtggtgg tccattgatt atgaggttgt actttgttca tggtggttcc    180

agagtttggt tatcttctgt tttacaaact gctggcttcc cattcattat tgccgttatt    240

atcatcctgt atttctgcag atcagccgtt gctaagaatc aaaacaacaa gactaccaag    300

ctgttctata tgaggccaag attattctta gccgccgttt tcattggttt gattactggt    360

ttggacaact acttgtatgc ttacggtgtt gctagattgc cagtttctac ttcctctttg    420

attatcgctt tccaattggc tttcactgct ttctttgctt acttggttgt caagttgaag    480

ttcaccccat actctgttaa tgccgttgtt ttgttgactg ttggtgctgg tgttttggct    540

ttacatgctt cttcagatag accagaaggt gagtctaaga aagaatacac tatgggtttc    600

gtcatgactt tgatggctgc tttggtttac ggtttttttgt tgccattgat cgagttgact    660

tacaacaagg cccaacaaga aattacctac accttggttt tggaaatcca gatggttttg    720

tctttgtttg ctaccgtttt ctgcgttgtt ggtatgatcg ttaacaacga tttccaagtc    780

attccaagag aagcctctaa gtttgaattt ggtgctacca agtactatat catcttgtgt    840

gcttcagcct tgatttggca atgttacttt ttgggtgcta tcggcgttat tttctgttct    900

tctgctttgt tgtccggcat catcatttct gttttgctgc cagttattga agttttggct    960

gtcgtgttct acaaagaaaa gttccaagct gaaaagggtg tctctttggt tttatcttta   1020

tggggtttcg cctcttactt ttacggtgag tacaaggtta ctaagaaagc caagagatgt   1080

aacaccttct cctctactat taacggtgct tgtttgtcct ga                      1122
```

<210> SEQ ID NO 52
<211> LENGTH: 365
<212> TYPE: PRT
<213> ORGANISM: Musa acuminata

<400> SEQUENCE: 52

```
Met Glu Val Glu Gly Gln Asn Ser Asn His Gln Asn Gln Asp Ala Ala
1               5                   10                  15

Pro Gln Met Ser Lys Gly Leu Arg Arg Ala Leu Ile Val Leu Asn Cys
            20                  25                  30

Val Leu Met Ala Leu Gly Asn Thr Gly Ser Pro Leu Leu Leu Arg Leu
        35                  40                  45

Tyr Tyr Arg Ser Gly Gly Lys Arg Gln Trp Leu Ser Ser Trp Leu Glu
    50                  55                  60

Thr Ala Gly Trp Pro Phe Ile Phe Val Pro Leu Leu Ile Thr Tyr Leu
65                  70                  75                  80

His Arg Arg Arg Arg Cys Gln Leu Arg Pro Gly Asn Cys His Pro Thr
                85                  90                  95

Lys Leu Phe Phe Ile Thr Pro Arg Leu Phe Leu Ala Cys Ala Phe Ile
            100                 105                 110

Gly Leu Ile Thr Gly Phe Asp Asp Phe Leu Tyr Ala Tyr Gly Leu Ser
        115                 120                 125

Phe Leu Pro Val Ser Thr Ser Ser Leu Leu Ile Ser Thr Gln Leu Ala
    130                 135                 140

Phe Thr Ala Phe Phe Ala Phe Leu Ile Val Lys Gln Lys Phe Thr Pro
145                 150                 155                 160

Tyr Ser Ile Asn Ser Val Ala Leu Leu Thr Val Gly Ala Val Val Leu
                165                 170                 175

Gly Leu His Val Ser Ser Asp Arg Pro Asp Asn Val Thr Arg Gly Gln
            180                 185                 190
```

```
Tyr His Leu Gly Phe Ile Leu Thr Leu Gly Ala Ala Ala Leu Tyr Gly
        195                 200                 205

Leu Ile Leu Pro Leu Val Glu Leu Met Tyr Ser Lys Ser Lys Gln Ala
    210                 215                 220

Ile Thr Tyr Thr Leu Val Met Glu Met Gln Leu Val Met Gly Phe Phe
225                 230                 235                 240

Ala Thr Ala Phe Cys Thr Val Gly Met Leu Val Asn Lys Asp Phe Gln
                245                 250                 255

Ala Ile Pro Arg Glu Ala Arg His Phe Glu Leu Gly Glu Phe Arg Tyr
            260                 265                 270

Tyr Val Val Leu Val Trp Ser Ala Val Phe Trp Gln Phe Phe Phe Leu
        275                 280                 285

Gly Thr Val Gly Ile Ile Phe Cys Val Asn Thr Leu Leu Ala Gly Ile
    290                 295                 300

Leu Ile Ala Leu Phe Ile Pro Val Thr Glu Val Leu Gly Val Val Phe
305                 310                 315                 320

Phe Lys Glu Asn Phe Ser Ser Glu Lys Gly Ile Ala Leu Val Leu Ser
                325                 330                 335

Leu Trp Gly Leu Ala Ser Tyr Ser Tyr Gly Glu Tyr Arg Gln Glu Lys
            340                 345                 350

Asp Lys Lys Asp Lys Ala Ala Pro Ser Asn Gln Val Ala
        355                 360                 365
```

<210> SEQ ID NO 53
<211> LENGTH: 1098
<212> TYPE: DNA
<213> ORGANISM: Musa acuminata

<400> SEQUENCE: 53

```
atggaagtcg agggtcaaaa ctccaaccac caaaatcaag atgctgctcc acaaatgtct      60

aaaggtttga gaagggcttt gatcgttttg aactgtgttt tgatggcttt gggtaatact     120

ggttcacctt tgttgttgag gttgtactat agatctggtg gtaagagaca atggttgtca     180

tcttggttgg aaactgctgg ttggccattc atttttgttc ctttgttgat cacctacttg     240

cacagacgta gaagatgtca actaagacca ggtaattgtc acccaactaa gttgttcttt     300

attacgccaa ggttgttctt ggcttgtgct ttcattggtt tgattaccgg tttcgatgat     360

ttcttgtatg cctacggttt gtctttcttg ccagtttcta cttcctcctt gttgatttct     420

actcaattgg ctttcactgc tttcttcgct ttcttgatcg ttaagcaaaa gttcacccca     480

tactccatta actctgttgc tttgttaact gttggtgctg ttgttttggg tctgcatgtt     540

tcttcagata gaccagataa tgttaccaga ggtcaatacc atttgggttt cattttgact     600

ttgggtgctg ctgcattata tggtttgata ttgccattgg tcgagctgat gtactctaaa     660

tctaagcaag ctattaccta caccttggtc atggaaatgc aattggttat gggtttttc     720

gctaccgctt tctgtactgt tggtatgttg gttaacaagg acttccaagc tattccaaga     780

gaagctagac attttgaatt gggtgaattc aggtactacg ttgtcttggt ttggtcagct     840

gttttttggc aatttttctt cttgggtact gtcggtatta tcttctgcgt taatactttg     900

ttggccggta ttttgattgc cttgttcatt ccagttaccg aagttttggg tgtcgttttc     960

ttcaaagaga acttctcatc cgaaaagggt attgccttgg ttttgtcttt gtggggttta    1020

gcttcttatt cttacggtga gtacagacaa gaaaaggata agaaagataa ggctgctcca    1080

tccaatcaag ttgcttaa                                                  1098
```

<210> SEQ ID NO 54
<211> LENGTH: 365
<212> TYPE: PRT
<213> ORGANISM: Nelumbo nucifera

<400> SEQUENCE: 54

Met Ala Arg Asn Ile Glu Thr Ile Glu Asn Gly Val Leu Asn Glu Lys
1 5 10 15

Thr Cys Tyr Tyr Thr Lys Ile Pro Asp Gly Asp Ser Ser Ile Lys Ser
20 25 30

Asn Met Ala Lys Trp Trp Leu Leu Gly Ile Asn Cys Val Cys Thr Val
35 40 45

Leu Gly Thr Ile Ala Gly Pro Leu Phe Leu Arg Leu Tyr Phe Leu His
50 55 60

Gly Gly Asn Arg Lys Trp Ile Pro Ser Trp Leu Gln Thr Ala Gly Val
65 70 75 80

Pro Val Leu Leu Gly Pro Leu Thr Val Leu Tyr Leu Arg Glu Arg Ala
85 90 95

Ser Gly Val Arg Phe Leu Ala Pro Thr Lys Leu Leu Leu Leu Ser Ala
100 105 110

Gly Ile Gly Ile Leu Val Gly Leu Asn Asp Phe Met Tyr Ser His Gly
115 120 125

Leu Ser Phe Leu Pro Val Ser Thr Ser Ala Leu Leu Leu Ser Thr Gln
130 135 140

Leu Gly Phe Thr Ala Leu Phe Ala Leu Leu Ile Ala Lys Gln Lys Phe
145 150 155 160

Thr Pro Tyr Ser Ile Asn Ala Val Val Leu Met Thr Leu Gly Ala Ala
165 170 175

Leu Leu Gly Leu Ser Lys Ser Gly Asp Arg Leu Leu Gly Val Ser Asn
180 185 190

Arg Asp Tyr Trp Leu Gly Phe Val Leu Thr Leu Gly Ala Ala Gly Leu
195 200 205

Leu Gly Phe Ile Leu Pro Cys Cys Glu Val Ala Tyr Ala Thr Ala Arg
210 215 220

Lys Thr Ile Thr Tyr Ser Val Val Leu Gln Phe Gln Phe Gly Val Asn
225 230 235 240

Phe Phe Ala Thr Val Phe Cys Thr Ile Gly Met Leu Ile Asn Lys Asp
245 250 255

Phe Gln Ala Ile Pro Arg Glu Ala Asn Ala Phe Glu Leu Gly Ala Val
260 265 270

Lys Tyr Tyr Leu Val Leu Val Ser Ile Ala Ile Val Trp Gln Met Ala
275 280 285

Gly Val Gly Thr Leu Gly Val Val Phe Ser Thr Thr Ser Leu Phe Ala
290 295 300

Gly Val Leu Asn Ala Thr Leu Leu Pro Leu Thr Glu Thr Ala Ala Val
305 310 315 320

Ile Val Tyr His Glu Lys Phe Thr Gly Glu Lys Gly Met Ala Leu Ala
325 330 335

Leu Cys Ser Trp Gly Phe Ile Ser Tyr Phe Tyr Gly Ser Tyr Lys Glu
340 345 350

Lys Lys Lys Gln Asp Ala Leu Phe Glu Thr Gly Ser Arg
355 360 365

<210> SEQ ID NO 55

<211> LENGTH: 1098
<212> TYPE: DNA
<213> ORGANISM: Nelumbo nucifera

<400> SEQUENCE: 55
atggccagaa acatcgaaac catcgaaaac ggtgttttga acgaaaagac ttgctactac 60
accaagattc cagatggtga ttcctccatt aagtctaata tggctaaatg gtggttgttg 120
ggtattaact gtgtctgtac tgttttgggt actattgctg gtcctttgtt tttgaggttg 180
tacttcttgc atggtggtaa cagaaaatgg attccatctt ggttgcaaac tgctggtgtt 240
ccagttttgt tgggtccatt gactgtcttg tatttgagag aaagagcttc tggcgttaga 300
tttttggctc caactaagtt gttgttgctg tctgctggta ttggtatttt ggttggtttg 360
aacgacttca tgtactccca tggtttgtct tttttgccag tttctacttc cgctttgttg 420
ttgtctactc aattgggttt tactgctttg ttcgccttgt tgattgctaa gcaaaagttc 480
actccatact ccattaacgc cgttgttttg atgactttgg gtgctgcttt attgggtttg 540
tctaaatccg gtgatagact gttgggtgtt tctaatagag attactggtt gggtttcgtt 600
ttgacattag gtgctgctgg tttgttgggc tttattttgc catgttgtga agttgcttat 660
gctactgcta gaaagaccat tacttactcc gttgtcttgc aattccaatt cggtgttaat 720
ttcttcgcta ccgttttctg taccatcggc atgttgatta acaaggattt ccaagccatt 780
ccaagagaag ctaatgcttt tgaattgggt gcagtcaagt actacttggt cttggtttct 840
attgctatcg tttggcaaat ggccggtgtt ggtactttag gtgttgtttt ttctaccacc 900
tctttgtttg ctggtgtctt gaatgctact ttgttgccat taactgaaac cgctgctgtt 960
atcgtttacc acgaaaagtt tactggtgaa aaaggtatgg ctttggcttt gtgttcttgg 1020
ggttttatct cttacttcta cggctcctac aaagaaaaga aaaagcaaga tgccttgttc 1080
gaaaccggtt ctagataa 1098

<210> SEQ ID NO 56
<211> LENGTH: 406
<212> TYPE: PRT
<213> ORGANISM: Papaver somniferum

<400> SEQUENCE: 56

Met Asp Ile Glu Leu Ala Ser Thr Asn Ala Gly Ser Ala Thr Asn Tyr
1 5 10 15

Asn His Gly Ala Gly Asn His His Ser Asn Leu Val Val Pro Asn Asp
20 25 30

Ser Thr Gly Glu Asp Asp Leu Gln Lys Ser Ile Asn Pro Ile Thr Gln
35 40 45

Lys Ile Val Arg Asn Trp Lys Leu Ile Leu Phe Cys Phe Phe Thr Ala
50 55 60

Phe Gly Tyr Ile Gly Gly Pro Met Leu Gln Arg Leu Tyr Phe Thr Gln
65 70 75 80

Gly Gly Gly Arg Lys Trp Leu Ser Ser Met Leu Gln Thr Val Gly Phe
85 90 95

Pro Val Leu Val Ala Pro Leu Ser Tyr Ile Tyr Met Lys Lys Val Asn
100 105 110

Gly Pro Ser Tyr Asp Ser Ser Trp Val Phe Ile Met Glu Pro Lys Leu
115 120 125

Phe Met Tyr Ser Ala Ile Leu Gly Val Ala Leu Gly Leu Asp Asn Tyr
130 135 140

```
Met Tyr Ser Ala Gly Leu Phe Tyr Leu Pro Val Ser Thr Ser Ser Leu
145                 150                 155                 160

Leu Phe Ser Thr Gln Leu Ala Phe Thr Ala Ile Phe Ala Phe Ile Ile
                165                 170                 175

Val Arg Gln Lys Phe Thr Phe Cys Ser Phe Asn Ser Val Val Leu Met
            180                 185                 190

Thr Leu Gly Ala Val Val Leu Ala Leu Asn Thr Ser Ser Asp Thr Pro
        195                 200                 205

Pro Gly Thr Thr Gln Gln Gln Tyr Tyr Leu Gly Phe Phe Leu Thr Leu
    210                 215                 220

Ala Gly Ala Ala Leu Ala Gly Leu Ile Met Pro Leu Val Glu Leu Ala
225                 230                 235                 240

Tyr Gly Lys Ser Ser Lys Pro Ile Thr Tyr Ser Val Val Met Gln Phe
                245                 250                 255

Gln Phe Val Leu Ser Leu Phe Ala Thr Leu Val Ser Ile Ile Gly Met
            260                 265                 270

Ala Ile Asn Lys Asp Phe Gln Val Ile Gln Arg Glu Gly Arg Asn Phe
        275                 280                 285

Gly Leu Gly Gln Val Lys Tyr Tyr Leu Leu Leu Ile Ala Val Ala Val
    290                 295                 300

Ala Trp Gln Ile Ala Ser Ala Gly Phe Leu Gly Ile Ile Tyr Cys Thr
305                 310                 315                 320

Ser Ser Leu Phe Ser Gly Ile Phe Thr Thr Cys Leu Leu Pro Phe Thr
                325                 330                 335

Gln Val Ala Ala Ser Ile Ala Phe His Glu Lys Phe Thr Gly Gln Lys
            340                 345                 350

Gly Met Ser Leu Ala Leu Cys Leu Trp Gly Phe Ala Ser Tyr Phe Val
        355                 360                 365

Gly Glu His Lys Lys Thr Lys Lys Pro His Pro Ile Val Tyr Asp Lys
    370                 375                 380

Glu Lys Ser Glu Leu Thr Asp Asn Asn Asp Thr Lys Glu Gly Gly Lys
385                 390                 395                 400

Gln Tyr Asn Val Thr Gln
                405
```

<210> SEQ ID NO 57
<211> LENGTH: 1221
<212> TYPE: DNA
<213> ORGANISM: Papaver somniferum

<400> SEQUENCE: 57

```
atggacatcg aattggcttc taccaatgct ggttctgcta ctaattacaa tcatggtgct      60

ggtaaccatc actccaattt ggttgttcca aatgattcta ctggtgagga tgacttgcaa     120

aagtctatta acccaatcac tcagaagatc gtcagaaact ggaagttgat tttgttctgt     180

ttcttcaccg ccttcggtta tattggtggt ccaatgttgc aaaggttgta ctttactcaa     240

ggtggtggta gaaaatggct gtcatctatg ttacaaactg ttggtttccc agttttggtt     300

gctccattgt cttatatcta catgaagaag gttaacggtc cctcctatga ttcttcttgg     360

gttttcatta tggaacccaa gctgtttatg tactccgcta ttttgggtgt tgctttgggt     420

ttagataact acatgtattc cgctggcttg ttctatttgc cagtttctac ttcttccctg     480

ttgttctcta ctcaattggc tttcactgct attttcgcct tcattatcgt cagacaaaag     540

ttcaccttct gctcattcaa ctccgttgtt ttgatgactt tgggtgctgt tgttttggct     600
```

```
ttgaacactt cttctgatac tccaccaggt actactcaac aacaatatta cttgggtttc    660

ttcttgactt tggctggtgc tgctttagct ggtttgatta tgccattggt tgaattggca    720

tacggcaaat cttctaagcc aattacctac tctgttgtca tgcaattcca attcgtcttg    780

tctttgttcg ctaccttggt ttccattatt ggtatggcca ttaacaagga cttccaggtt    840

attcaaagag agggtagaaa tttcggtttg ggtcaagtta agtactacct gttgttgatt    900

gctgttgcag ttgcttggca aattgcttct gctggttttt tgggtattat ctactgtacc    960

tcctctttgt tctctggtat tttcaccact tgtctgttgc cattcactca agttgctgct   1020

tctattgctt ttcatgagaa gttcactggt caaaagggta tgtctttggc tttatgtttg   1080

tggggttttg cctcttactt tgttggtgaa cacaaaaaga ctaagaagcc acatccaatc   1140

gtctacgaca aagaaaagtc tgaattgacc gataacaacg acacaaaaga aggtggtaag   1200

cagtacaacg ttacccaatg a                                             1221


<210> SEQ ID NO 58
<211> LENGTH: 383
<212> TYPE: PRT
<213> ORGANISM: Papaver somniferum

<400> SEQUENCE: 58

Met Val Thr Ser Ala Met Asp Ile Glu Lys Leu Glu Ile Leu Gly Thr
1               5                   10                  15

Thr His Asn Gly Asn Ser Asn Thr Arg Ile Glu Lys Pro Lys Lys Thr
            20                  25                  30

Lys Asn Trp Leu Leu Val Ile Ile Asn Cys Ala Ile Val Phe Val Gly
        35                  40                  45

Ala Ile Gly Ser Pro Leu Leu Met Arg Leu Tyr Tyr Leu His Gly Gly
    50                  55                  60

Ser His Ile Trp Leu Ser Ser Phe Ile Ala Ser Ala Gly Phe Pro Ile
65                  70                  75                  80

Leu Ile Ile Pro Leu Met Phe Leu Phe Ile Arg Ser Arg Ser Ser Ala
                85                  90                  95

Asp Lys Ile Ser Ser Ser Phe Trp Met Glu His Lys Leu Phe Leu Trp
            100                 105                 110

Gly Ala Ile Leu Gly Val Leu Tyr Gly Leu Val Thr Phe Met Tyr Ala
        115                 120                 125

Leu Gly Leu Ser Tyr Ile Pro Val Ser Thr Ser Ser Leu Leu Met Ala
    130                 135                 140

Thr Gln Leu Cys Phe Ile Ala Phe Phe Ser Trp Leu Ile Val Lys Gln
145                 150                 155                 160

Lys Phe Thr Ala Phe Ile Ile Asn Ala Val Val Val Met Thr Leu Gly
                165                 170                 175

Ser Val Leu Leu Gly Ile Asn Thr Asp Gly Asp Arg Pro Val Gly Val
            180                 185                 190

Ser Lys Ala Gln Tyr Leu Leu Gly Phe Val Leu Thr Leu Ser Ala Ala
        195                 200                 205

Ala Leu Ala Gly Leu Ile Met Pro Leu Ile Glu Leu Ala Phe Ser Lys
    210                 215                 220

Ala Ile Arg Asn Leu Ser Tyr Ser Ser Leu Leu Gln Phe Gln Phe Val
225                 230                 235                 240

Leu Ser Val Phe Ser Ala Thr Val Cys Val Ile Gly Met Leu Ala Asn
                245                 250                 255

Lys Asp Phe Gln Ala Ile Pro Arg Glu Ala Asn Asp Phe Gly Leu Gly
```

```
            260                 265                 270

Lys Ala Asn Tyr Tyr Ile Ile Met Val Ala Thr Ala Ile Thr Trp Gln
        275                 280                 285

Leu Ser Gly Val Gly Thr Met Gly Val Ile Phe Tyr Ala Ser Ala Leu
    290                 295                 300

Phe Asn Gly Ile Leu Ser Ser Val Leu Ile Pro Leu Thr Gly Val Ala
305                 310                 315                 320

Ala Val Met Phe Tyr His Glu Ser Phe Thr Ser Leu Lys Gly Met Ala
                325                 330                 335

Leu Ala Leu Cys Leu Trp Gly Leu Cys Ser Tyr Phe Tyr Gly Glu Tyr
            340                 345                 350

Lys Met Met Asn Lys Val Met Asn Asn Glu Ser Thr Lys Arg Leu Asp
        355                 360                 365

Lys Val Glu Asn Glu Pro Lys Arg Leu Asp Asp Tyr Glu Glu Pro
    370                 375                 380
```

<210> SEQ ID NO 59
<211> LENGTH: 1152
<212> TYPE: DNA
<213> ORGANISM: Papaver somniferum

<400> SEQUENCE: 59

```
atggttacct ccgccatgga tatcgaaaag ttggaaattt tgggtactac ccacaacggt     60

aactctaaca ctagaattga gaagcccaaa aagaccaaga actggttgtt ggttattatc    120

aactgcgcca tcgttttcgt tggtgctatt ggttctccat tattgatgag gttgtactac    180

ttgcatggtg gttcccatat ttggctgtca tcttttattg cttcagctgg tttcccaatc    240

ttgatcattc cattgatgtt cttgtttatc aggtccagat cttccgccga taagatttct    300

tcttcttttt ggatggaaca caagttgttt ttgtggggtg ctattttggg tgtcttgtat    360

ggtttggtta ctttcatgta tgccttgggc ttgtcctata ttccagtttc tacatcctct    420

ttgttgatgg ctactcagtt gtgtttcatt gctttcttct cttggttgat cgtcaagcaa    480

aagttcaccg ccttcattat taacgccgtt gttgttatga ctttgggctc tgttttgttg    540

ggtattaaca ctgatggtga tagaccagtt ggtgtttcta aagctcaata cttgttgggt    600

ttcgtcttga ctttgtctgc tgctgctttg gctggtttga ttatgccatt gattgaattg    660

gctttctcca aggccattag gaacttgtct tattcgtctt tgttgcagtt ccagttcgtc    720

ttgtctgttt tttctgctac cgtttgcgtt attggtatgt tggctaacaa ggatttccaa    780

gccattccta gagaagctaa tgatttcggt ttgggtaaag ccaactacta cattattatg    840

gttgctaccg ctatcacctg gcaattgtct ggtgttggta ctatgggtgt tattttctat    900

gcttccgctt tgttcaacgg catcttgtca tctgttttga ttcctttgac tggtgttgct    960

gctgttatgt tctaccatga atctttcacc agcttgaaag gtatggcttt ggctttgtgt   1020

ttatggggtt tgtgttctta cttttacggc gagtacaaga tgatgaacaa ggtcatgaac   1080

aacgaatcca ctaagagatt ggataaggtc gaaaacgagc caaaaagatt ggatgattac   1140

gaggaaccat aa                                                       1152
```

<210> SEQ ID NO 60
<211> LENGTH: 389
<212> TYPE: PRT
<213> ORGANISM: Papaver somniferum

<400> SEQUENCE: 60

```
Met Ala Ile Ser Thr Leu Asn Ile Glu Thr Leu Glu Ser Leu Gly Thr
1               5                   10                  15

Ala Gln Tyr Gly Asn Ser Lys Thr His Thr Glu Lys Pro Thr Lys Thr
            20                  25                  30

Lys Asn Trp Leu Met Ile Ile Ile Asn Cys Ala Phe Ala Thr Ile Gly
        35                  40                  45

Val Val Gly Gly Pro Leu Leu Val Arg Leu Tyr Tyr Leu His Gly Gly
    50                  55                  60

Asn Arg Lys Trp Leu Thr Ser Phe Leu Gln Ser Ala Gly Phe Pro Ile
65                  70                  75                  80

Leu Ile Val Pro Leu Ile Phe Leu Phe Ile Gln Ser Lys Leu Leu Thr
                85                  90                  95

Arg Lys Asn Asp Gln Ser Ser Pro Phe Ser Tyr Ile Glu Pro Lys Leu
            100                 105                 110

Phe Leu Ser Ser Ala Ala Ile Gly Val Leu Phe Gly Val Asp Asn Phe
        115                 120                 125

Met Tyr Ser Leu Gly Leu Ser Tyr Leu Pro Val Ser Thr Ser Thr Leu
    130                 135                 140

Leu Phe Ala Thr Asn Leu Cys Phe Ile Ala Phe Phe Ser Trp Leu Ile
145                 150                 155                 160

Val Lys Gln Lys Phe Thr Ala Phe Ile Ile Asn Ala Val Val Val Met
                165                 170                 175

Thr Leu Gly Ser Val Leu Leu Gly Ile Asn Ile Asp Gly Asp Arg Pro
            180                 185                 190

Ile Gly Val Ser Lys Ser His Tyr Leu Leu Gly Phe Ile Leu Thr Leu
        195                 200                 205

Val Ala Ala Ala Leu Ala Gly Leu Ile Met Pro Leu Ile Glu Leu Ala
    210                 215                 220

Phe Gly Lys Ala Ile Arg Asn Leu Thr Tyr Ser Ser Leu Leu Gln Phe
225                 230                 235                 240

Gln Leu Val Leu Ser Leu Phe Ser Thr Ile Val Cys Gly Ile Gly Met
                245                 250                 255

Leu Val Asn Lys Asp Phe Gln Ala Ile Pro Arg Glu Ala Asn Glu Phe
            260                 265                 270

Glu Leu Gly Lys Ala Lys Tyr Tyr Ile Ile Met Val Val Thr Ala Ile
        275                 280                 285

Ile Trp Gln Phe Thr Ala Val Gly Ile Val Gly Val Ile Phe Tyr Thr
    290                 295                 300

Ser Ala Leu Phe Asn Gly Ile Phe Gly Ser Val Leu Val Pro Phe Thr
305                 310                 315                 320

Gly Val Ala Ala Ile Ile Phe Tyr His Glu Ser Phe Thr Gly Leu Lys
                325                 330                 335

Gly Met Ala Leu Ala Leu Cys Leu Trp Gly Phe Cys Ser Tyr Phe Tyr
            340                 345                 350

Gly Glu Tyr Lys Met Arg Lys Lys Val Ile Asn Asn Glu Thr Pro Glu
        355                 360                 365

Thr Ile Asp Asn Val Glu Asn Glu Pro Arg Lys Ser Asp Asp His Glu
    370                 375                 380

Gln Pro Leu Ile Val
385
```

<210> SEQ ID NO 61
<211> LENGTH: 1170
<212> TYPE: DNA

<213> ORGANISM: Papaver somniferum

<400> SEQUENCE: 61

```
atggccatct ccaccttgaa cattgaaacc ttggaatctt tgggtactgc tcaatacggt     60
aactctaaga ctcatactga aaagccaact aagaccaaga actggctgat gattattatc    120
aactgtgctt tcgctaccat cggtgttgtt ggtggtccat tattggttag gttgtattac    180
ttgcatggtg gcaatagaaa gtggttgact tctttcttgc aatctgctgg tttcccaatt    240
ttgatcgtcc cattgatttt cttgttcatc cagtctaagc tgctgaccag aaagaatgat    300
caatcttctc cattctccta catcgagcca aagttgtttt tatcctctgc tgctattggt    360
gttttgttcg gtgttgacaa cttcatgtat tccttgggtt tgtcttactt gccagtttct    420
acttctactt tgttgttcgc cactaacttg tgcttcattg ctttttttctc ttggttgatc    480
gtcaagcaaa agttcaccgc cttcattatt aacgccgttg ttgttatgac tttgggctct    540
gttttgttgg gtattaacat cgatggtgat agaccaatcg gtgtttctaa gtctcattac    600
ttgttgggtt tcatcttgac tttggttgct gctgctttgg ctggtttgat tatgccattg    660
attgaattgg ctttcggtaa ggccattaga aacttgactt actcctcttt gttgcaattc    720
cagttggtct tgtctttgtt ctctactatc gtttgcggta tcggtatgtt ggttaacaag    780
gattttcaag ccattccaag agaagccaat gaattcgaac taggtaaagc caagtactac    840
atcatcatgg ttgttaccgc tatcatttgg caattcactg ctgttggtat agtcggtgtt    900
attttctaca cctctgcttt gttcaacggt atctttggtt ctgttttggt tccattcaca    960
ggtgttgctg ccattatctt ttaccatgaa tctttcaccg gtttgaaagg tatggctttg   1020
gctttgtgtt tgtggggttt ttgttcttac ttttacggcg agtacaagat gcgtaaaaag   1080
gtcattaaca acgaaacccc agaaaccatc gataacgttg aaaatgaacc tagaaagtcc   1140
gatgatcacg aacaaccatt gatcgtttga                                    1170
```

<210> SEQ ID NO 62
<211> LENGTH: 359
<212> TYPE: PRT
<213> ORGANISM: Jatropha curcas

<400> SEQUENCE: 62

```
Met Asp Glu Asn Lys Glu Lys Pro Gln Pro Ala Lys Ala Thr Met Arg
1               5                   10                  15

Arg Ala Leu Leu Val Leu Asn Cys Val Ile Leu Ser Ile Gly Asn Cys
            20                  25                  30

Gly Gly Pro Leu Ile Met Arg Leu Tyr Phe Ile His Gly Gly Lys Arg
        35                  40                  45

Val Trp Leu Ser Ser Trp Leu Glu Thr Ala Gly Trp Pro Ile Ile Phe
    50                  55                  60

Ile Pro Leu Leu Ile Ser Tyr Phe His Arg Arg Ser Thr Thr Asp Pro
65                  70                  75                  80

Thr Thr Ala Lys Leu Phe Tyr Met Lys Pro Ser Leu Phe Leu Ala Ala
                85                  90                  95

Thr Gly Ile Gly Ile Leu Thr Gly Phe Asp Asp Tyr Leu Tyr Ala Tyr
            100                 105                 110

Gly Val Ala Arg Leu Pro Val Ser Thr Ser Ser Leu Ile Ile Ala Thr
        115                 120                 125

Gln Leu Ala Phe Thr Ala Gly Phe Ala Phe Leu Leu Val Lys Gln Lys
    130                 135                 140
```

```
Phe Thr Ser Tyr Ser Ile Asn Ala Val Val Leu Leu Thr Val Gly Ala
145                 150                 155                 160

Gly Val Leu Ala Leu His Thr Ser Ser Asp Arg Pro Glu His Glu Ser
                165                 170                 175

Lys Lys Glu Tyr Asn Leu Gly Phe Val Met Thr Leu Gly Ala Ala Val
            180                 185                 190

Leu Tyr Gly Leu Ile Leu Pro Leu Val Glu Leu Thr Tyr Arg Lys Ala
        195                 200                 205

Lys Gln Glu Ile Ser Tyr Thr Leu Val Met Glu Ile Gln Met Ile Met
    210                 215                 220

Cys Leu Phe Ala Thr Val Val Cys Thr Val Gly Met Leu Val Asn Asn
225                 230                 235                 240

Asp Phe Lys Val Ile Pro Arg Glu Ala Lys Glu Phe Glu Leu Gly Glu
                245                 250                 255

Thr Lys Tyr Tyr Val Ile Met Val Trp Ser Ala Ile Ile Trp Gln Cys
            260                 265                 270

Phe Phe Leu Gly Ala Ile Gly Ile Val Phe Cys Ala Ser Ser Leu Ala
        275                 280                 285

Ser Gly Val Val Ile Ala Val Leu Leu Pro Val Thr Glu Ile Leu Ala
    290                 295                 300

Val Ile Phe Tyr Gln Glu Lys Phe Gln Ala Glu Lys Gly Val Ala Leu
305                 310                 315                 320

Ala Leu Ser Leu Trp Gly Phe Leu Ser Tyr Phe Tyr Gly Glu Ile Lys
                325                 330                 335

Gln Ser Lys Lys Thr Asn Leu Thr Ser Glu Ile Glu Thr Ser Glu Ser
            340                 345                 350

Ser Ile Pro Thr Gln Asn Val
        355
```

<210> SEQ ID NO 63
<211> LENGTH: 1080
<212> TYPE: DNA
<213> ORGANISM: Jatropha curcas

<400> SEQUENCE: 63

```
atggacgaga acaaagaaaa gccacaacca gctaaagcta ctatgagaag ggctttgttg     60

gttttgaact gcgttatttt gtccattggt aattgtggtg gtccattgat tatgaggttg    120

tactttattc acggtggtaa gagagtttgg ttgtcatctt ggttggaaac tgctggttgg    180

ccaattatct ttatcccttt gttgatctcc tacttccaca gaagatctac tactgatcca    240

actactgcta agctgtttta catgaagcca tccttgtttt tggctgctac tggtattggt    300

attttgaccg gttttgatga ttacttgtac gcttatggtg ttgccagatt gccagtttct    360

acttcctctt tgattatcgc tactcaattg gcttttaccg ctggttttgc tttcttgttg    420

gttaagcaaa agttcacctc ctactccatt aacgctgttg ttttgttgac tgttggtgct    480

ggtgttttgg cattgcatac ttcatctgat agaccagaac acgagtctaa gaaagagtac    540

aatttgggtt tcgttatgac tttgggtgct gctgtcttgt atggtttgat tttgccatta    600

gtcgagctga cttacagaaa ggctaaacaa gaaatctcct acaccttggt catggaaatc    660

caaatgatta tgtgtttgtt cgctaccgtt gtctgtactg ttggtatgtt agttaacaac    720

gacttcaagg tcattccaag ggaagctaaa gaatttgaat tgggcgaaac taagtactac    780

gttatcatgg tttggtccgc cattatttgg caatgttttt tcttgggtgc catcggtata    840

gttttctgtg cttcttcttt ggcttccggt gttgttattg ctgttttgtt accagttacc    900
```

```
gaaatcttgg ccgttatctt ctaccaagaa aagttccaag ctgaaaaggg tgttgctttg    960

gctttgtctt tatggggttt tctgtcttac ttttacggtg agatcaagca gtctaaaaag   1020

accaacttga cctccgaaat tgaaacctcc gaatcttcta ttccaactca gaacgtttaa   1080


<210> SEQ ID NO 64
<211> LENGTH: 390
<212> TYPE: PRT
<213> ORGANISM: Cucurbita pepo subsp. pepo

<400> SEQUENCE: 64

Met Ser Ala Pro Leu Pro Asn Phe Val His Ser Gln Phe Leu Asp His
1               5                   10                  15

Asn Ser Lys Met His Ser Gln Pro Ser Glu Ser Phe Val His Asn Gln
            20                  25                  30

Thr Lys His Glu Gln Pro Asn Gln Ser Pro Asp Ala Ala Val Lys Lys
        35                  40                  45

Phe Leu Leu Ala Phe Asn Cys Val Leu Met Ser Ile Gly Asn Cys Gly
    50                  55                  60

Gly Pro Leu Ile Leu Arg Leu Tyr Phe Ile His Gly Gly Asn Arg Val
65                  70                  75                  80

Trp Leu Ser Ser Trp Leu Leu Thr Gly Gly Trp Pro Ile Ile Leu Leu
                85                  90                  95

Pro Leu Val Ile Ser Tyr Phe Gln Arg Arg Arg Thr Ser Ala Ala Gly
            100                 105                 110

Thr Thr Thr Glu Phe Ile Phe Ile Lys Pro Arg Leu Phe Phe Ala Ser
        115                 120                 125

Ala Val Ile Gly Leu Leu Thr Gly Leu Asp Asn Tyr Leu Tyr Ala Tyr
    130                 135                 140

Gly Val Ala Arg Leu Pro Val Ser Thr Ser Ser Leu Ile Ile Ala Ser
145                 150                 155                 160

Gln Leu Ala Phe Thr Ala Gly Phe Ala Phe Leu Leu Val Lys Gln Arg
                165                 170                 175

Phe Thr Ser Tyr Ser Val Asn Ala Val Val Leu Leu Thr Leu Gly Gly
            180                 185                 190

Ala Ile Leu Ala Leu His Ser Ser Gly Asp Arg Pro Ala Gly Glu Ser
        195                 200                 205

Asn Arg Glu Tyr Ile Ala Gly Phe Leu Met Thr Val Gly Ala Ser Val
    210                 215                 220

Leu Tyr Gly Phe Val Leu Pro Leu Ile Glu Leu Thr Tyr Lys Lys Ala
225                 230                 235                 240

Lys Gln Asn Leu Thr Tyr Thr Leu Val Leu Glu Thr Gln Phe Val Ile
                245                 250                 255

Ser Leu Phe Ala Thr Ile Leu Cys Thr Ile Gly Met Leu Ile Asn Asn
            260                 265                 270

Asp Phe Gln Ala Ile Pro Arg Glu Gly Thr Glu Phe Gly Leu Gly Lys
        275                 280                 285

Thr Lys Tyr Tyr Val Ile Leu Ala Leu Ser Thr Ile Ile Trp Gln Cys
    290                 295                 300

Phe Phe Leu Gly Ala Val Gly Val Ile Phe Tyr Ser Ser Ser Leu Phe
305                 310                 315                 320

Ser Gly Val Val Ile Ala Leu Leu Leu Pro Ala Thr Glu Ile Leu Ala
                325                 330                 335

Val Ile Phe Phe Arg Glu Lys Phe Gln Ala Glu Lys Gly Val Ser Leu
```

```
        340                 345                 350

Ala Leu Asn Leu Trp Gly Phe Val Ser Tyr Phe Tyr Gly Glu Phe Lys
        355                 360                 365

Gln Ser Ser Lys Lys Lys Leu Gln Leu Pro Arg Ala Gln Gly Ser Ala
    370                 375                 380

Ile Gln Ile Pro Asn Val
385                 390


<210> SEQ ID NO 65
<211> LENGTH: 1173
<212> TYPE: DNA
<213> ORGANISM: Cucurbita pepo subsp. pepo

<400> SEQUENCE: 65

atgtctgctc cattgccaaa cttcgttcac tctcaatttt tggaccacaa ctccaagatg      60

cattctcaac catctgaatc cttcgttcat aaccagacaa aacacgaaca gccaaatcaa     120

tctccagatg ctgctgttaa gaagttcttg ttggctttca actgcgtctt gatgtctatt     180

ggtaattgtg gtggtccatt gatcttgagg ttgtacttta ttcatggtgg taacagagtc     240

tggttgtcat cttggttgtt gactggtggt tggccaatta tcttgttgcc attggttatc     300

tcttacttcc agagaagaag aacatctgct gctggtacta ctaccgaatt cattttcatt     360

aagcccaggt tgtttttcgc ctctgctgtt attggtttgt taaccggttt ggacaattac     420

ttgtatgctt acggtgttgc tagattgcca gtttctactt cctctttgat tatcgcttct     480

caattggctt ttactgctgg ttttgctttc ctgttggtta agcaaagatt cacctcttac     540

tctgttaacg ccgttgtttt gttgacttta ggtggtgcta ttttggcctt gcattcttct     600

ggtgatagac ctgctggtga atctaataga gagtatattg ctggtttctt gatgaccgtt     660

ggtgcttctg tcttgtatgg ttttgttttg ccattgatcg agctgactta caagaaggct     720

aagcaaaact tgacttacac cttggttttg gaaacccaat tcgtcatttc tttgttcgct     780

accattttgt gcaccatcgg tatgttgatt aacaacgatt tccaagccat tccaagagaa     840

ggtactgaat ttggtttggg taagaccaag tactacgtta tcttggcttt gtccaccatt     900

atctggcaat gtttttcttt gggtgctgtc ggtgttatct tctactcttc atctttgttc     960

tccggtgttg ttattgcctt gttgttgcca gctactgaaa ttttggccgt cattttcttc    1020

agagaaaagt tccaagctga aaagggtgtt tctttggctt tgaatttgtg ggtttcgtg    1080

tcttactttt acggtgaatt caagcagtcc tccaagaaga aattacaatt gccaagagca    1140

caaggttccg ccattcaaat tccaaacgtt tag                                 1173


<210> SEQ ID NO 66
<211> LENGTH: 368
<212> TYPE: PRT
<213> ORGANISM: Lactuca sativa

<400> SEQUENCE: 66

Met Glu Gly Arg Glu Glu Leu Ala Ser Pro Ile Val Ala Thr Lys Val
1               5                   10                  15

Ser Pro Ser Ala Lys Lys Ala Leu Leu Ile Leu Asn Cys Ile Leu Leu
            20                  25                  30

Ser Leu Gly Asn Cys Gly Gly Pro Leu Ser Met Arg Leu Tyr Phe Leu
        35                  40                  45

His Gly Gly Asn Arg Val Trp Leu Ser Ala Phe Leu Glu Thr Gly Gly
    50                  55                  60
```

```
Trp Pro Phe Ile Leu Ile Val Leu Leu Val Leu Tyr Phe Cys Arg Arg
65                  70                  75                  80

Cys Ser Thr Ser Pro Thr Ser Thr Thr Val Val Phe Met Arg Pro Arg
                85                  90                  95

Leu Phe Phe Ala Ala Ala Val Ile Gly Val Leu Thr Gly Leu Asp Asp
            100                 105                 110

Phe Leu Tyr Ala Cys Gly Val Ser Arg Leu Pro Val Ser Thr Thr Ser
        115                 120                 125

Leu Ile Ile Ala Ser Gln Leu Gly Phe Thr Ala Phe Phe Ala Phe Leu
    130                 135                 140

Leu Val Lys Gln Lys Phe Thr Pro Tyr Ser Ile Asn Ala Val Met Leu
145                 150                 155                 160

Leu Thr Val Gly Ala Ala Val Leu Ala Leu His Thr Ser Ser Asp Leu
                165                 170                 175

Pro Asn Gly Glu Ser Arg Ala Glu Tyr Leu Lys Gly Phe Phe Met Thr
            180                 185                 190

Val Ala Ala Ala Ala Leu Tyr Gly Leu Val Leu Pro Met Val Glu Met
        195                 200                 205

Thr Tyr Asn Lys Ala Lys Gln Ala Ile Thr Tyr Thr Leu Val Leu Glu
    210                 215                 220

Ile Gln Met Val Ile Cys Leu Phe Ala Thr Ile Val Cys Thr Thr Gly
225                 230                 235                 240

Met Ile Ile Asp Asn Asp Phe Lys Ala Ile Pro Arg Glu Ala Lys Glu
                245                 250                 255

Tyr Glu Leu Gly Glu Thr Lys Tyr Tyr Ala Val Leu Cys Ile Asn Ala
            260                 265                 270

Ile Phe Trp Gln Ser Phe Phe Leu Gly Ala Ile Gly Val Val Phe Cys
        275                 280                 285

Ala Ser Ser Leu Leu Ser Gly Ile Ile Ile Ala Val Leu Leu Pro Val
    290                 295                 300

Thr Glu Val Leu Ala Val Val Phe Tyr Lys Glu His Phe Gln Ala Glu
305                 310                 315                 320

Lys Gly Ile Ala Leu Val Leu Ser Leu Trp Gly Phe Thr Ser Tyr Phe
                325                 330                 335

Tyr Gly Glu Tyr Lys Val Met Lys Thr Lys Asp Ile Glu Arg Glu Ser
            340                 345                 350

Leu His Asp Arg Ser Val Asp Leu Pro Gln Ile Asn Tyr Ser Ser Val
        355                 360                 365
```

<210> SEQ ID NO 67
<211> LENGTH: 1107
<212> TYPE: DNA
<213> ORGANISM: Lactuca sativa

<400> SEQUENCE: 67

```
atggaaggta gagaagaatt ggcctctcca atagttgcta caaaagtttc tccatctgct      60

aagaaggcct tgttgatttt gaactgcatc ttgttgtctt tgggtaattg tggtggtcca     120

ttgtccatga ggttgtactt tttacatggt ggtaacagag tttggttgtc cgctttttttg     180

gaaactggtg gttggccatt cattttgata gttttgttgg tcctgtactt ctgcagacgt     240

tgttctactt ctccaacttc tactaccgtt gtttttatga ggccaaggtt gttttttgct     300

gctgctgtta ttggtgtttt gaccggtttg gatgatttct tgtatgcttg tggtgtttcc     360

agattgccag tttctactac gtctttgatt atcgcttctc aattgggttt cactgctttc     420
```

```
tttgcctttt tgctggttaa gcaaaagttc accccatact ctattaacgc cgttatgttg    480

ttgactgttg gtgctgcagt tttggcattg catacttcat ctgatttgcc aaacggtgaa    540

tctagagctg aatacttgaa gggtttcttc atgactgttg cagctgctgc attatatggt    600

ttggttttgc caatggttga gatgacttac aacaaagcta agcaagctat tacctacacc    660

ttggtcttgg aaatccaaat ggttatttgt ttgttcgcca ccattgtctg tactaccggt    720

atgattattg acaacgattt caaggccatt ccaagggaag ctaaagaata tgaattgggc    780

gaaactaagt actacgctgt tttgtgcatt aacgccatct tttggcaatc tttttcttg     840

ggtgcaatcg gtgttgtttt ctgtgcttct tctttgttgt ccggtattat cattgccgtt    900

ttgttgccag ttactgaagt tttggctgtc gtgttctaca aagaacattt ccaagctgaa    960

aagggtatcg ccttggtttt gtctttgtgg ggttttactt cttacttcta cggtgagtac   1020

aaggtgatga agactaagga tattgagagg gaatccttgc acgatagatc tgttgatttg   1080

cctcaaatca actactcctc cgtttga                                       1107
```

```
<210> SEQ ID NO 68
<211> LENGTH: 382
<212> TYPE: PRT
<213> ORGANISM: Papaver somniferum

<400> SEQUENCE: 68

Met Glu Asn Glu Asn Thr Met Lys Arg Glu Ala Leu Asn Ser Asp Ser
1               5                   10                  15

Ser His Glu Gln His His Gln Gln Glu Lys Glu Thr Lys Lys Lys Lys
            20                  25                  30

Leu Val Leu Leu Ile Val Asn Cys Ile Leu Leu Ser Val Gly Gln Val
        35                  40                  45

Gly Gly Pro Met Met Leu Arg Leu Tyr Tyr Leu His Gly Gly Gln Arg
    50                  55                  60

Lys Trp Leu Ser Ser Trp Leu Gln Thr Ser Ala Phe Pro Ile Leu Leu
65                  70                  75                  80

Ile Pro Leu Met Val Ser Trp Phe Lys Ser Lys Ser Lys Phe His Ser
                85                  90                  95

Gln Ser Gln Ser Thr Asn Val Asp His Val Asn Pro Gly Phe Leu Leu
            100                 105                 110

Thr Arg Lys Leu Phe Ile Trp Ser Val Ile Val Gly Ile Ile Thr Gly
        115                 120                 125

Leu Asp Ser Phe Leu Phe Ala Val Gly Tyr Ser Tyr Leu Pro Val Ser
    130                 135                 140

Val Ala Ser Leu Leu Leu Ala Thr Gln Leu Ala Phe Thr Ala Val Phe
145                 150                 155                 160

Ala Leu Ile Leu Val Lys Gln Lys Phe Thr Pro Tyr Ser Ile Asn Ser
                165                 170                 175

Val Val Leu Leu Thr Leu Gly Ala Val Ile Leu Ala Phe His Thr Ser
            180                 185                 190

Ser Asp Lys Pro Ile Gly Val Ser Lys Ser Gln Tyr Phe Leu Gly Phe
        195                 200                 205

Phe Met Thr Leu Gly Gly Ala Ala Leu Leu Gly Phe Met Leu Pro Leu
    210                 215                 220

Ile Glu Phe Val Tyr Ala Asn Ala Cys Lys Val Ile Thr Tyr Asp Leu
225                 230                 235                 240

Val Met Gln Met Gln Phe Leu Val Ser Leu Phe Ala Thr Val Phe Ser
                245                 250                 255
```

```
Thr Ile Gly Met Leu Ile Asn Lys Asp Phe Gln Ala Ile Ser Arg Glu
            260                 265                 270

Ala Asn Glu Tyr Gly Leu Gly Glu Thr Lys Tyr Tyr Met Val Leu Val
        275                 280                 285

Phe Thr Ser Ile Leu Ile Gln Leu Ser Ile Val Gly Tyr Leu Gly Val
    290                 295                 300

Ile Phe Tyr Ala Thr Ser Leu Phe Thr Gly Ile Leu Val Thr Leu Leu
305                 310                 315                 320

Ile Pro Val Gln Gln Val Phe Ala Ile Ile Phe Phe His Glu Lys Phe
                325                 330                 335

Ser Ala Glu Lys Gly Met Ser Leu Ala Leu Ser Ile Trp Gly Phe Ala
            340                 345                 350

Ser Tyr Phe Tyr Gly Glu Tyr Arg Gln Thr Lys Lys Lys Lys Asn Arg
        355                 360                 365

Asp Lys Val Pro Ile Ser His Lys Glu Ile Pro Ser Glu Val
    370                 375                 380
```

<210> SEQ ID NO 69
<211> LENGTH: 1149
<212> TYPE: DNA
<213> ORGANISM: Papaver somniferum

<400> SEQUENCE: 69

```
atggaaaacg agaacaccat gaagagagaa gccttgaatt ctgattcctc tcatgaacaa      60

catcaccagc aagaaaaaga gactaagaag aagaagctgg tcttgttgat cgttaactgc     120

atcttgttgt ctgttggtca agttggtggt ccaatgatgt tgagactata ttacttgcat     180

ggtggtcaga gaaagtggtt atcttcttgg ttgcaaactt ctgctttccc cattttgttg     240

atcccattga tggtttcatg gttcaagtcc aagtctaagt tccactctca atctcaatct     300

accaacgttg atcatgttaa cccaggtttc ttgttgacca gaaagttgtt catttggtcc     360

gttatcgttg gtattatcac cggtttggat tctttcttat tcgccgttgg ttattcctac     420

ttgccagttt ctgttgcttc tttgttgttg gctactcaat tggcttttac tgctgttttc     480

gctttgatct tggtcaagca aaagttcact ccatactcca tcaactccgt tgttttgttg     540

actttgggtg ctgttatttt ggctttccat acctcttcag ataagccaat cggtgtttct     600

aagtcccaat actttttggg tttcttcatg actttaggtg gtgctgcttt gttgggtttt     660

atgttgccat tgatcgaatt cgtttacgct aacgcctgta aggttattac ctacgatttg     720

gtcatgcaaa tgcagttctt ggtttctttg ttcgctactg ttttctccac cattggcatg     780

ttgattaaca aggatttcca agccatttcc agagaagcta atgaatatgg tttgggcgaa     840

acgaagtact acatggtttt ggttttcacc tccatcttga tccaattgtc tattgtcggt     900

tacttgggcg ttattttcta cgctacatct ttgttcaccg gtatcttggt taccttgttg     960

attccagttc aacaagtttt cgccatcata ttcttccacg aaaagttctc tgctgagaag    1020

ggtatgtctt tggctttgtc tatttggggt tttgcctctt acttttacgg tgagtatagg    1080

cagaccaaaa aaaagaagaa tagagacaag gtccccatct ctcacaaaga aattccatct    1140

gaagtctaa                                                            1149
```

<210> SEQ ID NO 70
<211> LENGTH: 348
<212> TYPE: PRT
<213> ORGANISM: Papaver somniferum

<400> SEQUENCE: 70

Met Gly Lys Tyr Leu Leu Leu Phe Asn Cys Ile Leu Leu Ala Val Ser
1 5 10 15

Ser Ala Gly Gly Pro Leu Leu Leu Arg Leu Tyr Phe Ile His Gly Gly
20 25 30

Lys Arg Leu Trp Leu Ser Ser Trp Leu Glu Thr Ala Gly Trp Pro Ile
35 40 45

Leu Phe Leu Pro Leu Ser Leu Ser Tyr Phe Leu Lys Arg Arg Arg Phe
50 55 60

Lys Asn Gly Gln Asp Glu Lys Pro Ser Lys Phe Phe Met Ile Thr Pro
65 70 75 80

Phe Leu Phe Met Ala Ser Ala Phe Ile Gly Leu Leu Val Gly Leu Asp
85 90 95

Asp Tyr Leu Tyr Thr Tyr Gly Val Ser Leu Leu Pro Val Ser Thr Ser
100 105 110

Ala Leu Ile Met Ser Thr His Leu Ala Phe Thr Ala Gly Phe Ala Leu
115 120 125

Phe Met Val Lys Gln Lys Phe Thr Ser Tyr Ser Val Asn Ala Val Ile
130 135 140

Leu Leu Thr Val Gly Ala Ile Leu Leu Gly Leu His Ser Asn Gly Asp
145 150 155 160

Thr Pro Val His Glu Ser Asn Arg Asp Tyr Tyr Leu Gly Phe Val Met
165 170 175

Thr Ile Gly Ala Ser Ile Ile Gly Gly Leu Leu Leu Pro Leu Val Glu
180 185 190

Leu Met Tyr Lys Lys Ser Lys Gln Thr Ile Thr Tyr Ser Leu Val Ile
195 200 205

Glu Leu Gln Ile Val Ile Ser Val Phe Ala Thr Leu Leu Cys Thr Val
210 215 220

Gly Met Leu Val Asn Asn Asp Phe Lys Val Ile Gln Arg Glu Gly Lys
225 230 235 240

Glu Tyr Glu Leu Gly Glu Thr Asn Tyr Tyr Val Val Leu Val Ala Ser
245 250 255

Ser Ile Thr Trp Gln Leu Cys Tyr Leu Gly Thr Ile Gly Val Ile Phe
260 265 270

Cys Ser Thr Ser Leu Leu Ala Gly Val Ile Gly Ala Val Val Leu Pro
275 280 285

Val Ile Glu Ile Leu Ala Val Ile Phe Tyr His Glu Ser Phe Lys Ala
290 295 300

Glu Lys Gly Ile Ala Leu Phe Leu Ser Leu Trp Gly Phe Ile Ser Tyr
305 310 315 320

Phe Tyr Leu Glu Ile Lys Glu Ser Thr Lys Pro Lys Lys Lys Arg Ser
325 330 335

Leu Glu Leu Glu Gln Gly Asp Leu Thr Val Ser Ser
340 345

<210> SEQ ID NO 71
<211> LENGTH: 1047
<212> TYPE: DNA
<213> ORGANISM: Papaver somniferum

<400> SEQUENCE: 71
atgggcaaat acctgctgtt gttcaactgc attttgttgg ctgtttcttc tgctggtggt 60
cctttgttgt tgaggttgta ctttattcat ggtggtaaga ggttgtggtt gtcatcttgg 120

```
ttggaaactg ctggttggcc aattttgttt ttgccattgt ccttgtccta ctttttgaag    180

cgtagaagat tcaagaacgg tcaagacgaa aagccatcta agttcttcat gattacccct    240

ttcttgttca tggcttctgc tttcattggt ttgttggttg gtttggatga ttacttgtac    300

acctacggtg tttctttgtt gccagtttct acatccgctt tgattatgtc tactcatttg    360

gcttttaccg ctggttttgc tttgtttatg gtcaagcaaa agttcacctc ctactctgtt    420

aacgccgtta ttttgttaac cgttggtgct atcttgttgg gcttgcattc taatggtgat    480

actccagttc atgaatccaa cagagattac tacttgggtt tcgttatgac cattggtgcc    540

tctattattg gtggtttgtt attgcctttg gtcgagttga tgtacaagaa gtctaagcaa    600

accatcacct actcattggt catcgaattg caaatcgtca tttctgtttt cgctaccttg    660

ttgtgtactg ttggtatgtt ggtcaacaac gatttcaagg tcattcagcg tgaaggtaaa    720

gaatacgaat tgggtgaaac taactactac gttgttttgg ttgcctcttc tattacctgg    780

caattgtgtt acttgggtac tatcggtgtt attttctgct ctacctcttt gttagctggt    840

gttattggtg cagttgtttt gccagttatt gaaatcttgg ccgttatctt ctaccacgaa    900

tcttttaaag ccgaaaaggg tattgccctg tttttgtctt tgtggggttt catctcttac    960

ttctacttgg agatcaaaga gtctaccaag ccaaagaaga agaggtcttt ggaattggaa   1020

caaggtgatt tgaccgtcag ctcttaa                                       1047
```

<210> SEQ ID NO 72
<211> LENGTH: 383
<212> TYPE: PRT
<213> ORGANISM: Nandina domestica

<400> SEQUENCE: 72

```
Met Ser Met Asn Ile Asp Met Asn Val Glu Glu Gly Ser Ala Ile Ser
1               5                   10                  15

Lys Thr His Ile Gln Lys Gln Thr Thr Met Thr Thr Gln Ala Lys Lys
            20                  25                  30

Pro Ile Asn Leu Pro Leu Ile Leu Leu Asn Cys Ser Leu Met Thr Val
        35                  40                  45

Gly Val Leu Gly Gly Pro Leu Leu Leu Arg Leu Tyr Tyr Ile His Gly
    50                  55                  60

Gly Asn Arg Arg Trp Leu Thr Ser Cys Ile Gln Asn Ala Gly Phe Pro
65                  70                  75                  80

Ile Leu Leu Phe Pro Leu Ile Tyr Leu Tyr Ile Leu His Thr Lys Lys
                85                  90                  95

Thr Lys Leu Ser Asn Ala Ser Phe Phe Met Glu Pro Lys Leu Phe Val
            100                 105                 110

Ser Ser Ala Leu Ile Gly Val Leu Phe Gly Leu Asp Asn Phe Met Tyr
        115                 120                 125

Ala Leu Gly Leu Ser Tyr Ile Pro Val Ser Thr Ser Ser Leu Leu Phe
    130                 135                 140

Ala Thr Gln Leu Ala Phe Leu Ala Val Phe Ser Arg Leu Ile Val Lys
145                 150                 155                 160

Gln Lys Phe Thr Ala Phe Ser Ile Asn Ala Val Val Leu Met Thr Leu
                165                 170                 175

Gly Ser Ile Leu Leu Gly Ile Arg Asn Glu Gly Asp Arg Pro Leu Gly
            180                 185                 190

Val Thr Lys Ala Glu Tyr Leu Leu Gly Phe Leu Leu Thr Leu Gly Ser
        195                 200                 205
```

```
Ala Ala Leu Val Gly Phe Ile Leu Pro Leu Ile Glu Leu Ser Tyr Ser
    210                 215                 220

Arg Ala Thr Arg Thr Phe Asn Tyr Ser Thr Val Met Gln Phe Gln Phe
225                 230                 235                 240

Asn Ala Ala Ile Phe Ser Thr Ile Phe Asn Leu Ile Gly Met Leu Ile
                245                 250                 255

Asn Lys Asp Phe Gln Ala Ile Pro Gln Glu Ala Asn Glu Tyr Lys Leu
            260                 265                 270

Gly Ser Thr Met Tyr Tyr Phe Val Leu Val Ala Gly Ala Val Ile Trp
        275                 280                 285

Gln Leu Ser Phe Ile Gly Gly Leu Gly Val Ile Leu Tyr Thr Ser Ser
    290                 295                 300

Leu Phe Ser Gly Val Phe Thr Ala Val Leu Leu Pro Phe Thr Glu Val
305                 310                 315                 320

Ala Ala Val Ile Val Tyr His Glu Ser Phe Thr Gly Glu Lys Gly Met
                325                 330                 335

Ala Leu Ala Leu Cys Leu Trp Gly Phe Thr Asn Tyr Phe Tyr Gly Glu
            340                 345                 350

Tyr Arg Lys Met Lys His Met Glu Ile Thr Glu Pro Met Lys Gln Asp
        355                 360                 365

Gln Val Ile Ile Thr Pro His Asp Asp Glu Gln Ser Cys Thr Val
    370                 375                 380


<210> SEQ ID NO 73
<211> LENGTH: 1152
<212> TYPE: DNA
<213> ORGANISM: Nandina domestica

<400> SEQUENCE: 73

atgtccatga acatcgacat gaacgtcgaa gaaggttctg ctatttctaa gacccatatc      60

caaaagcaaa ctaccatgac tactcaagct aagaagccaa tcaacttgcc attgattttg     120

ctgaactgtt ccttgatgac cgttggtgtt ttaggtggtc ctttgttgtt gaggttgtac     180

tatattcatg gtggtaacag aagatggttg acctcttgta ttcaaaatgc tggtttcccc     240

attctgttgt tcccattgat atacttgtac atcctgcaca ccaaaaagac caagttgtct     300

aatgcttcat tcttcatgga acccaagctg tttgtttcct ctgctttgat aggtgttttg     360

ttcggtttgg acaatttcat gtatgccttg ggtttgtcct atattccagt ttctacttcc     420

tccttgttgt tcgctactca attggctttt ttggccgttt tctctagatt gatcgtcaag     480

caaaagttca ccgccttttc tattaacgcc gttgttttga tgactctggg ttctattttg     540

ttgggtatca gaaacgaagg tgatagacca ttgggtgtta ctaaggctga atacttgttg     600

ggtttcttgt tgacattggg ttctgctgct ttggttggtt tcattttgcc tttgatcgag     660

ttgtcttact ctagagctac tagaaccttc aactactcta ccgttatgca attccaattc     720

aacgctgcta ttttctccac catcttcaac ttgattggca tgttgattaa caaggacttc     780

caagctattc cacaagaagc taacgagtat aagttgggtt ctacgatgta ctacttcgtt     840

ttggttgctg gtgctgttat ttggcaattg tcttttattg gtggtctggg cgttatcttg     900

tacacttctt ctttgttttc tggtgttttc accgctgttt tgttgccatt cactgaagtt     960

gctgctgtta tcgtttacca tgaatctttc actggtgaaa aaggtatggc tttggctttg    1020

tgtttgtggg gttttaccaa ttacttttac ggcgagtaca gaaagatgaa gcacatggaa    1080

attaccgagc caatgaagca agatcaagtt attatcaccc cacacgatga tgaacaatct    1140
```

tgtactgttt aa 1152

<210> SEQ ID NO 74
<211> LENGTH: 384
<212> TYPE: PRT
<213> ORGANISM: Papaver bracteatum

<400> SEQUENCE: 74

Met Asn Ile Glu Thr Leu Asp Ile Leu Gly Pro Asn Gln Asn Gly Asn
1 5 10 15

Ser Gly Thr His Thr Glu Gln Pro Ile Lys Thr Arg Asn Trp Leu Leu
20 25 30

Ile Ile Ile Asn Cys Ala Leu Val Phe Cys Gly Val Ile Gly Gly Pro
35 40 45

Leu Leu Met Arg Leu Tyr Tyr Leu His Gly Gly Ser Arg Lys Trp Leu
50 55 60

Ser Ser Phe Leu Gln Thr Ala Gly Phe Pro Val Leu Ile Phe Pro Leu
65 70 75 80

Ile Phe Leu Tyr Ile Lys Ser Asn Ser Pro Thr Gln Asn Asn Asp Gln
85 90 95

Ser Phe Ser Phe Phe Met Glu Pro Lys Leu Phe Leu Trp Ser Ala Ile
100 105 110

Val Gly Ile Val Phe Gly Val Ser Asn Phe Met Tyr Ala Leu Gly Leu
115 120 125

Ser Tyr Leu Pro Val Ser Thr Ser Thr Ile Leu Phe Ala Thr Gln Leu
130 135 140

Cys Phe Thr Ala Phe Phe Ala Trp Leu Ile Val Lys Gln Glu Phe Thr
145 150 155 160

Ala Phe Ile Ile Asn Ala Val Ile Val Met Thr Leu Gly Ser Val Leu
165 170 175

Leu Gly Ile Asn Thr Asn Gly Asp Arg Pro Ile Gly Val Ser Lys Ala
180 185 190

Gln Tyr Leu Ile Gly Phe Leu Met Thr Leu Ala Ala Ala Ala Leu Thr
195 200 205

Gly Leu Gly Thr Pro Phe Ile Glu Leu Ala Phe Phe Lys Ala Thr Arg
210 215 220

Asn Ile Thr Tyr Ser Thr Phe Leu Gln Phe Gln Ile Thr Leu Gly Leu
225 230 235 240

Phe Gly Thr Cys Leu Asn Val Ile Gly Met Leu Ile Asn Lys Asp Phe
245 250 255

Gln Ala Ile Pro Arg Glu Ala Asp Asn Phe Glu Leu Gly Lys Gly Lys
260 265 270

Tyr Tyr Met Ile Ile Cys Leu Thr Ala Leu Thr Trp Gln Leu Ser Gly
275 280 285

Ile Gly Leu Ile Gly Leu Ile Phe Tyr Thr Asn Ala Leu Phe Asn Gly
290 295 300

Ile Tyr Val Ser Val Leu Val Pro Phe Thr Glu Val Ala Ala Val Ile
305 310 315 320

Phe Tyr His Glu Lys Phe Thr Gly Leu Lys Gly Met Ala Leu Ala Leu
325 330 335

Cys Leu Trp Gly Phe Ser Ser Tyr Phe Tyr Gly Glu Tyr Lys Met Met
340 345 350

Asn Lys Gly Gly Gly Asn Glu Thr Gln Glu Lys Thr Lys Ala Val Glu
355 360 365

```
Ser Glu Pro Lys Arg Leu Glu Asp Gln Glu Ala Pro Tyr Ser Thr Val
    370                 375                 380


<210> SEQ ID NO 75
<211> LENGTH: 1155
<212> TYPE: DNA
<213> ORGANISM: Papaver bracteatum

<400> SEQUENCE: 75

atgaacatcg aaaccttgga catcttgggt ccaaatcaaa atggtaactc tggtactcat      60

accgaacaac ctattaagac tagaaactgg ctgctgatta ttatcaactg cgctttggtt     120

ttctgcggtg ttattggtgg tccattattg atgaggttgt actacttgca tggtggttct     180

agaaaatggt tgtcctcttt cttgcaaact gctggttttc cagttctgat tttccctttg     240

atcttcctgt acatcaagtc caattctcca actcaaaaca acgaccagtc tttctcattt     300

ttcatggaac ccaagttgtt cttgtggtct gctatagttg gtatcgtttt cggtgtttcc     360

aatttcatgt atgccttggg tttgtcttac ttgccagttt ccacttccac tattttgttc     420

gctactcaat tgtgtttcac cgcttttttt gcttggttga tcgtcaagca agaattcact     480

gccttcatta ttaacgccgt tatcgttatg actttgggct ctgttttgtt gggtattaac     540

actaatggtg acagacctat tggtgtttct aaggcccaat acttgattgg tttcttgatg     600

actttagctg ctgctgcttt gactggtttg ggtactcctt ttattgaatt ggctttcttc     660

aaggccacca gaaacattac ttactccaca ttcttgcaat tccagattac cttgggtctg     720

tttggtactt gcttgaacgt tattggcatg ctgatcaaca aggatttcca agctattcca     780

agagaagccg acaatttcga attaggtaaa ggcaagtact acatgatcat ttgcttgaca     840

gctttgactt ggcaattgtc cggtattggt ttaattggct tgatcttcta caccaacgct     900

ttgtttaatg gcatctacgt ttctgttttg gtcccattca ctgaagttgc tgctgttatt     960

ttctaccacg aaaagttcac tggtttgaaa ggtatggctt tggctttgtg tttgtggggt    1020

ttttcttctt acttttacgg cgagtacaag atgatgaaca aaggtggtgg taacgaaact    1080

caagaaaaga ctaaggctgt tgaatccgaa cctaagagat tggaggatca agaagctcca    1140

tactctactg tttga                                                     1155


<210> SEQ ID NO 76
<211> LENGTH: 360
<212> TYPE: PRT
<213> ORGANISM: Cinnamomum micranthum f. kanehirae

<400> SEQUENCE: 76

Met Asp Ile Glu Arg Ala Ala Ala Pro Ser Ser Ser Asp Val Asp Asn
1               5                   10                  15

Thr Lys Leu Pro Pro Lys Arg Asn Ile Lys Trp Trp Leu Val Leu Ile
            20                  25                  30

Asn Val Val Cys Ile Gly Val Gly Thr Ile Gly Gly Pro Leu Leu Thr
        35                  40                  45

Arg Met Tyr Phe Leu His Gly Gly Ser Arg Lys Trp Leu Ser Ser Trp
    50                  55                  60

Leu Gln Thr Ala Gly Phe Pro Ile Leu Leu Gly Pro Leu Ile Phe Leu
65                  70                  75                  80

Tyr Lys Arg His Gln Ala Arg Gly Ile Arg Phe Ile Ala Glu Pro Lys
                85                  90                  95

Leu Ile Ala Ala Ser Ala Ala Val Gly Val Leu Ile Gly Leu Asp Asn
```

```
            100                 105                 110

Phe Met Tyr Ser His Gly Leu Ser Thr Leu Pro Val Ser Thr Ser Ser
        115                 120                 125

Leu Leu Phe Ser Thr Gln Leu Ala Phe Thr Ala Phe Phe Ala Leu Ile
    130                 135                 140

Ile Val Arg Gln Lys Phe Thr Pro Tyr Ser Ile Asn Ala Val Val Leu
145                 150                 155                 160

Met Thr Leu Gly Ala Val Leu Leu Gly Met Arg Lys Gly Gly Asp Arg
                165                 170                 175

Pro Ala Gly Val Ser Asn Ala Asp Tyr Leu Leu Gly Phe Ile Ile Thr
            180                 185                 190

Leu Gly Ala Ala Ala Val Leu Gly Phe Leu Leu Pro Cys Ile Glu Leu
        195                 200                 205

Ile Tyr Ala Lys Ala Ser Lys Val Ile Asn Tyr Ala Val Val Met Gln
    210                 215                 220

Phe Gln Leu Gly Val Ser Phe Phe Ala Thr Leu Phe Ser Thr Ile Gly
225                 230                 235                 240

Met Ile Ala Asn Lys Asp Phe Gln Ala Ile Ser Arg Glu Ala Lys Ala
                245                 250                 255

Phe Asp Ile Gly Glu Gly Lys Tyr Tyr Leu Val Ile Val Phe Val Ala
            260                 265                 270

Leu Thr Phe Gln Leu Val Tyr Ile Gly Ser Leu Gly Leu Val Phe Cys
        275                 280                 285

Thr Ser Ser Leu Phe Thr Gly Val Val Thr Ala Thr Leu Leu Pro Leu
    290                 295                 300

Thr Glu Ile Ala Ala Val Ile Phe Phe Lys Glu Lys Phe Thr Gly Glu
305                 310                 315                 320

Lys Gly Met Ser Leu Ala Leu Cys Leu Trp Gly Phe Ala Ser Tyr Phe
                325                 330                 335

Tyr Gly Thr Tyr Arg Ile Glu Lys Lys Gln Lys Glu Asn Ile Lys Thr
            340                 345                 350

Glu Thr Pro Glu Ala Glu Val Lys
        355                 360
```

<210> SEQ ID NO 77
<211> LENGTH: 1083
<212> TYPE: DNA
<213> ORGANISM: Cinnamomum micranthum f. kanehirae

<400> SEQUENCE: 77

```
atggacattg aaagagctgc tgctccatct tcttcagatg ttgataatac caaattgcca     60

cctaagagga acattaagtg gtggttggtt ttgattaacg ttgtctgtat tggtgtcggt    120

actattggtg gtccattatt gactagaatg tacttcttgc atggtggttc cagaaaatgg    180

ttatcttctt ggttgcaaac tgctggtttc ccaattttgt tgggtccatt gatctttctg    240

tacaagagac atcaagctag aggcattaga ttcattgctg aacctaaatt gattgctgct    300

tctgctgctg ttggtgtttt gattggtttg gataacttca tgtactccca tggtttgtct    360

actttgccag tttctacttc ctctttgttg ttctctactc aattggcttt cactgctttc    420

ttcgccttga ttatcgttag acaaaagttc accccatact ccattaacgc tgttgttttg    480

atgactttgg gtgccgtttt gctaggtatg agaaaaggtg gtgatagacc tgctggtgtt    540

tctaatgctg attacttgtt gggtttcatc attacattgg gtgctgctgc agttttgggt    600

tttttgttgc catgtatcga attgatctac gctaaggctt ccaaggttat taactacgca    660
```

```
gttgtcatgc aattccaatt gggtgtttct tttttcgcca ccttgttttc taccattggt    720

atgattgcta acaaggactt ccaagccatt tctagagaag ctaaggcctt tgatattggt    780

gaaggcaagt attacttggt catcgttttc gttgctttga ctttccagtt ggtttacatc    840

ggttctttgg gtttagtttt ctgcacctct tctttgttca ctggtgttgt tactgctact    900

ttgttgcctt tgactgaaat tgctgccgtc attttcttca aagaaaagtt tactggtgag    960

aagggtatgt ctttggcttt gtgtttgtgg ggttttgctt cttactttta cggcacctac   1020

agaatcgaaa agaagcagaa agaaaacatc aagactgaaa ccccagaagc cgaagttaag   1080

taa                                                                 1083


<210> SEQ ID NO 78
<211> LENGTH: 394
<212> TYPE: PRT
<213> ORGANISM: Papaver somniferum

<400> SEQUENCE: 78

Met Asp Ile Glu Ala Ala Ala Ser Thr Asn Val Gly Ala Ala Ala Thr
1               5                   10                  15

Asn Tyr Asn His Gly Thr Gly Asn His His Asn Asn Leu Val Val Gln
            20                  25                  30

Asn Asp Arg Glu Asp Asp Leu Pro Lys Thr Asp Asn Pro Ile Thr Lys
        35                  40                  45

Lys Ile Val Ile Asp Trp Lys Leu Ile Leu Leu Cys Leu Leu Phe Ala
    50                  55                  60

Phe Gly Tyr Ile Gly Gly Pro Ile Leu Gln Arg Leu Tyr Phe Thr His
65                  70                  75                  80

Gly Gly Gly Arg Lys Trp Phe Met Ser Met Leu Gln Cys Val Gly Phe
                85                  90                  95

Pro Val Leu Val Ala Pro Leu Ser Tyr Ile Tyr Ile Lys Lys Val Asn
            100                 105                 110

Gly Pro Ser Tyr Asp Ala Ser Trp Val Phe Leu Met Glu Pro Lys Leu
        115                 120                 125

Phe Ile Tyr Ser Ala Leu Leu Gly Val Ala Leu Gly Leu Asp Asn Tyr
    130                 135                 140

Met Tyr Ser Ala Gly Leu Phe Tyr Leu Pro Val Ser Thr Ser Ser Leu
145                 150                 155                 160

Leu Phe Ser Thr Gln Leu Ala Phe Thr Ala Ile Phe Ala Phe Ile Ile
                165                 170                 175

Val Arg Gln Lys Phe Thr Phe Tyr Ser Phe Asn Ser Val Val Leu Met
            180                 185                 190

Thr Leu Gly Ser Val Val Leu Ala Leu Asn Thr Gly Ser Asp Lys Pro
        195                 200                 205

Pro Gly Thr Thr Gln Gln Gln Tyr Tyr Ile Gly Phe Ala Leu Thr Ile
    210                 215                 220

Ala Gly Ala Ala Leu Leu Gly Leu Val Leu Pro Leu Val Glu Leu Ser
225                 230                 235                 240

Tyr Gly Arg Ser Ser Lys Pro Ile Thr Tyr Ser Val Val Met Gln Phe
                245                 250                 255

Gln Phe Val Leu Ser Leu Phe Gly Thr Ile Ala Thr Met Ile Gly Met
            260                 265                 270

Ala Ile Asn Asn Asp Phe Gln Val Ile Pro Arg Glu Gly Arg Asp Phe
        275                 280                 285
```

Gly Leu Gly Gln Gly Lys Tyr Tyr Leu Leu Ile Val Ala Leu Ala Val
    290                 295                 300

Val Trp Gln Leu Phe Thr Ile Gly Phe Leu Gly Leu Ile Tyr Cys Thr
305                 310                 315                 320

Ser Ser Leu Phe Ala Gly Ile Tyr Thr Thr Cys Leu Leu Pro Phe Thr
                325                 330                 335

Gln Val Ala Ala Ser Ile Ala Phe Gln Glu Lys Phe Thr Ser Gln Lys
            340                 345                 350

Gly Met Ser Leu Ala Leu Cys Leu Trp Gly Phe Val Ser Tyr Phe Ala
        355                 360                 365

Gly Glu Tyr Lys Lys Ser Lys Lys Pro Gln Pro Ile Ala Tyr Asp Lys
    370                 375                 380

Asp Lys Ser Glu Leu Ser Asp Asn Asp Ala
385                 390

<210> SEQ ID NO 79
<211> LENGTH: 1185
<212> TYPE: DNA
<213> ORGANISM: Papaver somniferum

<400> SEQUENCE: 79
atggatattg aagctgctgc ctctactaat gttggtgctg ctgctactaa ttacaatcat 60
ggtactggta accaccacaa caacttggtt gttcaaaacg atagagaaga tgacttgcca 120
aagactgata acccaattac caagaagatc gttatcgact ggaagttgat tctgttgtgt 180
ttgttgtttg ccttcggtta tattggtggt ccaatattgc aaaggttgta ctttactcat 240
ggtggtggta gaaagtggtt catgtctatg ttgcaatgtg ttggtttccc agttttggtt 300
gctccattgt cttacatcta catcaagaaa gttaacggtc catcttacga tgcctcttgg 360 gttttttga tggaacctaa gttgttcatc tactccgctt tgttgggtgt tgctttgggt 420
ttagataact acatgtattc cgctggcttg ttctatttgc cagtttctac ttcttccctg 480
ttgttctcta cacaattggc tttcactgct attttcgcct tcattatcgt cagacaaaag 540
ttcaccttct acagcttcaa ctccgttgtt ttgatgactt tgggttcagt tgttttggct 600
ttgaataccg gttctgataa gccaccaggt actactcaac aacaatatta cattggtttc 660
gccttgacta ttgctggtgc agctttgtta ggtttggttt tgccattggt tgaactgtct 720
tatggcagat cttctaagcc aattacctac tctgttgtca tgcaattcca attcgtcttg 780
tctttgttcg gtactattgc cactatgatt ggtatggcca ttaacaacga tttccaagtc 840
attccaagag agggtagaga ttttggttta ggtcaaggca agtactactt gttgatagtt 900
gctttagctg ttgtctggca gttgttcact attggttttt tgggtttgat ctactgcacc 960
tcttctttgt ttgctggtat ctacactaca tgcttgttgc cattcactca agttgctgct 1020
tctattgctt tccaagaaaa gtttaccagc caaaagggta tgtcattggc tttgtgttta 1080
tggggtttcg tttcttattt tgccggtgag tacaagaagt ctaaaaagcc acaacctatt 1140
gcctacgata aggacaaatc tgaattgtct gataacgacg cctga 1185

<210> SEQ ID NO 80
<211> LENGTH: 375
<212> TYPE: PRT
<213> ORGANISM: Papaver somniferum

<400> SEQUENCE: 80

Met Ala Thr Ser Glu Met Asn Leu Glu Thr Leu Glu Asn Leu Gly Ala
1               5                   10                  15

```
Thr Glu Asn Cys Lys Ser Lys Leu His Thr Glu Pro Pro Thr Lys His
            20                  25                  30

Lys Asn Trp Leu Leu Thr Cys Ile Asn Cys Ala Ile Val Phe Cys Gly
        35                  40                  45

Val Ile Gly Ser Pro Leu Leu Leu Arg Leu Tyr Phe Leu His Gly Gly
    50                  55                  60

Asp Arg Lys Trp Leu Ser Ser Trp Ile Gln Thr Ala Gly Phe Pro Val
65                  70                  75                  80

Leu Ile Leu Pro Leu Ile Phe Leu Tyr Ile Arg Ser Glu Leu Phe Ala
                85                  90                  95

Ser Arg Asn Asn Asp His Val Ser Ser Phe Phe Met Glu Gln Lys Leu
            100                 105                 110

Phe Leu Ser Ser Ala Ala Ile Gly Phe Leu Tyr Gly Val Val Asn Phe
        115                 120                 125

Met Tyr Ala Leu Gly Leu Ser Tyr Ile Pro Val Ser Thr Ser Ser Ile
    130                 135                 140

Leu Cys Ala Thr Gln Leu Cys Phe Ser Ala Phe Phe Ala Trp Leu Ile
145                 150                 155                 160

Val Lys Gln Lys Phe Thr Ala Phe Ile Ile Asn Ala Ile Val Ile Met
                165                 170                 175

Thr Leu Gly Ser Val Leu Leu Gly Ile Asn Ser Asn Gly Asp Arg Pro
            180                 185                 190

Val Gly Val Ser Lys Ala Gln Tyr Leu Ile Gly Phe Val Met Thr Leu
        195                 200                 205

Gly Ser Ala Ala Leu Ser Gly Leu Ile Met Pro Met Ile Glu Ile Ala
    210                 215                 220

Phe Ser Lys Ala Thr Arg Ser Ile Thr Tyr Ser Ser Leu Leu Gln Phe
225                 230                 235                 240

Gln Ile Thr Leu Ala Ile Ser Ala Asn Ala Leu Asn Ile Ile Gly Val
                245                 250                 255

Leu Ile Asn Lys Asp Phe Gln Ala Ile His Arg Glu Ala Asn Glu Tyr
            260                 265                 270

Glu Leu Gly Lys Thr Lys Tyr Tyr Ile Ile Leu Phe Phe Thr Ala Phe
        275                 280                 285

Thr Phe Gln Leu Met Thr Met Gly Val Leu Gly Val Ile Leu Tyr Thr
    290                 295                 300

Ser Ala Leu Phe Asn Gly Ile Phe Thr Ser Val Leu Ile Pro Phe Thr
305                 310                 315                 320

Gln Val Ala Ala Val Ile Phe Tyr His Glu Lys Phe Thr Gly Leu Lys
                325                 330                 335

Gly Met Ala Leu Ala Leu Cys Leu Trp Gly Phe Cys Ser Tyr Phe Tyr
            340                 345                 350

Gly Glu Tyr Lys Met Leu Gln Lys Val Val Asp Arg Glu Thr Pro Glu
        355                 360                 365

Lys Tyr Tyr Lys Ala Lys Lys
    370                 375
```

<210> SEQ ID NO 81
<211> LENGTH: 1128
<212> TYPE: DNA
<213> ORGANISM: Papaver somniferum

<400> SEQUENCE: 81

```
atggccacct ctgaaatgaa cttggaaacc ttggaaaatt tgggtgctac tgaaaactgc      60
```

```
aagtctaagt tgcatactga accaccaact aagcacaaga attggttgtt gacctgtatt    120

aactgcgcta tcgttttctg tggtgttatt ggttcacctt tgttgttgag gttgtacttc    180

ttgcatggtg gtgatagaaa atggttgtcc tcttggattc aaactgctgg ttttccagtt    240

ctgattttgc ctttgatctt cctgtacatc agatccgaat tattcgcctc tagaaacaac    300

gatcacgtgt catctttttt catggaacaa aaactgttct tgtcctccgc tgctattggt    360

ttcttgtatg gtgttgttaa cttcatgtac gccttgggtt tgtcctatat tccagtttct    420

acctcctcta ttttgtgcgc tactcaattg tgtttctctg ctttttttgc ctggttgatc    480

gtcaagcaaa agttcactgc tttcattatc aacgccatcg ttattatgac cttgggttct    540

gttttgttgg gcattaactc taacggtgat agaccagttg gtgtttctaa agcccaatac    600

ttgattggtt tcgtcatgac tttaggttct gctgctttgt ctggtttgat tatgccaatg    660

attgaaatcg ctttctccaa ggctactagg tctattactt actcctcttt gttgcaattc    720

caaatcacct tggctatttc tgctaacgcc ttgaacatta tcggtgtctt gattaacaag    780

gacttccaag ccattcatag agaagctaac gaatacgaat tgggcaagac caagtactac    840

atcattttgt ttttcaccgc cttcaccttc caattgatga ctatgggtgt tttgggtgtt    900

atcttgtaca cttctgcttt gttcaacggt atcttcacct ctgttttgat cccattcact    960

caagttgctg ccgttatctt ttaccacgaa aagtttactg gtttgaaagg tatggctttg   1020

gctttgtgtt tgtggggttt ctgttcttac ttttacggtg agtacaagat gttgcaaaag   1080

gttgttgata gagaaacccc tgagaagtat tacaaggcta agaagtga                1128
```

<210> SEQ ID NO 82
<211> LENGTH: 356
<212> TYPE: PRT
<213> ORGANISM: Rosa chinensis

<400> SEQUENCE: 82

```
Met Glu Thr Lys Gln Glu Pro Gln Ala Asn Thr Ser Thr Thr Lys Arg
1               5                   10                  15

Ala Leu Leu Ile Leu Asn Cys Ile Leu Leu Ser Ile Gly Asn Cys Gly
            20                  25                  30

Gly Pro Leu Ile Met Arg Leu Tyr Phe Ile His Gly Gly Lys Arg Val
        35                  40                  45

Trp Leu Ser Ser Trp Leu Glu Thr Gly Gly Trp Pro Ile Leu Leu Ile
    50                  55                  60

Pro Leu Phe Ile Ser Tyr Leu His Arg Arg Ser Thr Asn Pro Pro Thr
65                  70                  75                  80

Lys Leu Phe Tyr Met Lys Pro Arg Leu Phe Leu Ala Ala Thr Phe Ile
                85                  90                  95

Gly Val Leu Thr Gly Leu Asp Asp Tyr Leu Tyr Ala Tyr Gly Val Ala
            100                 105                 110

Arg Leu Pro Val Ser Thr Ser Ser Leu Ile Ile Ala Thr Gln Leu Ala
        115                 120                 125

Phe Thr Ala Ala Phe Ala Phe Leu Leu Val Lys Gln Lys Phe Thr Ser
    130                 135                 140

Phe Ser Ile Asn Ala Val Val Leu Leu Thr Ala Gly Ala Gly Val Leu
145                 150                 155                 160

Ala Leu His Thr Ser Ser Asp Arg Pro Gly His Glu Ser Thr Lys Gln
                165                 170                 175

Tyr Ala Leu Gly Phe Val Met Thr Leu Val Ala Ala Ala Leu Tyr Gly
```

```
            180                 185                 190

Phe Ile Leu Pro Leu Val Glu Leu Thr Tyr Lys Lys Ser Lys Gln Glu
        195                 200                 205

Ile Ser Tyr Thr Leu Val Met Glu Ile Gln Met Val Met Cys Leu Phe
    210                 215                 220

Ala Thr Ile Phe Cys Thr Ile Gly Met Leu Val Asn Lys Asp Phe Asn
225                 230                 235                 240

Val Ile Pro Arg Glu Ala Arg Glu Phe Gly Leu Gly Glu Thr Lys Tyr
                245                 250                 255

Tyr Val Ile Leu Val Trp Ser Ala Ile Ile Trp Gln Cys Phe Phe Leu
            260                 265                 270

Gly Ala Ile Gly Val Ile Phe Cys Ala Ser Ser Leu Leu Ser Gly Ile
        275                 280                 285

Leu Ile Ala Val Leu Leu Pro Val Thr Glu Val Leu Ala Val Ile Phe
    290                 295                 300

Tyr Gln Glu Asn Phe Gln Ala Glu Lys Gly Val Ala Leu Ala Leu Ser
305                 310                 315                 320

Leu Trp Gly Phe Val Ser Tyr Phe Tyr Gly Glu Val Lys Glu Ser Lys
                325                 330                 335

Lys Lys Asn Leu Ala Pro Gly Ser Glu Met Pro Arg Ser Ser Ser Pro
            340                 345                 350

Thr Glu Asn Val
        355
```

<210> SEQ ID NO 83
<211> LENGTH: 1071
<212> TYPE: DNA
<213> ORGANISM: Rosa chinensis

<400> SEQUENCE: 83

```
atggaaacga agcaagaacc acaagctaac acttctacta ctaagagagc cttgttgatc     60

ttgaactgca tcttgttgtc tattggtaat tgtggtggtc cattgatcat gaggttgtac    120

tttattcatg gtggtaagag agtctggttg tcatcttggt tggaaactgg tggttggcca    180

attttgttga ttcctttgtt catctcctac ctgcatagaa gatctactaa tccaccaacg    240

aagctgtttt acatgaagcc aagattattc ttagccgcca ctttcattgg tgttttgact    300

ggtttggatg attacttgta tgcttacggt gttgctagat tgccagtttc tacttcctct    360

ttgattatcg ctactcaatt ggcttttact gctgcttttg ctttcttgtt ggtcaagcaa    420

aagttcacct ccttctctat taacgccgtt gttttgttga ctgctggtgc tggtgtttta    480

gcattgcata cttcatctga tagaccaggt catgaatcta ctaagcaata cgctttgggt    540

ttcgttatga ctttggttgc tgctgcatta tacggtttca ttttgccatt ggttgagctg    600

acttacaaga agtccaaaca agaaatctcc tacaccttgg tcatggaaat ccaaatggtt    660

atgtgtttgt tcgccaccat tttctgtacc attggtatgt tggttaacaa ggacttcaac    720

gtcattccaa gagaagctag agaatttggt ttgggtgaaa ctaagtacta cgttatcttg    780

gtttggtccg ccattatttg gcaatgtttt ttcttgggtg ctatcggtgt tattttctgc    840

gcttcttctt tgttgtccgg tattttgatt gcagttttgt tgccagttac cgaagttttg    900

gctgttatct tctaccaaga aaacttccaa gctgaaaagg gtgttgcttt ggctttgtct    960

ttgtggggtt ttgtttctta cttttacggt gaggtcaaag agtccaagaa gaaaaatttg   1020

gctccaggtt ctgaaatgcc cagatcttct tctccaactg aaaacgtttg a            1071
```

<210> SEQ ID NO 84
<211> LENGTH: 358
<212> TYPE: PRT
<213> ORGANISM: Erythranthe guttata

<400> SEQUENCE: 84

Met Glu Ile Gln Thr Thr Ala Ala Ala Met Lys Arg Val Leu Leu Ile
1 5 10 15

Ile Asn Cys Ile Ile Leu Ala Val Gly Asn Cys Gly Gly Pro Leu Ile
20 25 30

Met Arg Leu Tyr Phe Val His Gly Gly Lys Arg Ile Trp Phe Ser Ser
35 40 45

Trp Leu Glu Thr Gly Gly Trp Pro Ile Leu Leu Val Pro Leu Leu Val
50 55 60

Ser Tyr Asn Arg Arg Arg Arg Thr Ala Ala Ser Gly Lys Ala Glu Leu
65 70 75 80

Tyr Leu Met Lys Pro Arg Val Phe Leu Ala Ala Ala Val Ile Gly Val
85 90 95

Leu Thr Gly Phe Asp Asp Tyr Leu Tyr Ala Tyr Gly Val Ala Lys Leu
100 105 110

Pro Val Ser Thr Ser Ala Leu Ile Ile Ala Ser Gln Leu Ala Phe Thr
115 120 125

Ala Ala Phe Ala Phe Leu Met Val Lys Gln Glu Phe Thr Ala Tyr Ser
130 135 140

Val Asn Ser Val Val Leu Leu Thr Leu Gly Ala Val Val Leu Gly Leu
145 150 155 160

His Thr Asn Gly Asp Arg Pro Glu Gly Glu Ser Ser Lys Glu Tyr Met
165 170 175

Val Gly Phe Phe Leu Thr Val Ala Ala Ala Ala Leu Cys Gly Phe Ile
180 185 190

Leu Pro Ala Val Glu Leu Thr Tyr Lys Lys Ala Lys Gln Ala Val Ser
195 200 205

Tyr Thr Leu Val Leu Glu Met Gln Leu Val Met Cys Val Phe Ala Thr
210 215 220

Ser Phe Cys Thr Leu Gly Met Leu Val Asn Asn Asp Phe Gln Ala Ile
225 230 235 240

Ala Arg Glu Ala Arg Ala Tyr Glu Leu Gly Glu Thr Lys Tyr Tyr Ile
245 250 255

Val Val Leu Trp Ser Ala Ile Val Trp Gln Cys Phe Phe Leu Gly Ala
260 265 270

Ile Gly Val Ile Phe Tyr Ser Ser Ser Leu Leu Ser Gly Ile Val Ile
275 280 285

Thr Val Leu Leu Pro Ala Thr Glu Ile Leu Ala Ile Ile Phe Tyr His
290 295 300

Glu Lys Phe Gln Ala Glu Lys Gly Leu Ser Leu Phe Leu Ser Leu Trp
305 310 315 320

Gly Phe Ile Ser Tyr Phe Tyr Gly Glu Met Lys Lys Asp Lys Asn Lys
325 330 335

Asn Lys Asn Asn Ile Asp Gln Ser Asn Asp Gln Thr Gln Ala Thr Glu
340 345 350

Thr Glu Leu Thr His Arg
355

<210> SEQ ID NO 85

<211> LENGTH: 1077
<212> TYPE: DNA
<213> ORGANISM: Erythranthe guttata

<400> SEQUENCE: 85

```
atggaaattc aaactaccgc tgctgccatg aagagagttt tgttgattat taactgcatc     60

atcttggccg ttggtaattg tggtggtcca ttgattatga ggttgtactt tgttcatggt    120

ggtaagagaa tctggttctc ttcttggttg gaaactggtg gttggccaat tttgttggtt    180

ccattattgg tgtcctacaa cagaagaaga aggactgctg cttctggtaa agctgaatta    240

tacttgatga agcccagagt ttttttggct gctgctgtta taggtgtttt gactggtttt    300

gatgattact tgtacgctta cggtgttgct aaattgccag tttctacttc cgctttgatt    360

atcgcttctc aattggcttt tacagctgct tttgcttttct tgatggtcaa gcaagaattc    420

accgcttact ctgttaactc cgttgttttg ttaactttgg gtgctgttgt tttgggcttg    480

catacaaatg gtgatagacc agaaggtgag tcatctaaag aatatatggt cggtttcttc    540

ttgactgttg ctgctgcagc tttgtgtggt ttcattttgc cagctgttga attgacttac    600

aagaaggcta aacaagccgt ttcttacacc ttggttttgg aaatgcaatt ggtcatgtgt    660

gttttcgcta cttctttctg tactttgggt atgttggtta acaacgactt ccaagctatt    720

gctagagaag ctagagctta tgaattgggt gaaacgaagt actacattgt cgttttgtgg    780

tctgctatag tttggcaatg ttttttcttg ggtgccatcg gtgttatctt ctactcttct    840

tctttattgt ccggtatcgt tatcaccgtt ttgttgccag ctactgaaat tttggccatc    900

attttctacc acgaaaagtt ccaagctgag aagggtttgt ctttgttttt gtcattgtgg    960

ggcttcatta gctacttcta tggtgaaatg aagaaggata agaacaaaaa caagaacaac   1020

atcgaccagt ccaacgatca aactcaagct acagaaactg aattgaccca cagatga      1077
```

<210> SEQ ID NO 86
<211> LENGTH: 377
<212> TYPE: PRT
<213> ORGANISM: Arachis duranensis

<400> SEQUENCE: 86

```
Met Ala Glu Pro Val Glu Ala Gln Gln Gln Gln Arg Lys Thr Thr Met
1               5                   10                  15

Lys Arg Thr Leu Leu Val Thr Asn Cys Ile Leu Leu Ser Val Gly Thr
            20                  25                  30

Ser Gly Gly Pro Leu Ile Met Arg Leu Tyr Phe Leu His Gly Gly His
        35                  40                  45

Arg Val Trp Leu Ser Ser Cys Leu Glu Thr Ala Gly Phe Pro Ile Met
    50                  55                  60

Leu Ile Pro Leu Ile Leu Ser Tyr Phe Arg Arg Lys Asn Asn Arg His
65                  70                  75                  80

Tyr Pro Ser Glu Thr Glu Lys Leu Lys Thr Thr Met Val Ser Met Lys
                85                  90                  95

Pro Pro Leu Phe Phe Ala Ala Ala Phe Ile Gly Ile Leu Thr Gly Leu
            100                 105                 110

Asp Asp Tyr Leu Tyr Ala Cys Gly Val Ala Arg Leu Pro Val Ser Thr
        115                 120                 125

Ser Ala Leu Ile Ile Ala Thr Gln Leu Ala Phe Thr Ala Val Phe Ala
    130                 135                 140

Phe Leu Leu Val Arg Gln Lys Phe Thr Pro Tyr Ser Val Asn Ala Val
145                 150                 155                 160
```

```
Val Leu Leu Thr Val Gly Ala Gly Val Leu Ala Leu His Thr Arg Ser
                165                 170                 175

Asp Arg Pro Thr Gly Glu Ser Thr Val Glu Tyr Val Lys Gly Phe Val
            180                 185                 190

Met Thr Leu Met Ala Ala Ala Leu Tyr Gly Phe Val Leu Pro Leu Val
        195                 200                 205

Glu Leu Thr Tyr Lys Lys Ala Lys Gln Asn Leu Thr Tyr Ser Leu Val
    210                 215                 220

Met Glu Ile Gln Phe Val Met Cys Phe Phe Ala Thr Val Phe Cys Val
225                 230                 235                 240

Ala Gly Met Ile Ile Asn Asn Asp Phe Lys Val Ile Pro Arg Glu Ala
                245                 250                 255

Arg Glu Phe Gly Leu Gly Arg Gly Asn Tyr Tyr Val Val Met Val Ala
            260                 265                 270

Ser Ala Ile Met Trp Gln Ala Phe Phe Leu Gly Ala Ile Gly Val Ile
        275                 280                 285

Phe Cys Ser Ser Ser Leu Leu Ser Gly Ile Leu Ile Ala Ile Leu Leu
    290                 295                 300

Pro Val Thr Gly Ile Leu Ala Val Ile Phe Tyr Lys Glu Lys Phe Gln
305                 310                 315                 320

Val Glu Lys Ala Val Ser Leu Val Leu Ser Leu Trp Gly Phe Val Ser
                325                 330                 335

Tyr Phe Tyr Gly Glu Ile Lys Gln Ala Asn Lys Glu Lys Met Thr Met
            340                 345                 350

Met Asp Ser Lys Asn Ser Val Pro Glu Thr Glu Gln Ile Gln Thr Leu
        355                 360                 365

Ala Val Ser His Ser Pro Asn Asn Ile
    370                 375
```

<210> SEQ ID NO 87
<211> LENGTH: 1134
<212> TYPE: DNA
<213> ORGANISM: Arachis duranensis

<400> SEQUENCE: 87

```
atggccgaac cagttgaagc tcaacaacaa caaagaaaga ctaccatgaa gagaaccttg      60

ttggttacca actgcatctt gttgtctgtt ggtacttctg gtggtccatt gattatgagg     120

ttgtatttct tgcatggtgg tcacagagtt tggttgtcat cttgtttgga aactgctggt     180

ttcccaatta tgttgatccc attgatcctg tcctacttca gaagaaagaa caacagacat     240

tacccatccg aaaccgaaaa gttgaaaacc actatggttt ctatgaagcc acctttgttt     300

tttgctgctg ccttcattgg tattttgacc ggtttggatg attacttgta tgcttgtggt     360

gttgctagat tgccagtttc tacttccgct ttgattattg ctactcaatt ggctttcact     420

gccgtttttg ctttttttgtt ggtcagacaa aagttcaccc catactctgt taatgccgtt     480

gttttgttaa ctgttggtgc tggtgttttg gcattgcata caagatctga tagaccaact     540

ggtgaatcta ctgttgaata cgttaagggt ttcgtcatga ctttgatggc tgctgcatta     600

tacggttttg ttttgccatt ggttgagctg acttacaaga aggctaagca aaacttgacc     660

tactccttgg ttatggaaat ccaattcgtt atgtgtttct tcgctaccgt tttttgtgtt     720

gccggtatga ttatcaacaa cgacttcaag gttattccaa gggaagctag agaattcggt     780

ttaggtagag gtaactacta cgttgttatg gttgcttctg ctattatgtg gcaagctttt     840
```

```
ttcttgggtg ctatcggtgt tatcttctgc tcatcttctt tgctgtctgg tatcttgatt    900

gccattttgt tgccagttac aggtattttg gccgtcatct tctacaaaga aaagttccaa    960

gtcgaaaagg ccgtttcctt ggttttgtct ttgtggggtt tcgtttctta cttctacggt   1020

gaaatcaagc aggccaacaa agaaaagatg actatgatgg actccaagaa ctctgttcca   1080

gaaaccgaac aaattcaaac cttggctgtt tctcattccc caaacaacat ttga         1134


<210> SEQ ID NO 88
<211> LENGTH: 382
<212> TYPE: PRT
<213> ORGANISM: Papaver somniferum

<400> SEQUENCE: 88

Met Glu Asn Glu Ser Thr Met Lys Arg Val Val Leu Asn Asn Asp Ser
1               5                   10                  15

Ser His Glu Gln His His Gln Gln Glu Lys Glu Thr Lys Lys Lys Lys
            20                  25                  30

Leu Val Leu Leu Ile Val Asn Cys Ile Leu Leu Ser Val Gly Gln Val
        35                  40                  45

Gly Gly Pro Met Met Leu Arg Leu Tyr Tyr Leu His Gly Gly Gln Arg
    50                  55                  60

Lys Trp Leu Ser Ser Trp Leu Gln Thr Ser Ala Phe Pro Ile Leu Leu
65                  70                  75                  80

Ile Pro Leu Met Val Ser Trp Phe Lys Ser Lys Ser Lys Phe His Ser
                85                  90                  95

Gln Ser Gln Ser Thr Asn Ile Asp His Val Asn Pro Gly Phe Leu Leu
            100                 105                 110

Thr Arg Lys Leu Phe Ile Trp Ser Val Ile Val Gly Ile Ile Thr Gly
        115                 120                 125

Leu Asp Ser Phe Leu Phe Ala Val Gly Tyr Ser Tyr Leu Pro Val Ser
    130                 135                 140

Val Ala Ser Leu Leu Leu Ala Thr Gln Leu Ala Phe Thr Ala Val Phe
145                 150                 155                 160

Ala Leu Val Leu Val Lys Gln Lys Phe Thr Pro Tyr Ser Ile Asn Ser
                165                 170                 175

Val Val Leu Leu Thr Leu Gly Ala Val Ile Leu Ala Phe His Thr Ser
            180                 185                 190

Ser Asp Lys Pro Ile Gly Val Ser Lys Ala Gln Tyr Phe Leu Gly Phe
        195                 200                 205

Phe Met Thr Leu Gly Gly Ala Ala Leu Leu Gly Phe Met Leu Pro Leu
    210                 215                 220

Ile Glu Phe Val Tyr Ala Asn Ala Cys Lys Val Ile Thr Tyr Asp Leu
225                 230                 235                 240

Val Met Gln Met Gln Phe Leu Val Ser Leu Phe Ala Thr Val Phe Ser
                245                 250                 255

Thr Ile Gly Met Ile Ile Asn Lys Asp Phe Gln Ala Ile Ser Arg Glu
            260                 265                 270

Ala Asn Glu Tyr Gly Leu Gly Glu Thr Lys Tyr Tyr Met Val Leu Val
        275                 280                 285

Phe Thr Ser Ile Leu Ile Gln Leu Ser Ile Val Gly Tyr Leu Gly Val
    290                 295                 300

Ile Phe Tyr Ala Thr Ser Leu Phe Thr Gly Ile Leu Val Thr Leu Leu
305                 310                 315                 320

Ile Pro Ile Gln Gln Ile Phe Ala Ile Ile Phe Phe His Glu Lys Phe
```

325 330 335

Ser Ala Glu Lys Gly Met Ser Leu Ala Leu Ser Val Trp Gly Phe Ala
340 345 350

Ser Tyr Phe Tyr Gly Glu Tyr Arg Gln Thr Lys Lys Lys Lys Asn Leu
355 360 365

Asp Lys Val Pro Ile Ser His Lys Lys Ile Pro Ser Glu Val
370 375 380

<210> SEQ ID NO 89
<211> LENGTH: 1149
<212> TYPE: DNA
<213> ORGANISM: Papaver somniferum

<400> SEQUENCE: 89
atggaaaacg agtccaccat gaagagggtt gttttgaaca atgattcctc tcatgaacaa 60
caccaccagc aagaaaaaga gactaagaag aagaagctgg tcttgttgat cgttaactgc 120
atcttgttgt ctgttggtca agttggtggt ccaatgatgt tgagactata ttacttgcat 180
ggtggtcaga gaaagtggtt atcttcttgg ttgcaaactt ctgctttccc cattttgttg 240
atcccattga tggtttcatg gttcaagtcc aagtctaagt tccactctca atctcaatcc 300
accaacatcg atcatgttaa tccaggtttc ttgttgaccc gtaagttgtt catttggtct 360
gttatcgttg gtatcatcac cggtttggat tctttttgt ttgccgttgg ttactcctac 420
ttgccagttt ctgttgcttc tttgttgttg gctactcaat tggcttttac tgctgttttc 480
gctttggttt tggtcaagca aaagttcact ccatactcca tcaactccgt tgttttgttg 540
actttgggtg ctgttatttt ggctttccat acctcttcag ataagccaat cggtgtttct 600
aaggctcaat actttttggg tttcttcatg actttaggtg gtgctgcttt gttgggtttt 660
atgttgccat tgatcgaatt cgtttacgct aacgcctgta aggttattac ctacgatttg 720
gtgatgcaaa tgcagttctt ggtttctttg ttcgctactg ttttctccac cattggtatg 780
atcatcaaca aggatttcca agccatttcc agagaagcta atgaatatgg tttgggcgaa 840
acgaagtact acatggtctt ggttttcacc tccatcttga tccaattgtc tattgtcggt 900
tacttgggcg ttattttcta cgctacatct ttgttcaccg gtatcttggt cactttgttg 960
attccaatcc aacaaatctt cgccatcata ttcttccacg aaaagttctc tgctgagaag 1020
ggtatgtctt tggctttgtc tgtttggggt tttgcttctt acttttacgg tgagtacagg 1080
cagaccaaaa aaaagaagaa cttggataag gtccccatct ctcataagaa gattccatct 1140
gaagtctaa 1149

<210> SEQ ID NO 90
<211> LENGTH: 348
<212> TYPE: PRT
<213> ORGANISM: Papaver alpinum

<400> SEQUENCE: 90

Met Asn Thr Tyr Leu Leu Leu Phe Asn Gly Ile Leu Leu Ala Val Ser
1 5 10 15

Ser Ile Ala Gly Pro Leu Leu Leu Arg Leu Tyr Phe Ile His Gly Gly
20 25 30

Lys Arg Ile Trp Leu Ser Ser Cys Leu Glu Thr Ala Gly Phe Pro Val
35 40 45

Leu Ile Phe Pro Leu Trp Leu Ser Tyr Phe Leu Arg Arg Arg Gly Phe
50 55 60

```
Ile Lys Gly Asp Asp Asp Glu Lys Pro Lys Lys Leu Phe Thr Ile Thr
65                  70                  75                  80

Leu Pro Leu Phe Ile Ala Ser Ala Val Ile Gly Leu Val Thr Gly Leu
                85                  90                  95

Asp Asp Tyr Leu Tyr Thr Tyr Gly Val Ser Leu Leu Pro Ile Ser Thr
            100                 105                 110

Ala Thr Ile Ile Met Ser Thr His Leu Ala Phe Thr Ala Gly Phe Ala
        115                 120                 125

Leu Val Met Val Lys Gln Lys Phe Thr Ser Phe Ser Val Asn Ala Val
    130                 135                 140

Val Leu Leu Thr Ile Gly Ala Ile Leu Leu Gly Leu His Gly Asn Gly
145                 150                 155                 160

Asp Lys Pro Val Asn Glu Ser Lys Lys Asp Tyr Tyr Leu Gly Phe Leu
                165                 170                 175

Ile Thr Ile Ala Ala Ser Val Phe Asn Gly Leu Met Leu Pro Met Val
            180                 185                 190

Glu Leu Met Tyr Met Lys Ser Lys Gln Thr Ile Thr Tyr Ser Leu Val
        195                 200                 205

Ile Glu Leu Gln Met Val Ile Ser Gly Phe Ala Thr Leu Phe Cys Thr
    210                 215                 220

Ile Gly Met Ile Ala Asn Asn Asp Phe Lys Val Ile Pro Arg Glu Gly
225                 230                 235                 240

Arg Glu Tyr Gly Leu Gly Glu Ile Asn Tyr Tyr Ile Val Leu Val Ala
                245                 250                 255

Ser Ala Ile Thr Trp Gln Met Tyr Phe Val Gly Thr Val Gly Val Ile
            260                 265                 270

Phe Cys Ser Thr Ser Leu His Ala Gly Val Ile Ser Val Val Val Leu
        275                 280                 285

Pro Leu Thr Glu Ile Leu Ser Val Val Phe Tyr His Glu Ser Phe Lys
    290                 295                 300

Ala Glu Lys Gly Ile Ala Leu Phe Leu Ser Leu Trp Gly Phe Ile Ser
305                 310                 315                 320

Tyr Phe Tyr Leu Glu Ile Lys Ala Ser Arg Lys Pro Lys Lys Gln Cys
                325                 330                 335

Ser Glu Leu Glu Gln Gly Gly Leu Thr Val Ser Ser
            340                 345
```

<210> SEQ ID NO 91
<211> LENGTH: 1047
<212> TYPE: DNA
<213> ORGANISM: Papaver alpinum

<400> SEQUENCE: 91

```
atgaacacct acctgttgtt gttcaacggt attttgttgg ccgtttcttc tattgctggt      60

cctttgttgt tgaggttgta ctttattcat ggtggtaaga ggatctggtt gtcctcttgt     120

ttggaaactg ctggttttcc agttctgatt tttccattgt ggctgtccta ctttttgaga     180

agaagaggtt tcatcaaggg tgatgatgac gaaaagccaa agaagttgtt cactattacc     240

ctgcctttgt tcattgcttc tgctgttatt ggtttggtta ccggtttgga tgattacttg     300

tatacctacg gtgtttcctt gttgccaatt tctactgcca ccattattat gtctacccat     360

ttggctttca cagctggttt tgctttggtt atggttaagc aaaagttcac ctccttctct     420

gttaacgctg ttgttttgtt gaccattggt gctatcttgt tgggtttaca tggtaatggt     480

gataagccag tcaacgaatc taagaaggat tactacttgg gtttcctgat tactattgct     540
```

```
gcctctgttt ttaacggttt gatgttgcct atggtcgagt tgatgtacat gaagtctaag    600

caaaccatca cctactcatt ggtcatcgaa ttgcaaatgg ttatttctgg tttcgctacc    660

ttgttctgta ccattggtat gattgctaac aacgacttca aggtcattcc aagagaaggt    720

agagaatatg gtttgggtga aatcaactac tatatcgttt tggttgcctc tgctattacc    780

tggcaaatgt actttgttgg tactgttggt gttatcttct gctctacttc tttacatgcc    840

ggtgtcattt ccgttgttgt tttaccattg accgaaatct tgtccgtcgt tttctaccat    900

gaatctttca aagccgaaaa gggtattgcc ttgtttttgt ctttgtgggg tttcatctct    960

tacttctact tggaaatcaa ggcctctaga aagcctaaaa agcaatgctc tgaacttgaa   1020

caaggtggtt tgactgtttc ctcttga                                       1047
```

<210> SEQ ID NO 92
<211> LENGTH: 377
<212> TYPE: PRT
<213> ORGANISM: Eschscholzia californica

<400> SEQUENCE: 92

```
Met Ala Ser Ser Met Asn Ile Glu Thr Asn Met Asn Gln Glu Thr Asn
1               5                   10                  15

His Thr Glu Lys Pro Asn Lys Thr Leu Val Gln Glu Gln Pro Thr Pro
            20                  25                  30

Lys Asn Trp Pro Ile Ile Ile Ile Asn Ser Val Ile Thr Gly Ile Gly
        35                  40                  45

Ala Ile Gly Gly Pro Leu Leu Met Arg Leu Tyr Tyr Leu His Gly Gly
    50                  55                  60

Asn Arg Arg Trp Leu Ser Ser Cys Val Gln Thr Ala Gly Phe Pro Ile
65                  70                  75                  80

Leu Ile Ile Pro Leu Thr Phe Leu Tyr Phe Gln His His Ser Lys Gln
                85                  90                  95

Asn Pro Lys Asn His Leu Ser Ser Thr Ser Phe Trp Met Glu Pro Lys
            100                 105                 110

Leu Phe Ile Ser Ser Ala Val Ile Gly Thr Leu Phe Gly Leu Asp Asn
        115                 120                 125

Phe Met Tyr Ala Leu Gly Leu Ser Tyr Ile Pro Ile Ser Thr Ser Ser
    130                 135                 140

Leu Leu Phe Ala Thr Gln Leu Ala Phe Val Ala Phe Phe Ala Trp Phe
145                 150                 155                 160

Ile Val Lys Gln Lys Phe Thr Pro Tyr Ser Ile Asn Ser Val Ile Leu
                165                 170                 175

Met Thr Leu Gly Ser Ile Leu Leu Gly Val Asp Asn Asp Gly Asp Arg
            180                 185                 190

Pro Met Gly Val Thr Lys Ala Gln Tyr Leu Leu Gly Phe Leu Leu Thr
        195                 200                 205

Leu Gly Ser Ala Ala Leu Ile Gly Phe Met Leu Pro Leu Val Glu Leu
    210                 215                 220

Cys Tyr Ser Lys Ala Thr Arg Thr Leu Ser Tyr Ser Thr Val Leu Gln
225                 230                 235                 240

Phe Gln Ile Thr Leu Ala Leu Phe Ser Thr Ile Phe Asn Ala Ile Gly
                245                 250                 255

Met Leu Ala Asn Lys Asp Phe Gln Ala Ile Pro Arg Glu Ala Arg Glu
            260                 265                 270

Phe Gly Leu Gly Glu Thr Met Tyr Tyr Val Val Leu Val Ala Gly Ala
```

```
        275                 280                 285

Ile Val Trp Gln Leu Ser Phe Ile Gly Gly Leu Gly Val Ile Leu Tyr
    290                 295                 300

Thr Ser Ser Leu Phe Ser Gly Ile Leu Thr Ser Val Leu Leu Pro Phe
305                 310                 315                 320

Thr Glu Val Ala Ala Val Ile Val Tyr His Glu Ser Phe Thr Gly Gln
                325                 330                 335

Lys Gly Met Ser Leu Ala Leu Cys Leu Trp Gly Phe Ser Ser Tyr Phe
            340                 345                 350

Tyr Gly Glu Tyr Lys Met Ser Lys Asp Ser Asn Pro Ile Ile Ser Glu
        355                 360                 365

Lys Glu Asp Asp Leu Pro Cys Leu Val
    370                 375


<210> SEQ ID NO 93
<211> LENGTH: 1134
<212> TYPE: DNA
<213> ORGANISM: Eschscholzia californica

<400> SEQUENCE: 93

atggcctcct ccatgaacat cgagactaac atgaatcaag aaactaacca caccgagaag      60

ccaaacaaaa ctttggttca agaacaaccc actccaaaga actggccaat tatcattatc     120

aactccgtta ttaccggtat tggtgctatt ggtggtccat tattgatgag gttgtattac     180

ttgcatggtg gtaacagaag atggttgtca tcttgtgttc aaactgctgg tttcccaatt     240

ttgattatcc ctttgacctt cttgtacttc caacaccatt ctaagcaaaa cccaaagaac     300

cacttgtcct ctacatcttt ttggatggaa cctaagctgt tcatttcctc tgctgttatt     360

ggtactttgt tcggtttgga caatttcatg tacgcattgg gtttgagcta tatcccaatt     420

tctacctcct ctttgttgtt cgctactcaa ttggcttttg ttgctttctt cgcttggttt     480

atcgtcaagc aaaagttcac tccatactcc attaactccg tcattttgat gaccttgggt     540

tccattttgt tgggtgttga taacgatggt gatagaccaa tgggtgttac taaggctcaa     600

tacttgttgg gtttcttgtt gactttaggt tccgctgctt tgattggttt tatgttgcca     660

ttggttgagc tgtgttactc taaagctact agaaccttgt cttactctac cgtcttgcaa     720

ttccaaatta ccttggcttt gttctccacc attttcaacg ctattggtat gttggctaac     780

aaggatttcc aagccattcc aagagaagct agagaatttg gtttgggtga aaccatgtac     840

tacgttgttt tggttgctgg tgctatagtt tggcaattgt ctttcattgg tggtttgggc     900

gttatcttgt acacttcttc tttgttttcc ggcatcttga cctctgtttt gttgcctttt     960

actgaagttg ctgccgttat cgtttaccat gaatctttta ctggtcaaaa gggtatgtct    1020

ttggcattgt gtttgtgggg tttttcctct tacttttacg gtgagtacaa gatgtccaag    1080

gattctaacc caatcatctc cgaaaaagaa gatgatttgc cttgcttggt ctaa          1134


<210> SEQ ID NO 94
<211> LENGTH: 371
<212> TYPE: PRT
<213> ORGANISM: Macleaya cordata

<400> SEQUENCE: 94

Met Ala Met Ser Ile Glu Arg Ile Glu Glu Gly Ala Leu Glu Gln Asn
1               5                   10                  15

Asn His His Asn Lys Leu Ser Asp Gly Asp Tyr Glu Glu Asp Ser Lys
            20                  25                  30
```

```
Lys Ser Leu Met Ala Lys Trp Gly Leu Leu Leu Leu Asn Cys Thr Cys
        35                  40                  45

Ser Ala Val Gly Thr Ile Gly Gly Pro Leu Leu Leu Arg Leu Tyr Phe
    50                  55                  60

Leu His Gly Gly Ser Arg Lys Trp Leu Ser Ser Trp Leu Gln Thr Ala
65                  70                  75                  80

Gly Phe Pro Ile Leu Leu Ile Pro Leu Leu Val Leu Tyr Phe Arg Asp
                85                  90                  95

Arg Ser Leu Gly Val Lys Phe Phe Ala Ser Pro Lys Leu Leu Leu Ser
            100                 105                 110

Ser Ala Val Ile Gly Val Leu Leu Gly Leu Asp Asn Phe Met Tyr Ser
        115                 120                 125

Tyr Gly Leu Ser Phe Leu Pro Val Ser Thr Ser Ser Leu Leu Ile Ser
    130                 135                 140

Thr Gln Leu Ile Phe Thr Ala Leu Phe Ala Phe Ile Met Val Arg Gln
145                 150                 155                 160

Lys Phe Thr Pro Tyr Ser Ile Asn Ser Val Val Leu Met Thr Leu Gly
                165                 170                 175

Ser Ile Leu Leu Gly Leu Arg Lys Ser Gly Asp Arg Pro Pro Gly Val
            180                 185                 190

Ser Thr Ser Gln Tyr Leu Leu Gly Phe Ile Leu Ser Ile Gly Ala Ala
        195                 200                 205

Ala Leu Gly Gly Phe Val Leu Pro Cys Thr Glu Val Ala Tyr Ala Lys
    210                 215                 220

Ala Ser Lys Ala Met Thr Tyr Ser Leu Val Leu Gln Tyr Gln Phe Cys
225                 230                 235                 240

Met Thr Phe Phe Ala Thr Val Phe Cys Thr Val Gly Met Leu Val Asn
                245                 250                 255

Lys Asp Phe Ser Ala Met Gln Arg Glu Ala Ser Glu Tyr Glu Leu Gly
            260                 265                 270

Ala Thr Lys Tyr Tyr Leu Val Leu Val Ser Ser Ala Val Val Trp Gln
        275                 280                 285

Leu Met Phe Val Gly Thr Leu Gly Ile Ile Phe Cys Thr Ser Ser Leu
    290                 295                 300

Phe Ala Gly Val Ile Thr Ala Thr Leu Leu Pro Leu Thr Glu Ile Ala
305                 310                 315                 320

Ala Val Ile Val Phe His Glu Lys Phe Thr Gly Glu Lys Gly Met Ala
                325                 330                 335

Leu Ala Leu Gly Ile Trp Gly Phe Ile Ser Tyr Phe Tyr Gly Ser Tyr
            340                 345                 350

Arg Glu Asn Lys Lys Asn Ile Gln Ser Pro His Glu Thr Asn Asn Thr
        355                 360                 365

Ser Ser Lys
    370
```

<210> SEQ ID NO 95
<211> LENGTH: 1116
<212> TYPE: DNA
<213> ORGANISM: Macleaya cordata

<400> SEQUENCE: 95

```
atggccatgt ccatcgaaag aattgaagaa ggtgctttgg aacaaaacaa ccaccataac      60

aaattgtccg atggtgacta cgaagaggac tctaaaaaat ctttgatggc taagtggggc     120
```

```
ctgttgttgt tgaactgtac ttgttctgct gttggtacta ttggtggtcc tttgttgtta    180

aggttgtact tcttgcatgg tggttccaga aaatggttat cttcttggtt gcaaactgct    240

ggtttcccaa ttttgttgat cccattattg gtcttgtact tcagagacag atctttgggt    300

gttaagtttt tcgcttctcc caagttgttg ttatcctctg ctgttatcgg tgtcttgttg    360

ggtttagata acttcatgta ctcctacggc ttgtcttttt tgccagtttc tacttcctcc    420

ttgttgatct ctacccaatt gattttcact gctttgttcg ccttcatcat ggtcagacaa    480

aagtttactc catactccat caactccgtt gttttgatga ctttgggttc catcttgctg    540

ggtttgagaa aatctggtga tagaccacca ggtgtttcta catctcaata cttgttaggc    600

ttcatcttgt ctattggtgc tgctgcttta ggtggttttg ttttgccatg tactgaagtt    660

gcttacgcta aagcttctaa ggctatgact tattccttgg tcttgcaata ccagttctgt    720

atgactttct tcgctactgt tttctgtacc gttggtatgt tggttaacaa ggatttctct    780

gctatgcaaa gggaagcttc tgaatatgaa ttgggtgcta ctaagtacta cctggtcttg    840

gtttcttcag ctgttgtttg gcaattgatg ttcgttggta ctctgggtat tatcttctgt    900

acctcttctt tgtttgccgg tgttattact gctactttgt tgccattgac agaaattgct    960

gccgttatcg tttttcacga aaagttcact ggtgaaaaag gtatggcttt ggctttaggt   1020

atttggggtt tcatctctta cttctacggt tcctacagag agaacaagaa gaacattcaa   1080

tctccacacg aaacgaacaa cacctcttct aagtaa                             1116
```

```
<210> SEQ ID NO 96
<211> LENGTH: 364
<212> TYPE: PRT
<213> ORGANISM: Cinnamomum micranthum f. kanehirae

<400> SEQUENCE: 96

Met Ser Leu Asp Ile Glu Arg Ala Glu Glu Thr Gln Phe Pro Thr Ser
1               5                   10                  15

Thr Asn Val Asp Asn Thr Lys Leu Glu Asp Ala Thr Pro Pro Lys Arg
            20                  25                  30

Lys Ile Asn Trp Leu Leu Ile Ala Met Asn Val Thr Cys Val Gly Leu
        35                  40                  45

Gly Thr Ile Gly Gly Pro Leu Met Val Arg Leu Tyr Phe Leu His Gly
    50                  55                  60

Gly Ser Lys Arg Trp Leu Ser Ser Trp Leu Gln Thr Ala Gly Phe Pro
65                  70                  75                  80

Ile Leu Leu Gly Pro Leu Ser Phe Leu Tyr Met Lys His Arg Ala Arg
                85                  90                  95

Gly Gln Arg Phe Phe Ala Glu Pro Lys Leu Met Ile Ala Ser Ala Val
            100                 105                 110

Ile Gly Val Ile Ile Gly Leu Asp Asn Phe Met Tyr Ser His Gly Leu
        115                 120                 125

Ser Val Leu Pro Val Ser Thr Ser Ser Leu Leu Phe Ser Thr Gln Leu
    130                 135                 140

Ala Phe Thr Ala Phe Phe Ala Leu Ile Ile Val Arg Gln Arg Phe Thr
145                 150                 155                 160

Pro Tyr Ser Val Asn Ala Val Val Leu Met Thr Leu Gly Ser Val Leu
                165                 170                 175

Leu Gly Leu Arg Lys Gly Gly Asp Arg Pro Ala Asn Val Ser Asn Gly
            180                 185                 190

Glu Tyr Met Val Gly Phe Ile Ile Thr Ile Gly Ala Ala Ala Leu Ile
```

```
        195                 200                 205

Gly Phe Val Leu Pro Cys Val Glu Leu Ala Tyr Ala Lys Ala Ser Lys
    210                 215                 220

Ala Ile Thr Tyr Pro Val Val Leu Gln Phe Gln Leu Gly Val Thr Phe
225                 230                 235                 240

Phe Ala Thr Val Phe Ser Thr Ile Gly Met Ile Ala His Lys Asp Phe
                245                 250                 255

Ser Ala Ile Ser Arg Glu Ala Lys Ala Tyr Thr Ile Gly Glu Ala Lys
            260                 265                 270

Tyr Tyr Leu Val Ile Val Trp Gly Ala Ile Leu Phe Gln Leu Val Tyr
        275                 280                 285

Ile Gly Ser Leu Gly Leu Val Phe Cys Thr Ser Ser Leu Phe Thr Gly
    290                 295                 300

Val Val Thr Ala Thr Leu Leu Pro Leu Thr Glu Ile Ala Ala Val Ile
305                 310                 315                 320

Phe Phe Lys Glu Lys Phe Thr Gly Glu Lys Gly Met Ser Leu Ala Leu
                325                 330                 335

Cys Leu Trp Gly Phe Met Ser Tyr Phe Tyr Gly Ala Tyr Ile Met Glu
            340                 345                 350

Arg Lys Gln Arg Lys Ala Gln Glu Glu Glu Pro Lys
        355                 360


<210> SEQ ID NO 97
<211> LENGTH: 1095
<212> TYPE: DNA
<213> ORGANISM: Cinnamomum micranthum f. kanehirae

<400> SEQUENCE: 97

atgtccttgg atatcgaaag agccgaagaa actcaattcc caacttctac caatgttgac     60

aacaccaaat tggaagatgc tactccacca aagagaaaga ttaactggtt gttgattgcc    120

atgaacgtta cctgtgttgg tttgggtact attggtggtc cattgatggt taggttgtat    180

ttcttgcatg gtggttccaa aagatggttg tcatcttggt tgcaaactgc tggttttcca    240

attttgttgg gtccattgtc tttcttgtac atgaagcaca gagctagagg tcaaagattt    300

tttgctgaac ccaagttgat gattgcctct gctgttattg gtgttattat cggtttggac    360

aatttcatgt actcccacgg tttgtctgtt ttgccagttt ctacttcttc cttgttgttc    420

tctactcaat tggctttcac tgctttcttc gccttgatta tagtcagaca aagattcacc    480

ccatactccg ttaatgctgt tgttttgatg actttgggtt ctgtcttgtt gggtttgaga    540

aaaggtggtg atagaccagc taatgtttct aatggtgagt acatggttgg tttcattatt    600

accattggtg ctgctgcttt gatcggtttt gttttaccat gtgttgaatt ggcttacgct    660

aaagcttcta aggctattac ttatccagtc gtcttgcaat ttcaattggg tgttactttt    720

ttcgccaccg ttttctctac tatcggtatg attgctcaca aggatttctc cgctatttct    780

agagaagcta aggcttacac aattggtgaa gctaagtact acttggttat agtttggggt    840

gccatcttgt tccaattggt ttacattggt tccttgggtt tagttttctg cacctcttct    900

ttgttcactg gtgttgttac tgctactttg ttgccattga ctgaaattgc tgccgtcatt    960

ttcttcaaag aaaagttcac aggtgagaag ggtatgtctt tggctttgtg tttgtggggt   1020

tttatgtctt acttttacgg tgcctacatc atggaaagaa agcaaagaaa ggctcaagaa   1080

gaggaaccta agtag                                                    1095
```

```
<210> SEQ ID NO 98
<211> LENGTH: 394
<212> TYPE: PRT
<213> ORGANISM: Papaver somniferum

<400> SEQUENCE: 98

Met Asp Ile Glu Ala Ala Ala Ser Thr Ile Val Gly Ala Ala Ala Thr
1               5                   10                  15

Asn Tyr Asn His Gly Thr Gly Asn His His Asn Asn Leu Ala Val Gln
            20                  25                  30

Asn Asp His Glu Asp Asp Leu Pro Lys Thr Gly Asn Pro Val Thr Lys
        35                  40                  45

Lys Ile Val Ile Asp Trp Lys Leu Ile Leu Phe Cys Leu Leu Phe Ala
    50                  55                  60

Phe Gly Tyr Ile Gly Gly Pro Met Leu Gln Arg Leu Tyr Phe Thr His
65                  70                  75                  80

Gly Gly Gly Arg Lys Trp Phe Met Ser Met Leu Gln Cys Val Gly Phe
                85                  90                  95

Pro Val Leu Val Ala Pro Leu Ser Tyr Ile Tyr Ile Lys Lys Val Asn
            100                 105                 110

Gly Pro Ser Tyr Asp Ala Ser Trp Val Phe Leu Met Glu Pro Lys Leu
        115                 120                 125

Phe Met Tyr Ser Ala Leu Leu Gly Val Ala Leu Gly Leu Asp Asn Tyr
    130                 135                 140

Met Tyr Ser Ala Gly Leu Phe Tyr Leu Pro Val Ser Thr Ser Ser Leu
145                 150                 155                 160

Leu Phe Ser Thr Gln Leu Ala Phe Thr Ala Ile Phe Ala Phe Ile Ile
                165                 170                 175

Val Arg Gln Lys Phe Thr Phe Tyr Ser Phe Asn Ser Val Val Leu Met
            180                 185                 190

Thr Leu Gly Ser Val Val Leu Ala Leu Asn Thr Gly Ser Asp Lys Pro
        195                 200                 205

Pro Gly Thr Thr Gln Gln Gln Tyr Tyr Leu Gly Phe Ala Leu Thr Ile
    210                 215                 220

Ala Gly Ala Ala Leu Leu Gly Leu Val Leu Pro Leu Val Glu Leu Ser
225                 230                 235                 240

Tyr Gly Arg Ser Ser Lys Pro Ile Thr Tyr Ser Val Val Met Gln Phe
                245                 250                 255

Gln Phe Val Leu Ser Leu Phe Gly Thr Ile Ala Thr Met Ile Gly Met
            260                 265                 270

Ala Ile Asn Asn Asp Phe Gln Val Ile Pro Arg Glu Gly Arg Asp Phe
        275                 280                 285

Gly Leu Gly Gln Gly Lys Tyr Tyr Leu Leu Ile Val Ala Leu Ala Val
    290                 295                 300

Val Trp Gln Leu Phe Thr Ile Gly Phe Leu Gly Leu Ile Tyr Cys Thr
305                 310                 315                 320

Ser Ser Leu Phe Ala Gly Ile Tyr Thr Thr Cys Leu Leu Pro Phe Thr
                325                 330                 335

Gln Val Ala Ala Ser Ile Ala Phe Gln Glu Lys Phe Thr Ser Gln Lys
            340                 345                 350

Gly Met Ser Leu Ala Leu Cys Leu Trp Gly Phe Val Ser Tyr Phe Ala
        355                 360                 365

Gly Glu Tyr Lys Lys Ser Lys Lys Pro His Pro Ile Ala Tyr Asp Lys
    370                 375                 380
```

Glu Lys Ser Glu Leu Ser Asp Asn Asp Ala
385 390

<210> SEQ ID NO 99
<211> LENGTH: 1185
<212> TYPE: DNA
<213> ORGANISM: Papaver somniferum

<400> SEQUENCE: 99
atggatattg aagctgctgc ctctactata gttggtgctg ctgctactaa ttacaatcat 60
ggtactggta accaccataa caacttggct gttcaaaacg atcacgaaga tgatttgcca 120
aagactggta atccagttac caagaagatc gttatcgatt ggaagttgat cctgttctgt 180
ttgttgtttg ccttcggtta tattggtggt ccaatgttgc aaaggttgta ctttactcat 240
ggtggtggta gaaagtggtt catgtctatg ttgcaatgtg ttggtttccc agttttggtt 300
gctccattgt cttacatcta catcaagaaa gttaacggtc catcttacga tgcctcttgg 360
gtttttttga tggaacctaa gttgttcatg tactccgctt tgttgggtgt tgctttgggt 420
ttagataact acatgtattc cgctggcttg ttctatttgc cagtttctac ttcttccctg 480
ttgttctcta ctcaattggc tttcactgct attttcgcct tcattatcgt cagacaaaag 540
ttcaccttct acagcttcaa ctccgttgtt ttgatgactt tgggttctgt tgttttggct 600
ttgaataccg gttctgataa gccaccaggt actactcaac aacaatatta cttgggtttc 660
gctttgacta ttgctggtgc agctttgtta ggtttggttt tgccattggt tgaactgtct 720
tatggcagat cttctaagcc aattacctac tctgttgtca tgcaattcca attcgtcttg 780
tctttgttcg gtactattgc cactatgatt ggtatggcca ttaacaacga tttccaagtc 840
attccaagag agggtagaga ttttggttta ggtcaaggca agtactactt gttgatagtt 900
gctttagctg ttgtctggca gttgttcact attggttttt tgggtttgat ctactgcacc 960
tcttctttgt ttgctggtat ctacactaca tgcttgttgc cattcactca agttgctgct 1020
tctattgctt tccaagaaaa gtttaccagc caaaagggta tgtcattggc tttgtgtttg 1080
tggggttttg tttcttattt tgccggtgag tacaagaagt ctaaaaagcc acatccaatt 1140
gcctacgaca aagaaaagtc tgaattgtct gataacgacg cctga 1185

<210> SEQ ID NO 100
<211> LENGTH: 383
<212> TYPE: PRT
<213> ORGANISM: Papaver somniferum

<400> SEQUENCE: 100

Met Ala Thr Ser Glu Met Asn Leu Glu Thr Leu Asp Asn Leu Gly Thr
1 5 10 15

Ile Glu Asn Cys Lys Ser Lys Pro Thr Lys His Lys Asn Trp Leu Leu
20 25 30

Ile Cys Ile Asn Cys Ala Ile Val Phe Cys Gly Val Ile Gly Ser Pro
35 40 45

Leu Leu Leu Arg Leu Tyr Phe Leu His Gly Gly Asn Arg Lys Trp Leu
50 55 60

Ser Ser Trp Ile Gln Thr Ala Gly Phe Pro Val Leu Ile Leu Pro Leu
65 70 75 80

Ile Phe Leu Tyr Ile Arg Ser Glu Leu Leu Ala Thr Arg Asn Asn Asp
85 90 95

His Val Ser Pro Phe Leu Met Glu Pro Arg Leu Phe Leu Ser Ser Ala
100 105 110

Ala Ile Gly Phe Leu Tyr Gly Val Val Asn Phe Met Tyr Ala Leu Gly
115 120 125

Leu Ser Tyr Ile Pro Val Ser Thr Ser Ser Ile Leu Cys Ala Thr Gln
130 135 140

Leu Cys Phe Ser Ala Phe Phe Ala Trp Leu Ile Val Lys Gln Lys Phe
145 150 155 160

Thr Ala Phe Ile Ile Asn Ala Ile Val Ile Met Thr Leu Gly Ser Val
165 170 175

Leu Leu Gly Ile Asn Ser Asp Gly Asp Arg Pro Val Gly Val Ser Lys
180 185 190

Ser Gln Tyr Leu Ile Gly Phe Leu Met Thr Leu Gly Ser Ala Ala Leu
195 200 205

Ser Gly Leu Ile Met Pro Leu Ile Glu Leu Ala Phe Ser Lys Ala Thr
210 215 220

Arg Ser Ile Thr Tyr Ser Thr Leu Leu Gln Phe Gln Ile Thr Leu Ala
225 230 235 240

Ile Ser Ala Asn Ala Leu Asn Ile Ile Gly Met Leu Ile Asn Lys Asp
245 250 255

Phe Gln Ala Ile His Arg Glu Ala Asn Glu Tyr Glu Leu Gly Lys Thr
260 265 270

Lys Tyr Tyr Ile Ile Leu Phe Phe Thr Ala Phe Thr Phe Gln Leu Met
275 280 285

Thr Met Gly Val Leu Gly Val Ile Leu Cys Thr Ser Ala Leu Phe Asn
290 295 300

Gly Ile Phe Thr Ser Ala Leu Ile Pro Phe Thr Gln Val Ala Ala Val
305 310 315 320

Ile Phe Tyr His Glu Gln Phe Thr Gly Leu Lys Gly Met Thr Leu Ala
325 330 335

Leu Cys Leu Trp Gly Phe Cys Ser Tyr Phe Tyr Gly Glu Tyr Lys Met
340 345 350

Leu His Lys Val Val Asn Arg Glu Ala Pro Glu Lys Asn Tyr Glu Val
355 360 365

Lys Arg Pro Cys Thr Thr Trp Gly Lys Asn Cys Ile Asp Glu Ala
370 375 380

<210> SEQ ID NO 101
<211> LENGTH: 1152
<212> TYPE: DNA
<213> ORGANISM: Papaver somniferum

<400> SEQUENCE: 101
atggccacct ctgaaatgaa cttggaaacc ttggataact tgggcaccat tgaaaattgc 60
aagtccaaac ctaccaagca caagaattgg ttgttgatct gtattaactg cgccatcgtt 120
ttctgtggtg ttattggttc acctttgttg ttgaggttgt acttcttgca tggtggtaac 180
agaaaatggt tgtcctcttg gattcaaact gctggttttc cagttctgat tttgcctttg 240
atcttcctgt acatcagatc cgaattattg gctaccagaa acaacgatca tgtctctcca 300
tttttgatgg aacccaggtt gtttttatcc tctgctgcta ttggtttctt gtacggtgtt 360
gttaatttca tgtacgcctt gggtttgtcc tatattccag tttctacctc ctctattttg 420
tgcgctactc aattgtgttt ctctgctttt tttgcctggt tgatcgtcaa gcaaaagttc 480
actgctttca ttattaacgc catcgtcatt atgaccttgg gttctgtttt gttgggtatc 540
aattctgatg gtgatagacc agttggtgtc tctaaatccc aatacttgat cggtttcttg 600

```
atgactttag gttctgctgc tttgtccggt ttgataatgc cattgattga attggctttc    660

tctaaggcca ctagatccat tacttactct accttgttgc aattccaaat caccttggct    720

atttctgcta acgccttgaa cattatcggc atgttgatta acaaggactt ccaagccatt    780

catagagaag ctaacgaata cgaattgggc aagaccaagt actacatcat tttgtttttc    840

accgccttca ccttccaatt gatgactatg ggtgttttgg gtgttatctt gtgtacttct    900

gctttgttca acggtatttt cacctctgct ttgatcccat tcactcaagt tgctgctgtt    960

atcttttacc acgaacaatt cactggtttg aagggtatga ctttggcttt gtgtttgtgg   1020

ggtttttgct cttactttta cggtgagtac aagatgttgc acaaggttgt taacagagaa   1080

gctccagaaa agaactacga agtcaaaaga ccatgtacca cttggggtaa gaactgtatt   1140

gatgaagctt aa                                                       1152
```

```
<210> SEQ ID NO 102
<211> LENGTH: 355
<212> TYPE: PRT
<213> ORGANISM: Manihot esculenta

<400> SEQUENCE: 102

Met Glu Thr Asn Asp Lys Pro Gln Val Asn Asn Thr Lys Arg Arg Ala
1               5                   10                  15

Leu Leu Ile Leu Asn Cys Ile Leu Leu Thr Val Gly Asn Cys Gly Gly
            20                  25                  30

Pro Leu Ile Leu Arg Leu Tyr Phe Ile His Gly Gly Lys Arg Val Trp
        35                  40                  45

Leu Ser Ser Trp Leu Gln Thr Gly Gly Trp Pro Ile Ile Phe Ile Leu
    50                  55                  60

Leu Leu Ile Ser Tyr Leu His Arg Arg Ser His Lys Pro Thr Thr Lys
65                  70                  75                  80

Phe Phe Tyr Met Asp Thr Ser Leu Phe Ile Ala Ala Thr Ile Val Gly
                85                  90                  95

Val Ile Thr Gly Phe Asp Asp Tyr Leu Tyr Ala Tyr Gly Ile Ala Arg
            100                 105                 110

Leu Pro Val Ser Thr Ser Ser Leu Ile Ile Ala Thr Gln Leu Ala Phe
        115                 120                 125

Thr Ala Gly Phe Ala Phe Leu Leu Val Lys Gln Lys Phe Asn Phe Tyr
    130                 135                 140

Ser Ile Asn Ala Val Ile Leu Leu Thr Val Gly Ala Gly Val Leu Ala
145                 150                 155                 160

Leu His Ser Asn Ser Asp Arg Pro Glu His Glu Ser Lys Gly Glu Tyr
                165                 170                 175

Ile Leu Gly Phe Val Thr Thr Leu Ala Ala Ala Ala Ile Tyr Gly Leu
            180                 185                 190

Ile Leu Pro Leu Val Glu Leu Ile Tyr Lys Lys Ser Lys Gln Glu Ile
        195                 200                 205

Ser Tyr Thr Leu Val Met Glu Ile Gln Leu Val Met Ser Leu Phe Ala
    210                 215                 220

Thr Val Val Cys Thr Val Gly Met Leu Val Asn Lys Asp Phe Glu Ala
225                 230                 235                 240

Ile Pro Gly Glu Ala Arg Gly Phe Gly Leu Gly Glu Thr Lys Tyr Tyr
                245                 250                 255

Val Ile Ile Val Cys Thr Ala Ile Ile Leu Gln Cys Phe Phe Leu Gly
            260                 265                 270
```

Ala Ile Gly Val Ile Phe Tyr Ser Ser Ser Leu Val Ser Ala Ile Ile
275 280 285

Ile Ala Val Leu Leu Pro Val Thr Glu Ile Leu Ala Val Ile Phe Tyr
290 295 300

Gln Glu Lys Phe Gln Ala Glu Lys Gly Val Ala Leu Ala Leu Ser Leu
305 310 315 320

Trp Gly Phe Ile Ser Tyr Phe Tyr Gly Glu Val Lys Gln Thr Lys Lys
325 330 335

Lys Asp Leu Ala Thr Glu Thr Glu Met Ser Gln Thr Ser Asn Pro Thr
340 345 350

Gln Asn Val
355

<210> SEQ ID NO 103
<211> LENGTH: 1068
<212> TYPE: DNA
<213> ORGANISM: Manihot esculenta

<400> SEQUENCE: 103
atggaaacga acgataagcc acaagtcaac aataccaaaa gaagggcctt gttgattctg 60
aactgtatct tgttgactgt tggtaattgt ggtggtccat tgattttgag gttgtacttt 120
attcacggtg gtaagagagt ttggttgtca tcttggttgc aaactggtgg ttggccaatt 180
atcttcatct tgttgttgat cagctacttg cacagaagat ctcataagcc aactaccaag 240
ttcttctaca tggacacgtc tttgtttatt gctgctacta tcgttggtgt tatcaccggt 300
tttgatgatt acttgtacgc ttacggtatt gccagattgc cagtttctac ttcctcattg 360
attatcgcta ctcaattggc ttttactgct ggttttgctt tcttgttggt caagcaaaag 420
ttcaacttct actccattaa cgccgtcatt ttgttaacag ttggtgctgg tgttttggcc 480
ttgcattcta attctgatag accagaacat gagtctaagg gtgagtacat tttgggtttc 540
gttactactt tggctgctgc tgctatctat ggtttgattt tgccattggt cgagctgatc 600
tacaagaagt ctaaacaaga aatctcctac accttggtca tggaaatcca attggttatg 660
tctttgttcg ctactgttgt ctgtacagtt ggtatgttgg ttaacaagga tttcgaagct 720
attccaggtg aagctagagg ttttggtttg ggtgaaacta agtactacgt tattattgtc 780
tgcaccgcca ttatcttgca gtgtttttc ttgggtgcta tcggtgttat cttctactct 840
tcttctttgg tttccgccat cattattgct gttttgttgc cagttaccga aatcttggct 900
gtcattttct accaagaaaa gttccaagct gaaaagggtg ttgctttggc tttgtctttg 960
tggggtttta tctcttactt ttacggtgaa gttaagcaga ccaagaagaa ggatttggct 1020
actgaaactg aaatgtccca aacttctaac ccaactcaaa acgtctga 1068

<210> SEQ ID NO 104
<211> LENGTH: 355
<212> TYPE: PRT
<213> ORGANISM: Handroanthus impetiginosus

<400> SEQUENCE: 104

Met Ala Val Glu Asn Thr Ser Pro Ala Met Gln Arg Thr Phe Leu Ile
1 5 10 15

Ile Asn Cys Ile Ile Leu Ala Val Gly Asn Cys Gly Gly Pro Leu Ile
20 25 30

Met Arg Leu Tyr Phe Ile His Gly Gly Gln Arg Ile Trp Phe Ser Ser
35 40 45

Trp Leu Glu Thr Gly Gly Trp Pro Ile Ile Leu Ile Pro Leu Leu Phe
50 55 60

Ser Tyr Thr Arg Arg Arg Ser Thr Thr Ala Asn Ala Lys Pro Ile Leu
65 70 75 80

Met Lys Pro Arg Val Phe Phe Ala Ala Ala Val Ile Gly Thr Val Thr
85 90 95

Gly Leu Asp Asp Tyr Leu Tyr Ala Tyr Gly Val Ala Lys Leu Pro Val
100 105 110

Ser Thr Ser Ala Leu Ile Ile Ala Thr Gln Leu Ala Phe Thr Ala Ala
115 120 125

Phe Ala Phe Val Leu Val Lys Gln Lys Phe Thr Ala Tyr Ser Ile Asn
130 135 140

Ala Val Val Leu Leu Thr Val Gly Ala Val Val Leu Gly Leu His Thr
145 150 155 160

Asn Gly Asp Arg Pro Ala Gly Glu Ser Asn Lys Glu Tyr Trp Leu Gly
165 170 175

Phe Cys Leu Thr Val Ala Ala Ala Ala Leu Tyr Gly Phe Ile Leu Pro
180 185 190

Leu Ile Glu Leu Met Tyr Lys Lys Ala Arg Gln Glu Leu Thr Tyr Ser
195 200 205

Leu Ile Met Glu Ile Gln Leu Val Met Cys Phe Phe Ala Thr Val Phe
210 215 220

Cys Thr Val Gly Met Ile Ile Asn Asn Asp Phe Gln Ala Ile Ser Arg
225 230 235 240

Glu Ala Lys Glu Tyr Glu Leu Gly Glu Thr Lys Tyr Tyr Leu Val Val
245 250 255

Val Trp Ser Ala Ile Ile Trp Gln Cys Phe Phe Leu Gly Ala Ile Gly
260 265 270

Val Ile Phe Tyr Ser Ser Ser Leu Leu Ser Ala Ile Ile Ile Thr Val
275 280 285

Leu Leu Pro Val Ile Glu Ile Leu Ala Val Ile Phe Tyr His Glu Lys
290 295 300

Phe Gln Val Glu Lys Gly Ile Ser Leu Phe Leu Ser Leu Trp Gly Phe
305 310 315 320

Ile Ser Tyr Phe Leu Gly Glu Ile Lys His Asn Lys Lys Asn Lys Asp
325 330 335

Asn Leu Asn Glu Asp Gln Pro Ser Glu Val Gln Leu Ala His Gln Asn
340 345 350

Ser Val Pro
355

<210> SEQ ID NO 105
<211> LENGTH: 1068
<212> TYPE: DNA
<213> ORGANISM: Handroanthus impetiginosus

<400> SEQUENCE: 105
atggccgttg aaaacacttc tccagctatg caaagaacct tcttgattat caactgcatc 60
attttggctg ttggtaattg tggtggtcca ttgatcatga ggttgtactt tattcatggt 120
ggtcagagaa tctggttctc ttcttggttg gaaactggtg gttggccaat tatcttgatt 180
cctttgttgt tctcctacac cagaagaaga tctactactg ctaatgccaa gccaattttg 240
atgaagccaa gagttttttt cgctgctgct gttattggta ctgttactgg tttggatgat 300

```
tacttgtatg cttacggtgt tgctaagttg ccagtttcta cttccgcttt gattattgct    360

actcaattgg cttttactgc tgctttcgct ttcgttttgg ttaagcaaaa gttcaccgcc    420

tactctatta acgctgttgt tttgttgact gttggtgcag ttgttttggg tttacacact    480

aatggtgata gacctgctgg tgaatctaac aaagaatact ggttgggttt ctgtttgaca    540

gttgcagctg ctgcattata cggtttcatt ttgccattga tcgagctgat gtacaagaag    600

gctagacaag aattgaccta ctccttgatc atggaaatcc aattggttat gtgtttcttc    660

gctaccgttt tctgtaccgt tggtatgatc attaacaacg atttccaagc catttccagg    720

gaagctaaag aatatgaatt gggcgaaacg aagtactact tggttgttgt ttggtccgct    780

attatttggc aatgtttttt cttgggtgcc atcggtgtta tcttctactc ttcttctttg    840

ttgtccgcca ttatcatcac agttttgttg ccagtcattg aaatcttggc cgttattttc    900

taccacgaaa agttccaagt tgagaagggt atctctctgt tttgtcttt gtggggtttt    960

atctcctact tttgggtgaa aatcaagcac aacaagaaaa acaaggacaa cttgaacgaa   1020

gatcagccat ctgaagttca attggcacat caaaactctg tcccatga                1068
```

```
<210> SEQ ID NO 106
<211> LENGTH: 369
<212> TYPE: PRT
<213> ORGANISM: Aquilegia coerulea

<400> SEQUENCE: 106

Met Glu Ile Glu Ser Gln Ala Asn Asn His Glu Glu Glu Phe Asn Lys
1               5                   10                  15

Gln Lys Thr Val Gln Lys Ile Phe Leu Lys Arg Met Ile Leu Leu Met
            20                  25                  30

Asn Cys Ala Ile Leu Ser Ile Gly Asn Thr Gly Gly Pro Leu Leu Leu
        35                  40                  45

Arg Leu Tyr Phe Ile Arg Gly Gly Lys Arg Val Trp Leu Ser Cys Trp
    50                  55                  60

Leu Glu Thr Gly Gly Trp Pro Ile Met Leu Ile Pro Leu Leu Gly Ser
65                  70                  75                  80

Tyr Ile Tyr Arg Val Arg Lys Ser Lys Glu Lys Ala Lys Leu Leu Phe
                85                  90                  95

Ile Thr Pro Phe Leu Phe Val Ala Gly Ala Val Leu Gly Val Leu Thr
            100                 105                 110

Gly Val Asp Asp Tyr Leu Tyr Ala Tyr Gly Val Ser Lys Leu Pro Val
        115                 120                 125

Ser Thr Ser Ala Leu Ile Ile Ser Thr Gln Leu Val Phe Thr Ala Gly
    130                 135                 140

Phe Ala Phe Leu Leu Val Lys Gln Lys Phe Thr Ser Tyr Thr Ile Asn
145                 150                 155                 160

Ala Ile Val Leu Leu Thr Val Ala Ala Val Val Leu Gly Val Arg Ala
                165                 170                 175

Ser Ser Asp Arg Pro Asn Gly Glu Ser Lys Met Glu Tyr Phe Thr Gly
            180                 185                 190

Phe Phe Met Thr Leu Gly Ala Ser Ala Leu Tyr Gly Phe Val Leu Pro
        195                 200                 205

Met Val Glu Leu Thr Tyr Lys Lys Ser Lys Thr Lys Ile Ser Tyr Thr
    210                 215                 220

Leu Val Ile Glu Met Gln Met Val Met Ser Leu Phe Ala Thr Ala Phe
225                 230                 235                 240
```

Cys Thr Ile Gly Met Leu Ile Asn Lys Asp Phe Gln Ala Ile Pro Arg
                245                 250                 255

Glu Ala Lys Ala Tyr Glu Leu Gly Glu Ala Lys Tyr Tyr Thr Val Leu
            260                 265                 270

Val Ser Asn Ala Ile Val Trp Gln Phe Phe Phe Leu Gly Ala Ile Gly
        275                 280                 285

Val Ile Phe Ser Ala Ser Ser Leu Leu Ser Gly Ile Met Ile Ala Val
    290                 295                 300

Leu Leu Pro Leu Thr Glu Ser Leu Ala Val Val Phe Tyr His Glu Lys
305                 310                 315                 320

Phe Ser Ser Glu Lys Gly Ile Ala Leu Ala Leu Ser Leu Trp Gly Phe
                325                 330                 335

Val Ser Tyr Phe Tyr Gly Glu Tyr Lys Gln Thr Lys Gln Leu Gln Gln
            340                 345                 350

Ser Ile Ile Glu Ser Lys Thr Asn Thr Val Val Asn Ala Ser Ser Pro
        355                 360                 365

Thr

<210> SEQ ID NO 107
<211> LENGTH: 1110
<212> TYPE: DNA
<213> ORGANISM: Aquilegia coerulea

<400> SEQUENCE: 107
atggaaatcg aatcccaagc caacaaccac gaagaagaat tcaacaagca aaagaccgtc 60
caaaagatct tcttgaagag gatgatcttg ttgatgaact gcgccatttt gtctattggt 120
aatactggtg gtcctctgtt gttgaggttg tactttatta gaggtggtaa gagagtttgg 180
ttgtcttgtt ggttggaaac tggtggttgg ccaattatgt tgattccatt attgggctcc 240
tacatctaca gagtgagaaa gtctaaagaa aaggccaagt tgttgttcat caccccattt 300
ttgtttgttg ctggtgctgt tttgggtgtt ttgactggtg ttgatgatta cttgtatgcc 360
tacggtgttt ctaagttgcc agtttctact tccgccttga ttatttctac ccaattggtt 420
tttactgccg gtttcgcttt tttgttggtg aagcaaaagt tcacctccta cactattaac 480
gccatcgttt tgttgactgt tgctgcagtt gttttaggtg ttagagcttc ttctgataga 540
ccaaacggtg aatctaagat ggaatacttc actggtttct ttatgacctt gggtgcttct 600
gcattatacg gttttgtttt gccaatggtc gaactgactt acaagaagtc taagaccaag 660
atctcttaca ccttggtcat cgaaatgcaa atggtcatgt ctttgtttgc tactgctttc 720
tgtaccatcg gcatgttgat taacaaggat ttccaagcca ttccaagaga agctaaagct 780
tatgaattgg gtgaagctaa gtactacacc gtcttggttt ctaatgctat cgtttggcag 840 tttttttttct tgggtgcaat cggtgttatt ttctccgctt cttctttgtt gtccggtatt 900
atgattgcag tcttgttgcc attgactgaa tctttggctg ttgttttcta ccacgagaag 960
ttctcttcag aaaagggtat tgctttggct ttgtctttgt ggggtttcgt ttcttacttt 1020
tacggtgagt acaagcagac caagcaattg caacaatcca tcattgaatc caagaccaat 1080
accgttgtta atgcttcttc tccaacctaa 1110

<210> SEQ ID NO 108
<211> LENGTH: 397
<212> TYPE: PRT
<213> ORGANISM: Papaver somniferum

<400> SEQUENCE: 108

```
Met Lys His Ile Val Glu Asn Asp Gln Ser Asn Met Lys Gly Gly Val
1               5                   10                  15

Leu Val Ser Ser Asn Ser His Glu His His His His Gln Gly Ala Asp
            20                  25                  30

Asn Lys Lys Lys Lys Lys Met Lys Leu Val Ile Leu Ile Val Asn Cys
        35                  40                  45

Ile Leu Leu Ser Val Ala Gln Ile Ser Gly Pro Leu Leu Leu Arg Ile
    50                  55                  60

Tyr Tyr Leu His Gly Gly Gln Arg Lys Trp Leu Ser Ser Trp Leu Gln
65                  70                  75                  80

Thr Val Ala Phe Pro Phe Leu Leu Ile Pro Ile Ser Val Ser Trp Phe
                85                  90                  95

Arg Ser Lys Ser Lys Ser His Asp Ser Arg Ser Ile Ser Ala Ile Asp
            100                 105                 110

Val Asn Pro Thr Thr Asp Arg Lys Leu Arg Phe Gly Gly Phe Ser Pro
        115                 120                 125

Lys Leu Phe Ile Ser Cys Ile Phe Leu Gly Ile Ile Val Gly Leu Asp
    130                 135                 140

Ser Phe Leu Tyr Ala Tyr Gly Val Ser Tyr Leu Pro Val Ser Thr Ser
145                 150                 155                 160

Ser Leu Leu Met Ser Thr Gln Leu Ala Phe Thr Ala Ala Phe Ala Leu
                165                 170                 175

Leu Leu Val Arg Gln Lys Phe Thr Pro Tyr Ser Ile Asn Ser Val Val
            180                 185                 190

Leu Leu Thr Leu Gly Ala Val Val Leu Ala Phe His Thr Asn Gly Asp
        195                 200                 205

Lys Pro Ile Gly Val Ser Lys Ala Gln Tyr Phe Leu Gly Phe Phe Leu
    210                 215                 220

Thr Leu Gly Ala Ala Ala Leu Phe Gly Phe Met Leu Pro Phe Ile Glu
225                 230                 235                 240

Leu Val Tyr Arg Lys Ala Ser Glu Ala Ile Thr Tyr Asp Leu Val Met
                245                 250                 255

Arg Met Gln Phe Ile Thr Ser Met Val Ala Thr Val Phe Cys Thr Ile
            260                 265                 270

Ala Met Leu Ile Asn Lys Asp Phe Gln Ala Ile Ser Arg Glu Ala Lys
        275                 280                 285

Gly Phe Glu Leu Gly Glu Thr Lys Tyr Tyr Ile Val Leu Ile Cys Thr
    290                 295                 300

Ala Val Ser Met Gln Cys Ala Val Val Gly Thr Leu Gly Val Ile His
305                 310                 315                 320

Cys Ala Thr Ser Leu Phe Ser Gly Val Leu Met Thr Leu Leu Leu Pro
                325                 330                 335

Ile Gln Gln Ile Cys Ala Ile Phe Phe Phe Asn Glu Lys Phe Ser Ala
            340                 345                 350

Glu Lys Gly Met Ser Leu Gly Leu Ser Ile Trp Gly Phe Ala Ser Tyr
        355                 360                 365

Phe Tyr Gly Glu Tyr Lys Gln Thr Lys Lys Lys Thr Asn Gln His Lys
    370                 375                 380

Ala Val Ser Thr Lys Ser Gln Glu Ile Pro Asp Glu Val
385                 390                 395
```

<210> SEQ ID NO 109
<211> LENGTH: 1194

<212> TYPE: DNA
<213> ORGANISM: Papaver somniferum

<400> SEQUENCE: 109
atgaagcaca tcgtcgaaaa cgaccagtct aatatgaaag gtggtgtctt ggtttcctcc 60
aactctcatg aacatcatca tcaccaaggt gccgataaca aaaagaaaaa gaagatgaag 120
ctggtcatcc tgatcgttaa ctgcattttg ttgtccgttg ctcaaatttc tggtcccttg 180
ttgttgagaa tctactactt gcatggtggt caaagaaagt ggttatcttc ttggttgcaa 240
actgttgctt tccccttttt gttgatccca atttccgttt cctggttcag atctaagtct 300
aagtctcacg attccagatc catttccgct attgatgtta acccaactac cgacagaaag 360
ttgagatttg gtggtttttc acccaagttg ttcatcagct gtattttctt gggtatcatc 420
gtcggtttgg actcattctt gtatgcttat ggtgtttcct acttgccagt ttctacttcc 480
tctttgttga tgtctactca attggctttt actgctgctt tcgctttgtt gttggttaga 540
caaaagttca ccccatactc catcaactct gttgttttgt tgactttggg tgcagttgtt 600
ttggcttttc ataccaatgg tgataagcca atcggtgttt ctaaggctca atactttttg 660
ggtttcttct taacattggg tgctgcagct ttgtttggtt ttatgttgcc attcatcgag 720
ctggtttaca gaaaagcttc tgaagctatt acctacgact tggttatgag aatgcaattc 780
atcacctcta tggttgctac tgttttctgt accattgcca tgttgattaa caaggatttc 840
caagccattt ccagagaagc taagggtttt gaattaggcg aaacgaagta ctacatcgtt 900
ttgatctgta ccgctgtttc tatgcaatgt gccgttgttg gtactttagg tgttattcat 960
tgtgccacgt ctttgttctc tggtgtttta atgaccctgt tgttgccaat tcaacaaatt 1020
tgcgctatct tcttcttcaa cgaaaaattc tctgccgaga agggtatgtc tttgggtttg 1080
tctatttggg gttttgcctc ttacttttac ggtgagtaca agcagaccaa aaaaaagacc 1140
aatcaacaca aagccgtgtc cacaaagtct caagaaattc cagatgaagt ctaa 1194

<210> SEQ ID NO 110
<211> LENGTH: 347
<212> TYPE: PRT
<213> ORGANISM: Papaver atlanticum

<400> SEQUENCE: 110

Met Glu Lys Tyr Leu Leu Leu Phe Asn Cys Ile Leu Leu Ala Val Cys
1               5                   10                  15

Ser Ala Gly Gly Pro Leu Leu Leu Arg Leu Tyr Phe Ile His Gly Gly
            20                  25                  30

Lys Arg Leu Trp Leu Ser Ser Trp Leu Glu Thr Ala Gly Trp Pro Ile
        35                  40                  45

Leu Phe Leu Pro Leu Ser Leu Ser Tyr Phe Leu Lys Arg Arg Arg Phe
    50                  55                  60

Lys Asn Gly Gln Asp Glu Lys Pro Ser Lys Phe Phe Met Ile Thr Pro
65                  70                  75                  80

Phe Leu Phe Met Ala Ser Ala Phe Ile Gly Leu Leu Val Gly Leu Asp
                85                  90                  95

Asp Tyr Leu Tyr Thr Tyr Gly Val Ser Leu Leu Pro Val Ser Thr Ala
            100                 105                 110

Ser Leu Ile Met Ser Thr His Val Ala Phe Thr Ala Gly Phe Ala Leu
        115                 120                 125

Phe Met Val Lys Gln Lys Phe Thr Ser Tyr Ser Val Asn Ala Val Ile
    130                 135                 140

```
Leu Leu Thr Val Gly Ala Val Leu Leu Gly Leu His Ser Asn Gly Asp
145                 150                 155                 160

Arg Ser Val His Glu Ser Asn Arg Asp Tyr Tyr Leu Gly Phe Val Met
                165                 170                 175

Thr Ile Gly Ala Ser Val Ile Gly Gly Leu Leu Leu Pro Leu Val Glu
            180                 185                 190

Leu Met Tyr Lys Lys Ser Lys Gln Thr Ile Thr Tyr Thr Leu Val Thr
        195                 200                 205

Glu Leu Gln Ile Val Ile Ser Val Phe Ala Thr Leu Phe Cys Thr Val
    210                 215                 220

Gly Met Leu Val Asn Asn Asp Phe Lys Val Ile Gln Arg Glu Gly Lys
225                 230                 235                 240

Glu Tyr Asp Leu Gly Glu Thr Lys Tyr Tyr Val Val Leu Val Ala Ser
                245                 250                 255

Ser Ile Thr Trp Gln Leu Cys Phe Leu Gly Thr Ile Gly Val Ile Phe
            260                 265                 270

Cys Ser Thr Ser Leu Leu Ala Gly Val Ile Gly Ala Ala Val Leu Pro
        275                 280                 285

Val Ile Glu Ile Leu Gly Val Ile Phe Tyr His Glu Ser Phe Lys Ala
    290                 295                 300

Glu Lys Gly Ile Ala Leu Phe Leu Ser Leu Trp Gly Phe Ile Ser Tyr
305                 310                 315                 320

Phe Tyr Leu Glu Ile Lys Ala Ser Arg Lys Pro Lys Arg Gln Cys Ser
                325                 330                 335

Glu Leu Glu Gln Gly Gly Leu Thr Val Ser Ser
            340                 345
```

<210> SEQ ID NO 111
<211> LENGTH: 1044
<212> TYPE: DNA
<213> ORGANISM: Papaver atlanticum

<400> SEQUENCE: 111

```
atggaaaagt acctgctgct gttcaactgc attttgttgg ctgtttgttc tgctggtggt     60

cctttgttgt tgaggttgta ctttattcat ggtggtaaga ggttgtggtt gtcatcttgg    120

ttggaaactg ctggttggcc aattttgttt ttgccattgt ccttgtccta ctttttgaag    180

cgtagaagat tcaagaacgg tcaagacgaa aagccatcta agttcttcat gattacccct    240

ttcttgttca tggcttctgc tttcattggt ttgttggttg gtttggatga ttacttgtac    300

acctacggtg tttctttgtt gccagtttct actgcctctt tgattatgtc tactcatgtt    360

gcttttaccg ctggttttgc tttgtttatg gtcaagcaaa agttcacctc ctactctgtt    420

aacgccgtta ttttgttaac tgttggtgct gtcttgttgg gcttgcattc taatggtgat    480

agatctgttc acgaatccaa cagagattac tacttgggtt tcgttatgac tattggtgcc    540

tctgttattg gtggtttgtt attgcctttg gtcgagttga tgtacaagaa gtctaagcaa    600

actatcacct acaccttggt taccgaattg caaatcgtta tttctgtttt cgctaccttg    660

ttctgtaccg ttggtatgtt agttaacaac gacttcaagg tcattcagcg tgaaggtaaa    720

gaatacgatt tgggtgaaac taagtactac gttgttttgg ttgcctcttc tattacctgg    780

caattgtgtt tcttgggtac tatcggtgtt attttctgct ctacctcttt gttagctggt    840

gttattggag ctgctgtttt gccagttatt gaaatcttgg gtgttatctt ctaccacgaa    900

tctttcaaag ccgaaaaggg tattgccttg tttttgtctt tgtggggttt catctcttac    960
```

ttctacttgg aaatcaaggc ctccagaaag ccaaaaagac aatgttctga attggagcaa 1020
ggtggtttga ctgtttcttc ttga 1044

<210> SEQ ID NO 112
<211> LENGTH: 385
<212> TYPE: PRT
<213> ORGANISM: Glaucium Flavum

<400> SEQUENCE: 112

Met Glu Thr Pro Ile Asn Ile Ala Ala Asn Glu Glu Lys Thr Gln Asp
1 5 10 15

Glu Lys Ser Lys Thr Tyr Thr Glu Tyr Pro Ala Lys Thr Lys Asn Trp
20 25 30

Pro Leu Ile Ile Leu Asn Thr Val Ile Met Thr Ile Gly Val Ile Gly
35 40 45

Gly Pro Leu Leu Met Arg Leu Tyr Tyr Ile His Gly Gly Asn Arg Arg
50 55 60

Trp Leu Ser Ser Cys Ile Gln Asn Ala Gly Phe Pro Ile Leu Leu Ile
65 70 75 80

Pro Leu Thr Phe Leu Phe Phe Gln Tyr Ser Lys Thr Pro His Gln Glu
85 90 95

Asn His His Leu Ser Ser Ser Pro Leu Ser Ser Lys Pro Ser Ser Phe
100 105 110

Leu Met Glu Pro Lys Leu Phe Leu Ser Ser Ser Phe Val Gly Ile Leu
115 120 125

Phe Gly Leu Asn Asn Phe Met Tyr Ser Leu Gly Leu Ser Tyr Ile Pro
130 135 140

Ile Ser Thr Ser Ser Leu Leu Phe Ala Thr Gln Leu Ala Phe Val Ala
145 150 155 160

Phe Phe Ala Trp Leu Ile Val Lys Gln Gln Phe Thr Ala Tyr Ser Ile
165 170 175

Asn Ser Val Val Leu Met Thr Leu Gly Ser Ile Leu Leu Gly Val Lys
180 185 190

Asn Asp Gly Asp Arg Pro Val Gly Val Thr Lys Ala Glu Tyr Met Leu
195 200 205

Gly Phe Leu Leu Thr Leu Gly Ser Ala Ala Leu Val Gly Phe Ile Leu
210 215 220

Pro Leu Val Glu Leu Ser Tyr Ser Lys Ala Thr Arg His Val Asn Tyr
225 230 235 240

Thr Thr Ile Leu Gln Tyr Gln Leu Asn Leu Ala Leu Phe Ser Thr Ile
245 250 255

Phe Asn Ser Ile Gly Met Val Ile Asn Lys Asp Phe Gln Ala Ile Pro
260 265 270

Arg Glu Ala Ser Glu Phe Glu Leu Gly Lys Thr Met Tyr Tyr Thr Ile
275 280 285

Leu Ile Thr Gly Ala Ile Ile Trp Gln Leu Ser Phe Ile Gly Gly Leu
290 295 300

Gly Val Ile Leu Tyr Thr Ser Ser Leu Phe Ser Gly Ile Leu Thr Ser
305 310 315 320

Val Leu Leu Pro Phe Thr Glu Ile Ala Ala Val Ile Val Tyr Arg Glu
325 330 335

Ser Phe Thr Gly Leu Lys Gly Met Ala Leu Ala Leu Cys Leu Trp Gly
340 345 350

Phe Thr Ser Tyr Phe Tyr Gly Glu Tyr Lys Met Met Lys Asn Met Lys
        355                 360                 365

Thr Lys Thr Ser Glu Lys Val Val Asp Asn Asp Glu Glu Pro Cys Thr
    370                 375                 380

Val
385

<210> SEQ ID NO 113
<211> LENGTH: 1158
<212> TYPE: DNA
<213> ORGANISM: Glaucium Flavum

<400> SEQUENCE: 113
atggaaacgc caatcaacat tgctgccaac gaagaaaaaa ctcaggacga aaaatctaag 60
acctacactg aatacccagc taagacaaaa aactggccat tgattatctt gaacaccgtc 120
attatgacca tcggtgttat tggtggtcca ttattgatga ggttgtacta cattcatggt 180
ggtaacagaa gatggttgtc ctcttgtatt caaaatgctg gtttccccat tctgttgatc 240
ccattgactt ttttgttctt ccagtactct aagaccccac atcaagaaaa ccatcacttg 300
tcatcttctc cattgtcctc taagccatcc tcatttttga tggaacctaa gctgttcctg 360
tcctcttctt ttgttggtat tttgttcggc ttgaacaact tcatgtacag cttgggtttg 420
agctatattc caatctccac ttcgtctttg ttgttcgcta ctcaattggc ttttgttgct 480
tttttcgctt ggttgatcgt caagcaacaa ttcactgctt actccatcaa ctccgttgtt 540
ttgatgactt tgggttccat tttgttgggt gttaagaacg atggtgatag accagttggt 600
gttacaaaag ctgagtacat gttgggtttc ttgttgactt taggttctgc tgctttggtt 660
ggtttcattt tgccattggt tgagctgtct tactctaagg ctactagaca tgttaactac 720
accaccatct tgcaatacca attgaacttg gctttgttca gcaccatctt caactctatt 780
ggtatggtta tcaacaagga cttccaagct attccaagag aagcctctga atttgaattg 840
ggtaagacta tgtactacac gatcttgatt accggtgcca ttatttggca attgtctttc 900
attggtggtt tgggcgttat cttgtacaca tcttctttgt tctccggtat cttgacctct 960
gttttgttgc cattcactga aattgctgcc gttatcgttt acagagaatc tttcactggt 1020
ttgaaaggta tggctttggc tttatgtttg tggggtttta cctcttactt ttacggtgag 1080
tacaagatga tgaagaatat gaagaccaag acctccgaaa aggttgttga caacgatgaa 1140
gaaccatgta ccgtttga 1158

<210> SEQ ID NO 114
<211> LENGTH: 368
<212> TYPE: PRT
<213> ORGANISM: Papaver somniferum

<400> SEQUENCE: 114

Met Ala Ile Asp Ile Glu Arg Ile Glu Glu Gly Asp Leu Asp Asp Asn
1               5                   10                  15

His Asp Asn Asn His Ala Lys Ser Gly Asp Glu Asn Ser Asp Phe Asn
            20                  25                  30

Ser Met Met Ala Lys Trp Gly Leu Leu Leu Leu Asn Cys Met Leu Ser
        35                  40                  45

Ala Val Gly Thr Ile Gly Gly Pro Leu Leu Leu Arg Leu Tyr Phe Leu
    50                  55                  60

His Gly Gly Gly Arg Lys Trp Ile Ser Ser Ala Leu Gln Thr Ala Gly
65                  70                  75                  80

```
Phe Pro Ile Leu Leu Ile Pro Leu Ala Val Leu Tyr Phe Arg Asp Arg
                85                  90                  95

Lys Thr Ile Gly Val Gly Lys Phe Phe Ala Ser Pro Lys Leu Leu Leu
            100                 105                 110

Ser Ala Ala Val Ile Gly Val Leu Leu Gly Leu Glu Thr Phe Met Tyr
        115                 120                 125

Ser Tyr Gly Leu Ser Phe Leu Pro Val Ser Thr Ser Ser Leu Leu Ile
    130                 135                 140

Ser Thr Gln Leu Val Phe Thr Ala Cys Phe Ala Phe Val Met Val His
145                 150                 155                 160

Gln Lys Phe Thr Pro Tyr Ser Ile Asn Ala Ala Val Leu Met Thr Leu
                165                 170                 175

Gly Ser Ile Leu Leu Ala Ile Arg Lys Asn Gly Asp Arg Pro Pro Gly
            180                 185                 190

Val Thr Thr Ser Gln Tyr Leu Leu Gly Phe Ile Leu Ser Ile Ala Ala
        195                 200                 205

Ala Gly Leu Ala Gly Phe Ile Leu Pro Cys Thr Glu Val Ala Tyr Ala
    210                 215                 220

Lys Ser Ser Lys Pro Met Thr Tyr Cys Leu Val Leu Gln Tyr Gln Phe
225                 230                 235                 240

Cys Met Thr Phe Phe Ala Thr Ala Phe Cys Ala Val Gly Met Phe Val
                245                 250                 255

Asn Asn Asp Phe Ser Ala Met Gln Arg Glu Ala Asn Ala Tyr Glu Leu
            260                 265                 270

Gly Ala Thr Lys Tyr Tyr Met Val Leu Val Ser Ser Ala Val Val Trp
        275                 280                 285

Gln Leu Met Phe Val Gly Thr Leu Gly Ile Ile Phe Cys Thr Ser Ser
    290                 295                 300

Leu Phe Ser Gly Val Ile Thr Ala Thr Leu Leu Pro Leu Thr Glu Ile
305                 310                 315                 320

Ala Ala Leu Ile Ile Phe His Glu Lys Phe Thr Gly Glu Lys Gly Met
                325                 330                 335

Ala Leu Ala Leu Ser Leu Trp Gly Phe Thr Ser Tyr Phe Tyr Gly Ser
            340                 345                 350

Tyr Arg Glu Thr Lys Asn Gln Thr Gln Thr Asn Leu Glu Ala Lys Thr
        355                 360                 365
```

<210> SEQ ID NO 115
<211> LENGTH: 1107
<212> TYPE: DNA
<213> ORGANISM: Papaver somniferum

<400> SEQUENCE: 115

```
atggccatcg acatcgaaag aattgaagaa ggtgatttgg acgataacca cgataacaat      60

catgctaaat ctggtgacga aaactccgac tttaattcca tgatggctaa atggggtctg     120

ttgttgttga actgtatgtt gtctgctgtt ggtactattg gtggtccttt gttgttaagg     180

ttgtacttct tgcatggtgg tggtagaaaa tggatttctt ctgctttaca aactgctggc     240

ttcccaattt tgttgattcc attggctgtc ttgtacttca gagatagaaa aaccattggt     300

gtcggtaagt ttttcgcttc tccaaagttg ttgttatccg ctgctgttat cggtgttttg     360

ttgggtttag aaaccttcat gtactcctac ggtttgtctt ttttgccagt ttctacctcc     420

tccttgttga tttctactca attggttttc accgcttgct tcgcttttgt tatggttcat     480
```

```
caaaagttca cgccctactc tatcaatgct gctgttttga tgactttggg ctctattttg    540

ttggccatta gaaagaatgg tgatagacca ccaggtgtta ctacttctca atacttgtta    600

ggcttcatct tgtctattgc tgctgctggt ttggctggtt tcattttgcc atgtactgaa    660

gttgcttacg ccaaatcttc taagccaatg acttactgtt tggtcttgca ataccagttc    720

tgtatgactt ttttcgctac tgctttttgt gccgttggta tgttcgttaa caatgatttc    780

tctgccatgc aaagggaagc taatgcttat gaattgggtg ctactaagta ctatatggtc    840

ttggtttctt cagccgttgt ttggcaattg atgttcgttg gtactctggg tattatcttc    900

tgtacctctt ctttgttctc cggtgttatt actgctactt tgttgccatt gacagaaatt    960

gctgccttga ttatcttcca tgagaagttc actggtgaaa aaggtatggc tttggctttg   1020

tctttatggg gttttacctc ttacttctac ggttcctatc gtgaaactaa gaaccagact   1080

caaactaact tggaagctaa gacctga                                       1107
```

```
<210> SEQ ID NO 116
<211> LENGTH: 366
<212> TYPE: PRT
<213> ORGANISM: Cinnamomum micranthum f. kanehirae

<400> SEQUENCE: 116

Met Ala Met Asp Ile Glu Lys Val Glu Glu Gly Val Val Pro Arg Thr
1               5                   10                  15

Glu Tyr Asn Asn Lys Ala Pro Pro Ser Ser Glu Glu Lys Ala Gln Lys
            20                  25                  30

Lys Ser Ser Ile Asn Trp Leu Leu Leu Leu Leu Asn Phe Thr Leu Thr
        35                  40                  45

Ala Ile Gly Thr Ile Gly Gly Pro Leu Leu Leu Arg Leu Tyr Phe Leu
    50                  55                  60

His Gly Gly Gly Arg Lys Trp Leu Thr Ser Trp Leu Gln Thr Ala Gly
65                  70                  75                  80

Phe Pro Phe Leu Ile Leu Pro Leu Ser Ile Leu Tyr Ile Arg Glu Arg
                85                  90                  95

Ala Arg Gly Thr His Thr His Phe Leu Ala Glu Pro Lys Leu Leu Ile
            100                 105                 110

Ser Ser Ala Ala Ile Gly Leu Leu Leu Gly Leu Asp Asn Phe Leu Tyr
        115                 120                 125

Ser Tyr Gly Val Ser Leu Leu Pro Val Ser Thr Ser Ser Leu Leu Phe
    130                 135                 140

Ser Thr Gln Leu Ala Phe Thr Ala Phe Phe Ala Leu Ile Ile Val Arg
145                 150                 155                 160

Gln Lys Phe Ser Pro Phe Ser Ile Asn Ala Val Val Leu Met Thr Leu
                165                 170                 175

Gly Ser Val Leu Leu Gly Ile Arg Lys Ser Gly Asp Arg Pro Ala Asn
            180                 185                 190

Val Thr Asn Gly Glu Tyr Leu Leu Gly Phe Val Ile Thr Leu Gly Ala
        195                 200                 205

Ala Ala Leu Leu Gly Phe Val Leu Pro Cys Ile Glu Met Thr Tyr Ala
    210                 215                 220

Lys Ala Ser Arg Ala Ile Ser Phe Thr Val Val Met Gln Phe Gln Leu
225                 230                 235                 240

Gly Val Thr Phe Phe Ala Thr Leu Phe Cys Thr Ile Gly Met Ile Ile
                245                 250                 255

Asn Lys Asp Phe Thr Ala Ile Gly Arg Glu Ala Ser Ala Tyr Gly Leu
```

```
            260                 265                 270

Gly Glu Thr Lys Tyr Tyr Met Val Leu Thr Ala Ile Ala Ile Leu Phe
        275                 280                 285

Gln Met Val Phe Val Gly Ser Leu Gly Ile Val Phe Cys Thr Ser Ser
    290                 295                 300

Leu Phe Ala Gly Val Val Ala Ala Thr Leu Leu Pro Ile Thr Glu Ile
305                 310                 315                 320

Ala Ala Val Ile Val Tyr His Glu Lys Phe Thr Gly Glu Lys Gly Met
                325                 330                 335

Ala Leu Ala Leu Cys Leu Trp Gly Phe Thr Ser Tyr Phe Tyr Gly Ala
            340                 345                 350

Tyr Arg Thr Glu Lys Lys Gln Thr Pro Gln Thr Glu Ser Asp
        355                 360                 365


<210> SEQ ID NO 117
<211> LENGTH: 1101
<212> TYPE: DNA
<213> ORGANISM: Cinnamomum micranthum f. kanehirae

<400> SEQUENCE: 117

atggccatgg atatcgaaaa ggttgaagaa ggtgttgttc caagaactga gtacaacaac     60

aaagctccac catcctctga agaaaaggct caaaagaaat cctccatcaa ctggttgctg    120

ttgttgttga atttcacctt gactgccatt ggtactattg gtggtccttt gttattgagg    180

ttgtacttct tgcatggtgg tggtagaaaa tggttaactt cttggttgca aactgctggt    240

ttcccatttt tgattctgcc attgtccatc ttgtacatca gagaaagagc tagaggtact    300

catacccatt ttttggctga acctaagctg ttgatttcct ctgctgctat tggtttgttg    360

ttaggtttgg acaacttctt gtactcctac ggtgtttctt tgttgccagt ttctacttcc    420

tccttgttgt tctctactca attggctttt actgctttct tcgccttgat tatcgtcaga    480

caaaagttct ctccattctc cattaacgcc gttgttttga tgactttggg ttctgttttg    540

ttgggcatta gaaagtctgg tgatagacca gctaatgtta ccaatggtga atacttgttg    600

ggtttcgtta ttactttggg tgctgctgct ttattgggtt ttgtcttgcc atgtattgaa    660

atgacttacg ctaaagcctc cagagctatt tctttcactg ttgtcatgca attccaattg    720

ggtgttactt ttttcgctac cttgttctgc actatcggta tgattatcaa caaggatttc    780

accgctattg gtagagaagc ttcagcttat ggtttgggtg aaactaagta ctacatggtt    840

ttgaccgcca ttgccatttt gttccaaatg gtttttgttg gctctctggg tatcgttttc    900

tgtacctctt ctttgttcgc tggtgttgtt gctgctacat tattgccaat tactgaaatt    960

gctgccgtta tcgtttacca cgaaaagttc actggtgaaa aaggtatggc tttggctttg   1020

tgtttgtggg gttttacttc ttacttttac ggtgcttaca ggaccgaaaa aaagcaaact   1080

ccacaaaccg aatccgactg a                                              1101


<210> SEQ ID NO 118
<211> LENGTH: 390
<212> TYPE: PRT
<213> ORGANISM: Papaver somniferum

<400> SEQUENCE: 118

Met Ala Thr Ser Ala Met Asp Ile Glu Thr Ile Gly Ile Leu Gly Thr
1               5                   10                  15

Thr Gln Asn Gly Asn Ser Glu Thr His Thr Glu Lys Thr Ile Glu Thr
            20                  25                  30
```

```
Lys Asn Trp Leu Leu Ile Thr Ile Asn Cys Ala Phe Thr Ile Cys Gly
        35                  40                  45

Ala Val Gly Gly Pro Leu Leu Met Arg Leu Tyr Tyr Leu His Gly Gly
    50                  55                  60

Ser Arg Ile Trp Leu Ser Ser Phe Glu Ala Ser Ala Gly Phe Pro Ile
65                  70                  75                  80

Leu Ile Phe Pro Leu Ile Phe Leu Phe Phe Arg Ser Lys Ser Ser Ala
                85                  90                  95

Asp Lys Ile Leu Ser Ser Phe Trp Leu Glu Thr Lys Leu Phe Leu Trp
            100                 105                 110

Gly Ala Ile Leu Gly Ile Leu Tyr Gly Leu Val Thr Phe Met Tyr Ala
        115                 120                 125

Leu Gly Leu Ser Tyr Ile Pro Leu Ser Thr Ser Ser Leu Leu Met Ala
    130                 135                 140

Thr Gln Leu Cys Phe Thr Ala Phe Phe Ala Trp Leu Ile Val Lys Gln
145                 150                 155                 160

Lys Phe Thr Ala Phe Val Ile Asn Ala Val Val Val Met Thr Leu Gly
                165                 170                 175

Ser Val Val Leu Gly Ile Asn Thr Asp Gly Asp Arg Pro Val Gly Val
            180                 185                 190

Ser Lys Ala Gln Tyr Leu Leu Gly Phe Leu Leu Thr Leu Gly Ala Ala
        195                 200                 205

Ala Leu Ala Gly Leu Ile Thr Pro Leu Ile Glu Leu Ala Phe Ser Lys
    210                 215                 220

Ala Thr Arg Asn Leu Cys Tyr Ser Ser Leu Leu Asn Phe Gln Val Ile
225                 230                 235                 240

Leu Ser Val Phe Ser Thr Ile Val Cys Val Ile Gly Met Leu Val Asn
                245                 250                 255

Lys Asp Phe Gln Ala Ile Pro Arg Glu Ala Asn Asp Phe Glu Leu Gly
            260                 265                 270

Lys Ala Asn Tyr Tyr Ile Ile Met Ile Val Thr Ala Ile Ile Trp Gln
        275                 280                 285

Leu Leu Gly Val Gly Thr Val Gly Val Ile Phe Tyr Thr Ser Ala Leu
    290                 295                 300

Phe Ser Gly Ile Leu Gly Ser Val Leu Val Pro Leu Thr Gly Val Thr
305                 310                 315                 320

Ala Ile Met Phe Tyr His Glu Ser Phe Thr Gly Leu Lys Gly Met Ala
                325                 330                 335

Leu Ala Leu Cys Phe Trp Gly Leu Cys Ser Tyr Phe Tyr Gly Glu Tyr
            340                 345                 350

Lys Met Met Lys Lys Val Val His Asp Glu Thr Pro Glu Thr Ile Asp
        355                 360                 365

Asn Ile Glu Asn Asp Pro Asn Arg Leu Asp Asn Gln Asp Ala Pro Tyr
    370                 375                 380

Thr Leu Asn Gln Val Leu
385                 390
```

<210> SEQ ID NO 119
<211> LENGTH: 1173
<212> TYPE: DNA
<213> ORGANISM: Papaver somniferum

<400> SEQUENCE: 119

```
atggctacct ccgctatgga tattgaaacc attggtattt tgggtactac ccagaatggt      60
```

```
aactctgaaa ctcataccga aaagaccatc gaaactaaga actggttgtt gattaccatt    120

aactgcgctt tcactatttg tggtgctgtt ggtggtccat tattgatgag actatattac    180

ttgcacggtg gttccagaat ttggttgtct agttttgaag cttctgctgg tttcccaatt    240

ttgatcttcc cactgatttt cttgttcttc aggtccaaat cttccgccga taagattttg    300

tcatctttct ggttggagac taagttgttt ttgtggggtg ctatattggg tatcttgtac    360

ggtttggtta ctttcatgta tgccttgggt ttgtcctata ttccattgtc tacttcgtct    420

ttgttgatgg ctactcaatt gtgtttcact gctttttttcg cttggttgat cgtcaagcaa    480

aagtttactg ccttcgttat taacgccgtt gttgttatga ctttgggttc tgttgttttg    540

ggtattaaca ccgatggtga tagaccagtt ggtgtttcta aagctcaata cttgttgggt    600

ttcttgttga ctttaggtgc tgctgctttg gctggtttga ttactccatt gattgaattg    660

gctttctcca aggctactag aaacttgtgt tactcctcct tgttgaactt ccaagttatc    720

ctgtctgttt tctctaccat cgtttgcgtt attggtatgt tggttaacaa ggacttccaa    780

gccattccaa gagaagctaa tgatttcgaa ttgggcaaag ccaactacta catcattatg    840

atcgttaccg ctatcatctg gcaattatta ggtgttggta ctgtcggtgt tatcttctat    900

acttctgctt tgttctctgg tatcttgggt tcagttttgg ttccattgac tggtgttact    960

gccattatgt tctaccatga atctttcacc ggtttgaaag gtatggcttt ggctttgtgt   1020

ttttggggtt tgtgttctta cttttacggc gagtacaaga tgatgaagaa agttgttcat   1080

gacgaaaccc cagaaaccat cgataacatt gaaaacgatc caaacagatt ggataatcaa   1140

gatgctccct acaccttgaa tcaagtcttg taa                                1173
```

<210> SEQ ID NO 120
<211> LENGTH: 370
<212> TYPE: PRT
<213> ORGANISM: Rosa chinensis

<400> SEQUENCE: 120

```
Met Gln Met Glu Thr Thr Glu Asp Glu Gln Arg Lys Ala Thr Ala Leu
1               5                   10                  15

Lys Arg Leu Leu Leu Ile Leu Ser Cys Val Phe Leu Ser Ile Gly Asn
            20                  25                  30

Cys Gly Gly Pro Leu Ile Met Arg Leu Tyr Phe Ile His Gly Gly Lys
        35                  40                  45

Arg Val Trp Leu Ser Ser Met Leu Glu Thr Gly Gly Trp Pro Ile Ile
    50                  55                  60

Leu Val Pro Ile Ala Ile Ala Tyr Tyr His Arg Arg Lys Asn Gln Ala
65                  70                  75                  80

Pro Thr Glu Pro Pro Thr Lys Leu Phe Phe Met Lys Ile Pro Leu Phe
                85                  90                  95

Val Ala Ser Ala Val Ile Gly Val Leu Thr Gly Leu Asp Asp Tyr Leu
            100                 105                 110

Tyr Ala Tyr Gly Val Ala Arg Leu Pro Val Ser Thr Ser Ser Leu Ile
        115                 120                 125

Ile Ala Ala Gln Leu Ala Phe Thr Ala Leu Phe Ala Phe Ile Leu Val
    130                 135                 140

Lys Gln Lys Phe Thr Ser Tyr Ser Ile Asn Ala Ile Val Leu Leu Thr
145                 150                 155                 160

Val Gly Ala Ala Val Leu Gly Leu Asn Thr Asn Ser Asp Arg Pro Glu
                165                 170                 175
```

```
Gly Glu Ser Asn Ala Gln Tyr Met Leu Gly Phe Met Met Thr Val Ala
            180                 185                 190

Ala Ala Ala Leu Tyr Gly Phe Val Leu Pro Leu Val Glu Leu Met Tyr
        195                 200                 205

Lys Lys Ala Lys Gln Asn Ile Thr Tyr Ala Leu Val Leu Glu Ile Gln
    210                 215                 220

Leu Val Met Cys Leu Phe Ala Thr Ile Phe Cys Thr Val Gly Met Leu
225                 230                 235                 240

Val Asn Asn Asp Phe Lys Val Ile Pro Arg Glu Ala Arg Lys Phe Glu
                245                 250                 255

Leu Gly Glu Thr Thr Tyr Tyr Val Val Leu Val Val Ser Ala Ile Ile
            260                 265                 270

Trp Gln Gly Phe Phe Leu Gly Ala Ile Gly Ile Ile Phe Cys Ala Ser
        275                 280                 285

Ser Leu Leu Ser Gly Ile Val Ile Ala Val Leu Leu Pro Ile Thr Glu
    290                 295                 300

Ile Phe Ala Val Ile Phe Tyr His Glu Lys Phe Gln Ala Glu Lys Gly
305                 310                 315                 320

Val Ser Leu Val Leu Ser Leu Trp Gly Phe Val Ser Tyr Phe Tyr Gly
                325                 330                 335

Glu Ile Lys His Asn Lys Glu Ser Lys Arg Val Lys Lys Lys Glu Asn
            340                 345                 350

Asn Lys Asp Ser Ser Gly Gln Asp Thr Glu Asn Pro Gln Ser Val Pro
        355                 360                 365

Asn Pro
    370
```

<210> SEQ ID NO 121
<211> LENGTH: 1113
<212> TYPE: DNA
<213> ORGANISM: Rosa chinensis

<400> SEQUENCE: 121

```
atgcagatgg aaaccaccga agatgaacaa agaaaagcta ctgctttgaa gaggctgttg      60

ttgattttgt cttgcgtgtt cttgtctatt ggtaattgtg gtggtccatt gatcatgagg     120

ttgtacttta ttcatggtgg taagagagtc tggctgtcat ctatgttgga aactggtggt     180

tggccaatca ttttggttcc aattgctatt gcctactacc acagaagaaa aaatcaagct     240

ccaactgaac cacctaccaa gttgtttttt atgaagatcc ctttgttcgt tgcctccgct     300

gttattggtg ttttgactgg tttggatgat tacttgtatg cttacggtgt tgctagattg     360

ccagtttcta cttcctcttt gattattgct gctcaattgg ctttcactgc tttgttcgct     420

tttatcttgg tcaagcaaaa gttcacctcc tactctatta acgccatcgt tttgttgact     480

gttggtgctg ctgttttggg tttgaacact aattctgata gaccagaagg tgaatctaac     540

gctcagtata tgttgggttt catgatgaca gttgcagctg ctgcattata cggttttgtt     600

ttgccattgg tcgagctgat gtacaaaaaa gccaagcaaa acattaccta cgccttggtt     660

ttggaaatcc aattggttat gtgtttgttc gccaccattt tctgtactgt tggtatgttg     720

gttaacaacg acttcaaggt tattccaaga gaagccagaa agttcgaatt gggtgaaact     780

acttactacg ttgtcttggt tgtttccgcc attatttggc aaggtttttt cttgggtgct     840

atcggtatta tcttctgcgc ttcttcttta ttgtccggta tcgttattgc agtcttgttg     900

ccaattaccg aaattttcgc cgttatcttc taccacgaaa agttccaagc tgaaaagggt     960
```

gtttctttgg ttttgtcttt gtggggtttc gtgtcttact tttacggtga aatcaagcac 1020
aacaaagagt ccaagagagt caagaagaaa gagaacaaca aggactcttc tggtcaagat 1080
actgaaaacc cacaatctgt tccaaatcca taa 1113

<210> SEQ ID NO 122
<211> LENGTH: 357
<212> TYPE: PRT
<213> ORGANISM: Durio zibethinus

<400> SEQUENCE: 122

Met Glu Val Val Lys Glu His Lys Pro Gly Thr Thr Met Arg Lys Ser
1 5 10 15

Leu Leu Val Ile Asn Cys Ile Ile Leu Ser Ile Gly Asn Cys Gly Gly
20 25 30

Pro Leu Leu Met Arg Leu Tyr Phe Ile His Gly Gly Lys Arg Val Trp
35 40 45

Phe Ser Ser Trp Leu Glu Thr Gly Gly Trp Pro Ile Ile Leu Phe Pro
50 55 60

Ile Ala Cys Ala Tyr Met His Arg Ser Arg Thr Gln Pro Thr Ser Lys
65 70 75 80

Asn Lys Leu Phe Phe Ile Lys Pro Pro Leu Phe Ile Ala Ala Ala Val
85 90 95

Ile Gly Thr Leu Thr Gly Leu Asp Asp Tyr Leu Tyr Ala Tyr Gly Val
100 105 110

Ala Arg Leu Pro Val Ser Thr Ser Ser Leu Ile Ile Ala Ser Gln Leu
115 120 125

Ala Phe Thr Ala Gly Phe Ala Phe Leu Leu Val Lys Gln Lys Phe Thr
130 135 140

Ser Tyr Ser Ile Asn Ala Val Phe Leu Leu Thr Ile Gly Ala Gly Val
145 150 155 160

Leu Ala Leu His Thr Ser Gly Asp Arg Pro Ala Asn Glu Ser Asn Arg
165 170 175

Glu Tyr Val Leu Gly Phe Leu Met Thr Leu Ala Ala Ser Ala Leu Tyr
180 185 190

Gly Phe Ile Leu Pro Leu Val Glu Leu Met Tyr Lys Lys Ala Asn Gln
195 200 205

Glu Ile Ser Tyr Ala Leu Val Met Glu Ile Gln Met Val Met Cys Leu
210 215 220

Ser Ala Thr Gly Phe Cys Thr Val Gly Met Leu Val Asn Lys Asp Phe
225 230 235 240

Lys Val Ile Pro Arg Glu Ala Arg Glu Phe Glu Leu Gly Glu Thr Lys
245 250 255

Tyr Tyr Val Val Ala Ile Trp Ser Ala Ile Ile Trp Gln Cys Phe Phe
260 265 270

Leu Gly Ala Ile Gly Val Ile Phe Cys Ala Ser Ser Leu Leu Ser Gly
275 280 285

Ile Ile Ile Ala Val Leu Leu Pro Val Thr Glu Ile Leu Ala Val Ile
290 295 300

Phe Tyr Lys Glu Lys Phe Gln Ala Glu Lys Gly Val Ala Leu Ala Leu
305 310 315 320

Ser Leu Trp Gly Phe Ile Ser Tyr Phe Tyr Gly Glu Ile Lys Gln Ile
325 330 335

Lys Lys Lys Lys Pro Ala Pro Glu Thr Glu Met Pro Ser Val Pro Asn 340 345 350

Ser Val Glu Ser Val
355

<210> SEQ ID NO 123
<211> LENGTH: 1074
<212> TYPE: DNA
<213> ORGANISM: Durio zibethinus

<400> SEQUENCE: 123
atggaagtcg tcaaagaaca caagccaggt actactatga gaaagtcttt gttggttatc 60
aactgcatca tcttgtccat tggtaattgt ggtggtccat tattgatgag gttgtacttt 120
attcacggtg gtaagagagt ttggttctct tcttggttgg aaactggtgg ttggccaatt 180
atcttgtttc caattgcttg tgcctacatg catagatcta gaactcaacc tacttccaag 240
aacaagctgt ttttcattaa gccacctttg ttcattgctg ctgctgttat tggtactttg 300
actggtttgg atgattactt gtatgcttac ggtgttgcta gattgccagt ttctacttcc 360
tctttgatta tcgcttctca attggctttt actgctggtt ttgctttctt gttggtcaag 420
caaaagttca cctcctactc tattaacgcc gtttttttgt tgactattgg tgctggtgtt 480
ttggccttgc atacttctgg tgatagacca gctaatgaat ccaacagaga atacgttttg 540
ggtttcttga tgactttggc tgcttctgca ttatacggtt tcattttgcc attggtcgag 600
ctgatgtaca agaaggctaa tcaagaaatc tcctacgcct tggttatgga aatccaaatg 660
gttatgtgtt tgtctgctac tggtttctgt actgttggta tgttggttaa caaggacttc 720
aaggttattc caagagaagc cagggaattt gaattgggtg aaactaagta ttacgttgtc 780
gctatttggt ccgccattat ttggcaatgt tttttcttgg gtgctatcgg tgttattttc 840
tgcgcttctt ctttgttgtc cggtattatc attgctgttt tgttgccagt taccgaaatt 900
ttggctgtca tcttctacaa agaaaagttc caagctgaaa agggtgttgc tttggctttg 960
tctttgtggg gttttatctc ttacttctac ggtgaaatca agcagatcaa gaaaaagaaa 1020
ccagctccag aaactgaaat gccatctgtt ccaaattccg ttgaatccgt ttga 1074

<210> SEQ ID NO 124
<211> LENGTH: 359
<212> TYPE: PRT
<213> ORGANISM: Olea europaea var. sylvestris

<400> SEQUENCE: 124

Met Asp Thr Ala Asn Thr Glu Thr Gln Thr Asn Thr Gly Met Lys Lys
1 5 10 15

Ala Leu Leu Gly Leu Asn Cys Ile Ile Leu Ala Ile Gly Asn Cys Gly
20 25 30

Gly Pro Leu Val Met Arg Leu Tyr Phe Ile Arg Gly Gly Lys Arg Ile
35 40 45

Trp Phe Ser Ser Trp Leu Gln Thr Val Gly Trp Pro Ile Ile Phe Ile
50 55 60

Pro Leu Thr Ile Ala Tyr Ile His Arg Arg Lys Thr Gly Gly Ser Thr
65 70 75 80

Thr Lys Thr Gln Phe Phe Leu Met Lys Pro Arg Leu Phe Ile Ala Ser
85 90 95

Ala Thr Ile Gly Val Leu Thr Gly Leu Asp Asp Tyr Leu Thr Ala Tyr
100 105 110

Gly Val Ala Lys Leu Pro Val Ser Thr Ser Ser Leu Ile Ile Ala Thr

```
        115                 120                 125

Gln Leu Ala Phe Thr Ala Gly Phe Ala Phe Leu Leu Val Lys Gln Lys
    130                 135                 140

Phe Thr Gly Tyr Ser Ile Asn Ala Val Val Leu Leu Thr Val Gly Ala
145                 150                 155                 160

Val Ile Leu Gly Leu His Thr Ser Ser Asp Arg Pro Glu Gly Glu Ser
                165                 170                 175

Lys Lys Glu Tyr Leu Leu Gly Phe Phe Leu Ile Leu Val Ala Ser Ala
            180                 185                 190

Leu Tyr Gly Phe Ile Leu Pro Leu Val Glu Tyr Met Tyr Ser Lys Ala
        195                 200                 205

Lys Gln Ala Ile Thr Tyr Thr Leu Val Leu Glu Ile Gln Met Val Met
    210                 215                 220

Cys Phe Phe Ala Thr Ala Phe Cys Thr Val Gly Met Leu Ile Asn Asn
225                 230                 235                 240

Asp Phe Gln Ala Ile Ser Arg Glu Ala Glu Glu Tyr Glu Leu Gly Glu
                245                 250                 255

Asp Lys Tyr Tyr Leu Val Val Val Trp Asn Ala Ile Val Trp Gln Cys
            260                 265                 270

Phe Phe Leu Gly Ser Ile Gly Val Ile Phe Tyr Ser Ser Ser Leu Leu
        275                 280                 285

Ser Gly Ile Val Leu Thr Phe Leu Leu Pro Val Thr Glu Val Leu Ala
    290                 295                 300

Val Ile Phe Tyr His Glu Lys Phe Gln Ala Glu Lys Gly Val Ser Leu
305                 310                 315                 320

Phe Leu Ser Leu Trp Gly Phe Ile Ser Tyr Phe Tyr Gly Glu Ile Lys
                325                 330                 335

His Gly Thr Asn Lys Lys Asn Asp Lys His Asp Ser Ser Gln Thr Glu
            340                 345                 350

Met Thr Pro Thr Val Val Pro
        355
```

<210> SEQ ID NO 125
<211> LENGTH: 1080
<212> TYPE: DNA
<213> ORGANISM: Olea europaea var. sylvestris

<400> SEQUENCE: 125

```
atggataccg ctaacactga aacccaaact aatactggta tgaagaaggc tttgttgggt      60

ttgaactgca ttattttggc tattggtaat tgcggtggtc cattggttat gaggttgtac     120

tttattagag gtggtaagag gatctggttc tcttcttggt tgcaaactgt tggttggcca     180

attatcttca tcccattgac cattgcctac atccatagaa gaaaaactgg tggttctact     240

actaagaccc agttcttttt gatgaagccc aggttgttta ttgcttctgc tactattggt     300

gttttgaccg gtttggatga ttacttgact gcttatggtg ttgctaagtt gccagtttct     360

acctcctctt tgattattgc tactcaattg gctttcactg ctggttttgc tttcttgttg     420

gttaagcaaa agttcaccgg ttactccatt aacgctgttg ttttgttgac tgttggtgct     480

gttattttgg gcttgcatac ttcttcagat agaccagaag gtgagtccaa gaaagaatac     540

ttgttaggct tcttcttgat cttggtcgct tctgcattat acggtttcat tttgccattg     600

gtcgagtata tgtactccaa agctaagcaa gctattacct acaccttggt cttggaaatc     660

caaatggtta tgtgtttctt cgctactgct ttctgtactg ttggcatgtt gattaacaac     720
```

gacttccaag ccatttccag agaagctgaa gaatatgaac taggtgagga caagtactac 780
ttggttgttg tttggaatgc tatcgtttgg cagtgttttt tcttgggttc aatcggtgtt 840
atcttctact cctcatcttt gttgtctggt atcgttctga ctttttgtt gccagtcact 900 gaagttttgg ccgttatttt ctaccacgaa aagttccaag ctgaaaaggg tgtttctctg 960
tttttgtctt tgtggggttt catctcttac ttctacggtg aaatcaaaca tggcacgaac 1020
aagaagaatg acaagcacga ttcttctcaa actgaaatga ctccaactgt tgtcccatga 1080

<210> SEQ ID NO 126
<211> LENGTH: 341
<212> TYPE: PRT
<213> ORGANISM: Coffea eugenioides

<400> SEQUENCE: 126

Met Glu Lys Phe Leu Leu Thr Val Asn Cys Phe Leu Leu Ala Phe Gly
1 5 10 15

Thr Thr Gly Gly Pro Leu Ile Met Arg Leu Tyr Phe Ile His Gly Gly
20 25 30

Glu Arg Val Trp Leu Ser Ala Trp Leu Glu Thr Gly Gly Trp Pro Ile
35 40 45

Ile Ile Ile Pro Leu Met Ile Ala Tyr Phe His Arg Arg Lys Asn Gln
50 55 60

Glu Ser Asn Ala Lys Leu Ile Tyr Ile Thr Pro Lys Ile Phe Ile Ser
65 70 75 80

Phe Val Val Ile Gly Val Leu Thr Gly Val Asp Asp Phe Leu Tyr Ala
85 90 95

His Gly Val Ala Lys Leu Pro Val Ser Thr Tyr Ser Leu Leu Ile Ala
100 105 110

Thr Gln Leu Ala Phe Thr Ala Phe Phe Ala Phe Ile Leu Val Arg Gln
115 120 125

Lys Phe Thr Pro Tyr Ser Ile Asn Ala Val Ala Met Leu Thr Leu Gly
130 135 140

Ala Gly Val Leu Ala Met His Thr Ser Ser Asp Arg Pro Glu Gly Val
145 150 155 160

Thr Lys Arg Glu Tyr Tyr Val Gly Phe Phe Met Thr Leu Gly Ala Ser
165 170 175

Ala Leu Tyr Gly Phe Val Leu Pro Leu Ile Glu Leu Thr Tyr Met Lys
180 185 190

Ala Lys Asn Ala Ile Thr Tyr Thr Leu Val Leu Glu Ile Gln Leu Val
195 200 205

Met Cys Phe Phe Ala Thr Ala Phe Cys Thr Ala Gly Met Leu Val Asn
210 215 220

Lys Asp Phe Gln Ala Ile Ser Arg Glu Ala Lys Thr Tyr Glu Leu Gly
225 230 235 240

Glu Val Thr Phe Tyr Val Val Leu Val Trp Thr Ala Ile Ser Trp Gln
245 250 255

Cys Phe Phe Leu Gly Ala Ile Gly Leu Ile Phe Ser Ala Ser Ser Leu
260 265 270

Leu Ser Gly Ile Ile Ile Ala Val Met Leu Pro Leu Thr Glu Ile Leu
275 280 285

Ala Val Ile Phe Tyr His Glu Ser Phe Lys Val Glu Lys Ala Leu Ala
290 295 300

Leu Val Leu Ser Leu Trp Gly Phe Val Ser Tyr Phe Tyr Gly Glu Ile
305 310 315 320

```
Lys His Asn Lys Lys Lys Ser Ser Ala Lys Asp Gln Thr Asp Ile Ala
                325                 330                 335

Glu Phe Val Ala Pro
            340


<210> SEQ ID NO 127
<211> LENGTH: 1026
<212> TYPE: DNA
<213> ORGANISM: Coffea eugenioides

<400> SEQUENCE: 127

atggaaaagt tcctgttgac cgtcaactgt tttttgttgg cttttggtac tactggtggt     60

ccattgatca tgaggttgta ctttattcat ggtggtgaaa gagtttggtt gtctgcttgg    120

ttggaaactg gtggttggcc aattatcatt atcccattga tgattgccta cttccacagg    180

cgtaaaaatc aagaatctaa cgccaagttg atctacatca ccccaaagat tttcatctcc    240

ttcgttgtta ttggtgtttt gaccggtgtt gatgatttct tgtatgctca tggtgttgct    300

aagttgccag tttctactta ctctttgttg atcgctactc aattggcttt cactgctttc    360

ttcgctttca ttttggtcag acaaaagttc accccatact ccattaacgc tgttgctatg    420

ttgactttag gtgctggtgt tttagctatg catacctctt cagatagacc agaaggtgtt    480

actaagagag aatattacgt cggtttcttt atgaccttgg gtgcttctgc attatacggt    540

tttgttttgc cattgatcga gctgacttac atgaaggcta agaacgctat tacttacacc    600

ttggtcttgg aaatccaact ggttatgtgt tttttcgcta ccgctttctg tactgctggt    660

atgttggtta acaaggactt ccaagctatt tccagagaag ctaagactta cgaattgggt    720

gaagttacct tctacgttgt tttggtttgg actgctattt cttggcaatg tttctttttg    780

ggtgccatcg gtttgatttt ctctgcttct tctttgttgt ccggtatcat tattgctgtc    840

atgttgcctt tgaccgaaat tttggctgtt atcttctacc acgaatcctt caaagttgaa    900

aaggctttgg ctttggtttt gtctttgtgg ggtttcgttt cttacttcta cggtgaaatc    960

aagcacaaca agaaaaagtc ctctgctaag gaccaaaccg atattgctga atttgttgct   1020

ccataa                                                              1026


<210> SEQ ID NO 128
<211> LENGTH: 397
<212> TYPE: PRT
<213> ORGANISM: Papaver somniferum

<400> SEQUENCE: 128

Met Lys Ser Ile Val Glu Asn Asp Gln Ser Asn Met Lys Gly Gly Val
1               5                   10                  15

Leu Val Ser Ser Asn Ser His Glu His His His His Gln Glu Glu Asp
            20                  25                  30

Asn Lys Lys Lys Lys Lys Met Lys Leu Val Ile Leu Ile Val Asn Cys
        35                  40                  45

Ile Phe Leu Ser Val Ala Gln Ile Thr Gly Pro Leu Leu Leu Arg Val
    50                  55                  60

Tyr Tyr Leu His Gly Gly Gln Arg Lys Trp Leu Ser Ser Trp Leu Gln
65                  70                  75                  80

Thr Val Ala Phe Pro Phe Leu Leu Ile Pro Ile Ser Val Ser Trp Phe
                85                  90                  95

Lys Ser Lys Ser Lys Ser His Asp Ser Arg Ser Ile Ser Ala Ile Asp
            100                 105                 110
```

Val Asn Pro Thr Thr Asp Arg Lys Leu Arg Phe Gly Gly Phe Ser Pro
        115                 120                 125

Lys Leu Phe Ile Ser Cys Ile Phe Leu Gly Ile Ile Val Gly Leu Asp
    130                 135                 140

Ser Phe Leu Tyr Ala Tyr Gly Val Ser Tyr Leu Pro Val Ser Thr Ser
145                 150                 155                 160

Ser Leu Leu Met Ser Thr Gln Leu Ala Phe Thr Ala Ala Phe Ala Leu
                165                 170                 175

Leu Leu Val Arg Gln Lys Phe Thr Pro Tyr Ser Ile Asn Ser Val Val
            180                 185                 190

Leu Leu Thr Leu Gly Ala Val Val Leu Ala Phe His Thr Asn Gly Asp
        195                 200                 205

Lys Pro Ile Gly Val Ser Lys Asp Gln Tyr Phe Leu Gly Phe Phe Val
    210                 215                 220

Thr Leu Gly Ala Ala Ala Leu Phe Gly Phe Met Leu Pro Phe Ile Glu
225                 230                 235                 240

Leu Val Tyr Arg Lys Ala Cys Glu Ala Val Thr Tyr Asp Leu Val Met
                245                 250                 255

Arg Met Gln Phe Ile Ile Ser Met Val Ala Thr Val Phe Cys Thr Ile
            260                 265                 270

Ala Met Leu Ile Asn Lys Asp Phe Gln Ala Ile Ser Arg Glu Ala Lys
        275                 280                 285

Gly Phe Glu Leu Gly Glu Thr Lys Tyr Tyr Ile Val Leu Ile Phe Thr
    290                 295                 300

Ala Val Ser Met Gln Cys Ala Val Val Gly Thr Leu Gly Val Ile His
305                 310                 315                 320

Cys Ala Ser Ser Leu Phe Ser Gly Val Leu Met Thr Leu Leu Leu Pro
                325                 330                 335

Ile Gln Gln Ile Cys Ala Ile Phe Phe Phe Asn Glu Lys Phe Ser Ala
            340                 345                 350

Glu Lys Gly Met Ser Leu Gly Leu Ser Ile Trp Gly Phe Ala Ser Tyr
        355                 360                 365

Phe Tyr Gly Glu Tyr Lys Gln Thr Lys Lys Lys Thr Asn Gln His Lys
    370                 375                 380

Ala Val Pro Ile Asn Ser Gln Glu Ile Pro Asp Glu Val
385                 390                 395

<210> SEQ ID NO 129
<211> LENGTH: 1194
<212> TYPE: DNA
<213> ORGANISM: Papaver somniferum

<400> SEQUENCE: 129
atgaagtcca tcgtcgaaaa cgaccagtct aatatgaaag gtggtgtctt ggtttcctcc 60
aactctcatg aacatcatca tcaccaagaa gaggacaaca aaaagaaaaa gaagatgaag 120
ctggtcatcc tgatcgttaa ctgcattttt ttgtccgttg ctcaaattac cggtcctttg 180
ttgttgagag tttactactt gcatggtggt caaagaaagt ggttgtcatc ttggttgcaa 240
actgttgctt ttcccttctt gttgatccca atttccgttt cctggttcaa gtccaaatct 300
aagtctcacg attccagatc catttccgct attgatgtta acccaactac cgacagaaag 360
ttgagatttg gtggtttttc acccaagttg ttcatcagct gtattttctt gggtatcatc 420
gtcggtttgg actcattctt gtatgcttat ggtgtttcct acttgccagt ttctacttcc 480

```
tctttgttga tgtctactca attggctttt actgctgctt tcgccttgtt gttggttaga    540

caaaagttta ccccatactc catcaactcc gttgttttgt tgactttggg tgctgttgtt    600

ttggcttttc ataccaatgg tgataagcca atcggtgttt ctaaggacca atactttttg    660

ggtttcttcg ttactttagg tgctgcagct ttgtttggtt ttatgttgcc attcatcgag    720

ctggtttaca gaaaagcttg tgaagctgtt acctacgatt tggttatgag aatgcagttc    780

atcatctcta tggttgctac tgttttctgc accattgcca tgttgattaa caaggatttc    840

caagccattt ccagagaagc taagggtttt gaattaggcg aaacgaagta ctacatcgtc    900

ttgattttta ccgccgtttc tatgcaatgt gcagttgttg gtacattggg tgttattcat    960

tgtgcctcat ctttgttctc tggtgttttg atgaccctgt tgttgccaat tcaacaaatt   1020

tgcgctatct tcttcttcaa cgaaaaattc tctgccgaga agggtatgtc tttgggtttg   1080

tctatttggg gttttgcctc ttacttttac ggtgagtaca agcagactaa gaagaaaact   1140

aatcaacaca aggccgtgcc aatcaactct caagaaattc cagatgaagt ctaa         1194


<210> SEQ ID NO 130
<211> LENGTH: 351
<212> TYPE: PRT
<213> ORGANISM: Papaver miyabeanum

<400> SEQUENCE: 130

Met Glu Lys Tyr Leu Leu Leu Phe Asn Cys Ile Leu Leu Ala Val Gly
1               5                   10                  15

Ser Thr Ala Gly Pro Leu Leu Leu Arg Leu Tyr Phe Ile His Gly Gly
            20                  25                  30

Lys Arg Leu Trp Leu Ser Ser Trp Leu Glu Thr Ala Gly Trp Pro Ile
        35                  40                  45

Leu Phe Leu Pro Leu Ser Leu Ser Tyr Phe Leu Lys Arg Arg Arg Phe
    50                  55                  60

Lys Thr Gly Gln Asp Glu Lys Pro Ser Lys Phe Phe Met Ile Thr Pro
65                  70                  75                  80

Phe Leu Phe Met Ala Ser Ala Phe Ile Gly Ile Leu Val Gly Leu Asp
                85                  90                  95

Asp Tyr Leu Tyr Thr Tyr Gly Val Ser Leu Leu Pro Val Ser Thr Ser
            100                 105                 110

Ala Leu Ile Met Ser Thr His Leu Ala Phe Thr Ala Gly Phe Ala Leu
        115                 120                 125

Phe Met Val Lys Gln Lys Phe Thr Ser Tyr Ser Val Asn Ala Val Val
    130                 135                 140

Leu Leu Thr Val Gly Ala Ile Leu Leu Gly Leu His Ser Asn Gly Asp
145                 150                 155                 160

Arg Pro Leu Tyr Glu Ser Asn Arg Asp Tyr Tyr Leu Gly Phe Val Met
                165                 170                 175

Thr Ile Gly Ala Ser Val Ile Gly Gly Leu Leu Thr Pro Leu Val Glu
            180                 185                 190

Leu Met Tyr Lys Lys Ser Lys Gln Thr Ile Thr Tyr Thr Leu Val Ile
        195                 200                 205

Glu Leu Gln Ile Val Met Ser Val Phe Ala Thr Leu Phe Cys Thr Val
    210                 215                 220

Gly Met Leu Val Asn Asn Asp Phe Lys Val Ile Gln Arg Glu Gly Lys
225                 230                 235                 240

Glu Tyr Asp Leu Gly Glu Thr Lys Tyr Tyr Val Val Leu Val Ala Ser
                245                 250                 255
```

Ser Ile Thr Trp Gln Leu Cys Phe Leu Gly Ile Val Gly Val Val Phe
260 265 270

Cys Ser Thr Ser Leu Leu Ala Gly Val Ile Gly Ala Val Val Val Pro
275 280 285

Val Ile Glu Ile Leu Gly Val Ile Phe Tyr His Glu Ser Phe Lys Ala
290 295 300

Glu Lys Gly Ile Ala Leu Phe Leu Ser Leu Trp Gly Phe Ile Ser Tyr
305 310 315 320

Phe Tyr Leu Glu Leu Lys Glu Ile Lys Lys Pro Lys Asn His His Ser
325 330 335

Glu Leu Glu Glu Asp Leu Thr Val Ser Ser Gln Ser Asn Leu Ala
340 345 350

<210> SEQ ID NO 131
<211> LENGTH: 1056
<212> TYPE: DNA
<213> ORGANISM: Papaver miyabeanum

<400> SEQUENCE: 131
atggaaaagt acctgctgct gttcaactgc attttgttgg ctgttggttc tactgctggt 60
cctttgttgt tgaggttgta ctttattcat ggtggtaaga ggttgtggtt gtcatcttgg 120
ttggaaactg ctggttggcc aattttgttt ttgccattgt ccttgtccta ctttctgaag 180
agaagaagat tcaagactgg tcaagacgaa aagccatcta agttcttcat gattacccct 240
ttcttgttca tggcttctgc cttcattggt attttggttg gtttggatga ttacttgtac 300
acctacggtg tttctttgtt gccagtttct acttccgctt tgattatgtc tactcatttg 360
gcttttaccg ctggttttgc tttgtttatg gtcaagcaaa agttcacctc ctactctgtt 420
aatgccgttg ttttgttaac cgttggtgct atcttgttgg gcttgcattc taatggtgat 480
agaccactgt acgaatccaa cagagattac tacttgggtt tcgttatgac tattggtgcc 540
tctgttattg gtggtttgtt gactccattg gtcgaattga tgtacaagaa gtccaagcaa 600
actatcacct acaccttggt tatcgaattg caaatcgtca tgtctgtttt cgctactttg 660
ttctgtactg ttggtatgtt ggtcaacaac gatttcaagg tcattcagcg tgaaggtaaa 720
gaatacgatt tgggtgaaac taagtactac gttgtcttgg ttgcttcttc tattacctgg 780
caattgtgtt tcttgggtat cgttggtgtt gttttctgtt ctacctcttt gttggccggt 840
gttataggtg ctgttgttgt tccagttatt gaaatcttgg gtgtcatctt ctaccacgaa 900
tcttttaaag ccgaaaaggg tattgccctg tttttgtctt tgtggggttt catctcttac 960
ttctacttgg agttgaaaga gatcaagaag ccaaagaacc atcactccga attggaagaa 1020
gatctgactg tttcttccca atctaacttg gcttga 1056

<210> SEQ ID NO 132
<211> LENGTH: 382
<212> TYPE: PRT
<213> ORGANISM: Papaver bracteatum

<400> SEQUENCE: 132

Met Asn Ile Glu Thr Leu Asp Ile Leu Gly Pro Asn Gln Asn Gly Asn
1 5 10 15

Ser Gly Thr His Thr Glu Gln Pro Ile Lys Thr Arg Asn Trp Leu Leu
20 25 30

Ile Ile Ile Asn Cys Ala Leu Val Phe Cys Gly Val Ile Gly Gly Pro
35 40 45

```
Leu Leu Met Arg Leu Tyr Tyr Leu His Gly Gly Ser Arg Lys Trp Leu
    50                  55                  60

Ser Ser Phe Leu Gln Thr Ala Gly Phe Pro Val Leu Ile Phe Pro Leu
65                  70                  75                  80

Ile Phe Leu Tyr Ile Lys Ser Asn Ser Pro Thr Gln Asn Asn Asp Gln
                85                  90                  95

Ser Phe Ser Phe Phe Met Glu Pro Lys Leu Phe Leu Trp Ser Ala Ile
            100                 105                 110

Val Gly Ile Val Phe Gly Val Ser Asn Phe Met Tyr Ala Leu Gly Leu
        115                 120                 125

Ser Tyr Leu Pro Val Ser Thr Ser Thr Ile Leu Phe Ala Thr Gln Leu
    130                 135                 140

Cys Phe Thr Ala Phe Phe Ala Trp Leu Ile Val Lys Gln Glu Phe Thr
145                 150                 155                 160

Ala Phe Ile Ile Asn Ala Val Ile Val Met Thr Leu Gly Ser Val Leu
                165                 170                 175

Leu Gly Ile Asn Thr Asn Gly Asp Arg Pro Ile Gly Val Ser Lys Ala
            180                 185                 190

Gln Tyr Leu Ile Gly Phe Leu Met Thr Leu Ala Ala Ala Ala Leu Thr
        195                 200                 205

Gly Leu Gly Thr Pro Phe Ile Glu Leu Ala Phe Phe Lys Ala Thr Arg
    210                 215                 220

Asn Ile Thr Tyr Ser Thr Phe Leu Gln Phe Gln Ile Thr Leu Gly Leu
225                 230                 235                 240

Phe Gly Thr Cys Leu Asn Val Ile Gly Met Leu Ile Asn Lys Asp Phe
                245                 250                 255

Gln Ala Ile Pro Arg Glu Ala Asp Asn Phe Glu Leu Gly Lys Gly Lys
            260                 265                 270

Tyr Tyr Met Ile Ile Cys Leu Thr Ala Leu Thr Trp Gln Leu Ser Gly
        275                 280                 285

Ile Gly Leu Ile Gly Leu Ile Phe Tyr Thr Asn Ala Leu Phe Asn Gly
    290                 295                 300

Ile Tyr Val Ser Val Leu Val Pro Phe Thr Glu Val Ala Ala Val Ile
305                 310                 315                 320

Phe Tyr His Glu Lys Phe Thr Gly Leu Lys Gly Met Ala Leu Ala Leu
                325                 330                 335

Cys Leu Trp Gly Phe Ser Ser Tyr Phe Tyr Gly Glu Tyr Lys Met Met
            340                 345                 350

Asn Lys Val Gly Asp Asn Asp Asn Glu Thr His Glu Lys Ile Gln Glu
        355                 360                 365

Val Glu Ser Asp Pro Lys Arg Leu Glu Asp Gln Glu Ala Pro
    370                 375                 380
```

<210> SEQ ID NO 133
<211> LENGTH: 1149
<212> TYPE: DNA
<213> ORGANISM: Papaver bracteatum

<400> SEQUENCE: 133

```
atgaacatcg aaaccttgga catcttgggt ccaaatcaaa atggtaactc tggtactcat      60

accgaacaac ctattaagac tagaaactgg ctgctgatta ttatcaactg cgctttggtt     120

ttctgcggtg ttattggtgg tccattattg atgaggttgt actacttgca tggtggttct     180

agaaaatggt tgtcctcttt cttgcaaact gctggttttc cagttctgat tttccctttg     240
```

```
atcttcctgt acatcaagtc caattctcca actcaaaaca acgaccagtc tttctcattt    300

ttcatggaac ccaagttgtt cttgtggtct gctatagttg gtatcgtttt cggtgtttcc    360

aatttcatgt atgccttggg tttgtcttac ttgccagttt ccacttccac tattttgttc    420

gctactcaat tgtgtttcac cgcttttttt gcttggttga tcgtcaagca agaattcact    480

gccttcatta ttaacgccgt tatcgttatg actttgggct ctgttttgtt gggtattaac    540

actaatggtg acagacctat tggtgtttct aaggcccaat acttgattgg tttcttgatg    600

actttagctg ctgctgcttt gactggtttg ggtactcctt ttattgaatt ggctttcttc    660

aaggccacca gaaacattac ttactccaca ttcttgcaat tccagattac cttgggtctg    720

tttggtactt gcttgaacgt tattggcatg ctgatcaaca aggatttcca agctattcca    780

agagaagccg acaatttcga attaggtaaa ggcaagtact acatgatcat ttgcttgaca    840

gctttgactt ggcaattgtc cggtattggt ttaattggct tgatcttcta caccaacgct    900

ttgtttaatg gcatctacgt ttctgttttg gtcccattca ctgaagttgc tgctgttatt    960

ttctaccacg aaaagttcac tggtttgaaa ggtatggctt tggctttgtg tttgtggggt   1020

ttttcttctt acttttacgg cgagtacaag atgatgaaca aggttggtga taacgacaac   1080

gaaactcacg aaaagatcca agaagttgaa tccgatccaa agagattgga ggatcaagaa   1140

gctccataa                                                            1149
```

<210> SEQ ID NO 134
<211> LENGTH: 386
<212> TYPE: PRT
<213> ORGANISM: Papaver somniferum

<400> SEQUENCE: 134

```
Met Ser Ala Leu His Ile Gln Met Met Glu Glu Gly Val Leu Ser Pro
1               5                   10                  15

Glu Ile Lys Pro Ser Thr Pro Ser Lys Asn Ile Lys Leu Ser Asp Gly
            20                  25                  30

Ile His Gly Asp Asp Gly Gly Asp Leu Lys Leu Lys Met Asn Lys Gln
        35                  40                  45

Ser Ile Met Glu Lys Trp Gly Leu Leu Val Leu Tyr Cys Ile Phe Ala
    50                  55                  60

Ala Val Gly Phe Ile Gly Gly Pro Leu Leu Leu Arg Val Tyr Phe Leu
65                  70                  75                  80

His Gly Gly Ser Arg Lys Trp Leu Ser Ser Ala Leu Gln Thr Ala Gly
                85                  90                  95

Phe Pro Ile Leu Leu Met Pro Leu Ala Ile His Tyr Ala Lys Arg Asp
            100                 105                 110

Lys Ala Val Pro Gln Ile Asp Phe Phe Ala Ser Pro Lys Leu Leu Leu
        115                 120                 125

Ser Ser Ile Phe Ile Gly Ile Leu Leu Gly Val Ser Asn Phe Met Tyr
    130                 135                 140

Ser Tyr Gly Leu Ser Phe Leu Pro Val Ser Thr Ser Ser Ile Leu Leu
145                 150                 155                 160

Ser Thr Asn Leu Ile Phe Thr Ala Leu Phe Ala Leu Ile Leu Val Arg
                165                 170                 175

Gln Lys Phe Ser Pro Phe Ser Ile Asn Ala Ile Val Ile Met Thr Leu
            180                 185                 190

Gly Ser Val Leu Leu Gly Val Gly Gln Asn Gly Asp Arg Pro Glu Gly
        195                 200                 205
```

```
Val Thr Ser Leu Gln Tyr Leu Leu Gly Phe Ile Leu Cys Ile Gly Ala
    210                 215                 220

Ala Ala Ser Gly Gly Leu Ala Leu Pro Cys Ile Glu Val Ala Tyr Thr
225                 230                 235                 240

Lys Ala Asn Gln Val Met Thr Tyr Pro Ile Val Leu Gln Tyr Gln Phe
                245                 250                 255

Phe Met Ala Leu Ser Ala Thr Val Phe Ser Ile Ile Gly Met Ala Val
            260                 265                 270

Asn Lys Asp Phe Gln Ala Met Gln Arg Glu Ala Asp Glu Phe Gly Leu
        275                 280                 285

Gly Lys Met Glu Tyr Tyr Leu Val Leu Val Ser Ser Ala Val Val Trp
    290                 295                 300

Gln Ile Ser Tyr Ile Gly Thr Leu Gly Ile Ile Phe Tyr Ala Thr Ser
305                 310                 315                 320

Ile Phe Ala Gly Val Val Ser Ala Val Leu Leu Pro Leu Thr Glu Ile
                325                 330                 335

Ala Ala Val Ile Val Phe His Glu Lys Phe Thr Gly Glu Lys Gly Met
            340                 345                 350

Ala Leu Ala Met Ser Val Trp Gly Phe Leu Ser Tyr Phe Tyr Gly Thr
        355                 360                 365

Tyr Lys Glu Ser Lys Val Gln Thr Gln Ile Asp Ser Thr Lys Asn Gln
    370                 375                 380

Pro Lys
385


<210> SEQ ID NO 135
<211> LENGTH: 1161
<212> TYPE: DNA
<213> ORGANISM: Papaver somniferum

<400> SEQUENCE: 135

atgtccgcct tgcatatcca gatgatggaa gaaggtgttt tgtctccaga aatcaaacca     60

tctactccct ccaagaacat caaattgtct gatggtattc acggtgatga tggtggtgat    120

ttgaaactga aaatgaacaa gcagtccatc atggaaaaat ggggtttgtt ggtcttgtac    180

tgtatttttg ctgccgttgg ttttattggt ggtcctttgt tgttgagagt ttacttcttg    240

catggtggtt ccagaaaatg gttgtcatct gctttacaaa ctgctggttt cccaattttg    300

ttgatgccat tggctattca ttacgccaaa agagataagg ccgttccaca aattgatttc    360

tttgcttctc caaagctgct gctgtcctct attttcattg gtattttgtt gggcgtgtcc    420

aacttcatgt attcttacgg tttgtctttc ttgccagtct ccacttcttc tatcttgttg    480

tctaccaact tgattttcac cgctttgttc gccttgattt tggtcagaca aaagttctct    540

ccattctcca ttaacgccat cgttattatg actttgggtt ccgttttgtt aggtgttggt    600

caaaatggtg atagacctga aggtgttact tccttgcaat atttgttggg tttcatcttg    660

tgtattggtg ctgctgcttc tggtggtttg gctttgccat gtattgaagt tgcttacacc    720

aaggccaatc aagttatgac ttatccaatc gtcttgcagt accaattctt catggctttg    780

tctgctaccg ttttctctat tattggtatg gccgttaaca aggatttcca agctatgcaa    840

agagaagctg acgaatttgg tttgggtaag atggaatatt acctggtctt ggtttcttct    900

gctgttgttt ggcaaatttc ctacattggt actttgggca ttattttcta cgccacttct    960

attttcgctg gtgttgtttc agctgttttg ttgccattga ctgaaattgc tgctgttatc   1020
```

gttttccacg aaaagttcac tggtgaaaaa ggtatggctt tggctatgtc tgtttggggt 1080
tttttgtctt acttctacgg cacctacaaa gaatctaagg ttcaaaccca aatcgactct 1140
accaagaatc aacctaagta a 1161

<210> SEQ ID NO 136
<211> LENGTH: 360
<212> TYPE: PRT
<213> ORGANISM: Aquilegia coerulea

<400> SEQUENCE: 136

Met Ala Thr Asn Met His Gly Leu Glu Asn Gly Ile Gln Glu Asn Gln
1 5 10 15

Gln Asn Lys Gln Ser Ala Glu Ser Ser Lys Met Ser Leu Phe Ile Ala
20 25 30

Lys Trp Trp Leu Leu Phe Leu Asn Phe Ala Cys Cys Ala Val Gly Thr
35 40 45

Ile Gly Gly Pro Leu Leu Leu Arg Leu Tyr Tyr Leu His Gly Gly Ser
50 55 60

Arg Lys Trp Ile Pro Gly Trp Leu Gln Thr Val Gly Phe Pro Ile His
65 70 75 80

Leu Ile Pro Ile Leu Ile Leu Tyr Ser Arg Arg Ser Pro Gly Val Lys
85 90 95

Phe Phe Ala Ser Pro Lys Leu Leu Leu Cys Ala Ala Val Ile Gly Val
100 105 110

Phe Thr Gly Leu Asp Asn Phe Met Tyr Ser Leu Gly Leu Ser Tyr Leu
115 120 125

Pro Val Ser Thr Ser Ser Leu Leu Leu Ala Thr Gln Leu Val Phe Thr
130 135 140

Ala Phe Phe Ser Phe Ile Ile Ala Arg Gln Lys Phe Thr Pro Phe Ser
145 150 155 160

Ile Asn Ala Val Val Leu Met Thr Leu Gly Ala Val Met Leu Gly Leu
165 170 175

Arg Asn Asn Gly Asp Arg Pro Gln Gly Val Thr Ser Ser Glu Tyr Met
180 185 190

Leu Gly Tyr Ile Leu Thr Ile Ala Ala Ala Gly Leu Leu Gly Phe Val
195 200 205

Leu Pro Val Thr Glu Val Thr Tyr Ala Lys Ala Thr His Ser Ile Thr
210 215 220

Tyr Ala Ile Val Leu Gln Phe Gln Phe Cys Thr Ala Leu Phe Ala Thr
225 230 235 240

Ile Phe Cys Ser Ile Gly Met Ile Ala Asn Lys Asp Phe Gln Ala Ile
245 250 255

Pro Arg Glu Ala Thr Gln Phe Asp Leu Gly Ala Gly Lys Tyr Tyr Leu
260 265 270

Leu Leu Ala Ser Ser Ala Val Val Trp Gln Leu Met Phe Leu Gly Ile
275 280 285

Met Gly Thr Ile Phe Cys Thr Ser Ser Leu Phe Ala Gly Ile Met Asn
290 295 300

Ala Thr Leu Leu Pro Phe Thr Gln Ile Ala Gly Val Ile Val Tyr Lys
305 310 315 320

Glu Lys Phe Thr Gly Glu Lys Gly Met Ala Leu Ala Leu Ser Leu Trp
325 330 335

Gly Phe Ala Ser Tyr Phe Tyr Gly Ala Tyr Arg Asp Asn Lys Lys Gln
340 345 350

Thr Gln Lys Glu Val Glu Glu Lys
355 360

<210> SEQ ID NO 137
<211> LENGTH: 1083
<212> TYPE: DNA
<213> ORGANISM: Aquilegia coerulea

<400> SEQUENCE: 137
atggccacta acatgcacgg tttggaaaac ggtattcaag aaaaccagca aaacaagcaa 60
tccgccgaat cttctaagat gtctttgttt attgctaagt ggtggctgct gtttttgaac 120
tttgcttgtt gtgcagttgg tactattggt ggtcctttgt tgttgaggtt gtattacttg 180
catggtggtt ccagaaaatg gattccaggt tggttgcaaa ctgttggttt tccaattcat 240
ctgatcccca tcttgatcct gtattctaga agatctccag gtgttaagtt tttcgcttct 300
ccaaagttgt tgttgtgcgc tgctgttatt ggtgttttta ctggtttgga caacttcatg 360
tacagcttgg gtttgtctta tttgccagtt tctacctcct ctttgttatt ggctactcaa 420
ttggttttta ccgccttctt ctcattcatt atcgccagac aaaagttcac cccattctct 480
attaacgccg ttgttttgat gactttgggt gctgttatgt tgggtttgag aaacaatggt 540
gatagacctc aaggtgttac ttcttctgag tacatgttag gttacatctt gactattgct 600
gctgctggtt tgttaggttt tgttttgcct gttactgaag ttacctacgc taaagctact 660
cattccatta cttacgccat tgtcttgcaa ttccaattct gtactgcttt gttcgctacc 720
atcttctgtt ccattggtat gattgctaac aaggacttcc aagccattcc aagagaagct 780
acacaatttg acttaggtgc tggtaagtac tacttgttgt tggcttcttc tgctgttgtt 840
tggcaattga tgttcttggg tattatgggt actatcttct gcacctcttc tttattcgct 900
ggtattatga acgctacctt gttgccattc actcaaattg ctggtgttat cgtctacaaa 960
gaaaagttta ccggtgaaaa aggtatggct ttggctttgt ctttatgggg ttttgcttct 1020
tacttttacg gtgcctacag agacaacaaa aagcaaactc aaaaagaggt cgaagagaag 1080
taa 1083

<210> SEQ ID NO 138
<211> LENGTH: 372
<212> TYPE: PRT
<213> ORGANISM: Papaver somniferum

<400> SEQUENCE: 138

Met Asp Thr Ser Thr Met Asn Ile Glu Thr Pro Glu Thr Leu Gly Pro
1 5 10 15

Asn Gln Asn His Val Glu Glu Thr Arg Lys Ala Arg Asn Trp Pro Leu
20 25 30

Ile Ile Ile Asn Cys Ala Leu Val Phe Cys Gly Val Ile Gly Gly Pro
35 40 45

Leu Leu Met Arg Leu Tyr Tyr Leu His Gly Gly Ser Arg Lys Trp Leu
50 55 60

Ser Ser Cys Leu Gln Thr Ala Gly Phe Pro Val Leu Leu Phe Pro Leu
65 70 75 80

Ile Phe Leu Tyr Ile Lys Ser Lys Pro Ser Met Gln Lys Asn Asp Gln
85 90 95

Ser Cys Ser Phe Phe Met Glu Pro Met Val Phe Val Trp Ser Ala Ile
100 105 110

```
Ile Gly Ile Val Phe Gly Val Ser Asn Phe Met Tyr Ala Leu Gly Leu
        115                 120                 125

Ser Tyr Leu Pro Val Ser Thr Ser Ile Ile Leu Phe Ala Thr Gln Leu
    130                 135                 140

Cys Phe Thr Ala Phe Phe Ala Trp Leu Ile Val Lys Gln Lys Phe Thr
145                 150                 155                 160

Ala Phe Ile Ile Asn Ala Val Ile Val Met Thr Leu Gly Ser Val Leu
                165                 170                 175

Leu Gly Ile Asn Thr Asp Gly Asp Arg Pro Ile Gly Val Ser Lys Ala
            180                 185                 190

Gln Tyr Leu Leu Gly Phe Leu Leu Thr Leu Ala Ala Ala Ala Leu Thr
        195                 200                 205

Gly Leu Gly Met Pro Phe Val Glu Leu Ala Leu Ser Lys Ala Thr Arg
    210                 215                 220

Asn Ile Thr Tyr Ser Thr Leu Leu Gln Phe Gln Ile Ile Leu Gly Leu
225                 230                 235                 240

Phe Gly Thr Gly Leu Asn Val Ile Gly Met Leu Ile Asn Lys Asp Phe
                245                 250                 255

Gln Ala Ile Pro Arg Glu Ala Asp Glu Phe Glu Leu Gly Lys Gly Lys
            260                 265                 270

Tyr Tyr Met Ile Ile Ile Leu Thr Ala Leu Thr Trp Gln Leu Ala Ser
        275                 280                 285

Leu Gly Ser Leu Gly Ile Ile Leu Tyr Thr Asn Ala Leu Phe Asn Gly
    290                 295                 300

Ile Tyr Thr Ser Val Leu Val Pro Phe Thr Glu Val Gly Ala Val Ile
305                 310                 315                 320

Phe Phe His Glu Ser Phe Thr Gly Leu Lys Gly Met Ala Leu Ala Leu
                325                 330                 335

Cys Leu Trp Gly Phe Ser Ser Tyr Phe Tyr Gly Glu Tyr Lys Met Met
            340                 345                 350

Asn Lys Val Gly Asn Asn Asp Ser Thr His Glu Glu Thr Glu Lys Val
        355                 360                 365

Glu Asn Glu Thr
    370


<210> SEQ ID NO 139
<211> LENGTH: 1119
<212> TYPE: DNA
<213> ORGANISM: Papaver somniferum

<400> SEQUENCE: 139

atggacacct ccaccatgaa cattgaaact ccagaaactt tgggtccaaa ccagaatcat      60

gttgaagaaa ctagaaaggc tagaaactgg ccattgatta ttatcaactg cgctttggtt     120

ttctgcggtg ttattggtgg tccattattg atgaggttgt actacttgca tggtggttct     180

agaaaatggt tgtcatcttg tttacaaacc gctggttttc cagttttgtt gttcccattg     240

attttcttgt acatcaagag caagccatcc atgcaaaaga acgatcaatc ttgctcattc     300

ttcatggaac ctatggtttt tgtttggtcc gccattattg gtatcgtttt cggtgtttct     360

aacttcatgt atgccttggg tttgtcttac ttgccagttt ccacttccat tattttgttc     420

gctacccaat tgtgtttcac cgcttttttt gcttggttga tcgtcaagca aaagttcact     480

gccttcatta ttaacgccgt tatcgttatg actttgggct ctgttttgtt gggtattaac     540

actgatggtg atagacctat tggtgtctct aaagctcaat acttgttggg tttcttgttg     600
```

```
actttggctg ctgctgcttt gactggtttg ggtatgccat ttgttgaatt ggctttgtct    660

aaggccacta gaaacattac ttactccacc ttgttgcagt tccaaattat cttgggttta    720

ttcggtactg gcttgaacgt tataggcatg ttgattaaca aggacttcca agccattcca    780

agagaagctg acgaatttga attaggtaaa ggcaagtact acatgatcat tatcttgacc    840

gctttgactt ggcaattggc ttctttgggt tctttaggta ttatcttgta caccaacgct    900

ctgttcaatg gtatctacac ttctgttttg gttccattca ctgaagttgg tgccgttatt    960

ttcttccatg aatctttcac aggtttgaaa ggtatggctt tggctttatg tttgtggggt   1020

ttttcctctt actttttacgg tgagtacaag atgatgaaca aggttggtaa caacgattct   1080

actcacgaag aaaccgaaaa ggttgaaaac gaaacctaa                          1119
```

<210> SEQ ID NO 140
<211> LENGTH: 373
<212> TYPE: PRT
<213> ORGANISM: Fragaria vesca subsp. vesca

<400> SEQUENCE: 140

```
Met Gln Met Glu Thr Thr Asp Asn Glu Gln Arg Lys Ala Ala Ala Leu
1               5                   10                  15

Lys Arg Leu Leu Leu Ile Leu Ser Ser Val Leu Leu Ser Ile Gly Thr
            20                  25                  30

Cys Gly Gly Pro Leu Ile Met Arg Leu Tyr Phe Ile His Gly Gly Lys
        35                  40                  45

Arg Val Trp Leu Ser Ser Met Leu Glu Thr Gly Gly Trp Pro Val Ile
    50                  55                  60

Leu Val Pro Ile Ala Ile Ala Tyr Tyr His Arg Arg Lys Asn Gln Ala
65                  70                  75                  80

Pro Thr Asp Pro Pro Thr Lys Leu Phe Phe Met Lys Leu Pro Leu Phe
                85                  90                  95

Val Ala Ser Ala Val Ile Gly Val Leu Thr Gly Leu Asp Asp Tyr Leu
            100                 105                 110

Tyr Ala Tyr Gly Val Ala Arg Leu Pro Val Ser Thr Ser Ala Leu Ile
        115                 120                 125

Ile Ala Ala Gln Leu Ala Phe Thr Ala Leu Phe Ala Phe Ile Leu Val
    130                 135                 140

Lys Gln Lys Phe Thr Ser Tyr Ser Ile Asn Ala Val Val Leu Leu Thr
145                 150                 155                 160

Val Gly Ala Ala Val Leu Gly Leu Asn Thr Ser Ser Asp Arg Pro Lys
                165                 170                 175

Gly Glu Ser Asn Ala Gln Tyr Met Leu Gly Phe Val Met Thr Val Ala
            180                 185                 190

Ala Ala Ala Leu Tyr Gly Phe Val Leu Pro Leu Val Glu Leu Met Tyr
        195                 200                 205

Lys Lys Ala Lys Gln Asn Ile Thr Tyr Ala Leu Val Leu Glu Ile Gln
    210                 215                 220

Met Val Met Ser Leu Phe Ala Thr Ile Phe Cys Thr Val Gly Met Leu
225                 230                 235                 240

Val Asn Asn Asp Phe Lys Val Ile Pro Arg Glu Ala Arg Lys Phe Glu
                245                 250                 255

Leu Gly Glu Thr Thr Tyr Tyr Val Val Leu Val Val Ser Ala Ile Val
            260                 265                 270

Trp Gln Thr Phe Phe Leu Gly Ala Ile Gly Leu Ile Phe Cys Ala Ser
        275                 280                 285
```

```
Ser Leu Leu Ser Gly Ile Val Ile Ala Val Leu Leu Pro Val Thr Glu
    290                 295                 300

Ile Phe Ala Val Ile Phe Tyr His Glu Lys Phe Gln Ala Glu Lys Gly
305                 310                 315                 320

Val Ser Leu Ala Leu Ser Leu Trp Gly Phe Val Ser Tyr Phe Tyr Gly
                325                 330                 335

Glu Ile Lys His Asn Lys Gln Lys Lys Gln Ala Asp Ala Val Lys Glu
            340                 345                 350

Lys Glu Asn Asn Lys Glu Gly Cys Thr Pro Asp Val Glu Asn Leu Gln
        355                 360                 365

Thr Val Pro Asn Pro
    370
```

<210> SEQ ID NO 141
<211> LENGTH: 1122
<212> TYPE: DNA
<213> ORGANISM: Fragaria vesca subsp. vesca

<400> SEQUENCE: 141

```
atgcagatgg aaaccaccga caacgaacaa agaaaagctg ctgctttgaa aaggctgttg      60

ttgatcttat cctccgtctt gttgtctatt ggtacttgtg gtggtccatt gattatgagg     120

ttgtacttta ttcacggtgg taagagagtt tggctgtcat ctatgttgga aactggtggt     180

tggccagtta ttttggttcc aattgctatt gcctactacc acagaagaaa aaatcaagct     240

ccaactgatc cacctaccaa gttgtttttt atgaagttgc ctttgtttgt tgcctccgct     300

gttattggtg ttttgactgg tttggatgat tacttgtatg cttacggtgt tgctagattg     360

ccagtttcta cttccgcttt gattattgct gctcaattgg cttttactgc tttgttcgct     420

ttcatcttgg tcaagcaaaa gttcacctcc tactctatta acgccgttgt tttgttgact     480

gttggtgctg ctgttttggg tttgaatact tcttctgata gaccaaaggg tgaatctaat     540

gctcagtaca tgttgggttt cgttatgaca gttgcagctg ctgcattata cggttttgtt     600

ttgccattgg tcgagctgat gtacaaaaaa gccaagcaaa acattaccta cgccttggtt     660

ttggaaatcc aaatggttat gtctctgttc gctaccattt tctgtactgt tggtatgttg     720

gttaacaacg acttcaaggt tattccaaga gaagccagaa agttcgaatt gggtgaaact     780

acttattacg tcgtcttggt tgtttctgct atagtttggc aaactttctt cttgggtgct     840

atcggtttga ttttctgtgc ttcatctttg ttgtccggta tcgttattgc agttttgttg     900

ccagttaccg aaattttcgc cgttattttc taccacgaaa agttccaagc tgaaaagggt     960

gtttctttgg ctttgtcttt gtggggtttt gtctcttact tttacggtga aatcaagcac    1020

aacaagcaaa aaaagcaagc tgatgccgtc aaagagaaag agaacaacaa agaaggttgt    1080

accccagacg ttgaaaactt gcaaactgtt ccaaatccat aa                       1122
```

<210> SEQ ID NO 142
<211> LENGTH: 355
<212> TYPE: PRT
<213> ORGANISM: Ziziphus jujuba

<400> SEQUENCE: 142

```
Met Glu Leu Glu Asp Gln Ser Asn Thr Lys Thr Lys Lys Ala Leu Leu
1               5                   10                  15

Ile Leu Asn Cys Ile Leu Leu Ser Ile Gly Asn Cys Gly Gly Pro Leu
            20                  25                  30
```

```
Ile Met Arg Leu Tyr Tyr Ile His Gly Gly Lys Arg Ile Trp Leu Ser
        35                  40                  45

Ser Trp Leu Glu Thr Gly Gly Trp Pro Ile Met Leu Ile Pro Ile Thr
    50                  55                  60

Val Asn Tyr Phe Arg Arg Arg Lys Thr Ala Ser Ala Thr Glu Gly Thr
65                  70                  75                  80

Thr Lys Phe Phe Gln Ile Lys Leu Pro Leu Phe Leu Ala Ser Ala Leu
                85                  90                  95

Ile Gly Leu Met Thr Gly Phe Asp Asp Tyr Leu Tyr Ala Tyr Gly Leu
            100                 105                 110

Ala Arg Leu Pro Val Ser Thr Ser Ala Leu Ile Ile Ala Ser Gln Leu
        115                 120                 125

Ala Phe Thr Ala Gly Phe Ala Tyr Leu Leu Val Arg Gln Lys Phe Thr
    130                 135                 140

Ser Tyr Ser Val Asn Ala Ile Val Leu Leu Thr Val Gly Gly Ala Val
145                 150                 155                 160

Leu Ala Leu His Thr Ser Gly Asp Arg Pro Lys Gly Glu Ser Asn Lys
                165                 170                 175

Glu Tyr Val Met Gly Phe Leu Phe Thr Val Gly Ala Ser Ala Leu Tyr
            180                 185                 190

Gly Phe Val Leu Pro Leu Met Glu Leu Thr Tyr Lys Lys Ser Arg Gln
        195                 200                 205

Ser Ile Thr Tyr Ser Leu Val Leu Glu Ile Gln Met Val Met Ser Leu
    210                 215                 220

Phe Ala Thr Ile Phe Cys Thr Val Gly Met Leu Ile Asn Lys Asp Phe
225                 230                 235                 240

Gln Ala Ile Pro Arg Glu Ala Arg Lys Phe Glu Leu Gly Glu Thr Met
                245                 250                 255

Tyr Tyr Val Leu Leu Val Val Thr Gly Ile Thr Trp Gln Thr Phe Phe
            260                 265                 270

Leu Gly Ala Ile Gly Ile Ile Phe Cys Ala Ser Ser Leu Leu Ser Ala
        275                 280                 285

Ile Val Ile Ala Val Leu Leu Pro Val Thr Glu Ile Leu Ala Val Ile
    290                 295                 300

Phe Tyr Ser Glu Ser Phe Lys Ala Glu Lys Gly Val Ser Leu Val Leu
305                 310                 315                 320

Ser Leu Trp Gly Phe Val Ser Tyr Phe Tyr Gly Asp Ile Lys Arg Ala
                325                 330                 335

Lys Lys Lys Lys Pro Gln Asn Pro Glu Thr Glu Ile Pro Thr Pro Ile
            340                 345                 350

Ala Gly Pro
        355
```

<210> SEQ ID NO 143
<211> LENGTH: 1068
<212> TYPE: DNA
<213> ORGANISM: Ziziphus jujuba

<400> SEQUENCE: 143

```
atggaattgg aggaccagtc taacactaag actaagaagg ctttgttgat cctgaactgc      60

atcttgttgt ctattggtaa ttgtggtggt ccattgatca tgaggttgta ctatattcat     120

ggtggtaaga ggatctggtt gtcatcttgg ttggaaactg gtggttggcc aattatgttg     180

attccaatta ccgtcaacta cttcagaaga agaaaaactg cttctgctac tgaaggtact     240
```

```
actaagttct tccaaatcaa gttgcctttg ttcttggctt ctgctttgat tggtttgatg    300

actggtttcg acgattactt gtatgcttat ggtttggcta gattgccagt ttctacatcc    360

gctttgatta ttgcttctca attggctttt actgctggtt tcgcttactt gttggttaga    420

caaaagttca cctcctactc tgttaacgct atcgttttgt tgactgttgg tggtgctgtt    480

ttggcattgc atacttcagg tgatagacca aaaggtgagt ccaacaaaga atacgttatg    540

ggtttcttgt ttaccgttgg tgcttctgca ttatacggtt ttgttttgcc attgatggaa    600

ctgacctaca agaagtccag acaatctatt acctactcct tggtcttgga aatccaaatg    660

gttatgtctt tgttcgccac cattttctgt actgttggca tgttgattaa caaggacttc    720

caagctattc caagagaagc tagaaagttc gaattgggtg aaaccatgta ttacgtcttg    780

ttagttgtta ccggtattac ctggcaaact tttttcttgg gtgccatcgg tattatcttt    840

tgcgcttctt ctttgctgtc tgctatcgtt attgctgtct tgttgccagt tactgaaatt    900

ttggccgtta tcttctactc cgaatctttc aaagctgaaa agggtgtttc cctggttttg    960

tctttatggg gtttcgtttc ttacttctac ggtgatatta agagggctaa gaaaaagaag   1020

ccacaaaacc cagaaaccga aattccaact ccaattgctg gtccataa                1068
```

<210> SEQ ID NO 144
<211> LENGTH: 376
<212> TYPE: PRT
<213> ORGANISM: Lactuca sativa

<400> SEQUENCE: 144

```
Met Met Glu Lys Val Thr Thr Thr Thr Thr Thr Thr Gly Thr Thr Ala
1               5                   10                  15

Pro Met Ala Ala Lys Val Ser Pro Ala Ala Lys Lys Thr Leu Leu Ile
            20                  25                  30

Leu Asn Cys Ile Leu Leu Ser Ile Gly Asn Cys Gly Gly Pro Leu Ile
        35                  40                  45

Met Arg Leu Tyr Phe His His Gly Gly Asn Arg Val Trp Leu Ser Ser
    50                  55                  60

Phe Leu Glu Thr Ala Gly Trp Pro Phe Ile Val Ile Val Leu Ile Ile
65                  70                  75                  80

Leu Tyr Phe His Arg Arg Ala Ala Gly Lys Asn Gly Asn Asn Lys Arg
                85                  90                  95

Thr Thr Phe Ile Tyr Met Arg Pro Arg Leu Phe Phe Ala Val Ala Phe
            100                 105                 110

Val Gly Val Ile Thr Gly Phe Asp Asp Tyr Leu Tyr Ala Tyr Gly Val
        115                 120                 125

Ala Arg Leu Pro Val Ser Thr Ser Ala Leu Ile Ile Ala Ser Gln Leu
    130                 135                 140

Ala Phe Thr Ala Phe Phe Ala Tyr Leu Leu Val Lys Gln Lys Phe Thr
145                 150                 155                 160

Ala Tyr Ser Val Asn Ala Val Val Leu Leu Thr Val Gly Ala Gly Val
                165                 170                 175

Leu Ala Leu His Thr Asn Ser Asp Arg Pro Glu Gly Glu Thr Lys Lys
            180                 185                 190

Gln Tyr Val Met Gly Phe Val Leu Thr Val Ala Ala Ala Val Leu Tyr
        195                 200                 205

Gly Phe Ile Leu Pro Leu Ile Glu Leu Thr Tyr Asn Lys Ala Lys Gln
    210                 215                 220

Ala Ile Thr Tyr Thr Leu Val Leu Glu Ile Gln Met Val Met Cys Leu
```

```
225                 230                 235                 240

Phe Ala Thr Ile Phe Cys Met Val Gly Met Ile Ile Asn Asn Asp Phe
                245                 250                 255

Lys Val Ile Pro Arg Glu Ala Arg Asp Phe Asp Leu Gly Glu Thr Lys
            260                 265                 270

Tyr Tyr Ile Ile Met Cys Phe Ser Ala Leu Ile Trp Gln Cys Phe Phe
        275                 280                 285

Leu Gly Ala Ile Gly Val Ile Phe Cys Ala Ser Ser Leu Leu Ser Gly
    290                 295                 300

Ile Ile Ile Ala Val Leu Leu Pro Val Thr Glu Val Leu Ala Val Val
305                 310                 315                 320

Phe Tyr Lys Glu Lys Phe Gln Ala Glu Lys Gly Val Ala Leu Val Leu
                325                 330                 335

Ser Leu Trp Gly Phe Ala Ser Tyr Phe Tyr Gly Glu Tyr Lys Phe Met
            340                 345                 350

Lys Lys Ser Lys Asp Asn Thr Gln Ser Thr Gln Gln Ser Met Glu Leu
        355                 360                 365

Ala Gln Ala Asn Tyr Ser Ser Val
    370                 375


<210> SEQ ID NO 145
<211> LENGTH: 1131
<212> TYPE: DNA
<213> ORGANISM: Lactuca sativa

<400> SEQUENCE: 145

atgatggaaa aggttactac caccactact acaactggta ctactgctcc aatggctgct      60

aaagtttctc cagctgctaa aaagaccttg ttgattttga actgcatcct gttgtctatt     120

ggtaattgtg gtggtccatt gatcatgagg ttgtactttc atcatggtgg taacagagtt     180

tggctgtcct ctttttgga aactgctggt tggcctttta tcgttatcgt tttgatcatc     240

ttgtacttcc atagacgtgc tgctggtaaa aatggtaaca acaagagaac taccttcatc     300

tatatgaggc caaggttgtt ttttgctgtt gctttcgttg gtgttatcac cggttttgat     360

gattacttgt atgcttacgg tgttgccaga ttgccagttt ctacttctgc tttgattatc     420

gcttctcaat tggctttcac tgctttcttt gcttacttgt tggtcaagca aaagttcacc     480

gcttactctg ttaatgccgt tgttttgtta actgttggtg ctggtgtttt ggccttgcat     540

acaaattctg atagaccaga aggtgagaca aaaaagcaat acgttatggg tttcgttttg     600

acagttgctg ctgctgtctt gtatggtttc attttgccat tgatcgagct gacttacaac     660

aaagctaagc aagctattac ctacaccttg gtcttggaaa tccaaatggt tatgtgtttg     720

ttcgccacca ttttctgtat ggttggtatg atcatcaaca acgacttcaa ggttattcca     780

agagaagcca gagatttcga tttgggtgaa actaagtact acatcatcat gtgcttctcc     840

gctttgattt ggcaatgttt tttcttgggt gctatcggtg ttattttctg cgcttcttct     900

ttgttgtccg gtattatcat tgctgttttg ttgccagtta ccgaagtttt ggctgtggtt     960

ttctacaaag aaaagttcca agctgaaaag ggtgttgcct tggttttgtc tttgtggggt    1020

tttgcttctt acttttacgg tgagtacaag ttcatgaaga agtccaagga taacacccaa    1080

tctacccaac aatctatgga attggctcaa gctaactact cctctgtttg a             1131


<210> SEQ ID NO 146
<211> LENGTH: 350
<212> TYPE: PRT
```

<213> ORGANISM: Macleaya cordata

<400> SEQUENCE: 146

```
Met Asn Leu Val Met Lys Lys Arg Tyr Leu Leu Leu Phe Asn Cys Ile
1               5                   10                  15

Leu Leu Ala Ile Gly Asn Thr Gly Gly Pro Leu Leu Leu Arg Leu Tyr
            20                  25                  30

Phe Ile His Gly Gly Thr Arg Ile Trp Leu Ser Ser Trp Leu Glu Thr
        35                  40                  45

Gly Gly Trp Pro Ile Met Leu Leu Pro Leu Ser Ile Ser Tyr Leu Leu
    50                  55                  60

His Arg Phe Asn Asn Lys Gly Asp Glu Asn Ala Ala Asn Lys Phe Phe
65                  70                  75                  80

Thr Met Thr Pro Pro Leu Phe Thr Ala Ser Val Val Leu Gly Leu Leu
                85                  90                  95

Thr Gly Phe Asp Asp Tyr Leu Tyr Ala Tyr Gly Val Ser Leu Leu Pro
            100                 105                 110

Ile Ser Thr Ala Ser Leu Ile Ile Ser Thr His Leu Ala Phe Thr Ala
        115                 120                 125

Gly Phe Ala Leu Phe Ile Val Lys Gln Lys Phe Thr Ser Tyr Ser Val
    130                 135                 140

Asn Ser Val Val Leu Leu Thr Ile Gly Ala Ile Val Leu Gly Leu His
145                 150                 155                 160

Ser Ser Gly Asp Arg Pro Ile Gly Glu Ser Asp Lys Gln Tyr Tyr Leu
                165                 170                 175

Gly Phe Phe Met Thr Val Ala Ala Ala Ala Leu Asn Gly Phe Leu Leu
            180                 185                 190

Pro Met Ile Glu Leu Met Tyr Lys Lys Ser Lys Gln Ala Ile Thr Tyr
        195                 200                 205

Ser Leu Val Ile Glu Leu Gln Ile Val Met Cys Ile Phe Ala Thr Leu
    210                 215                 220

Phe Cys Thr Val Gly Met Leu Val Asn Lys Asp Phe Lys Ala Ile Pro
225                 230                 235                 240

Arg Glu Gly Lys Glu Tyr Lys Leu Gly Glu Ala Lys Tyr Tyr Thr Val
                245                 250                 255

Leu Val Ala Ser Ala Ile Ala Trp Gln Leu Phe Phe Leu Gly Gln Ile
            260                 265                 270

Gly Val Ile Phe Cys Ala Thr Ser Leu Leu Ser Gly Val Ile Thr Ala
        275                 280                 285

Val Leu Leu Pro Phe Thr Glu Ile Leu Ala Val Ile Phe Tyr His Glu
    290                 295                 300

Lys Phe Lys Ala Glu Lys Gly Ile Ala Leu Ser Leu Ser Phe Trp Gly
305                 310                 315                 320

Phe Ile Ser Tyr Phe Tyr Gly Glu Phe Lys Glu Ser Arg Asn Lys Lys
                325                 330                 335

Lys Gln Thr Ser Asp Ser Glu Gln Ala Ser Ser Ser Leu Thr
            340                 345                 350
```

<210> SEQ ID NO 147
<211> LENGTH: 1053
<212> TYPE: DNA
<213> ORGANISM: Macleaya cordata

<400> SEQUENCE: 147

```
atgaacctgg tcatgaagaa gaggtacttg ttgttgttca actgcatttt gttggccatt      60
```

```
ggtaatactg gtggtccttt gttgttgagg ttgtacttta ttcatggtgg caccagaatt    120

tggttgtcat cttggttgga aactggtggt tggccaatta tgttgttgcc attgtctatc    180

tcttacctgt tgcacaggtt taacaacaag ggtgacgaaa atgctgctaa caagttcttt    240

actatgaccc ctcctttgtt cactgcttct gttgttttgg gtttgttgac tggtttcgat    300

gattacttgt atgcctacgg tgtttccttg ttgccaattt ctactgcctc cttgattatc    360

tctactcatt tggcttttac tgctggtttc gctttgttta tcgtcaagca aaagttcacc    420

tcctactccg ttaattccgt tgtcttgttg actattggtg ctatcgtttt gggtctacat    480

tcttctggtg atagacctat tggtgaatct gataagcaat attacctggg ctttttcatg    540

actgttgctg ctgctgcatt gaatggtttt ttgttgccta tgatcgagct gatgtacaag    600

aaatccaagc aagctattac ctactccttg gtcattgaat tgcaaatcgt tatgtgcatc    660

ttcgctactt tgttctgtac tgttggtatg ttggttaaca aggacttcaa ggctattcca    720

agagaaggta aagagtacaa attgggcgaa gctaagtact atactgtttt ggttgcttct    780

gctattgctt ggcagttgtt tttcttgggt caaatcggtg ttattttctg cgctacttct    840

ttgttgtctg gtgttattac tgccgtcttg ttgcctttca ctgaaatttt ggctgttatc    900

ttctaccacg aaaagttcaa ggctgaaaag ggtattgctc tgtctttgtc tttttggggt    960

ttcatctctt acttctacgg tgagttcaaa gagtccagaa acaagaagaa gcaaacctcc   1020

gattctgaac aagcttcttc ctctttgact taa                                1053


<210> SEQ ID NO 148
<211> LENGTH: 379
<212> TYPE: PRT
<213> ORGANISM: Aquilegia coerulea

<400> SEQUENCE: 148

Met Asp Glu Glu Ala Ile Asp Ala Arg Ile Lys Glu Glu Gln Val Asp
1               5                   10                  15

Glu Gln Gln His Lys Ile Lys Lys Lys Lys Lys Gln Ile Lys Leu Phe
            20                  25                  30

Leu Leu Leu Leu Asn Cys Ala Leu Val Cys Leu Gly Gln Val Gly Gly
        35                  40                  45

Pro Leu Leu Ile Arg Leu Tyr Tyr Leu His Gly Gly Lys Arg Ile Trp
    50                  55                  60

Leu Thr Ser Trp Ile Gln Thr Ala Ala Phe Pro Leu Leu Leu Ile Pro
65                  70                  75                  80

Pro Leu Leu Ser Arg Ala Arg Asp Arg Ala Arg Ala Gln Ser Arg Val
                85                  90                  95

Leu Ser Gln Ser Ile Ser Pro Lys Asp Thr Lys Val Leu Leu Asn Pro
            100                 105                 110

Lys Leu Leu Ile Ala Ser Ile Val Met Gly Leu Ile Val Gly Val Asp
        115                 120                 125

Ser Tyr Met Phe Gly Leu Gly Leu Ser Tyr Leu Pro Val Ser Thr Ser
    130                 135                 140

Ser Leu Leu Met Ser Thr Gln Leu Ala Phe Thr Ala Val Phe Ser Leu
145                 150                 155                 160

Leu Leu Val Arg Gln Lys Phe Thr Ser Tyr Ser Ile Asn Ala Val Val
                165                 170                 175

Leu Met Thr Leu Gly Ser Val Ile Leu Ala Phe His Thr Asn Gly Asp
            180                 185                 190
```

Arg Pro Val Gly Val Ser Lys Gly Glu Tyr Phe Val Gly Phe Phe Met
        195                 200                 205

Thr Leu Gly Ala Ala Ala Leu Leu Gly Phe Met Leu Pro Leu Ile Glu
    210                 215                 220

Leu Ser Tyr Ser Lys Ala Cys Lys Val Ile Thr Tyr Asp Leu Val Leu
225                 230                 235                 240

Gln Val Gln Phe Val Val Ser Met Val Ala Thr Ile Phe Cys Thr Val
                245                 250                 255

Ala Met Val Ile Asn Lys Asp Phe Gln Ala Met Thr Arg Glu Ala Gln
            260                 265                 270

Glu Tyr Gly Leu Gly Glu Gly Lys Tyr Tyr Met Val Ile Thr Leu Ala
        275                 280                 285

Ala Leu Ala Met Gln Cys Met Leu Ala Gly Asn Leu Gly Val Val Phe
    290                 295                 300

Cys Ser Thr Ala Leu Phe Gly Gly Val Leu Leu Ala Leu Leu Leu Pro
305                 310                 315                 320

Ile Gln Gln Ile Phe Ala Val Ile Phe Phe His Glu Lys Phe Asn Pro
                325                 330                 335

Glu Lys Gly Ile Ser Leu Ala Leu Ser Leu Trp Gly Phe Val Ser Tyr
            340                 345                 350

Phe Tyr Gly Glu His Lys Leu Ile Lys Lys Gln Lys Gln Ala Ser Leu
        355                 360                 365

Leu Thr Gln Gln Leu His Ser Thr Thr Gly His
    370                 375

<210> SEQ ID NO 149
<211> LENGTH: 1140
<212> TYPE: DNA
<213> ORGANISM: Aquilegia coerulea

<400> SEQUENCE: 149
atggatgaag aagctatcga cgccaggatc aaagaagaac aagttgacga acaacagcac 60
aagatcaaaa agaagaagaa gcagatcaag ctgttcctgt tgttgttgaa ttgtgctttg 120
gtttgcttgg gtcaagttgg tggtccatta ttgattaggt tgtactactt gcatggtggt 180
aagagaattt ggttgacctc ttggattcaa actgctgctt ttccattgct attgatccca 240
ccattattgt ccagagctag agatagagca agagcacaat ctagagtttt gtcccaatct 300
atttctccaa aggataccaa ggttctgttg aacccaaagt tgttgattgc ctctatagtc 360
atgggtttga tcgttggtgt tgactcttat atgtttggtt tgggcttgtc ttacttgcca 420
gtttctacat catctctgtt gatgtctact caattggctt ttaccgctgt gttcagtttg 480
ttgttggtta gacaaaagtt cacctcctac tccattaacg ctgttgtttt gatgacattg 540
ggttccgtta ttttggcttt tcataccaat ggtgatagac cagttggtgt ttctaagggt 600
gaatactttg ttggtttctt catgactttg ggtgctgcag ctttgttggg ttttatgttg 660
ccattgatcg agctgtctta ctctaaagct tgtaaggtta tcacctacga cttggtcttg 720
caagttcaat tcgttgtttc tatggttgcc accattttct gtactgttgc catggttatt 780
aacaaggatt tccaagctat gaccagagaa gctcaagaat atggtttagg tgaaggcaag 840
tactacatgg ttataacttt ggctgctttg gctatgcaat gtatgttggc tggtaatttg 900
ggtgttgttt tctgttctac tgctttgttt ggtggtgttt tgttggcttt gttgctgcca 960
atccaacaaa ttttcgctgt tatcttcttc cacgaaaaat tcaacccaga gaagggtatt 1020
tctttggcat tgtctttatg ggcttcgtg tcatactttt acggtgaaca taagctgatc 1080
aagaagcaaa agcaagcttc tttgttgacc caacaattgc attctactac cggtcattga 1140

<210> SEQ ID NO 150
<211> LENGTH: 355
<212> TYPE: PRT
<213> ORGANISM: Papaver nudicale

<400> SEQUENCE: 150

```
Met Asn Thr Cys Leu Leu Trp Phe Asn Gly Leu Leu Leu Ala Ile Ser
1               5                   10                  15

Ser Ile Gly Gly Pro Leu Leu Leu Arg Leu Tyr Phe Ile His Gly Gly
            20                  25                  30

Lys Arg Ile Trp Leu Ser Ser Cys Leu Glu Thr Ala Gly Phe Pro Val
        35                  40                  45

Leu Phe Leu Pro Leu Trp Leu Ser Tyr Phe Leu Lys Arg Arg Gly Val
    50                  55                  60

Ile Lys Gly Asp Glu Gly Glu Lys Pro Ser Lys Leu Phe Thr Ile Thr
65                  70                  75                  80

Arg Pro Leu Phe Ile Ala Ser Ala Gly Ile Gly Leu Ile Thr Gly Leu
                85                  90                  95

Asp Asp Tyr Leu Tyr Thr Tyr Gly Val Ser Leu Leu Pro Ile Ser Thr
            100                 105                 110

Ala Thr Ile Ile Met Ser Thr His Leu Ala Phe Thr Ala Gly Phe Ala
        115                 120                 125

Leu Val Met Val Lys Gln Lys Phe Thr Ser Phe Ser Val Asn Ala Val
    130                 135                 140

Val Leu Leu Thr Val Gly Ala Ile Leu Leu Gly Leu His Ser Asn Gly
145                 150                 155                 160

Asp Arg Pro Ala Asn Glu Ser Thr Lys Glu Tyr Tyr Leu Gly Phe Leu
                165                 170                 175

Ile Thr Ile Ala Ala Ser Val Ile Asn Gly Leu Met Leu Pro Leu Val
            180                 185                 190

Glu Leu Met Tyr Met Lys Ser Lys Gln Val Ile Thr Tyr Ser Leu Val
        195                 200                 205

Ile Glu Leu Gln Ile Val Ile Ser Ala Phe Ala Thr Leu Phe Cys Thr
    210                 215                 220

Ile Gly Met Ile Val Asp Asn Asp Phe Lys Val Ile Pro Arg Glu Gly
225                 230                 235                 240

Arg Glu Tyr Gly Leu Gly Glu Val Asn Tyr Tyr Val Val Leu Val Ser
                245                 250                 255

Ser Ala Ile Met Trp Gln Met Tyr Phe Val Gly Thr Val Gly Val Ile
            260                 265                 270

Phe Cys Ser Thr Ser Leu Leu Ala Gly Val Ile Ala Val Val Val Leu
        275                 280                 285

Pro Leu Thr Glu Ile Leu Ser Val Val Phe Tyr His Glu Ser Phe Lys
    290                 295                 300

Ala Glu Lys Gly Ile Ala Leu Phe Leu Ser Leu Trp Gly Phe Ile Ser
305                 310                 315                 320

Tyr Phe Trp Gly Glu Leu Lys Gly Ser Arg Lys Ala Lys Lys Gln Ile
                325                 330                 335

Ser Glu Leu Glu Gln Asp Ser Ser Asn Ser Pro Thr Ser Leu His Ile
            340                 345                 350

Leu Asp Tyr
        355
```

<210> SEQ ID NO 151
<211> LENGTH: 1068
<212> TYPE: DNA
<213> ORGANISM: Papaver nudicale

<400> SEQUENCE: 151
atgaacacgt gcttgttgtg gttcaacggt ttgttgttgg ccatttcttc tattggtggt 60
cctttgttgt taaggttgta cttcattcat ggtggtaaga ggatttggtt gtcctcttgt 120
ttggaaactg ctggttttcc agttttgttt ttgccattgt ggctgtccta ctttttgaag 180
agaagaggtg ttatcaaggg tgacgaaggt gaaaaaccat ctaagttgtt cactatcacc 240
aggcctttgt ttattgcttc tgctggtatt ggtttgatca ccggtttgga tgattacttg 300
tatacctacg gtgtttcctt gttgccaatt tctactgcca ccattattat gtctacccat 360
ttggctttta ccgctggttt tgctttggtt atggttaagc aaaagttcac ctccttctct 420
gttaacgctg ttgttttgtt gactgttggt gctatcttgt tgggcttgca ttctaatggt 480
gatagaccag ctaatgagtc taccaaagaa tattacttgg gcttcttgat taccattgct 540
gcctctgtta ttaacggttt gatgctacca ttggtcgagt tgatgtacat gaagtccaag 600
caagttatca cctactcatt ggtcatcgaa ttgcaaatcg ttatttctgc tttcgctacc 660
ttgttctgca ctattggtat gatcgttgat aacgacttca aggtcattcc aagagaaggt 720
agagaatatg gtttgggtga agttaactac tacgtcgtct tggtttcttc tgctattatg 780
tggcaaatgt acttcgttgg tacagttggt gttattttct gctctacttc tttgttggct 840
ggtgtcattg ctgttgttgt tttaccattg accgaaatct tgtccgttgt tttctaccac 900
gaatctttca aagccgaaaa gggtattgct ctgtttttgt ctttgtgggg ttttatctct 960
tacttctggg gtgaattgaa gggttctaga aaagccaaga agcagatctc tgaattggaa 1020
caagattcct ctaactctcc aacctccttg catattttgg actactga 1068

<210> SEQ ID NO 152
<211> LENGTH: 403
<212> TYPE: PRT
<213> ORGANISM: Papaver bracteatum

<400> SEQUENCE: 152

Met Asp Ile Glu Ala Val Ser Thr Asn Glu Gly Ala Ala Thr Asn Tyr
1               5                   10                  15

Asn His Gly Gly Asn His Gln Ser Asn Leu Ile Val Pro Asn Asn His
            20                  25                  30

Glu Asp Asp Leu Gln Ser Thr Ala Asn Pro Ile Thr Gln Lys Arg Val
        35                  40                  45

Ile Lys Trp Lys Leu Leu Val Leu Phe Cys Leu Phe Ser Ala Ser Gly
    50                  55                  60

Asn Leu Gly Gly Pro Met Leu Gln Arg Leu Tyr Phe Ile His Gly Gly
65                  70                  75                  80

Gly Arg Lys Trp Phe Ser Ser Met Ile Gln Thr Ala Gly Phe Pro Val
                85                  90                  95

Leu Val Ala Pro Leu Ser Tyr Ile Tyr Val Lys Lys Ile Asn Gly Pro
            100                 105                 110

Ser Tyr Asp Ser Ser Trp Val Phe Met Met Glu Pro Lys Leu Phe Ile
        115                 120                 125

Tyr Ser Ala Ile Ile Gly Ala Val Leu Gly Leu Ala Asn Tyr Met Tyr
    130                 135                 140

Ser Ala Gly Leu Phe Tyr Leu Pro Val Ser Thr Ser Ser Leu Leu Phe
145 150 155 160

Ser Thr Gln Leu Ala Phe Thr Ala Ile Phe Ala Phe Ile Phe Val Arg
165 170 175

Gln Lys Phe Thr Phe Tyr Ser Phe Asn Ser Val Val Leu Met Thr Leu
180 185 190

Gly Ser Val Val Leu Ala Leu Asn Thr Ser Gly Asp Lys Pro Pro Gly
195 200 205

Thr Thr Gln Gln Gln Tyr Tyr Leu Gly Phe Phe Leu Thr Leu Gly Gly
210 215 220

Ala Ala Leu Gly Gly Leu Cys Met Pro Leu Ile Glu Leu Ala Tyr Gly
225 230 235 240

Lys Ser Ser Lys Pro Ile Thr Tyr Ser Val Val Leu Gln Phe Gln Phe
245 250 255

Val Leu Ser Leu Phe Ser Thr Leu Val Cys Met Ile Gly Met Ala Ile
260 265 270

Asn Asn Asp Phe Gln Val Ile Pro Ile Glu Gly Arg Asn Phe Gly Leu
275 280 285

Gly Glu Arg Arg Tyr Tyr Phe Leu Ile Val Ala Thr Ala Ile Val Trp
290 295 300

Gln Leu Leu Asn Val Gly Phe Leu Gly Ile Ile Tyr Cys Thr Ser Ser
305 310 315 320

Leu Phe Ser Gly Ile Phe Ser Thr Cys Leu Leu Pro Phe Ser Gln Val
325 330 335

Ala Ala Thr Ile Ala Phe Asn Glu Lys Phe Thr Gly Gln Lys Gly Met
340 345 350

Ser Leu Ala Leu Cys Leu Trp Gly Phe Val Ser Tyr Phe Val Gly Glu
355 360 365

Tyr Lys Lys Thr Lys Asn Pro His Pro Ile Ala Tyr Asp Asp Asn Ala
370 375 380

Glu Glu Leu Lys Asp Leu Asp Gln Leu Thr Asp Ser Asn Thr Met Glu
385 390 395 400

Gly Lys Pro

<210> SEQ ID NO 153
<211> LENGTH: 1212
<212> TYPE: DNA
<213> ORGANISM: Papaver bracteatum

<400> SEQUENCE: 153
atggacatcg aagctgtctc tactaatgaa ggtgctgcta ctaattacaa tcatggtggt 60
aaccatcagt ccaacttgat cgttccaaac aatcatgaag atgacttgca atctactgct 120
aacccaatca ctcaaaaaag ggttatcaag tggaagctgt tggttttgtt ctgtttgttt 180
tctgcctctg gtaacttagg tggtccaatg ttgcaaaggt tgtactttat ccatggtggt 240
ggtagaaagt ggttctcctc tatgattcaa actgctggtt ttccagtttt ggttgctcca 300
ttgtcttaca tctacgtcaa gaaaatcaac ggtccatcct atgattcctc ttgggttttt 360
atgatggaac ccaagttgtt catctactcc gctattattg gtgccgtttt gggtttagct 420
aactacatgt attcagccgg tttgttctat ttgccagttt ctacttcttc cctgttgttc 480
tctacacaat tggctttcac tgctattttc gccttcattt tcgtcagaca aaagttcacc 540
ttctacagct tcaactccgt tgttttgatg actttgggtt cagttgtttt ggctttgaat 600

```
acctctggtg ataagccacc aggtactact caacaacaat attacttggg tttcttcttg    660

acacttggtg gtgctgcttt aggtggtttg tgtatgccat tgattgaatt ggcttacggc    720

aaatcttcca agccaattac ttattccgtt gtcttgcaat tccagttcgt cttgtctttg    780

ttttccactt tggtctgcat gattggtatg gccattaaca acgatttcca agtcattcca    840

atcgagggta gaaattttgg tttgggtgaa agacgttact acttcttgat agttgctact    900

gctatcgttt ggcagttgtt gaatgttggt ttcctgggta ttatctactg cacctcttct    960

ttgttctccg gtattttctc tacttgcttg ttgccatttt ctcaagttgc tgctaccatt   1020

gctttcaacg aaaagtttac tggtcaaaag ggtatgtcct tggctttgtg tttgtggggt   1080

tttgtttctt actttgtcgg cgagtacaaa aagactaaga acccacatcc aattgcctac   1140

gatgataatg ctgaagaatt gaaggatttg gaccaattga ctgactctaa cactatggaa   1200

ggtaagccat ga                                                       1212


<210> SEQ ID NO 154
<211> LENGTH: 386
<212> TYPE: PRT
<213> ORGANISM: Papaver somniferum

<400> SEQUENCE: 154

Met Ser Ala Leu His Ile Glu Met Met Glu Glu Gly Val Leu Ser Pro
1               5                   10                  15

Asn Ile Lys Pro Ser Thr Pro Ser Lys Asn Ile Lys Leu Ser Asp Asp
            20                  25                  30

Ile His Gly Asp Asp Asp Gly Asp Leu Lys Met Ile Asn Lys Gln Ser
        35                  40                  45

Leu Met Glu Lys Trp Gly Leu Leu Val Met Tyr Cys Ile Phe Ala Ala
    50                  55                  60

Val Gly Phe Thr Gly Gly Pro Leu Leu Leu Arg Val Tyr Phe Leu His
65                  70                  75                  80

Gly Gly Ser Arg Lys Trp Leu Ser Ser Ala Leu Gln Thr Ala Gly Phe
                85                  90                  95

Pro Ile Leu Leu Leu Pro Leu Ala Ile Leu Tyr Ala Lys Arg Asp Lys
            100                 105                 110

Ala Ala Pro Gln Thr Asn Phe Phe Ala Ser Pro Lys Leu Leu Leu Ser
        115                 120                 125

Ser Ile Phe Ile Gly Ile Leu Leu Gly Val Ser Asn Phe Met Tyr Ser
    130                 135                 140

Tyr Gly Leu Ser Phe Leu Pro Val Ser Thr Ser Ser Ile Leu Leu Ser
145                 150                 155                 160

Thr Asn Leu Ile Phe Thr Ala Leu Cys Ala Leu Ile Leu Val Arg Gln
                165                 170                 175

Lys Phe Ser Pro Phe Ser Ile Asn Ala Ile Val Ile Met Thr Leu Gly
            180                 185                 190

Ser Val Leu Leu Gly Val Gly Gln Asn Gly Asp Arg Pro Glu Gly Val
        195                 200                 205

Thr Ser Leu Gln Tyr Leu Leu Gly Phe Ile Leu Ser Ile Gly Ala Ala
    210                 215                 220

Ala Ser Gly Gly Leu Ala Leu Pro Cys Ile Glu Val Ala Tyr Thr Lys
225                 230                 235                 240

Ala Asn Gln Val Met Thr Tyr Pro Ile Val Leu Gln Tyr Gln Phe Phe
                245                 250                 255

Met Ala Leu Ser Ala Thr Val Phe Ser Ile Ile Gly Met Ala Val Asn
```

```
            260                 265                 270

Lys Asp Phe Gln Ala Met Gln Arg Glu Ala Asp Glu Phe Gly Leu Gly
        275                 280                 285

Lys Met Glu Tyr Tyr Leu Val Leu Val Ser Ser Ala Val Val Trp Gln
    290                 295                 300

Ile Ser Tyr Ile Gly Thr Leu Gly Ile Ile Phe Tyr Ala Thr Ser Ile
305                 310                 315                 320

Phe Ala Gly Val Val Ser Ala Val Leu Leu Pro Leu Thr Glu Ile Ala
                325                 330                 335

Ala Val Ile Val Phe His Glu Lys Phe Thr Gly Glu Lys Gly Met Ala
            340                 345                 350

Leu Ala Met Ser Val Trp Gly Phe Leu Ser Tyr Phe Tyr Gly Thr Tyr
        355                 360                 365

Lys Glu Ser Lys Ile Gln Thr Gln Ile Asp Ser Thr Lys Thr Ser Thr
    370                 375                 380

Arg Glu
385
```

<210> SEQ ID NO 155
<211> LENGTH: 1161
<212> TYPE: DNA
<213> ORGANISM: Papaver somniferum

<400> SEQUENCE: 155

```
atgtccgcct tgcatatcga aatgatggaa gaaggtgttc tgtccccaaa tatcaaacca      60

tctactccat ccaagaacat caagttgtcc gatgatattc acggtgatga tgatggtgat     120

ctgaagatga ttaacaagca gtccttgatg gaaaagtggg gtttgttggt tatgtactgt     180

atttttgctg ctgttggttt tactggtggt cctttgttgt tgagagttta cttcttgcat     240

ggtggttcca gaaaatggtt gtcatctgct ttacaaactg ctggtttccc aatcttgttg     300

ttgccattgg ctatcttgta tgccaaaaga gataaggctg ctcctcaaac taatttcttt     360

gcttctccaa agctgctgct gtcctctatt ttcattggta ttttgttggg cgtgtccaac     420

ttcatgtatt cttacggttt gtctttcttg ccagtctcca cttcttcaat tttgttgtcc     480

accaacttga ttttcaccgc tttgtgtgct ttgatcttgg tcagacaaaa gttctctcca     540

ttctccatta acgccatcgt tattatgact ttgggttccg ttttgttagg tgttggtcaa     600

aatggtgata gacctgaagg tgttacttcc ttgcaatatt tgttgggttt catcttgtct     660

attggtgctg ctgcttctgg tggtttggct ttgccatgta ttgaagttgc ttacaccaag     720

gccaatcaag ttatgactta tccaatcgtc ttgcagtacc aattcttcat ggctttgtct     780

gctaccgttt tctctattat tggtatggcc gttaacaagg atttccaagc tatgcaaaga     840

gaagctgacg aatttggttt gggtaagatg gaatattacc tggtcttggt ttcttctgct     900

gttgtttggc aaatttccta cattggtact ttgggcatta ttttctacgc cacttctatt     960

ttcgctggtg ttgtttcagc tgttttgttg cctttgactg aaattgctgc cgttatcgtt    1020

tttcacgaaa agttcactgg tgaaaaaggt atggctttgg ctatgtctgt ttggggtttt    1080

ttgtcttact tctacggcac ctacaaagag tctaagattc aaacccaaat cgactctact    1140

aagacttcca ctagagagtg a                                               1161
```

<210> SEQ ID NO 156
<211> LENGTH: 368
<212> TYPE: PRT
<213> ORGANISM: Aquilegia coerulea

<400> SEQUENCE: 156

```
Met Ser Ser Ser Leu Asn Val Glu Gly Ala Thr Ser Pro Lys Val Asp
1               5                   10                  15

Thr Lys Thr Arg Lys Thr Thr Asn Trp Pro Leu Leu Leu Leu Ser Cys
            20                  25                  30

Ser Phe Val Ala Ile Gly Ile Ile Gly Gly Pro Leu Leu Ser Arg Leu
        35                  40                  45

Tyr Phe Leu His Gly Gly Ser Arg Ser Trp Leu Ser Ser Cys Met Gln
    50                  55                  60

Thr Ala Gly Phe Pro Ile Leu Phe Leu Pro Leu Leu Ser Leu Phe Leu
65                  70                  75                  80

Gln Ser Arg Ser Gln Gly Glu Ser Ala Ser Val Phe Phe Met Glu Pro
                85                  90                  95

Lys Leu Phe Ile Leu Ser Ala Ile Ile Gly Leu Leu Leu Gly Leu Asp
            100                 105                 110

Asn Phe Met Tyr Ser Leu Gly Leu Ser Tyr Thr Pro Val Ser Thr Ser
        115                 120                 125

Ser Ile Leu Phe Ser Thr Gln Leu Ala Phe Leu Ala Val Phe Ala Phe
    130                 135                 140

Phe Ile Val Lys Gln Lys Phe Thr Pro Tyr Ser Ile Asn Ala Val Ile
145                 150                 155                 160

Leu Met Thr Leu Gly Ser Val Leu Leu Gly Leu Arg Ser Asp Gly Asp
                165                 170                 175

Arg Pro Ala Gly Val Ser Asn Ala Gln Tyr Trp Leu Gly Phe Ile Leu
            180                 185                 190

Thr Leu Gly Ser Ala Ala Val Leu Gly Leu Ile Trp Pro Leu Ile Glu
        195                 200                 205

Leu Ser Tyr Ser Lys Ser Lys Arg Pro Val Asn Tyr Gly Val Val Leu
    210                 215                 220

Gln Phe Gln Thr Asn Leu Ala Ile Phe Ala Thr Leu Phe Ser Leu Thr
225                 230                 235                 240

Gly Met Ala Ile Asn Lys Asp Phe Gln Ala Met Gly Lys Glu Ser Asn
                245                 250                 255

Glu Tyr Gly Leu Gly Asn Gly Met Tyr Tyr Leu Val Leu Ala Ala Gly
            260                 265                 270

Ala Val Val Trp Gln Leu Ser Phe Ile Gly Gly Leu Gly Val Ile Phe
        275                 280                 285

Cys Ala Asn Ser Leu Leu Asn Gly Val Leu Ser Ala Val Leu Leu Pro
    290                 295                 300

Ile Thr Asn Ile Ala Ala Val Ile Phe Tyr His Glu Asn Phe Asn Gly
305                 310                 315                 320

Leu Lys Ala Met Ser Leu Val Leu Cys Leu Trp Gly Phe Val Ser Tyr
                325                 330                 335

Phe Tyr Gly Glu Tyr Thr Met Asn Lys Lys Leu Lys Asn Ser Pro Gln
            340                 345                 350

Thr Gln Leu Ser Asp Asp Ser Asn Lys Asn Glu Val Leu Ser Pro Val
        355                 360                 365
```

<210> SEQ ID NO 157
<211> LENGTH: 1107
<212> TYPE: DNA
<213> ORGANISM: Aquilegia coerulea

<400> SEQUENCE: 157

```
atgtcctcct cattgaacgt tgaaggtgct acttctccaa aagttgatac caagactaga     60

aagactacca actggccttt gttgttgttg agctgttctt ttgttgccat tggtattatt    120

ggtggtccat tgctgtctag gttgtatttc ttgcatggtg gttctagatc atggttgtca    180

tcttgtatgc aaactgctgg tttcccaatt ttgtttttgc ccttgttgtc cttgttcctg    240

caatctagat ctcaaggtga atctgcttct gttttcttca tggaacctaa gctgtttatc    300

ttgtccgcca ttatcggttt gttgttaggt ttggacaact tcatgtacag cttgggtttg    360

tcttatactc cagtttccac ctcctctatt ttgttctcta ctcaattggc tttcttggct    420

gttttcgctt tctttatcgt caagcaaaag ttcaccccat actccattaa cgccgttatt    480

ttgatgactt tgggttccgt tttgctgggt ttgagatctg atggtgatag acctgctggt    540

gtttctaatg ctcaatattg gttgggtttc atcttgacat tgggttcagc tgctgttttg    600

ggtttgattt ggccattgat tgagctgtct tactctaaat ccaaaagacc agttaactac    660

ggtgtcgtct tgcaatttca aactaacttg gctatcttcg ccaccttgtt ttctttgact    720

ggtatggcta ttaacaagga ctttcaagcc atgggcaaag aatctaacga atacggttta    780

ggtaacggca tgtactattt ggttttggct gctggtgctg ttgtttggca attgtctttc    840

attggtggtt tgggtgttat ttctgcgct aactctttgt tgaacggtgt tttgtcagct     900

gtcttgttgc caattactaa tattgctgcc gttatcttct accacgaaaa ctttaatggt    960

ctgaaggcca tgtcattggt tttgtgtttg tggggttttg tctcttactt ttacggtgag   1020

tacaccatga acaagaagtt gaagaattct ccacagactc aattgtccga tgactctaac   1080

aagaacgaag ttttgtcccc agtttaa                                       1107
```

<210> SEQ ID NO 158
<211> LENGTH: 370
<212> TYPE: PRT
<213> ORGANISM: Papaver somniferum

<400> SEQUENCE: 158

```
Met Ala Thr Ser Thr Met Asn Ile Glu Thr Pro Glu Thr Ile Val Pro
1               5                   10                  15

Asn Gln Asn Gly Asn Ser Lys Pro His Val Glu Glu Thr Gly Lys Ala
            20                  25                  30

Arg Asn Trp Pro Leu Ile Ile Ile Asn Cys Ala Leu Val Phe Cys Gly
        35                  40                  45

Val Ile Gly Gly Pro Leu Leu Met Arg Leu Tyr Tyr Leu His Gly Gly
    50                  55                  60

Ser Arg Lys Trp Leu Ser Ser Cys Leu Gln Thr Ala Gly Phe Pro Val
65                  70                  75                  80

Leu Leu Phe Pro Leu Asn Phe Leu Tyr Ile Lys Ser Lys Ser Ser Thr
                85                  90                  95

Gln Lys Asn Asp Gln Ser Cys Ser Phe Phe Met Glu Pro Met Val Phe
            100                 105                 110

Phe Trp Ser Ala Ile Ile Gly Ile Val Phe Gly Val Ala Asn Phe Met
        115                 120                 125

Tyr Ala Leu Gly Leu Ser Tyr Leu Pro Val Ser Thr Ser Thr Ile Leu
    130                 135                 140

Phe Ala Thr Gln Leu Cys Phe Thr Ala Phe Phe Ala Trp Leu Val Val
145                 150                 155                 160

Lys Gln Lys Phe Thr Ala Phe Ile Ile Asn Ala Val Ile Val Met Thr
                165                 170                 175
```

-continued

```
Leu Gly Ser Val Leu Leu Gly Ile Asn Thr Asn Gly Asp Arg Pro Ile
            180                 185                 190

Gly Val Ser Lys Ala Gln Tyr Leu Leu Gly Phe Leu Leu Thr Leu Ala
        195                 200                 205

Ala Ala Ala Leu Thr Gly Leu Gly Met Pro Phe Ile Glu Leu Ala Phe
    210                 215                 220

Ser Lys Ala Thr Arg Asn Ile Thr Tyr Ser Thr Leu Leu Gln Phe Gln
225                 230                 235                 240

Ile Ile Ile Gly Leu Phe Gly Thr Val Leu Asn Val Ile Gly Met Leu
                245                 250                 255

Ile Asn Lys Asp Phe Gln Ala Ile Pro Arg Glu Ala Asp Glu Phe Glu
            260                 265                 270

Leu Gly Lys Gly Lys Tyr Tyr Met Ile Ile Ile Leu Thr Ala Leu Thr
        275                 280                 285

Trp Gln Leu Ser Ser Val Gly Phe Leu Gly Leu Ile Ser Tyr Thr Asn
    290                 295                 300

Ala Leu Phe Asn Gly Ile Tyr Thr Ser Val Leu Val Pro Phe Thr Glu
305                 310                 315                 320

Val Gly Ala Val Ile Phe Phe His Glu Ser Phe Thr Gly Leu Lys Gly
                325                 330                 335

Met Ala Leu Ala Leu Cys Leu Trp Gly Phe Ser Ser Tyr Phe Tyr Gly
            340                 345                 350

Glu Tyr Lys Thr Met Asn Lys Val Leu Asn Gly Lys Met Pro Gln Asn
        355                 360                 365

Gly Pro
    370
```

<210> SEQ ID NO 159
<211> LENGTH: 1113
<212> TYPE: DNA
<213> ORGANISM: Papaver somniferum

<400> SEQUENCE: 159

```
atggctacct ccaccatgaa cattgaaact ccagaaacta tcgttccaaa ccagaatggt     60

aattccaagc cacatgttga agaaactggt aaggctagaa attggccatt gattattatc    120

aactgcgcct tggttttctg cggtgttatt ggtggtccat tattgatgag gttgtactac    180

ttgcatggtg gttctagaaa atggttgtca tcttgtttac aaaccgctgg ttttccagtt    240

ttgttgttcc cattgaattt cttgtacatc aagtccaagt cctccactca aaagaacgat    300

caatcttgct cattcttcat ggaacccatg gttttttcct ggtccgctat tattggtatc    360

gttttcggtg ttgctaactt catgtatgct ttgggtttgt cttacttgcc agtttctact    420

tccactattt tgttcgctac ccaattgtgt ttcactgctt tttttgcttg gttggtcgtc    480

aagcaaaagt ttaccgcttt cattattaac gccgttatcg ttatgacctt gggttctgtt    540

ttgttgggta ttaacactaa cggtgataga ccaatcggtg tttctaaagc tcaatacttg    600

ttgggtttct tgttgacttt ggctgctgct gctttgactg gtttgggtat gccttttatt    660

gaattggctt tctctaaggc caccagaaac attacttact ctaccttgtt gcagttccag    720

atcattattg gtttgttcgg tactgtcttg aacgtcattg gtatgttgat taacaaggac    780

ttccaagcta ttccaagaga agctgatgaa ttcgaactag gtaaaggcaa gtactacatg    840

atcattatct tgaccgcttt gacctggcaa ttatcttctg ttggtttttt gggcttgatc    900

tcttacacta acgctttgtt taacggcatc tacacctctg ttttggttcc attcactgaa    960
```

gttggtgccg ttattttctt ccatgaatct ttcacaggtt tgaaaggtat ggctttggct 1020
ttatgtttgt ggggtttttc ctcttacttt tacggtgagt acaagacgat gaacaaggtt 1080
ttgaatggta agatgccaca aaacggtcca tga 1113

<210> SEQ ID NO 160
<211> LENGTH: 373
<212> TYPE: PRT
<213> ORGANISM: Papaver somniferum

<400> SEQUENCE: 160

Met Ala Thr Ser Ala Met Asp Ile Glu Thr Pro Glu Thr Leu Val Pro
1 5 10 15

Asn Gln Asn Gly Asn Ser Lys Thr Lys Pro Ile Lys Thr Arg Asn Trp
20 25 30

Leu Leu Ile Leu Ile Asn Cys Ala Leu Val Ser Cys Gly Ser Ile Gly
35 40 45

Gly Pro Leu Leu Met Arg Leu Tyr Tyr Leu His Gly Gly Asn Arg Lys
50 55 60

Trp Phe Ser Ser Phe Ile Ala Ser Ala Gly Phe Pro Ile Leu Ile Phe
65 70 75 80

Pro Leu Met Phe His Phe Phe Arg Ser Glu Ser Ser Thr Asp Lys Ile
85 90 95

Trp Ser Cys Phe Trp Leu Glu His Lys Leu Phe Leu Arg Gly Val Ile
100 105 110

Leu Gly Ile Leu Tyr Gly Leu Val Thr Phe Met Tyr Ala Leu Gly Leu
115 120 125

Ser Tyr Ile Pro Val Ser Thr Ser Ser Leu Leu Met Ala Thr Gln Leu
130 135 140

Cys Phe Ile Ala Phe Phe Ser Trp Leu Ile Val Lys Gln Lys Phe Thr
145 150 155 160

Ala Phe Ile Ile Asn Ala Val Val Val Met Thr Leu Gly Ser Val Leu
165 170 175

Leu Gly Ile Asn Thr Asn Gly Asp Arg Pro Val Gly Val Thr Lys Ser
180 185 190

Gln Tyr Leu Leu Gly Phe Leu Leu Thr Leu Ala Ala Ala Ala Leu Ala
195 200 205

Gly Leu Ile Met Pro Leu Ile Glu Leu Ser Phe Ser Lys Ala Ile Asn
210 215 220

Asn Leu Thr Tyr Ser Ser Leu Leu Gln Phe Gln Phe Ile Leu Ser Leu
225 230 235 240

Ser Ser Thr Ile Val Cys Val Ile Gly Met Leu Ala Asn Lys Asp Phe
245 250 255

Gln Ala Ile Pro Arg Glu Ala Asn Asp Phe Glu Leu Gly Lys Ala Arg
260 265 270

Tyr Tyr Ile Ile Met Val Val Thr Ala Ile Val Trp Gln Leu Ser Gly
275 280 285

Val Gly Thr Val Gly Val Ile Phe Tyr Thr Ser Ala Leu Phe Asn Gly
290 295 300

Ile Leu Gly Ser Val Leu Ile Pro Leu Thr Gly Val Ala Ala Val Ile
305 310 315 320

Phe Tyr His Glu Ser Phe Thr Gly Leu Lys Gly Met Ala Leu Ala Leu
325 330 335

Cys Leu Trp Gly Phe Cys Ser Tyr Phe Tyr Gly Glu Tyr Lys Met Thr

```
        340                 345                 350

Lys Lys Val Ile Val Lys Val Glu Asn Glu Pro Lys Arg Leu Leu Gly
    355                 360                 365

Asp Gln Glu Glu Pro
    370
```

<210> SEQ ID NO 161
<211> LENGTH: 1122
<212> TYPE: DNA
<213> ORGANISM: Papaver somniferum

<400> SEQUENCE: 161

```
atggctacct ccgctatgga tattgaaact ccagaaactt tggttccaaa ccagaatggt      60

aactctaaga ctaagccaat caagaccaga aactggttgt tgattttgat taactgcgcc     120

ttggtttcct gtggttctat tggtggtcca ttattgatga ggttgtacta cttgcatggt     180

ggtaatagaa agtggttctc ctcttttatt gcttctgctg gtttcccaat tctgatcttt     240

ccattgatgt tccatttctt caggtccgaa tcttccactg ataagatttg gtcttgtttt     300

tggttggagc acaagttgtt tttgagaggt gttatcttgg gtatcttgta cggtttggtt     360

actttcatgt atgccttggg tttgtcctat attccagttt ctacttcctc tttgttgatg     420

gctactcagt tgtgtttcat tgctttcttc tcttggttga tcgtcaagca aaagttcacc     480

gcctttatta tcaacgccgt tgttgttatg actttgggtt ctgttttgtt gggtattaac     540

accaatggtg atagacctgt tggtgttact aagtcccaat acttgttggg tttcttgttg     600

actttggctg ctgctgcttt ggctggtttg attatgccat tgattgagct gtctttctca     660

aaggccatta acaacttgac ctactcgtct ttgttgcagt tccaattcat cctgtctttg     720

tcctctacta tcgtttgcgt tattggtatg ttggctaaca aggatttcca agccattcct     780

agagaagcta acgatttcga attgggtaaa gccaggtact acatcattat ggttgttact     840

gctatcgtct ggcaattgtc tggtgttggt actgtcggtg ttattttcta tacttctgct     900

ttgttcaacg gcatcttagg ttcagttttg attccattaa ctggtgttgc tgccgttatc     960

ttctaccatg aatctttcac tggtttgaaa ggtatggctt tggctttgtg tttgtggggt    1020

ttttgttctt acttttacgg cgagtacaag atgactaaga aggttatcgt taaggtcgaa    1080

aacgagccaa aaagattatt gggtgatcaa gaggaaccct aa                       1122
```

<210> SEQ ID NO 162
<211> LENGTH: 370
<212> TYPE: PRT
<213> ORGANISM: Prunus yedoensis var. nudiflora

<400> SEQUENCE: 162

```
Met His Met Glu Ala Asn His Glu Glu Lys Arg Asn Ala Ala Leu Lys
1               5                   10                  15

Arg Ala Leu Leu Ile Leu Ser Cys Val Leu Leu Ser Ile Gly Ala Cys
            20                  25                  30

Gly Gly Pro Leu Ile Met Arg Leu Tyr Phe Ile His Gly Gly Lys Arg
        35                  40                  45

Val Trp Leu Ser Ser Trp Leu Glu Thr Gly Gly Trp Pro Ile Ile Phe
    50                  55                  60

Ile Pro Ile Ala Leu Ala Tyr Tyr His Arg Arg Thr Thr Glu Gly Pro
65                  70                  75                  80

Ser Thr Lys Leu Phe Phe Met Lys Leu Pro Leu Phe Ile Ala Ser Ala
                85                  90                  95
```

```
Val Ile Gly Leu Leu Thr Gly Ile Asp Asp Tyr Leu Tyr Ala Tyr Gly
            100                 105                 110

Val Ala Arg Leu Pro Val Ser Thr Ala Ser Leu Ile Thr Ala Ala His
        115                 120                 125

Leu Ala Phe Thr Ala Leu Phe Ala Phe Leu Leu Val Lys Gln Lys Phe
    130                 135                 140

Thr Ser Tyr Ser Ile Asn Cys Ile Phe Leu Leu Thr Ile Gly Ala Ala
145                 150                 155                 160

Val Leu Gly Leu Asn Thr Ser Ala Asp Arg Pro Lys Gly Glu Ser Asp
                165                 170                 175

Lys Gln Tyr Ile Ala Gly Phe Met Met Thr Leu Ser Ala Ala Ala Leu
            180                 185                 190

Tyr Gly Phe Val Leu Pro Leu Val Glu Leu Thr Tyr Lys Lys Ala Lys
        195                 200                 205

Gln Thr Ile Thr Tyr Ala Leu Val Leu Glu Val Gln Leu Val Met Cys
    210                 215                 220

Leu Phe Ala Thr Ile Phe Cys Thr Val Gly Met Leu Ile Asn Asn Asp
225                 230                 235                 240

Phe Lys Val Ile Pro Arg Glu Ala Arg Asn Phe Glu Leu Gly Glu Ser
                245                 250                 255

Lys Tyr Tyr Val Val Leu Val Phe Ser Ala Ile Val Trp Gln Gly Phe
            260                 265                 270

Phe Leu Gly Ala Ile Gly Ile Ile Phe Cys Ala Ser Ser Leu Leu Ser
        275                 280                 285

Gly Ile Val Ile Ala Val Leu Leu Pro Val Thr Glu Ile Leu Ala Val
    290                 295                 300

Ile Phe Tyr His Glu Lys Phe Gln Ala Glu Lys Gly Val Ala Leu Ala
305                 310                 315                 320

Leu Ser Leu Trp Gly Phe Val Ser Tyr Phe Tyr Gly Glu Arg Lys Tyr
                325                 330                 335

Ser Lys Gln Lys Glu Ser Glu Met Lys Asn Glu Lys Glu Lys Glu Val
            340                 345                 350

Glu Ile Gly Lys Lys Asp Thr Pro Glu Thr Ala Glu Val Ser Gln Leu
        355                 360                 365

Asp Pro
    370
```

```
<210> SEQ ID NO 163
<211> LENGTH: 1113
<212> TYPE: DNA
<213> ORGANISM: Prunus yedoensis var. nudiflora

<400> SEQUENCE: 163

atgcacatgg aagccaacca cgaagaaaaa agaaatgctg ctttgaagag agccctgttg      60

attttgtctt gtgtcttgtt gtctattggt gcttgtggtg gtccattgat catgaggttg     120

tactttattc atggtggtaa gagagtctgg ttgtcatctt ggttggaaac tggtggttgg     180

ccaattatct ttattccaat tgctttggcc tactaccata gaagaactac tgaaggtcca     240

tctaccaagc tgttttttat gaagttgcct ctgttcattg cctccgctgt tattggtttg     300

ttgactggta ttgatgatta cttgtacgct tacggtgttg ctagattgcc agtttctact     360

gcttctttga ttactgctgc tcatttggct tttactgctt tgtttgcttt cttgttggtc     420

aagcaaaagt tcacctccta ctccattaac tgcatctttt tgttgacaat tggtgccgct     480
```

```
gttttgggtt taaatacttc tgctgataga ccaaagggtg aatctgataa gcagtacatt    540

gctggtttca tgatgacttt gtctgctgct gcattatacg gttttgtttt gccattggtt    600

gagctgactt acaagaaggc taagcaaact attacctacg ccttggtttt ggaagttcaa    660

ttggttatgt gtttgttcgc caccattttc tgtactgttg gcatgttgat taacaacgac    720

ttcaaggtta ttccaaggga agctagaaat ttcgaattgg gtgaatccaa gtactacgtc    780

gttttggttt tttctgctat agtctggcaa ggtttcttct tgggtgctat tggtattatc    840

ttctgcgctt cttctttgtt gtccggtata gttattgctg ttttgttgcc agttaccgaa    900

attttggccg ttattttcta ccacgaaaag ttccaagctg aaaagggtgt tgctttagct    960

ttgtctttgt ggggtttcgt ttcttacttt tacggtgaga gaaagtactc caagcagaaa   1020

gaatctgaaa tgaagaacga aaaagagaaa gaggtcgaga tcggtaaaaa ggatactcca   1080

gaaactgctg aagtttccca attggatcca tga                                1113


<210> SEQ ID NO 164
<211> LENGTH: 353
<212> TYPE: PRT
<213> ORGANISM: Macleaya cordata

<400> SEQUENCE: 164

Met Asp Lys Glu Gln Gln Arg Asp Ala Ala Met Lys Arg Ala Leu Leu
1               5                   10                  15

Ile Phe Asn Cys Val Leu Leu Ala Ile Gly Asn Cys Gly Gly Pro Leu
            20                  25                  30

Val Met Arg Leu Tyr Phe Val His Gly Gly Lys Arg Val Trp Leu Ser
        35                  40                  45

Ser Trp Leu Glu Thr Gly Gly Trp Pro Ile Ile Phe Ile Pro Leu Ala
    50                  55                  60

Ile Ser Tyr Phe His Arg Arg Arg Ala Ala Ala Gly Glu Ser Thr Thr
65                  70                  75                  80

Leu Ile Phe Met Lys Pro Arg Leu Phe Leu Ala Ala Thr Val Ile Gly
                85                  90                  95

Val Ile Thr Gly Phe Asp Asp Tyr Leu Tyr Ala Tyr Gly Val Ala Arg
            100                 105                 110

Leu Pro Val Ser Thr Ser Ala Leu Ile Ile Ala Cys Gln Leu Ala Phe
        115                 120                 125

Thr Ala Val Phe Ala Tyr Leu Leu Val Lys Gln Lys Phe Thr Ser Tyr
    130                 135                 140

Ser Ile Asn Ala Val Val Leu Met Thr Ile Gly Gly Ala Val Leu Ala
145                 150                 155                 160

Leu His Thr Ser Gly Asp Arg Pro Ala Gly Glu Ser Thr Lys Ala Tyr
                165                 170                 175

Val Ala Gly Phe Leu Met Thr Val Ala Ala Ala Leu Leu Tyr Gly Phe
            180                 185                 190

Val Leu Pro Leu Val Glu Leu Thr Tyr Lys Lys Ala Lys Gln Gln Ile
        195                 200                 205

Thr Tyr Thr Leu Val Leu Glu Ile Gln Leu Val Met Ser Leu Phe Ala
    210                 215                 220

Thr Leu Val Cys Thr Val Gly Met Leu Ile Asn Asn Asp Phe Gln Val
225                 230                 235                 240

Ile Pro Arg Glu Ala Arg Glu Phe Gly Leu Gly Glu Thr Lys Tyr Tyr
                245                 250                 255

Val Val Leu Ala Phe Ser Ala Ile Ile Trp Gln Gly Phe Phe Leu Gly
```

```
            260                 265                 270

Ala Ile Gly Val Ile Phe Cys Ser Ser Ser Leu Phe Ser Gly Ile Val
        275                 280                 285

Ile Ala Val Leu Leu Pro Val Thr Glu Ile Leu Ala Val Val Ile Phe
    290                 295                 300

Ser Glu Lys Phe Gln Ala Glu Lys Gly Val Ser Leu Ala Leu Asn Leu
305                 310                 315                 320

Trp Gly Phe Val Ser Tyr Phe Tyr Gly Glu Ile Lys His Asp Lys Lys
                325                 330                 335

Arg Lys Leu Glu Leu Gln Asn Ala Glu Ser Ala Cys Gln Ile Thr Ser
            340                 345                 350

Val
```

<210> SEQ ID NO 165
<211> LENGTH: 1062
<212> TYPE: DNA
<213> ORGANISM: Macleaya cordata

<400> SEQUENCE: 165

```
atggacaaag aacaacaaag ggatgctgct atgaagagag ctttgttgat tttcaactgc     60

gttttgttgg ctattggtaa ttgtggtggt ccattggtta tgaggttgta ctttgttcat    120

ggtggtaaga gagtttggtt gtcatcttgg ttggaaactg gtggttggcc aattatcttt    180

attccattgg ccatctctta cttccataga cgtagagctg ctgctggtga atctactact    240

ttgattttta tgaagcccag gttgttcttg gctgctactg ttattggtgt tattaccggt    300

ttcgatgatt acttgtatgc ttacggtgtt gctagattgc cagtttctac ttccgctttg    360

attattgctt gtcaattggc tttcactgct gttttcgctt acttgttggt taagcaaaag    420

ttcacctcct actccattaa cgctgttgtt ttgatgacaa ttggtggtgc tgttttggca    480

ttgcatactt caggtgatag accagccggt gaatcaacta aggcttatgt tgctggtttc    540

ttgatgactg ttgctgctgc tttgttgtac ggttttgttt tgccattggt tgagttgact    600

tacaagaagg ccaagcaaca aattacctac accttggttt tggaaatcca gttggtcatg    660

tctttgtttg ctactttggt atgtaccgtc ggcatgttga ttaacaacga tttccaagtt    720

attcccaggg aagctagaga atttggtttg ggtgaaacta agtactacgt tgtcttggct    780

ttttccgcca ttatttggca aggtttttttc ttgggtgcta tcggtgttat tttctgctca    840

tcttctttgt tctccggtat cgttattgca gttttgttgc cagttaccga aattttggct    900

gtcgttatct tctccgaaaa gttccaagct gaaaagggtg tttctttggc tttgaatttg    960

tggggtttcg tgtcttactt ttacggtgaa atcaagcacg acaagaagag aaagttggaa   1020

ttgcaaaatg ctgaatccgc ctgccaaatt acttctgttt aa                      1062
```

<210> SEQ ID NO 166
<211> LENGTH: 375
<212> TYPE: PRT
<213> ORGANISM: Helianthus annuus

<400> SEQUENCE: 166

```
Met Asn Asn His Lys Gln Asn Thr Thr Thr Asn Thr Thr Ala Gly Thr
1               5                   10                  15

Thr Ala Pro Ala Thr Ala Lys Val Ser Pro Ala Ala Lys Asn Thr Leu
            20                  25                  30

Leu Ile Leu Asn Cys Val Leu Leu Ser Ile Gly Asn Cys Gly Gly Pro
        35                  40                  45
```

```
Leu Ile Met Arg Leu Tyr Phe Leu His Gly Gly Glu Arg Val Trp Leu
    50                  55                  60

Ser Ser Phe Leu Glu Thr Ala Gly Trp Pro Val Ile Ile Leu Val Leu
65                  70                  75                  80

Ala Val Leu Tyr Phe Asp Arg Arg Arg Lys Asn Thr Asn Thr Lys Thr
                85                  90                  95

Thr Phe Val Tyr Met Arg Pro Arg Leu Phe Phe Ala Val Ala Val Ile
            100                 105                 110

Gly Ile Leu Thr Gly Leu Asp Asp Tyr Leu Tyr Ala Tyr Gly Val Ala
        115                 120                 125

Arg Leu Pro Val Ser Thr Ser Ser Leu Ile Ile Ala Ser Gln Leu Gly
    130                 135                 140

Phe Thr Ala Phe Phe Ala Tyr Val Leu Val Lys Gln Lys Phe Thr Pro
145                 150                 155                 160

Tyr Ser Val Asn Ala Val Val Leu Leu Thr Val Gly Ala Ala Val Leu
                165                 170                 175

Ala Leu His Thr Asn Gly Asp Arg Pro Glu Gly Glu Ser Lys Lys Ala
            180                 185                 190

Tyr Val Met Gly Phe Val Met Thr Val Gly Ala Ser Leu Leu Tyr Gly
        195                 200                 205

Phe Val Leu Pro Leu Ile Glu Leu Thr Tyr Asn Lys Ala Lys Gln Glu
    210                 215                 220

Ile Thr Tyr Thr Leu Val Leu Glu Ile Gln Met Val Met Cys Leu Phe
225                 230                 235                 240

Ala Thr Ile Phe Cys Ala Val Gly Met Phe Ile Asn Asn Asp Phe Lys
                245                 250                 255

Ala Ile Pro Val Glu Ala Thr Glu Phe Gly Leu Gly Glu Thr Lys Tyr
            260                 265                 270

Tyr Val Ile Leu Cys Ala Ser Ala Leu Ile Trp Gln Cys Phe Phe Leu
        275                 280                 285

Gly Ala Ile Gly Val Ile Phe Cys Ala Ser Ser Leu Leu Ser Gly Ile
    290                 295                 300

Ile Ile Ala Val Leu Leu Pro Val Ile Glu Val Leu Ala Val Val Phe
305                 310                 315                 320

Tyr Lys Glu Asn Phe Gln Ala Glu Lys Gly Val Ala Leu Val Leu Ser
                325                 330                 335

Leu Trp Gly Phe Ala Ser Tyr Phe Tyr Gly Glu Tyr Lys Phe Ala Lys
            340                 345                 350

Lys Leu Lys Glu Lys Thr Arg Ser Ser Gln Gln Ser Met Glu Leu Gly
        355                 360                 365

Gln Ala Tyr Ile Ser Ser Val
    370                 375
```

<210> SEQ ID NO 167
<211> LENGTH: 1128
<212> TYPE: DNA
<213> ORGANISM: Helianthus annuus

<400> SEQUENCE: 167

```
atgaacaacc acaagcaaaa cactactacc aacactactg ctggtactac tgctccagct      60

actgctaaag tttctccagc tgctaagaac accttgttga ttttgaactg cgtcttgttg     120

tctattggta attgtggtgg tccattgatc atgaggttgt atttcttgca tggtggtgaa     180

agagtttggc tgtcatcttt tttggaaact gctggttggc cagttatcat tttggtttta     240
```

gctgtcttgt acttcgacag aagaagaaag aacactaaca ctaagaccac cttcgtttac 300
atgaggccaa gattattctt tgccgttgcc gttattggta ttttgactgg tttggatgat 360
tacttgtacg cttatggtgt tgctagattg ccagtttcta cctcctcttt gattattgct 420
tctcaattgg gtttcaccgc tttctttgct tacgttttgg ttaagcaaaa gttcacccca 480
tactctgtta acgctgttgt tttgttgact gttggtgctg ctgttttggc attgcataca 540
aatggtgata gaccagaagg tgaatccaaa aaggcttacg ttatgggttt cgttatgaca 600
gttggtgcat ctttgttgta cggttttgtt ttgccattga tcgagttgac ttacaacaag 660
gccaagcaag aaattaccta caccttggtt ttggaaatcc aaatggttat gtgtttgttc 720
gccaccattt tttgtgctgt tggtatgttc atcaacaacg actttaaggc cattccagtt 780
gaagctactg aatttggttt gggtgaaact aagtactacg ttattttgtg cgcttccgct 840
ttgatttggc aatgtttttt cttgggtgcc atcggtgtta ttttctgtgc ttcttctttg 900
ctgtccggta ttatcattgc tgttctgttg ccagtcattg aagttttggc agtcgttttc 960
tacaaagaaa acttccaagc tgaaaagggt gttgctttgg ttttgtcttt gtggggtttt 1020
gcttcttact tttacggtga gtacaagttc gccaagaagt tgaaagaaaa gaccagatcc 1080
tctcagcagt ctatggaatt gggtcaagct tacatttcct ccgtttga 1128

<210> SEQ ID NO 168
<211> LENGTH: 342
<212> TYPE: PRT
<213> ORGANISM: Carica papaya

<400> SEQUENCE: 168

Met Glu Ala Ala Met Lys Arg Ala Leu Leu Val Leu Asn Cys Ile Leu
1               5                   10                  15

Leu Phe Ile Gly Gly Ser Gly Gly Pro Leu Leu Thr Arg Leu Tyr Phe
            20                  25                  30

Ile His Gly Gly Ser Arg Leu Trp Phe Ser Ser Trp Leu Gln Thr Gly
        35                  40                  45

Gly Phe Pro Ile Phe Leu Leu Pro Leu Ser Ile Ala Tyr Ile Gln His
    50                  55                  60

His Arg Arg Asn Pro Ser Pro Gly Asn Arg Phe Phe Ile Gly Pro Arg
65                  70                  75                  80

Leu Phe Ile Ala Ser Val Ile Ile Gly Ile Leu Thr Gly Leu Asp Asp
                85                  90                  95

Phe Leu Met Ala Asn Gly Met Ala Arg Leu Pro Ile Ser Thr Ser Ala
            100                 105                 110

Leu Ile Ser Ala Thr Gln Leu Ala Phe Thr Ala Gly Phe Ala Phe Leu
        115                 120                 125

Leu Val Arg Gln Lys Phe Thr Ala Tyr Ser Val Asn Ala Leu Val Leu
    130                 135                 140

Leu Thr Ile Gly Ala Ala Val Leu Ala Met His Gly Ser Ser Asp Arg
145                 150                 155                 160

Pro Glu Gly Glu Ser Ser Lys Glu Tyr Met Phe Gly Phe Val Met Met
                165                 170                 175

Ile Gly Ala Ala Ala Leu Tyr Gly Phe Ile Met Pro Phe Leu Glu Leu
            180                 185                 190

Val Tyr Ala Lys Ala Gly Gln Glu Ile Thr Tyr Ala Val Val Met Gln
        195                 200                 205

Ile Gln Met Val Ile Cys Val Phe Ala Thr Gly Phe Ser Thr Val Gly

```
    210                 215                 220

Met Val Ile Asn Asn Asp Phe Lys Val Ile Pro Arg Glu Ala Arg Glu
225                 230                 235                 240

Phe Glu Ile Gly Glu Thr Lys Tyr Tyr Leu Val Val Val Trp Ser Ala
                245                 250                 255

Val Ala Trp Gln Phe Ser Phe Leu Gly Val Val Gly Ile Val Phe Cys
            260                 265                 270

Ala Ser Ser Leu Leu Ser Gly Val Met Val Ser Leu Leu Ile Pro Val
        275                 280                 285

Thr Glu Val Leu Gly Val Ile Phe Leu Asp Glu Lys Phe Arg Pro Glu
    290                 295                 300

Lys Gly Val Ala Leu Ala Leu Ser Ile Trp Gly Phe Ile Ser Tyr Phe
305                 310                 315                 320

Tyr Gly Glu Ala Arg Thr Leu Lys Lys Gln Lys His Val Asp Gln Asp
                325                 330                 335

Thr Glu Met Gln Gln Val
            340
```

<210> SEQ ID NO 169
<211> LENGTH: 1029
<212> TYPE: DNA
<213> ORGANISM: Carica papaya

<400> SEQUENCE: 169

```
atggaagctg ctatgaagag agccttgttg gttttgaact gcatcttgtt gtttatcggt     60

ggttctggtg gtccattatt gactaggttg tactttattc atggtggctc tagattgtgg    120

ttctcttctt ggttgcaaac tggtggtttt ccaattttct tgctgccatt gtccattgcc    180

tacatccaac atcatagaag aaatccatct ccaggtaaca gattctttat tggtccaagg    240

ttgttcattg cctccgttat tattggtatt ttgaccggtt tggacgattt cttgatggct    300

aatggtatgg ctagattgcc aatttctacc tccgctttga tttctgctac tcaattggct    360

tttactgctg gttttgcctt tttgttggtc agacaaaagt tcaccgctta ctctgttaat    420

gccttggttt tgttgactat tggtgctgct gttttggcta tgcatggttc ttcagataga    480

ccagaaggtg aatcttctaa agagtacatg ttcggtttcg tcatgatgat tggtgcagct    540

gccttatatg gtttcattat gccattcttg gaactggttt atgctaaggc tggtcaagaa    600

attacttacg ccgttgttat gcaaatccaa atggttattt gtgttttcgc cactggtttc    660

tctactgttg gtatggttat taacaacgac ttcaaggtca ttccaagaga agctagagaa    720

ttcgaaatcg gtgaaacgaa gtactacttg gttgttgttt ggtcagctgt tgcttggcaa    780

ttttcatttt tgggtgttgt cggtatcgtt ttctgtgctt cttctttgtt gtctggtgtc    840

atggtgtctt tgttgattcc agttactgaa gtcttgggtg ttatcttctt ggacgaaaaa    900

ttcagaccag aaaagggtgt tgctttggct ttgtctattt ggggtttcat ctcttacttt    960

tacggtgaag ctaggaccct gaaaaaacaa aaacacgttg atcaagacac cgaaatgcaa   1020

caagtttaa                                                           1029
```

<210> SEQ ID NO 170
<211> LENGTH: 341
<212> TYPE: PRT
<213> ORGANISM: Papaver radicatum

<400> SEQUENCE: 170

```
Met Lys Lys Ser Leu Met Leu Phe Asn Thr Ile Leu Leu Gly Ile Gly
```

```
1               5                   10                  15

Ala Thr Gly Gly Pro Leu Leu Leu Arg Leu Tyr Phe Val Arg Gly Gly
            20                  25                  30

Lys Arg Ile Trp Leu Ser Ser Ala Leu Gly Ser Ala Gly Trp Pro Val
        35                  40                  45

Leu Ile Leu Pro Leu Ser Leu Ser Tyr Phe Phe Asn Arg Gly Gly Arg
    50                  55                  60

Gly Gly Asp Lys Arg Trp Tyr Lys Phe Tyr Thr Ile Thr Pro Pro Leu
65                  70                  75                  80

Ile Val Phe Ser Ala Phe Ile Gly Ile Ile Leu Gly Ser Asn Asp Tyr
                85                  90                  95

Leu Tyr Thr His Gly Ile Ser Leu Leu Pro Val Ser Thr Ser Thr Leu
            100                 105                 110

Ile Met Ser Thr His Leu Ala Phe Thr Ala Gly Phe Ala Phe Val Ile
        115                 120                 125

Val Lys His Lys Phe Thr Pro Tyr Ser Ile Asn Ala Val Val Leu Leu
    130                 135                 140

Thr Val Gly Ala Val Leu Leu Gly Leu Asn Ser Ser Gly Asp Lys Pro
145                 150                 155                 160

Val Asn Gln Ser Lys Lys Asp Tyr Tyr Leu Gly Phe Phe Leu Thr Val
                165                 170                 175

Gly Ala Ser Val Ile Ser Gly Phe Leu Phe Pro Leu Ser Glu Leu Met
            180                 185                 190

Tyr Met Lys Ala Lys Glu Arg Leu Thr Tyr Ser Leu Val Ile Glu Met
        195                 200                 205

Gln Ile Val Thr Ala Val Val Ala Ser Leu Phe Cys Ile Val Gly Met
    210                 215                 220

Ile Val Asn Asn Asp Phe Gln Ala Ile Pro Arg Glu Gly Arg Asp Tyr
225                 230                 235                 240

Glu Leu Gly Glu Val Lys Tyr Tyr Val Val Leu Val Ala Ile Ala Ile
                245                 250                 255

Met Trp Gln Ile Tyr Phe Val Gly Thr Ala Gly Val Ile Phe Cys Ser
            260                 265                 270

Thr Ser Leu Tyr Ala Gly Ile Ile Thr Ala Val Ile Leu Pro Val Thr
        275                 280                 285

Glu Ile Leu Ser Val Val Phe Tyr His Glu Ser Phe Lys Ser Glu Lys
    290                 295                 300

Gly Leu Ala Leu Phe Leu Ser Cys Trp Gly Phe Ile Ser Tyr Leu Tyr
305                 310                 315                 320

Gly Asp Tyr Lys Glu Asn Leu Lys Leu Lys Lys Ala Gln Lys Gln Ser
                325                 330                 335

Ser Glu Met Glu Leu
            340


<210> SEQ ID NO 171
<211> LENGTH: 1026
<212> TYPE: DNA
<213> ORGANISM: Papaver radicatum

<400> SEQUENCE: 171

atgaagaaat ccctgatgct gttcaacacc atcttgttag gtattggtgc tactggtggt      60

cctttgttgt tgagattata ctttgttaga ggtggcaaga ggatctggtt atcttctgct     120

ttgggttctg ctggttggcc agttttgatt ttgccattgt ctctgtccta ctttttttaac    180
```

-continued

```
agaggtggta gaggcggtga taagagatgg tacaaattct acactattac cccaccactg    240

atcgttttct ctgctttcat tggtattatc ttgggctcca acgattactt gtacacccat    300

ggtatttctt tgttgccagt ttctacctcc accttgatta tgtctactca tttggctttt    360

actgctggtt tcgctttcgt tatcgttaag cacaagttta ccccatactc cattaacgct    420

gttgttttgt tgactgttgg tgcagttttg ttgggtttga attcttctgg tgataagcca    480

gttaaccagt ccaaaaagga ttactacttg ggtttctttt taaccgttgg tgcctctgtt    540

atttccggtt ttttgtttcc attgtccgag ctgatgtaca tgaaggctaa agaaagattg    600

acctactcct tggtcatcga aatgcaaata gttactgctg ttgttgcctc tttgttctgt    660

atagttggta tgatcgttaa caacgacttc caagctattc caagagaagg tagagattac    720

gaattgggtg aagttaagta ctacgttgtt ttggttgcca ttgccattat gtggcaaatc    780

tactttgttg gtacagccgg tgttattttc tgttctactt cattatacgc cggtatcatt    840

accgcagtta ttttgccagt taccgaaatc ttgtccgttg ttttctacca cgaatccttc    900

aagtctgaaa aaggtttggc tttgttcttg tcttgctggg gttttatctc ttacttgtat    960

ggtgactaca aagagaacct gaagttgaag aaagcccaaa agcaatcttc cgagatggaa   1020

ttgtga                                                              1026
```

```
<210> SEQ ID NO 172
<211> LENGTH: 384
<212> TYPE: PRT
<213> ORGANISM: Sanguinaria canadensis

<400> SEQUENCE: 172

Met Gly Arg Arg Ser Arg Arg Ala Ala Pro Pro Asn Gly Glu Thr Thr
1               5                   10                  15

Gln Asn Glu Lys Ser Lys Thr Gln Ile Glu Ser Ser Pro Thr Ser Cys
            20                  25                  30

Arg Thr Lys Asn Trp Pro Leu Ile Ile Leu Asn Ala Ala Ile Met Thr
        35                  40                  45

Thr Gly Val Ile Gly Gly Pro Leu Leu Met Arg Leu Tyr Tyr Ile His
    50                  55                  60

Gly Gly Asn Arg Arg Trp Leu Ser Ser Cys Val Gln Thr Ala Gly Phe
65                  70                  75                  80

Pro Ile Leu Ile Ile Pro Leu Thr Phe Leu Tyr Phe Phe His Ser Lys
                85                  90                  95

Lys Ile Ser His His His Asn Ser Ser Ser Ser Ser Ser Ser Phe Trp
            100                 105                 110

Met Glu Pro Lys Leu Phe Val Ser Ser Ser Leu Ile Gly Ile Leu Phe
        115                 120                 125

Gly Leu Thr Asn Phe Met Tyr Ser Leu Gly Leu Ser Tyr Ile Pro Ile
    130                 135                 140

Ser Thr Ser Ser Leu Leu Tyr Ala Thr Gln Leu Val Phe Val Ala Phe
145                 150                 155                 160

Phe Ala Trp Phe Ile Val Lys Gln Gln Phe Thr Ala Phe Ser Ile Asn
                165                 170                 175

Ser Val Val Leu Met Thr Leu Gly Ser Ile Leu Leu Gly Ile Lys Thr
            180                 185                 190

Asp Gly Asp Arg Pro Val Gly Val Thr Lys Ala Glu Tyr Leu Leu Gly
        195                 200                 205

Phe Leu Leu Thr Leu Gly Ser Ala Ala Val Val Gly Phe Ile Leu Pro
    210                 215                 220
```

```
Met Val Glu Leu Ser Tyr Ser Lys Ala Thr Arg Thr Val Asn Tyr Thr
225                 230                 235                 240

Thr Val Leu Gln Tyr Gln Phe Asn Leu Ala Leu Phe Ser Thr Ile Phe
                245                 250                 255

Asn Ser Ile Gly Met Leu Ile Asn Lys Asp Phe Gln Ala Ile Pro Arg
            260                 265                 270

Glu Ala Ser Glu Phe Glu Leu Gly Lys Thr Met Tyr Tyr Val Val Leu
        275                 280                 285

Ile Gly Gly Ala Ile Thr Trp Gln Phe Ala Ser Ile Gly Gly Leu Gly
    290                 295                 300

Val Ile Leu Tyr Thr Ser Ser Leu Phe Ser Gly Ile Leu Ser Ser Val
305                 310                 315                 320

Leu Leu Pro Phe Thr Glu Ile Ala Ala Val Ile Val Tyr His Glu Arg
                325                 330                 335

Phe Thr Gly Leu Lys Gly Met Ala Leu Ala Leu Cys Phe Trp Gly Phe
            340                 345                 350

Thr Ser Tyr Phe Tyr Gly Glu Tyr Lys Leu Met Met Asn Asp Thr Lys
        355                 360                 365

Thr Lys Pro Pro Glu Lys Asn Ile Pro Asp Asp Pro Cys Thr Ser Val
    370                 375                 380
```

<210> SEQ ID NO 173
<211> LENGTH: 1155
<212> TYPE: DNA
<213> ORGANISM: Sanguinaria canadensis

<400> SEQUENCE: 173

```
atgggcagaa gatctagaag ggctgctcca ccaaatggtg aaactactca aaacgaaaag     60

tctaagaccc agatcgaatc ttctccaact tcttgtagaa ctaagaactg gccattgatt    120

attttgaacg ctgctattat gaccaccggt gttattggtg gtccattgct aatgaggttg    180

tactatattc atggtggtaa cagaaggtgg ttgtcctctt gtgttcaaac tgctggtttc    240

ccaattttga ttatcccttt gaccttcctg tacttcttcc actctaagaa gatctcccat    300

catcacaact cttccagttc ttcatcttca ttttggatgg aacccaagct gttcgtttcc    360

tcttctttga ttggtatctt gttcggtttg accaacttca tgtattcctt gggtttgagc    420

tatatcccaa tctccacttc ttctttgttg tacgctactc aattggtttt cgttgctttc    480

ttcgcttggt ttatcgtcaa gcaacaattc actgccttct ccattaactc cgttgttttg    540

atgactttgg gctccatttt gttgggtatt aagactgatg gtgatagacc agttggtgtt    600

actaaggctg aatacttgtt gggtttcttg ttgactttag gttctgctgc tgttgttggt    660

ttcattttgc caatggttga gctgtcttac tctaaggcta ctagaactgt taactacact    720

accgtcttgc aataccaatt caacttggct ttgttctcca ccatcttcaa ctctattggc    780

atgttgatta acaaggactt ccaagctatt ccaagagaag cctctgaatt tgaattgggt    840

aagaccatgt attacgtcgt tttaattggt ggtgctatca cttggcaatt cgcttctata    900

ggtggtttgg gtgttatctt gtacacctct tcattattct ccggcatctt gtcatctgtt    960

ttgttgccat tcactgaaat tgctgccgtt atcgtttatc acgaaagatt cactggtttg   1020

aaaggtatgg ctttggcatt gtgtttttgg ggttttacct cttactttta cggcgagtac   1080

aagttgatga tgaatgatac caaaactaag ccaccagaga agaacattcc agatgatcca   1140

tgtacctctg tctga                                                    1155
```

<210> SEQ ID NO 174
<211> LENGTH: 378
<212> TYPE: PRT
<213> ORGANISM: Aquilegia coerulea

<400> SEQUENCE: 174

Met Ser Ser Ser Ile His Leu Glu Ser Val Glu Glu Gly Thr Gln Thr
1               5                   10                  15

Pro Lys Ile Ala Thr Gln Met Gln Asn Lys Arg Lys Leu Thr Asn Trp
            20                  25                  30

Pro Leu Leu Leu Leu Ser Cys Thr Phe Val Ala Ile Gly Ile Ile Gly
        35                  40                  45

Gly Pro Leu Val Ser Arg Leu Tyr Tyr Ile His Gly Gly Lys Arg Arg
    50                  55                  60

Trp Leu Ser Ser Cys Met Gln Thr Ala Gly Phe Pro Ile Leu Phe Val
65                  70                  75                  80

Pro Leu Leu Ser Leu Phe Leu Gln Ser Lys Ser Gln Gly Val Ser Pro
                85                  90                  95

Ser Leu Phe Phe Met Glu Pro Lys Leu Phe Val Leu Ser Gly Leu Ile
            100                 105                 110

Gly Leu Leu Leu Gly Leu Asp Asn Phe Leu Tyr Ser Leu Gly Leu Ser
        115                 120                 125

Tyr Thr Pro Val Ser Thr Ser Ser Ile Leu Phe Ala Thr Gln Leu Ala
    130                 135                 140

Phe Leu Ala Val Phe Ala Phe Phe Met Val Lys Gln Lys Phe Thr Ala
145                 150                 155                 160

Tyr Ser Ile Asn Ser Val Ile Leu Met Thr Leu Gly Ser Val Leu Leu
                165                 170                 175

Gly Leu Arg Thr Ser Gly Asp Arg Pro Ala Gly Val Ser Asp Gly Gln
            180                 185                 190

Tyr Trp Leu Gly Phe Phe Leu Thr Leu Ala Ser Ala Ala Leu Leu Gly
        195                 200                 205

Leu Ile Trp Pro Leu Ile Glu Leu Ser Tyr Gly Lys Ala Lys Arg Pro
    210                 215                 220

Val Asn Tyr Gly Ile Val Leu Gln Phe Gln Thr Asn Leu Ala Ile Phe
225                 230                 235                 240

Ala Thr Leu Phe Ser Leu Thr Gly Met Val Ile Asn Lys Asp Phe Gln
                245                 250                 255

Ala Met Gly Arg Glu Ala Asn Glu Tyr Ala Leu Gly Asn Asn Met Tyr
            260                 265                 270

Tyr Leu Val Leu Ala Ala Ile Ala Val Val Trp Gln Leu Ser Phe Ile
        275                 280                 285

Gly Gly Leu Gly Val Ile Phe Cys Ala Asn Ser Leu Leu Asn Gly Val
    290                 295                 300

Leu Ser Ala Val Leu Leu Pro Ile Thr Asn Val Ala Ala Val Ile Phe
305                 310                 315                 320

Tyr His Glu Asn Phe Asn Gly Leu Lys Ala Met Ser Leu Val Leu Cys
                325                 330                 335

Leu Trp Gly Phe Val Ser Tyr Phe Tyr Gly Glu Tyr Lys Met Ser Gln
            340                 345                 350

Met Asn Lys Lys Leu Glu Asn Ser Thr Lys Ile Glu His Glu Gly Asp
        355                 360                 365

Ser Ala Pro Asn Ala Ala Leu Ser Ser Val
    370                 375

<210> SEQ ID NO 175
<211> LENGTH: 1137
<212> TYPE: DNA
<213> ORGANISM: Aquilegia coerulea

<400> SEQUENCE: 175

```
atgtcctcct ccatccactt ggaatctgtt gaagaaggta ctcaaactcc aaagattgct     60

acccaaatgc agaacaagag aaagttgact aattggccct tgctgttgtt gtcttgtact    120

tttgttgcca ttggtattat cggtggtcca ttggtttcta ggttgtacta tattcatggt    180

ggtaagagaa ggtggttgtc ctcttgtatg caaactgctg gttttccaat tttgttcgtc    240

ccattgctat ccttgttctt gcaatctaaa tcccaaggtg tttccccatc tttgtttttc    300

atggaaccta agctgttcgt cttgtctggt ttgattggtt tgttgttggg tctagacaac    360

ttcttgtatt ccttgggttt gtcttatacc ccagtttcca cttcctctat tttgtttgct    420

actcaattgg ctttcttggc tgttttcgct ttctttatgg tcaagcaaaa gttcaccgcc    480

tactccatta actccgttat tttgatgact ttgggctccg ttttgttggg tttgagaaca    540

tctggtgata gacctgctgg tgtttctgat ggtcaatatt ggttgggttt cttcttgact    600

ttggcttctg ctgctttatt gggtttaatt tggccattga tcgagttgtc ttacggtaaa    660

gctaaaagac cagttaacta cggtatcgtc ttgcaattcc aaactaactt ggctatcttc    720

gccaccttgt tttctttgac tggtatggtt atcaacaagg actttcaagc tatgggtaga    780

gaagctaatg aatacgcttt gggtaacaac atgtactact tggttttggc tgctattgca    840

gttgtttggc aattgtcttt tattggtggt ttgggtgtta ttttctgcgc caattctttg    900

ttgaacggtg ttttgtctgc tgtcttgttg ccaattacta atgttgctgc tgttatcttc    960

taccacgaaa actttaatgg tctgaaggcc atgtctttgg ttttgtgttt gtggggtttt   1020

gtctcttact tttacggtga gtacaagatg tcccagatga acaaaaagtt ggagaactcc   1080

accaagatcg aacatgaagg tgattctgct ccaaatgctg ctttgtcatc tgtttga      1137
```

<210> SEQ ID NO 176
<211> LENGTH: 375
<212> TYPE: PRT
<213> ORGANISM: Papaver somniferum

<400> SEQUENCE: 176

```
Met Ser Ile Glu Thr Pro Glu Thr Leu Gly Arg Asn Gln Asn Gly Asn
1               5                   10                  15

Ser Lys Thr Asp Ile Glu Lys Pro Ile Lys Thr Arg Asn Trp Leu Ile
            20                  25                  30

Ile Ile Ile Asn Cys Ala Leu Val Ser Cys Gly Ala Ile Gly Gly Pro
        35                  40                  45

Leu Leu Met Arg Leu Tyr Tyr Leu His Gly Gly Ser Arg Lys Trp Leu
    50                  55                  60

Ser Ser Cys Leu Gln Thr Ala Gly Phe Pro Ile Leu Ile Phe Pro Leu
65                  70                  75                  80

Ile Phe Leu Tyr Ile Lys Ser Lys Ser Ser Thr Pro Asn Lys Asp Gln
                85                  90                  95

Thr Ser Ser Phe Tyr Ile Glu Pro Lys Leu Phe Leu Ser Gly Ile Ala
            100                 105                 110

Ile Gly Ile Leu Phe Gly Phe Ala Asn Phe Met Tyr Ala Leu Gly Leu
        115                 120                 125
```

```
Ser Tyr Leu Pro Val Ser Thr Ser Ser Ile Leu Phe Ala Thr Gln Leu
    130                 135                 140

Cys Phe Thr Ala Phe Phe Ala Trp Leu Ile Val Lys Gln Lys Phe Ser
145                 150                 155                 160

Ala Phe Ile Ile Asn Ala Val Val Val Met Thr Leu Gly Ser Val Leu
                165                 170                 175

Leu Gly Ile Asn Thr Asn Gly Asp Arg Pro Ile Gly Val Ser Lys Ala
            180                 185                 190

Gln Tyr Leu Ile Gly Phe Leu Met Thr Leu Ala Ala Ala Ala Leu Thr
        195                 200                 205

Gly Leu Thr Met Pro Leu Ile Glu Leu Ala Phe Ser Lys Ala Thr Arg
    210                 215                 220

Arg Val Thr Tyr Ser Ser Leu Leu Gln Leu Gln Phe Thr Tyr Ser Leu
225                 230                 235                 240

Phe Ala Thr Gly Leu Asn Val Ile Gly Met Leu Ile Asn Lys Asp Phe
                245                 250                 255

Gln Ala Ile Pro Arg Glu Ala Glu Val Phe Glu Phe Gly Lys Arg Lys
            260                 265                 270

Tyr Tyr Met Ile Ile Val Leu Thr Ala Ile Thr Trp Gln Leu Ala Thr
        275                 280                 285

Leu Gly Phe Phe Gly Leu Ile Leu Tyr Thr Ser Ala Leu Phe Asn Gly
    290                 295                 300

Ile Tyr Gly Ser Leu Leu Phe Pro Phe Thr Gly Val Ala Ala Val Ile
305                 310                 315                 320

Phe Tyr His Glu Ser Phe Thr Gly Leu Lys Gly Met Ala Leu Ala Leu
                325                 330                 335

Cys Leu Trp Gly Phe Ser Ser Tyr Phe Tyr Gly Glu Tyr Lys Met Met
            340                 345                 350

Asn Lys Val Asn Asn Asn Glu Arg His Glu Lys Ile Glu Glu Val Glu
        355                 360                 365

Asn Asp Pro Lys Ser Thr Val
    370                 375
```

<210> SEQ ID NO 177
<211> LENGTH: 1128
<212> TYPE: DNA
<213> ORGANISM: Papaver somniferum

<400> SEQUENCE: 177

```
atgtccatcg aaactccaga aaccttgggt agaaatcaaa acggtaactc caagaccgat     60

atcgaaaagc caatcaagac tagaaactgg ctgattatca ttatcaactg cgctttggtt    120

tcttgcggtg ctattggtgg tccattattg atgagactgt attacttgca tggtggttcc    180

agaaaatggt tgtcctcttg tttacaaact gctggtttcc caattctgat cttcccattg    240

attttcttgt acatcaagtc caagtcctcc actccaaaca aagatcaaac ttcctcattc    300

tacatcgagc ccaagttgtt tttgtccggt attgcaattg gtatcttgtt cggttttgcc    360

aactttatgt atgccttggg tttgtcttat ttgccagtct ctacttcctc tattttgttc    420

gctactcaat tgtgtttcac cgcttttttt gcttggttga tcgtcaagca aaagttctcc    480

gctttcatta ttaacgccgt tgttgttatg actttgggct ctgttttgtt gggtattaac    540

actaatggtg acagaccaat cggtgtttct aaagcccaat atttgatcgg tttcttgatg    600

actttagctg ctgctgcttt gactggtttg actatgccat tgattgaatt ggctttctct    660

aaggctacta gaagggttac ttactcctct ttgttgcaac tgcaattcac ctattccttg    720
```

```
tttgctaccg gtttgaacgt tatcggtatg ttgattaaca aggacttcca agccattcca    780

agagaagctg aagtttttga attcggcaag agaaagtact acatgatcat cgttttgacc    840

gctattactt ggcaattggc tactttgggt tttttcggct tgatcttgta tacctctgct    900

ttgtttaatg gcatctacgg cagtttgttg tttccattca ctggtgttgc tgccgttatt    960

ttctaccatg aatctttcac aggtttgaaa ggtatggctt tggctttgtg tttgtggggt   1020

ttttcttctt acttttacgg cgagtacaag atgatgaaca aggtcaacaa caatgagagg   1080

cacgaaaaga ttgaagaagt tgaaaacgat ccaaagtcca ccgtttga                1128


<210> SEQ ID NO 178
<211> LENGTH: 365
<212> TYPE: PRT
<213> ORGANISM: Malus domestica

<400> SEQUENCE: 178

Met Glu Thr Asp His Val Glu Lys Arg Asn Ala Ala Ile Lys Lys Leu
1               5                   10                  15

Leu Leu Val Ile Ser Cys Ile Leu Leu Ser Ile Gly Thr Ala Gly Gly
            20                  25                  30

Pro Leu Val Met Arg Leu Tyr Phe Ile His Gly Gly Lys Arg Val Trp
        35                  40                  45

Leu Ser Ser Trp Leu Glu Thr Gly Gly Trp Pro Ile Thr Phe Ile Pro
    50                  55                  60

Leu Val Met Ala Tyr Tyr His Arg Arg Lys Thr Glu Gly Ala Ser Thr
65                  70                  75                  80

Lys Ile Ile Phe Met Lys Leu Pro Leu Phe Ile Ala Ser Ala Val Ile
                85                  90                  95

Gly Val Leu Thr Gly Leu Asp Asp Tyr Leu Tyr Ala Tyr Gly Val Ala
            100                 105                 110

Arg Leu Pro Val Ser Thr Ser Ala Leu Ile Ile Ala Gly Gln Leu Ala
        115                 120                 125

Phe Thr Ala Leu Phe Ala Phe Ile Leu Val Lys Gln Lys Phe Thr Ser
    130                 135                 140

Phe Ser Ile Asn Ala Val Val Leu Leu Thr Ile Gly Ala Ala Val Leu
145                 150                 155                 160

Gly Leu Asn Thr Ser Ser Asp Arg Pro Glu Gly Glu Ser Asn Lys Glu
                165                 170                 175

Tyr Ile Ala Gly Phe Phe Met Thr Val Ala Ala Ala Ala Leu Tyr Gly
            180                 185                 190

Phe Val Leu Pro Leu Ile Glu Leu Thr Tyr Lys Lys Ala Lys Gln Thr
        195                 200                 205

Ile Thr Tyr Ala Leu Val Leu Glu Ile Gln Leu Val Met Cys Leu Phe
    210                 215                 220

Ala Thr Leu Phe Cys Thr Val Gly Met Phe Ile Asp Asn Asp Phe Lys
225                 230                 235                 240

Val Ile Pro Arg Glu Ala Arg Asn Phe Gly Leu Gly Glu Thr Ser Tyr
                245                 250                 255

Tyr Val Val Leu Val Phe Ser Ala Ile Val Trp Gln Gly Phe Phe Leu
            260                 265                 270

Gly Ala Val Gly Val Ile Phe Cys Ala Ser Ser Leu Phe Ser Gly Ile
        275                 280                 285

Leu Ile Ala Val Leu Leu Pro Val Thr Glu Val Leu Ala Val Ile Phe
    290                 295                 300
```

Tyr His Glu Lys Phe Gln Ala Val Lys Gly Val Ser Leu Ala Leu Ser
305 310 315 320

Leu Trp Gly Phe Val Ser Tyr Phe Tyr Gly Glu Ile Lys His Ser Lys
325 330 335

Gln Glu Glu Lys Gly Lys Gln Ala Glu Ile Ser Glu Lys Lys Lys Glu
340 345 350

Thr Pro Glu Ala Thr Gln Val Pro Gln Gln Leu Glu Pro
355 360 365

<210> SEQ ID NO 179
<211> LENGTH: 1098
<212> TYPE: DNA
<213> ORGANISM: Malus domestica

<400> SEQUENCE: 179
atggaaaccg atcacgtcga aaagagaaac gctgctatta agaagttgct gttggttatc 60
tcctgcatct tgttgtctat tggtactgct ggtggtccat tggttatgag gttgtacttt 120
attcatggtg gtaagagagt ctggttgtca tcttggttgg aaactggtgg ttggccaatt 180
acttttattc ctttggttat ggcctactac catagaagaa aaactgaagg tgcttccacc 240
aagatcattt tcatgaagtt gcctttgttc attgcctccg ctgttattgg tgttttgact 300
ggtttggatg attacttgta tgcttacggt gttgctagat tgccagtttc tacttccgct 360
ttgattattg ctggtcaatt ggcttttact gctttgttcg ctttcatttt ggtcaagcaa 420
aagttcacct ccttctccat taacgctgtt gttttgttaa ctattggtgc tgcagttttg 480
ggtttgaaca cttcttctga tagaccagaa ggtgagtcta acaaagagta cattgctggt 540
ttcttcatga ctgttgctgc tgctgcatta tacggttttg ttttgccatt gatcgagctg 600
acttacaaga aagctaagca aactattacc tacgccttgg tcttggaaat tcaattggtc 660
atgtgtttgt tcgccacttt gttctgtact gttggtatgt tcatcgacaa cgatttcaag 720
gttattccaa gagaagctag gaatttcggt ttgggtgaaa cttcttacta cgtcgttttg 780
gttttctctg ctatagtttg gcaaggtttt ttcttgggtg ccgttggtgt tattttctgt 840
gcttcttctt tgttctccgg tattttgatt gctgttttgt tgccagttac cgaagttttg 900
gctgttatct tttaccacga aaagttccaa gctgttaagg gtgtttcttt ggctttgtct 960
ttgtggggtt tcgtttctta tttctacggt gaaatcaagc actccaagca agaagaaaag 1020
ggtaagcaag ctgaaatctc cgaaaagaag aaagaaactc cagaagctac tcaagtccca 1080
caacaattgg aaccataa 1098

<210> SEQ ID NO 180
<211> LENGTH: 352
<212> TYPE: PRT
<213> ORGANISM: Cinnamomum micranthum f. kanehirae

<400> SEQUENCE: 180

Met Lys Arg Ala Leu Leu Ile Phe Asn Cys Leu Leu Leu Ala Val Gly
1 5 10 15

Asn Cys Gly Gly Pro Leu Ile Met Arg Leu Tyr Phe Val His Gly Gly
20 25 30

Lys Arg Val Trp Leu Ser Ser Trp Leu Glu Thr Gly Gly Trp Pro Met
35 40 45

Ile Phe Ile Pro Leu Ile Phe Ser Tyr Phe His Arg Arg Arg Ser Ala
50 55 60

```
Ala Leu Glu Ser Ser Glu Ser Ala Asn Lys Thr Lys Met Ile Phe Met
65                  70                  75                  80

Lys Pro Arg Leu Phe Leu Ala Ser Ala Val Ile Gly Ile Ile Thr Gly
                85                  90                  95

Phe Asp Asp Tyr Leu Tyr Ala Tyr Gly Val Ala Arg Leu Pro Val Ser
            100                 105                 110

Thr Ser Ala Leu Ile Ile Ala Thr Gln Leu Ala Phe Thr Ala Gly Phe
        115                 120                 125

Ala Tyr Leu Leu Val Lys Gln Lys Phe Thr Ser Tyr Ser Ile Asn Ala
    130                 135                 140

Val Val Leu Ile Thr Ile Gly Gly Ala Val Leu Ala Leu His Thr Ser
145                 150                 155                 160

Gly Asp Arg Pro Ala Gly Val Ser Thr Lys Gln Tyr Ile Ala Gly Phe
                165                 170                 175

Leu Met Thr Leu Ala Ala Ala Ala Leu Tyr Gly Phe Val Leu Pro Leu
            180                 185                 190

Val Glu Leu Thr Tyr Lys Lys Ser Arg Gln Arg Ile Thr Tyr Thr Leu
        195                 200                 205

Val Leu Glu Ile Gln Leu Val Leu Ser Phe Phe Ala Thr Val Val Cys
    210                 215                 220

Thr Val Gly Met Leu Ala Asn Asn Asp Phe Lys Val Ile Pro Arg Glu
225                 230                 235                 240

Ala Ala Glu Phe Gly Leu Gly Glu Thr Ala Tyr Tyr Val Val Leu Ala
                245                 250                 255

Cys Ser Ala Ile Ala Trp Gln Gly Phe Phe Leu Gly Ala Ile Gly Val
            260                 265                 270

Ile Phe Ser Ser Ser Ser Leu Phe Ser Gly Ile Val Ile Ala Val Leu
        275                 280                 285

Leu Pro Val Thr Glu Ile Leu Ala Val Ile Ile Phe Lys Glu Lys Phe
    290                 295                 300

Lys Ala Glu Lys Gly Val Ser Leu Ala Leu Asn Leu Trp Gly Phe Val
305                 310                 315                 320

Ser Tyr Phe Tyr Gly Asp Ile Lys Asn Asn Lys Thr Asn Asn Leu Gln
                325                 330                 335

Leu Gln Leu His Lys Thr Glu Ala Thr Ala Thr Gln Ile Ser Ser Val
            340                 345                 350
```

<210> SEQ ID NO 181
<211> LENGTH: 1059
<212> TYPE: DNA
<213> ORGANISM: Cinnamomum micranthum f. kanehirae

<400> SEQUENCE: 181

```
atgaagaggg ccttgttgat cttcaactgt ttgttgttgg ctgttggtaa ttgtggtggt      60

ccattgatta tgaggttgta ctttgttcat ggtggtaaga gagtttggtt gtcatcttgg     120

ttggaaactg gtggttggcc aatgattttt atcccattga tcttctcgta cttccacaga     180

agaagatctg ctgctttgga atcttctgaa tctgctaaca agacgaagat gattttcatg     240

aagccaaggt tgtttttggc ctctgctgtt attggtatta tcaccggttt tgacgattac     300

ttgtatgctt atggtgttgc cagattgcca gtttctactt ccgctttgat tattgctact     360

caattggctt ttactgctgg tttcgcttac ttgttggtta agcaaaagtt cacctcctac     420

tccattaacg ccgttgtttt gattactatt ggtggtgctg ttttggcctt gcatacttct     480

ggtgatagac ctgctggtgt ttctactaag cagtatattg ctggtttttt gatgactttg     540
```

```
gctgctgctg cattatacgg ttttgttttg ccattggttg agctgactta caagaagtcc    600

agacaaagaa ttacctacac cttggtcttg gaaatccaat tggttttgtc tttcttcgct    660

actgttgtct gtactgttgg tatgttggca aacaacgatt tcaaggttat tccaagagaa    720

gctgctgaat ttggtttggg tgaaactgct tactatgttg tcttggcttg ttctgctatt    780

gcttggcaag gtttttttctt gggtgctatt ggtgtgatct tcagctcatc ttctttgttc   840

tctggtatcg ttattgccgt tttgttgcca gttactgaaa ttttggccgt catcatcttc    900

aaagaaaagt tcaaggctga aaagggtgtc tctttggctt tgaatttgtg gggtttcgtt    960

tcttacttct acggtgatat caagaacaac aagaccaaca acttgcaact acaattgcat   1020

aagactgaag ctactgctac ccaaatctct tctgtttga                          1059
```

<210> SEQ ID NO 182
<211> LENGTH: 369
<212> TYPE: PRT
<213> ORGANISM: Artemisia annua

<400> SEQUENCE: 182

```
Met Asp Asn His Lys Ser Ala Thr Thr Thr Thr Asn Thr Glu Pro Met
1               5                   10                  15

Thr Ala Lys Val Ser Pro Ala Ala Lys Lys Thr Leu Leu Ile Leu Asn
            20                  25                  30

Cys Ile Leu Leu Ser Val Gly Ile Cys Gly Gly Pro Leu Ile Met Arg
        35                  40                  45

Leu Tyr Phe Val His Gly Gly Asn Arg Val Trp Leu Ser Ser Phe Leu
    50                  55                  60

Glu Thr Ala Gly Trp Pro Phe Ile Val Pro Val Leu Ile Val Leu Phe
65                  70                  75                  80

Phe Ile Arg Arg Asn Ser Asn Thr Lys Thr Thr Thr Ile Tyr Met Arg
                85                  90                  95

Pro Arg Leu Phe Phe Ala Thr Ala Phe Val Gly Ile Leu Thr Gly Leu
            100                 105                 110

Asp Asp Tyr Leu Tyr Ala Tyr Gly Leu Ala Arg Leu Pro Val Ser Thr
        115                 120                 125

Ser Ser Leu Ile Ile Ala Ser Gln Leu Gly Phe Thr Ala Phe Phe Ala
    130                 135                 140

Tyr Leu Leu Val Lys Gln Lys Phe Thr Pro Tyr Ser Ile Asn Ala Val
145                 150                 155                 160

Val Leu Leu Thr Val Gly Ala Gly Val Leu Ala Leu His Thr Ser Ser
                165                 170                 175

Asp Arg Pro Lys Gly Glu Ser Lys Lys Glu Tyr Met Leu Gly Phe Val
            180                 185                 190

Met Thr Val Gly Ala Ala Leu Leu Tyr Gly Phe Ile Leu Pro Leu Val
        195                 200                 205

Glu Leu Thr Tyr Asn Lys Ala Lys Gln Ala Ile Thr Tyr Thr Leu Val
    210                 215                 220

Leu Glu Ile Gln Met Val Met Cys Leu Phe Ala Thr Ile Phe Cys Thr
225                 230                 235                 240

Val Gly Met Ile Val Asn Asn Asp Phe Lys Val Ile Pro Arg Glu Ala
                245                 250                 255

Thr Glu Phe Gly Leu Gly Lys Thr Asn Tyr Tyr Thr Ile Leu Cys Ala
            260                 265                 270

Ser Ala Leu Thr Trp Gln Cys Phe Phe Leu Gly Ala Ile Gly Val Ile
```

```
        275                 280                 285

Phe Cys Ala Ser Ser Leu Leu Ser Gly Ile Ile Ile Ala Val Ala Leu
    290                 295                 300

Pro Val Thr Glu Val Leu Ala Val Val Phe Phe Ser Glu Lys Phe Gln
305                 310                 315                 320

Ala Glu Lys Gly Val Ala Leu Val Leu Ser Leu Trp Gly Phe Ala Ser
                325                 330                 335

Tyr Phe Tyr Gly Glu Tyr Lys Ser Thr Lys Lys Pro Lys Asp Ile Asn
            340                 345                 350

Glu Ser Thr Arg Gln Thr Met Glu Leu Pro Gln Ser Asp Tyr Ser Arg
        355                 360                 365

Val


<210> SEQ ID NO 183
<211> LENGTH: 1110
<212> TYPE: DNA
<213> ORGANISM: Artemisia annua

<400> SEQUENCE: 183

atggacaacc ataagtctgc tactactacc actaatactg aacctatgac tgctaaagtt      60

tctccagctg ctaaaaagac cttgttgatt ttgaactgca tcttgttgtc cgttggtatt     120

tgtggtggtc cattgattat gaggttgtac tttgttcatg gtggtaacag agtttggctg     180

tcctcttttt tggaaactgc tggttggcct tttatcgttc cagttttgat cgttctgttc     240

ttcatcagaa gaaactctaa cactaagacc accactatct atatgaggcc aagattattc     300

ttcgctactg cttttgttgg tatcttgact ggtttggatg attacttgta tgcttacggt     360

ttggctagat tgccagtttc tacttcctct ttgattatcg cttctcaatt gggtttcact     420

gctttctttg cttacttgtt ggtcaagcaa aagttcaccc catactctat taacgccgtt     480

gttttgttga ctgttggtgc tggtgttttg gcattgcata cttcatctga tagaccaaag     540

ggtgagtcta agaaagagta catgttgggt ttcgttatga cagttggtgc agctttgttg     600

tacggtttca ttttgccatt ggttgagttg acttacaaca aggctaagca agctattacc     660

tacaccttgg ttttggaaat ccaaatggtt atgtgtttgt tcgccaccat tttctgtact     720

gttggtatga tcgttaacaa cgacttcaag gttattccaa gagaagctac tgaattcggt     780

ttgggtaaga ctaactacta taccattttg tgtgcctctg ctttgacttg gcaatgtttt     840

ttcttgggtg ctatcggtgt tattttctgc gcttcttctt tgttgtctgg tatcattata     900

gctgttgctt tgccagttac tgaagttttg gctgttgttt tcttcagcga aaagttccaa     960

gctgaaaaag gtgttgcatt ggttttgtct ttgtggggtt ttgcttctta cttttacggt    1020

gagtacaagt ctaccaaaaa gccaaaggat atcaacgaat ccactagaca aactatggaa    1080

ttgccacaat ccgattactc cagagtttga                                     1110


<210> SEQ ID NO 184
<211> LENGTH: 353
<212> TYPE: PRT
<213> ORGANISM: Capsicum chinense

<400> SEQUENCE: 184

Met Glu Pro Gln Val Ser Ser Arg Met Lys Lys Leu Leu Leu Val Ile
1               5                   10                  15

Asn Cys Ile Ile Leu Ala Val Gly Thr Cys Gly Gly Pro Leu Ile Met
            20                  25                  30
```

```
Arg Leu Tyr Phe Ile Lys Gly Gly Lys Arg Ile Trp Leu Ser Ser Trp
        35                  40                  45

Leu Gln Thr Ala Ala Trp Pro Ile Asn Phe Ile Pro Leu Val Ile Ser
    50                  55                  60

Tyr Ile Tyr Arg Arg Lys Ser Asn Asn Asn Asn Thr Thr Lys Leu Ile
65                  70                  75                  80

Leu Met Thr Pro Gln Ile Leu Val Val Thr Ile Gly Ile Gly Ile Leu
                85                  90                  95

Gln Gly Tyr Ala Asn Tyr Phe Tyr Ala Tyr Gly Ile Ala Lys Leu Pro
            100                 105                 110

Val Ser Thr Ser Gly Leu Leu Phe Ala Thr Gln Leu Ala Phe Thr Ala
        115                 120                 125

Phe Phe Ala Phe Leu Ile Val Lys Leu Lys Phe Thr Ser Tyr Ser Val
    130                 135                 140

Asn Ser Val Phe Leu Leu Thr Ile Gly Ala Val Val Leu Ala Leu Arg
145                 150                 155                 160

Ser Ser Gly Asp Gln Pro Glu Gly Glu Pro Lys Lys Glu Tyr Ile Leu
                165                 170                 175

Gly Phe Ile Met Thr Leu Ala Ala Ala Ala Leu Ser Gly Leu Ile Phe
            180                 185                 190

Pro Leu Val Glu Leu Ile Tyr Lys Lys Ala Gln Gln Ala Ile Thr Tyr
        195                 200                 205

Thr Leu Val Leu Glu Phe Gln Thr Val Tyr Cys Phe Ile Ala Thr Val
    210                 215                 220

Leu Ala Thr Ile Gly Met Ile Ile Asn Lys Asp Phe Gln Ala Ile Ser
225                 230                 235                 240

Arg Glu Ala Asn Ser Phe Glu Leu Gly Glu Ser Lys Tyr Tyr Ile Val
                245                 250                 255

Ile Val Trp Ser Ala Ile Val Leu Gln Phe Tyr Phe Leu Gly Val Ile
            260                 265                 270

Gly Val Ile Tyr Ser Ala Ser Ser Leu Val Ser Gly Ile Leu Ile Ser
        275                 280                 285

Val Leu Leu Pro Ala Thr Glu Val Leu Ala Val Phe Leu Tyr Gly Glu
    290                 295                 300

Lys Phe Asn Ala Glu Lys Gly Ile Ser Leu Ala Leu Ser Leu Trp Gly
305                 310                 315                 320

Phe Ala Ser Tyr Phe Tyr Gly Asp Tyr Lys Glu Asn Lys Lys Arg Glu
                325                 330                 335

Asn Asn Gln Ser Gln Glu Thr Glu Met Thr Asp Lys Ser Asn Cys Thr
            340                 345                 350

Pro
```

<210> SEQ ID NO 185
<211> LENGTH: 1062
<212> TYPE: DNA
<213> ORGANISM: Capsicum chinense

<400> SEQUENCE: 185

```
atggaacccc aagtctcctc tagaatgaag aagttgttgt tggttatcaa ctgcatcatt      60

ttggctgttg gtacttgtgg tggtccattg attatgaggt tgtactttat caaaggtggc     120

aagagaatct ggttgtcatc ttggttgcaa actgctgctt ggccaatcaa tttcattcca     180

ttggttatct cgtacatcta caggcgtaaa tcgaacaaca acaataccac caagttgatc     240

ttgatgaccc cacaaatttt ggttgttacc attggtatcg gtatcttgca aggttacgct     300
```

```
aattactttt acgcttacgg tattgccaag ttgccagttt ctacttctgg tttgttgttt    360

gctactcaat tggctttcac tgctttcttc gctttcttga tcgttaagtt gaagttcacc    420

tcctactccg ttaactctgt tttcttgttg actattggtg ctgttgtttt ggccttgaga    480

tcttctggtg atcaacctga aggtgaacct aagaaagagt acattttggg tttcattatg    540

accttggctg ctgctgcttt gtctggtttg atttttccat tagtcgagct gatctacaag    600

aaggctcaac aagctattac ttacaccttg gttttggagt tccaaaccgt ttactgtttc    660

attgctactg ttttggctac catcggtatg atcattaaca aggatttcca agccatttcc    720

agagaagcta actcttttga attgggcgaa tccaagtact acatcgttat agtttggtcc    780

gctatcgtct tgcagtttta ctttttgggt gttatcggcg ttatctactc tgcttcttct    840

ttggtttccg gcattttgat ctctgttttg ttgccagcta ctgaagtttt ggccgttttc    900

ttatacggtg aaaagttcaa tgccgagaag ggtatttctt tggctttgtc tttatggggt    960

ttcgcctctt acttttatgg tgactacaaa gagaacaaga agagggaaaa caaccagtct   1020

caagaaactg aaatgaccga taagtctaac tgtaccccat ga                      1062
```

```
<210> SEQ ID NO 186
<211> LENGTH: 345
<212> TYPE: PRT
<213> ORGANISM: Jatropha curcas

<400> SEQUENCE: 186

Met Arg Arg Ala Leu Leu Val Leu Asn Cys Val Ile Leu Ser Ile Gly
1               5                   10                  15

Asn Cys Gly Gly Pro Leu Ile Met Arg Leu Tyr Phe Ile His Gly Gly
            20                  25                  30

Lys Arg Val Trp Leu Ser Ser Trp Leu Glu Thr Ala Gly Trp Pro Ile
        35                  40                  45

Ile Phe Ile Pro Leu Leu Ile Ser Tyr Phe His Arg Arg Ser Thr Thr
    50                  55                  60

Asp Pro Thr Thr Ala Lys Leu Phe Tyr Met Lys Pro Ser Leu Phe Leu
65                  70                  75                  80

Ala Ala Thr Gly Ile Gly Ile Leu Thr Gly Phe Asp Asp Tyr Leu Tyr
                85                  90                  95

Ala Tyr Gly Val Ala Arg Leu Pro Val Ser Thr Ser Ser Leu Ile Ile
            100                 105                 110

Ala Thr Gln Leu Ala Phe Thr Ala Gly Phe Ala Phe Leu Leu Val Lys
        115                 120                 125

Gln Lys Phe Thr Ser Tyr Ser Ile Asn Ala Val Val Leu Leu Thr Val
    130                 135                 140

Gly Ala Gly Val Leu Ala Leu His Thr Ser Ser Asp Arg Pro Glu His
145                 150                 155                 160

Glu Ser Lys Lys Glu Tyr Asn Leu Gly Phe Val Met Thr Leu Gly Ala
                165                 170                 175

Ala Val Leu Tyr Gly Leu Ile Leu Pro Leu Val Glu Leu Thr Tyr Arg
            180                 185                 190

Lys Ala Lys Gln Glu Ile Ser Tyr Thr Leu Val Met Glu Ile Gln Met
        195                 200                 205

Ile Met Cys Leu Phe Ala Thr Val Val Cys Thr Val Gly Met Leu Val
    210                 215                 220

Asn Asn Asp Phe Lys Val Ile Pro Arg Glu Ala Lys Glu Phe Glu Leu
225                 230                 235                 240
```

```
Gly Glu Thr Lys Tyr Tyr Val Ile Met Val Trp Ser Ala Ile Ile Trp
                245                 250                 255

Gln Cys Phe Phe Leu Gly Ala Ile Gly Ile Val Phe Cys Ala Ser Ser
            260                 265                 270

Leu Ala Ser Gly Val Val Ile Ala Val Leu Leu Pro Val Thr Glu Ile
        275                 280                 285

Leu Ala Val Ile Phe Tyr Gln Glu Lys Phe Gln Ala Glu Lys Gly Val
    290                 295                 300

Ala Leu Ala Leu Ser Leu Trp Gly Phe Leu Ser Tyr Phe Tyr Gly Glu
305                 310                 315                 320

Ile Lys Gln Ser Lys Lys Thr Asn Leu Thr Ser Glu Ile Glu Thr Ser
                325                 330                 335

Glu Ser Ser Ile Pro Thr Gln Asn Val
            340                 345


<210> SEQ ID NO 187
<211> LENGTH: 1038
<212> TYPE: DNA
<213> ORGANISM: Jatropha curcas

<400> SEQUENCE: 187

atgagaaggg ccttgttggt tttgaactgc gttattttgt ctatcggtaa ttgtggtggt     60

ccattgatta tgaggttgta ctttattcac ggtggtaaga gagtttggtt gtcatcttgg    120

ttggaaactg ctggttggcc aattatcttt atccctttgt tgatctccta cttccacaga    180

agatctacta ctgatccaac tactgctaag ctgttttaca tgaagccatc tttgtttttg    240

gctgctaccg gtattggtat tttgactggt tttgatgatt acttgtacgc ttacggtgtt    300

gctagattgc cagtttctac ttcctctttg attatcgcta ctcaattggc ttttaccgct    360

ggttttgctt ttttgttggt caagcaaaag ttcacctcct actctattaa cgccgttgtt    420

ttgttgactg ttggtgctgg tgttttggca ttgcatactt catctgatag accagaacac    480

gagtctaaga aagagtacaa tttgggtttc gttatgactt tgggtgctgc tgtcttgtat    540

ggtttgattt tgccattggt tgagctgact tacagaaagg ctaaacaaga aatctcctac    600

accttggtca tggaaatcca aatgattatg tgtttgttcg ctaccgttgt ctgtactgtt    660

ggtatgttgg ttaacaacga tttcaaggtc attccaaggg aagccaaaga atttgaattg    720

ggtgaaacta agtactacgt catcatggtt tggtccgcta ttatttggca atgtttttc     780

ttgggtgcca tcggtatagt ttctgtgct tcttctttgg catccggtgt tgttattgct    840

gttttgttac cagttaccga aatcttggcc gttatcttct accaagaaaa gttccaagct    900

gaaaagggtg ttgctttggc tttgtctttg tggggttttt tgtcttactt ctacggtgaa    960

atcaagcagt ccaaaaagac taacttgacc tccgaaattg aaacctccga atcttctatt   1020

ccaactcaga acgtttaa                                                 1038


<210> SEQ ID NO 188
<211> LENGTH: 348
<212> TYPE: PRT
<213> ORGANISM: Papaver trinifolium

<400> SEQUENCE: 188

Met Gly Lys Tyr Leu Leu Leu Phe Asn Cys Ile Leu Leu Ala Val Ser
1               5                   10                  15

Ser Ala Ala Gly Pro Leu Leu Leu Arg Leu Tyr Phe Ile His Gly Gly
            20                  25                  30
```

```
Lys Arg Leu Trp Leu Leu Ser Trp Leu Glu Thr Ala Gly Trp Pro Ile
        35                  40                  45

Leu Phe Leu Pro Leu Ser Leu Ser Tyr Phe Leu Lys Arg Arg Arg Phe
    50                  55                  60

Lys Asn Gly Gln Asp Glu Lys Pro Ser Lys Phe Phe Met Ile Thr Pro
65                  70                  75                  80

Phe Leu Phe Met Ala Ser Ala Phe Ile Gly Leu Leu Ile Gly Leu Asp
                85                  90                  95

Asp Tyr Leu Tyr Thr Tyr Gly Val Ser Leu Leu Pro Val Ser Thr Ser
            100                 105                 110

Ala Leu Ile Met Ser Thr His Leu Ala Phe Thr Ala Gly Phe Ala Leu
        115                 120                 125

Phe Met Val Lys Gln Lys Phe Thr Ser Tyr Ser Val Asn Ala Val Ile
    130                 135                 140

Leu Leu Thr Val Gly Ala Val Leu Leu Gly Leu His Ser Asn Gly Asp
145                 150                 155                 160

Lys Pro Val His Glu Ser Asn Arg Asp Tyr Tyr Leu Gly Phe Val Ile
                165                 170                 175

Thr Ile Gly Ala Ser Val Ile Gly Gly Leu Leu Leu Pro Leu Val Glu
            180                 185                 190

Leu Met Tyr Lys Lys Ser Lys Gln Thr Ile Thr Tyr Ser Leu Val Ile
        195                 200                 205

Glu Leu Gln Ile Val Ile Ser Val Phe Ala Thr Leu Phe Cys Thr Val
    210                 215                 220

Gly Met Leu Val Asn Asn Asp Phe Lys Val Ile Gln Arg Glu Gly Lys
225                 230                 235                 240

Glu Tyr Asn Leu Gly Glu Thr Lys Tyr Tyr Val Val Leu Val Ala Ser
                245                 250                 255

Ser Ile Ser Trp Gln Leu Cys Phe Leu Gly Thr Ile Gly Val Ile Phe
            260                 265                 270

Cys Ser Thr Ser Leu Leu Ala Gly Val Ile Gly Ala Val Val Leu Pro
        275                 280                 285

Val Ile Glu Ile Leu Ala Val Ile Phe Tyr His Glu Ser Phe Lys Ala
    290                 295                 300

Glu Lys Gly Ile Ala Leu Phe Leu Ser Leu Trp Gly Phe Ile Ser Tyr
305                 310                 315                 320

Phe Tyr Leu Glu Leu Lys Ala Ser Arg Lys Pro Lys Lys Lys Gln Ser
                325                 330                 335

Leu Glu Leu Glu Gln Gly Asp Leu Thr Val Ser Ser
            340                 345
```

<210> SEQ ID NO 189
<211> LENGTH: 1047
<212> TYPE: DNA
<213> ORGANISM: Papaver trinifolium

<400> SEQUENCE: 189

```
atgggcaaat acctgctgtt gttcaactgc attttgttgg ctgtttcttc tgctgctggt      60

cctttgttgt tgaggttgta ctttattcat ggtggtaaga ggttgtggtt gttgtcttgg     120

ttggaaactg ctggttggcc aattttgttt ttgccattgt ccttgtccta ctttttgaag     180

cgtagaagat tcaagaacgg tcaagacgaa aagccatcta agttcttcat gattacccct     240

ttcttgttca tggcttctgc tttcattggt ttgttgatcg gtttggatga ttacttgtac     300
```

-continued

| | |
|---|---|
| acctacggtg tttctttgtt gccagtttct acatccgctt tgattatgtc tactcatttg | 360 |
| gcttttaccg ctggttttgc tttgtttatg gtcaagcaaa agttcacctc ctactctgtt | 420 |
| aacgccgtta ttttgttaac tgttggtgct gtcttgttgg gcttgcattc taatggtgat | 480 |
| aagccagttc atgaatccaa cagagattac tacttgggtt tcgtgattac tattggtgcc | 540 |
| tctgttattg gtggtttgtt attgcctttg gtcgagttga tgtacaagaa gtctaagcaa | 600 |
| accatcacct actcattggt catcgaattg caaatcgtca tttctgtttt cgctaccttg | 660 |
| ttctgtactg ttggtatgtt ggttaacaac gacttcaagg tcattcagag agaaggtaaa | 720 |
| gagtacaatt tgggcgaaac taagtactac gttgttttgg ttgcctcctc tatttcttgg | 780 |
| caattgtgtt tcttgggtac tatcggtgtt attttctgct ctacctcttt gttagctggt | 840 |
| gttattggag ctgttgtttt gccagttatt gaaatcttgg ccgttatctt ctaccacgaa | 900 |
| tcttttaaag ccgaaaaggg tattgccctg tttttgtctt tgtggggttt catctcttac | 960 |
| ttctacttgg aattgaaggc ctctagaaag ccaaagaaga agcaatcttt ggaattggaa | 1020 |
| caaggtgact tgactgtctc ttcttga | 1047 |